US009809813B2

(12) United States Patent
Robins et al.

(10) Patent No.: US 9,809,813 B2
(45) Date of Patent: Nov. 7, 2017

(54) METHOD OF MEASURING ADAPTIVE IMMUNITY

(71) Applicant: FRED HUTCHINSON CANCER RESEARCH CENTER, Seattle, WA (US)

(72) Inventors: Harlan S. Robins, Seattle, WA (US); Edus H. Warren, III, Bainbridge Island, WA (US); Christopher Scott Carlson, Kirkland, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 31 days.

(21) Appl. No.: 15/061,827

(22) Filed: Mar. 4, 2016

(65) Prior Publication Data

US 2016/0251721 A1    Sep. 1, 2016

Related U.S. Application Data

(63) Continuation of application No. 14/243,875, filed on Apr. 2, 2014, now abandoned, which is a continuation of application No. 12/794,507, filed on Jun. 4, 2010, now abandoned.

(60) Provisional application No. 61/220,344, filed on Jun. 25, 2009.

(51) Int. Cl.
*C12Q 1/68* (2006.01)
*G06F 19/24* (2011.01)
*C12N 15/10* (2006.01)

(52) U.S. Cl.
CPC ....... *C12N 15/1065* (2013.01); *C12Q 1/6869* (2013.01); *C12Q 1/6874* (2013.01); *C12Q 1/6881* (2013.01); *C12Q 1/6883* (2013.01); *G06F 19/24* (2013.01); *C12Q 2600/16* (2013.01)

(58) Field of Classification Search
None
See application file for complete search history.

(56) References Cited

U.S. PATENT DOCUMENTS

| | | |
|---|---|---|
| 3,270,960 A | 9/1966 | Phillips |
| 3,773,919 A | 11/1973 | Boswell et al. |
| 4,474,754 A | 10/1984 | Shimizu et al. |
| 4,683,195 A | 7/1987 | Mullis et al. |
| 4,683,202 A | 7/1987 | Mullis |
| 4,751,188 A | 6/1988 | Valet |
| 4,800,159 A | 1/1989 | Mullis et al. |
| 4,876,189 A | 10/1989 | Schetters |
| 4,942,124 A | 7/1990 | Church |
| 4,965,188 A | 10/1990 | Mullis et al. |
| 5,075,217 A | 12/1991 | Weber |
| 5,126,022 A | 6/1992 | Soane et al. |
| 5,149,625 A | 9/1992 | Church et al. |
| 5,168,038 A | 12/1992 | Tecott et al. |
| 5,189,147 A | 2/1993 | Saito et al. |
| 5,210,015 A | 5/1993 | Gelfand et al. |
| 5,213,960 A | 5/1993 | Chang |
| 5,231,012 A | 7/1993 | Mosmann et al. |
| 5,296,351 A | 3/1994 | Morley |
| 5,298,396 A | 3/1994 | Kotzin et al. |
| 5,326,696 A | 7/1994 | Chang |
| 5,336,598 A | 8/1994 | Kotzin et al. |
| 5,364,759 A | 11/1994 | Caskey et al. |
| 5,399,491 A | 3/1995 | Kacian et al. |
| 5,418,134 A | 5/1995 | Morley |
| 5,449,752 A | 9/1995 | Fujii et al. |
| 5,498,392 A | 3/1996 | Wilding et al. |
| 5,506,126 A | 4/1996 | Seed et al. |
| 5,587,128 A | 12/1996 | Wilding et al. |
| 5,627,037 A | 5/1997 | Ward |
| 5,627,052 A | 5/1997 | Schrader |
| 5,635,354 A | 6/1997 | Kourilsky et al. |
| 5,635,400 A | 6/1997 | Brenner |
| 5,667,967 A | 9/1997 | Steinman et al. |
| 5,698,396 A | 12/1997 | Pfreundschuh |
| 5,699,798 A | 12/1997 | Hochman et al. |
| 5,741,676 A | 4/1998 | Fuller |
| 5,776,708 A | 7/1998 | Kotzin et al. |
| 5,776,737 A | 7/1998 | Dunn |
| 5,837,447 A | 11/1998 | Gorski |
| 5,846,719 A | 12/1998 | Brenner et al. |
| 5,854,033 A | 12/1998 | Lizardi |
| 5,858,195 A | 1/1999 | Ramsey |
| 5,925,517 A | 7/1999 | Tyagi et al. |
| 5,935,793 A | 8/1999 | Wong |
| 5,969,108 A | 10/1999 | McCafferty et al. |
| 5,981,176 A | 11/1999 | Wallace |

(Continued)

FOREIGN PATENT DOCUMENTS

CN   101225441 A   7/2008
CN   102272327 A   12/2011
(Continued)

OTHER PUBLICATIONS

US 8,642,750, 02/2014, Faham et al. (withdrawn)
Abath et al. "Single-tubed nested PCR using immobilized internal primers", *Biotechniques*, 33(6): 1210-2, 1214 (2002).
Abbott, et al. "Design and use of signature primers to detect carry-over of amplified material", *J Virol Methods*, 46(1):51-59, Abstract Only (1994).
Ahmadzadeh et al. "FOXP3 expression accurately defines the population of intratumoral regulatory T cells that selectively accumulate in metastatic melanoma lesions", *Blood*, 112(13): 4953-4960 (2008).
Akatsuka, Y. et al., "Rapid screening of T-cell receptor (TCR) variable gene usage by multiplex PCR: Application for assessment of clonal composition", *Tissue Antigens*, 53:122-134 (1999).

(Continued)

*Primary Examiner* — Doug Schultz
(74) *Attorney, Agent, or Firm* — Cooley LLP

(57) ABSTRACT

A method of measuring immunocompetence is described. This method provides a means for assessing the effects of diseases or conditions that compromise the immune system and of therapies aimed to reconstitute it. This method is based on quantifying T-cell diversity by calculating the number of diverse T-cell receptor (TCR) beta chain variable regions from blood cells.

9 Claims, No Drawings

(56) References Cited

U.S. PATENT DOCUMENTS

| | | |
|---|---|---|
| 5,981,179 A | 11/1999 | Lorinez et al. |
| 6,001,229 A | 12/1999 | Ramsey |
| 6,010,607 A | 1/2000 | Ramsey |
| 6,033,546 A | 3/2000 | Ramsey |
| 6,054,034 A | 4/2000 | Soane et al. |
| 6,087,096 A | 7/2000 | Dau et al. |
| 6,090,592 A | 7/2000 | Adams et al. |
| 6,143,496 A | 11/2000 | Brown et al. |
| 6,172,214 B1 | 1/2001 | Brenner |
| 6,174,670 B1 | 1/2001 | Wittwer et al. |
| 6,258,540 B1 | 7/2001 | Lo et al. |
| 6,258,568 B1 | 7/2001 | Nyren |
| 6,300,070 B1 | 10/2001 | Boles et al. |
| 6,416,948 B1 | 7/2002 | Pilarski et al. |
| 6,440,706 B1 | 8/2002 | Vogelstein et al. |
| 6,458,530 B1 | 10/2002 | Morris et al. |
| 6,489,103 B1 | 12/2002 | Griffiths et al. |
| 6,524,829 B1 | 2/2003 | Seegar |
| 6,569,627 B2 | 5/2003 | Wittwer et al. |
| 6,596,492 B2 | 7/2003 | Avery et al. |
| 6,605,272 B2 | 8/2003 | Novak et al. |
| 6,613,525 B2 | 9/2003 | Nelson et al. |
| 6,667,159 B1 | 12/2003 | Walt |
| 6,753,147 B2 | 6/2004 | Vogelstein et al. |
| 6,787,308 B2 | 9/2004 | Balasubramanian et al. |
| 6,794,499 B2 | 9/2004 | Wengel et al. |
| 6,806,079 B1 | 10/2004 | McCafferty et al. |
| 6,858,412 B2 | 2/2005 | Willis et al. |
| 6,919,434 B1 | 7/2005 | Goto et al. |
| 6,964,850 B2 | 11/2005 | Bevilacqua |
| 7,068,874 B2 | 6/2006 | Wang et al. |
| 7,112,423 B2 | 9/2006 | Van Ness et al. |
| 7,115,400 B1 | 10/2006 | Adessi et al. |
| 7,148,040 B2 | 12/2006 | Meagher et al. |
| 7,157,228 B2 | 1/2007 | Hashmi et al. |
| 7,157,274 B2 | 1/2007 | Bohm et al. |
| 7,208,795 B2 | 4/2007 | Carver et al. |
| 7,232,653 B1 | 6/2007 | Austrup et al. |
| 7,306,906 B2 | 12/2007 | Maruyama et al. |
| 7,313,308 B2 | 12/2007 | Turner et al. |
| 7,323,305 B2 | 1/2008 | Leamon et al. |
| 7,329,731 B2 | 2/2008 | Jakobsen et al. |
| 7,351,578 B2 | 4/2008 | Cheo et al. |
| 7,365,179 B2 | 4/2008 | Brenner |
| 7,371,519 B2 | 5/2008 | Wolber |
| 7,375,211 B2 | 5/2008 | Kou |
| 7,393,665 B2 | 7/2008 | Brenner |
| 7,432,084 B2 | 10/2008 | Shoemaker |
| 7,537,897 B2 | 5/2009 | Brenner et al. |
| 7,544,473 B2 | 6/2009 | Brenner |
| 7,572,582 B2 | 8/2009 | Wengel et al. |
| 7,662,557 B2 | 2/2010 | McCafferty et al. |
| 7,666,604 B2 | 2/2010 | Jakobsen et al. |
| 7,691,994 B2 | 4/2010 | Brewer et al. |
| 7,700,323 B2 | 4/2010 | Willis et al. |
| 7,741,463 B2 | 6/2010 | Gormley et al. |
| 7,749,697 B2 | 7/2010 | Oleksiewicz et al. |
| 7,785,783 B2 | 8/2010 | Morley et al. |
| 7,833,716 B2 | 11/2010 | Becker et al. |
| 7,842,457 B2 | 11/2010 | Berka et al. |
| 7,862,999 B2 | 1/2011 | Zheng et al. |
| 7,879,324 B2 | 2/2011 | Saxon |
| 7,892,550 B2 | 2/2011 | Dennis et al. |
| 7,907,800 B2 | 3/2011 | Foquet et al. |
| 7,915,015 B2 | 3/2011 | Vogelstein et al. |
| 7,956,043 B2 | 6/2011 | Krieg et al. |
| 7,960,116 B2 | 6/2011 | Eid et al. |
| 8,012,690 B2 | 9/2011 | Berka et al. |
| 8,021,842 B2 | 9/2011 | Brenner |
| 8,030,023 B2 | 10/2011 | Adams et al. |
| 8,048,627 B2 | 11/2011 | Dressman et al. |
| 8,053,188 B2 | 11/2011 | Gullberg et al. |
| 8,053,235 B2 | 11/2011 | Buckner et al. |
| 8,137,569 B2 | 3/2012 | Harnack et al. |
| 8,137,936 B2 | 3/2012 | Macevicz |
| 8,153,375 B2 | 4/2012 | Travers et al. |
| 8,158,359 B2 | 4/2012 | Leamon et al. |
| 8,236,503 B2 | 8/2012 | Faham et al. |
| 8,283,294 B2 | 10/2012 | Kastrup et al. |
| 8,309,312 B2 | 11/2012 | Lang et al. |
| 8,313,625 B2 | 11/2012 | Rothberg et al. |
| 8,318,433 B2 | 11/2012 | Brenner |
| 8,394,590 B2 | 3/2013 | Kwong et al. |
| 8,445,205 B2 | 5/2013 | Brenner |
| 8,481,292 B2 | 7/2013 | Casbon et al. |
| 8,507,205 B2 | 8/2013 | Faham |
| 8,628,927 B2 | 1/2014 | Faham |
| 8,685,678 B2 | 4/2014 | Casbon |
| 8,691,510 B2 | 4/2014 | Faham |
| 8,699,361 B2 | 4/2014 | Jim et al. |
| 8,715,967 B2 | 5/2014 | Casbon |
| 8,722,368 B2 | 5/2014 | Casbon |
| 8,728,766 B2 | 5/2014 | Casbon |
| 8,741,606 B2 | 6/2014 | Casbon |
| 8,748,103 B2 | 6/2014 | Faham |
| 8,759,036 B2 | 6/2014 | Wang |
| 8,795,970 B2 | 8/2014 | Faham |
| 8,826,321 B2 | 9/2014 | Cronin et al. |
| 8,835,358 B2 | 9/2014 | Fodor |
| 9,012,148 B2 | 4/2015 | Han et al. |
| 9,043,160 B1 | 5/2015 | Moorhead et al. |
| 9,150,905 B2 | 10/2015 | Robins et al. |
| 9,217,176 B2 | 12/2015 | Faham et al. |
| 9,228,232 B2 | 1/2016 | Faham et al. |
| 9,416,420 B2 | 8/2016 | Faham et al. |
| 2002/0076725 A1 | 6/2002 | Toyosaki-Maeda et al. |
| 2002/0110807 A1 | 8/2002 | Pilarski et al. |
| 2003/0096277 A1 | 5/2003 | Chen |
| 2003/0120061 A1 | 6/2003 | Zhang |
| 2003/0162197 A1 | 8/2003 | Morley et al. |
| 2003/0207300 A1 | 11/2003 | Matray et al. |
| 2004/0033490 A1 | 2/2004 | Laird et al. |
| 2004/0132050 A1 | 7/2004 | Monforte |
| 2004/0146901 A1 | 7/2004 | Morris et al. |
| 2004/0170977 A1 | 9/2004 | Laird |
| 2004/0235061 A1 | 11/2004 | Wilkie et al. |
| 2004/0248172 A1 | 12/2004 | Samoszuk et al. |
| 2005/0037356 A1 | 2/2005 | Gullberg et al. |
| 2005/0064421 A1 | 3/2005 | Gehrmann et al. |
| 2005/0142577 A1 | 6/2005 | Jones et al. |
| 2005/0250147 A1 | 11/2005 | Macevicz |
| 2005/0255482 A1 | 11/2005 | Morley et al. |
| 2005/0260570 A1 | 11/2005 | Mao et al. |
| 2006/0019304 A1 | 1/2006 | Hardenbol et al. |
| 2006/0020397 A1 | 1/2006 | Kermani |
| 2006/0046258 A1 | 3/2006 | Lapidus et al. |
| 2006/0085139 A1 | 4/2006 | Collette et al. |
| 2006/0088876 A1 | 4/2006 | Bauer |
| 2006/0134125 A1 | 6/2006 | Luxembourg et al. |
| 2006/0147925 A1 | 7/2006 | Morley et al. |
| 2006/0199210 A1 | 9/2006 | Weichselbaum et al. |
| 2006/0211030 A1 | 9/2006 | Brenner |
| 2006/0216737 A1 | 9/2006 | Bodeau |
| 2006/0228350 A1 | 10/2006 | Wu et al. |
| 2006/0233812 A1 | 10/2006 | Burnie et al. |
| 2006/0234234 A1 | 10/2006 | Van Dongen et al. |
| 2006/0259248 A1 | 11/2006 | Collette et al. |
| 2006/0263789 A1 | 11/2006 | Kincaid |
| 2007/0020640 A1 | 1/2007 | McCloskey et al. |
| 2007/0020670 A1 | 1/2007 | Loken et al. |
| 2007/0105105 A1 | 5/2007 | Clelland et al. |
| 2007/0117134 A1 | 5/2007 | Kou |
| 2007/0160994 A1 | 7/2007 | Lim et al. |
| 2007/0161001 A1 | 7/2007 | Leshkowitz |
| 2007/0172873 A1 | 7/2007 | Brenner et al. |
| 2007/0238099 A1 | 10/2007 | Cohen et al. |
| 2007/0243564 A1 | 10/2007 | Lawson et al. |
| 2007/0264653 A1 | 11/2007 | Berlin et al. |
| 2007/0286849 A1 | 12/2007 | Chaturvedi |
| 2008/0050780 A1 | 2/2008 | Lee et al. |
| 2008/0069770 A1 | 3/2008 | Hercend et al. |
| 2008/0108509 A1 | 5/2008 | Haupl et al. |
| 2008/0166704 A1 | 7/2008 | Marche et al. |
| 2008/0166718 A1 | 7/2008 | Lim et al. |

(56) References Cited

U.S. PATENT DOCUMENTS

| | | |
|---|---|---|
| 2008/0199916 A1 | 8/2008 | Zheng et al. |
| 2008/0248484 A1 | 10/2008 | Bauer |
| 2008/0274904 A1 | 11/2008 | Gormley et al. |
| 2008/0280774 A1 | 11/2008 | Burczynski et al. |
| 2008/0286777 A1 | 11/2008 | Candeias et al. |
| 2009/0026082 A1 | 1/2009 | Rothberg et al. |
| 2009/0053184 A1 | 2/2009 | Morgan et al. |
| 2009/0098555 A1 | 4/2009 | Roth et al. |
| 2009/0105959 A1 | 4/2009 | Braverman et al. |
| 2009/0181859 A1 | 7/2009 | Muraguchi |
| 2009/0197257 A1 | 8/2009 | Harris |
| 2009/0208955 A1 | 8/2009 | Robins et al. |
| 2009/0226975 A1 | 9/2009 | Sabot et al. |
| 2009/0233301 A1 | 9/2009 | Lee |
| 2009/0253581 A1 | 10/2009 | Van Eijk et al. |
| 2009/0264299 A1 | 10/2009 | Drmanac et al. |
| 2009/0280489 A1 | 11/2009 | Devinder et al. |
| 2009/0286237 A1 | 11/2009 | Fitzgerald et al. |
| 2009/0298060 A1 | 12/2009 | Lal et al. |
| 2010/0008920 A1 | 1/2010 | Schneck et al. |
| 2010/0021896 A1 | 1/2010 | Han |
| 2010/0021984 A1 | 1/2010 | Edd |
| 2010/0027896 A1 | 2/2010 | Geva et al. |
| 2010/0034834 A1 | 2/2010 | Robbins et al. |
| 2010/0035764 A1 | 2/2010 | Chen |
| 2010/0040606 A1 | 2/2010 | Lantto et al. |
| 2010/0042329 A1 | 2/2010 | Hood et al. |
| 2010/0105886 A1 | 4/2010 | Wondenberg |
| 2010/0137143 A1 | 6/2010 | Rothberg et al. |
| 2010/0151471 A1 | 6/2010 | Faham et al. |
| 2010/0159456 A1 | 6/2010 | Albitar |
| 2010/0167353 A1 | 7/2010 | Walder et al. |
| 2010/0173394 A1 | 7/2010 | Colston, Jr. |
| 2010/0255471 A1 | 10/2010 | Clarke |
| 2010/0261204 A1 | 10/2010 | Goolsby et al. |
| 2010/0267043 A1 | 10/2010 | Braverman |
| 2010/0285975 A1 | 11/2010 | Mathies |
| 2010/0300895 A1 | 12/2010 | Nobile et al. |
| 2010/0304982 A1 | 12/2010 | Hinz et al. |
| 2010/0323348 A1 | 12/2010 | Hamady et al. |
| 2010/0330571 A1 | 12/2010 | Robins et al. |
| 2011/0003291 A1 | 1/2011 | Pasqual et al. |
| 2011/0014659 A1 | 1/2011 | Balazs et al. |
| 2011/0097712 A1 | 4/2011 | Cantor et al. |
| 2011/0104671 A1 | 5/2011 | Dornan et al. |
| 2011/0105343 A1 | 5/2011 | Puledran et al. |
| 2011/0129830 A1 | 6/2011 | Ladner et al. |
| 2011/0160078 A1 | 6/2011 | Fodor et al. |
| 2011/0195253 A1 | 8/2011 | Hinz et al. |
| 2011/0207134 A1 | 8/2011 | Faham et al. |
| 2011/0207135 A1 | 8/2011 | Faham et al. |
| 2011/0207617 A1 | 8/2011 | Faham et al. |
| 2011/0251099 A1 | 10/2011 | Visvanathan et al. |
| 2012/0035062 A1 | 2/2012 | Schultz et al. |
| 2012/0058902 A1 | 3/2012 | Livingston et al. |
| 2012/0071331 A1 | 3/2012 | Casbon et al. |
| 2012/0073667 A1 | 3/2012 | Schultz et al. |
| 2012/0122714 A1 | 5/2012 | Samuels |
| 2012/0135409 A1 | 5/2012 | Faham |
| 2012/0143531 A1 | 6/2012 | Davey et al. |
| 2012/0172241 A1 | 7/2012 | Rearick et al. |
| 2012/0173158 A1 | 7/2012 | Hubbell |
| 2012/0220466 A1 | 8/2012 | Fire et al. |
| 2013/0005584 A1 | 1/2013 | Faham |
| 2013/0017957 A1 | 1/2013 | Faham et al. |
| 2013/0065768 A1 | 3/2013 | Zheng |
| 2013/0116130 A1 | 5/2013 | Fu |
| 2013/0123120 A1 | 5/2013 | Zimmermann et al. |
| 2013/0136799 A1 | 5/2013 | Faham et al. |
| 2013/0150252 A1 | 6/2013 | Faham |
| 2013/0196328 A1 | 8/2013 | Pepin |
| 2013/0196861 A1 | 8/2013 | Quake |
| 2013/0202718 A1 | 8/2013 | Pepin |
| 2013/0236895 A1 | 9/2013 | Faham |
| 2013/0253842 A1 | 9/2013 | Sherwood et al. |
| 2013/0267427 A1 | 10/2013 | Faham |
| 2013/0288237 A1 | 10/2013 | Robins et al. |
| 2013/0302801 A1 | 11/2013 | Asbury |
| 2013/0324422 A1 | 12/2013 | Faham et al. |
| 2013/0344066 A1 | 12/2013 | Faham |
| 2014/0057799 A1 | 2/2014 | Johnson et al. |
| 2014/0094376 A1 | 4/2014 | Han |
| 2014/0127699 A1 | 5/2014 | Han |
| 2014/0155277 A1 | 6/2014 | Wiley |
| 2014/0186848 A1 | 7/2014 | Robins et al. |
| 2014/0194295 A1 | 7/2014 | Robins et al. |
| 2014/0206548 A1 | 7/2014 | Robins et al. |
| 2014/0206549 A1 | 7/2014 | Robins et al. |
| 2014/0213463 A1 | 7/2014 | Robins et al. |
| 2014/0221220 A1 | 8/2014 | Robins et al. |
| 2014/0234835 A1 | 8/2014 | Pepin |
| 2014/0235454 A1 | 8/2014 | Faham |
| 2014/0255929 A1 | 9/2014 | Zheng |
| 2014/0255944 A1 | 9/2014 | Carlton |
| 2014/0256567 A1 | 9/2014 | Robins et al. |
| 2014/0256592 A1 | 9/2014 | Faham |
| 2014/0315725 A1 | 10/2014 | Faham et al. |
| 2014/0322716 A1 | 10/2014 | Robins et al. |
| 2014/0336059 A1 | 11/2014 | Faham et al. |
| 2014/0342360 A1 | 11/2014 | Faham et al. |
| 2014/0342367 A1 | 11/2014 | Faham et al. |
| 2014/0349883 A1 | 11/2014 | Faham et al. |
| 2014/0356339 A1 | 12/2014 | Faham et al. |
| 2015/0017652 A1 | 1/2015 | Robins et al. |
| 2015/0031043 A1 | 1/2015 | Faham et al. |
| 2015/0031553 A1 | 1/2015 | Faham et al. |
| 2015/0031555 A1 | 1/2015 | Johnson et al. |
| 2015/0038346 A1 | 2/2015 | Faham et al. |
| 2015/0051089 A1 | 2/2015 | Robins et al. |
| 2015/0065352 A1 | 3/2015 | Faham et al. |
| 2015/0167080 A1 | 6/2015 | Moorhead et al. |
| 2015/0203897 A1 | 7/2015 | Robins et al. |
| 2015/0218656 A1 | 8/2015 | Kirsch et al. |
| 2015/0247198 A1 | 9/2015 | Klinger et al. |
| 2015/0247201 A1 | 9/2015 | Faham et al. |
| 2015/0252419 A1 | 9/2015 | Moorhead et al. |
| 2015/0252422 A1 | 9/2015 | Faham et al. |
| 2015/0259734 A1 | 9/2015 | Asbury et al. |
| 2015/0299785 A1 | 10/2015 | Livingston et al. |
| 2016/0115532 A1 | 4/2016 | Faham |
| 2016/0201133 A1 | 7/2016 | Faham et al. |
| 2016/0251728 A1 | 9/2016 | Faham et al. |

FOREIGN PATENT DOCUMENTS

| | | |
|---|---|---|
| EP | 0303459 A2 | 2/1989 |
| EP | 0799897 A1 | 10/1997 |
| EP | 1544308 A1 | 6/2005 |
| EP | 1549764 B1 | 7/2005 |
| EP | 0972081 B1 | 6/2007 |
| EP | 1544308 B1 | 1/2009 |
| EP | 2062982 A1 | 5/2009 |
| EP | 2088432 A1 | 8/2009 |
| EP | 2364368 B1 | 1/2014 |
| JP | 4262799 A | 9/1992 |
| JP | 2002-503954 A | 2/2001 |
| JP | 2005-245381 A | 9/2005 |
| JP | 2006-501842 A | 1/2006 |
| JP | 2007-515955 A | 6/2007 |
| JP | 2007-536939 A | 12/2007 |
| JP | 2008-099588 A | 5/2008 |
| WO | WO 93/01838 A1 | 2/1993 |
| WO | WO 95/28481 A1 | 10/1995 |
| WO | WO 97/13868 A1 | 4/1997 |
| WO | WO 97/13877 A1 | 4/1997 |
| WO | WO 97/18330 A1 | 5/1997 |
| WO | WO 97/46706 A1 | 12/1997 |
| WO | WO 98/01738 A2 | 1/1998 |
| WO | WO 98/44151 A1 | 10/1998 |
| WO | WO 99/19717 A1 | 4/1999 |
| WO | WO 99/20798 A1 | 4/1999 |
| WO | WO 02/24322 A2 | 3/2002 |
| WO | WO 03/008624 A2 | 1/2003 |
| WO | WO 03/044225 A2 | 5/2003 |

(56) References Cited

FOREIGN PATENT DOCUMENTS

| | | |
|---|---|---|
| WO | WO 03/052101 A1 | 6/2003 |
| WO | WO 03/059155 A2 | 7/2003 |
| WO | WO 2004/003820 A2 | 1/2004 |
| WO | WO 2004/033728 A2 | 4/2004 |
| WO | WO 2004/034031 A2 | 4/2004 |
| WO | WO 2004/044209 A1 | 5/2004 |
| WO | WO 2004/046098 A2 | 6/2004 |
| WO | WO 2004/063706 A2 | 7/2004 |
| WO | WO 2004/096985 A2 | 11/2004 |
| WO | WO 2005/003375 A2 | 1/2005 |
| WO | WO 2005/005651 A2 | 1/2005 |
| WO | WO 2005/042774 A2 | 5/2005 |
| WO | WO 2005/053603 A2 | 6/2005 |
| WO | WO 2005/056828 A1 | 6/2005 |
| WO | WO 2005/059176 A1 | 6/2005 |
| WO | WO 2005/084134 A2 | 9/2005 |
| WO | WO 2005/111242 A2 | 11/2005 |
| WO | WO 2005/113803 A1 | 12/2005 |
| WO | WO 2006/076025 A2 | 7/2006 |
| WO | WO 2006/076205 A2 | 7/2006 |
| WO | WO 2006/110855 A2 | 10/2006 |
| WO | WO 2006/116155 A2 | 11/2006 |
| WO | WO 2006/138284 A2 | 12/2006 |
| WO | WO 2007/134220 A2 | 11/2007 |
| WO | WO 2008/026927 A2 | 3/2008 |
| WO | WO 2008/039694 A2 | 4/2008 |
| WO | WO 2008/108803 A2 | 9/2008 |
| WO | WO 2008/147879 A1 | 12/2008 |
| WO | WO 2009/015296 A1 | 1/2009 |
| WO | WO 2009/017678 A2 | 2/2009 |
| WO | WO 2009/019657 A2 | 2/2009 |
| WO | WO 2009/021215 A1 | 2/2009 |
| WO | WO 2009/045898 A2 | 4/2009 |
| WO | WO 2009/070767 A2 | 6/2009 |
| WO | WO 2009/095567 A2 | 8/2009 |
| WO | WO 2009/108860 A2 | 9/2009 |
| WO | WO 2009/108866 A2 | 9/2009 |
| WO | WO 2009/137255 A2 | 11/2009 |
| WO | WO 2009/137832 A2 | 11/2009 |
| WO | WO 2009/145925 A1 | 12/2009 |
| WO | WO 2009/151628 A2 | 12/2009 |
| WO | WO 2009/152928 A2 | 12/2009 |
| WO | WO 2009/158521 A2 | 12/2009 |
| WO | WO 2010/011894 A1 | 1/2010 |
| WO | WO 2010/036352 A1 | 4/2010 |
| WO | WO 2010/053587 A2 | 5/2010 |
| WO | WO 2010/151416 A1 | 12/2010 |
| WO | WO 2011/083296 A1 | 7/2011 |
| WO | WO 2011/083996 A2 | 7/2011 |
| WO | WO 2011/106738 A2 | 9/2011 |
| WO | WO 2011/107595 A1 | 9/2011 |
| WO | WO 2011/139371 A1 | 11/2011 |
| WO | WO 2011/139372 A1 | 11/2011 |
| WO | WO 2011/140433 A1 | 11/2011 |
| WO | WO 2012/027503 A2 | 3/2012 |
| WO | WO 2012/048340 A2 | 4/2012 |
| WO | WO 2012/048341 A1 | 4/2012 |
| WO | WO 2012/055929 A1 | 5/2012 |
| WO | WO 2012/061832 A1 | 5/2012 |
| WO | WO 2012/083069 A2 | 6/2012 |
| WO | WO 2012/083225 A2 | 6/2012 |
| WO | WO 2012/142213 A2 | 10/2012 |
| WO | WO 2012/159754 A2 | 11/2012 |
| WO | WO 2013/033721 A1 | 3/2013 |
| WO | WO 2013/036459 A2 | 3/2013 |
| WO | WO 2013/055595 A1 | 4/2013 |
| WO | WO 2013/059725 A1 | 4/2013 |
| WO | WO 2013/066726 A1 | 5/2013 |
| WO | WO 2013/085855 A1 | 6/2013 |
| WO | WO 2013/086450 A1 | 6/2013 |
| WO | WO 2013/086462 A1 | 6/2013 |
| WO | WO 2013/090390 A2 | 6/2013 |
| WO | WO 2013/090469 A1 | 6/2013 |
| WO | WO 2013/096480 A2 | 6/2013 |
| WO | WO 2013/130512 A2 | 9/2013 |
| WO | WO 2013/131074 A1 | 9/2013 |
| WO | WO 2013/134162 A2 | 9/2013 |
| WO | WO 2013/134302 A1 | 9/2013 |
| WO | WO 2013/155119 A1 | 10/2013 |
| WO | WO 2013/158936 A1 | 10/2013 |
| WO | WO 2013/169957 A1 | 11/2013 |
| WO | WO 2013/181428 A2 | 12/2013 |
| WO | WO 2013/188471 A2 | 12/2013 |
| WO | WO 2013/188831 A1 | 12/2013 |
| WO | WO 2014/018460 A1 | 1/2014 |
| WO | WO 2014/026031 A1 | 2/2014 |
| WO | WO 2014/062945 A1 | 4/2014 |
| WO | WO 2014/062959 A1 | 4/2014 |
| WO | WO 2014/066184 A1 | 5/2014 |
| WO | WO 2014/130685 A1 | 8/2014 |
| WO | WO 2015/002908 A1 | 1/2015 |
| WO | WO 2015/013461 A2 | 1/2015 |
| WO | WO 2015/058159 A1 | 4/2015 |
| WO | WO 2015/160439 A2 | 10/2015 |
| WO | WO 2016/069886 A1 | 5/2016 |

OTHER PUBLICATIONS

Alatrakchi et al. "T-cell clonal expansion in patients with B-cell lymphoproliferative disorders", *Journal of Immunotherapy*, 21(5):363-370 (1998).

Alexandre, D. et al. "*H. sapiens* rearranged T-cell receptor gamma chain gene, V2-JP1", GenBank accession No: X57737, NCBI, Nov. 14, 2006, 8 pages [online] [retrieved on Jun. 26, 2013] Retrieved from the internet <URL:http://www.ncbi.nlm.nih.gov/nuccore/x57737>.

Alexandre, D. et al. "*H. sapiens* rearranged T-cell receptor gamma chain gene, V3RS-J1 (hybrid joint)", GenBank accession No: X57740, NCBI, Feb. 11, 1997, 8 pages [online] [retrieved on Jun. 26, 2013] Retrieved from the internet <URL:http://www.ncbi.nlm.nih.gov/nuccore/x57740>.

Al-Lazikani, B. et al., "Standard Conformations for the Canonical Structures of Immunoglobulins," *J. Mol. Biol.*, 273:927-948 (1997).

Altin et al. "The role of CD45 and CD45-associated molecules in T cell activation", *Immunology and Cell Biology*, 75: 430-445 (1997).

Altman, et al. "Phenotypic analysis of antigen-specific T lymphocytes", The *Journal of Immunology*, 187(1):7-9 (2011).

Altschul, et al. "Basic local alignment search tool", *J Mol Biol.*, 215(3):403-410 (1990).

Andreasson, et al. "The human IgE-encoding transcriptome to assess antibody repertoires and repertoire evolution", *J Mol Biol.*, 362(2):212-227 (2006). Epub Aug. 14, 2006.

Arnaout. "Specificity and overlap in gene segment-defined antibody repertoires", *BMC Genomics*, 6: 148 (2005).

Arden, et al. "Human T-cell receptor variable gene segment families", *Immunogenetics*, 42(6):455-500, Abstract Only (1995).

Armand, P. et al., "Detection of circulating tumour DNA in patients with aggressive B-cell non-Hodgkin lymphoma", *Brit. J. Haematol.*, vol. 163, pp. 123-126 (2013).

Arstila, T.P., et al., "A direct estimate of the human αβ T cell receptor diversity," *Science*, 286(5441): 958-961 (1999).

Aslanzadeh. "Preventing PCR amplification carryover contamination in a clinical laboratory", *Ann Clin Lab Sci.*, 34(4):389-396 (2004).

Assaf, et al. "High Detection Rate of T-Cell Receptor Beta Chain Rearrangements in T-Cell Lymphoproliferations by Family Specific Polymerase Chain Reaction in Combination with the Genescan Technique and DNA Sequencing", *Blood*, 96(2): 640-646 (2000).

Ateya, et al. "The good, the bad, and the tiny: a review of microflow cytometry", *Anal Bioanal Chem.*, 391(5): 1485-1498 (2008). doi: 10.1007/s00216-007-1827-5. Epub Jan. 29, 2008.

Babrzadeh et al. "Development on High-throughput Sequencing Technology: emPCR Titration and Barcode Design", *Stanford School of Medicine*, 2 pages (2011).

Bagnara, et al. "IgV gene intraclonal diversification and clonal evolution in B-cell chronic lymphocytic leukaemia", *British Journal of Haematology*, 133(1):50-58 (2006).

Bahloul, M. et al., "Clinical impact of molecular diagnostics in low-grade lymphoma," Best Practice & Research Clinical Haematology, 18(1):97-111 (2005).

(56) References Cited

OTHER PUBLICATIONS

Baldauf, "Phylogeny for the faint of heart: a tutorial," Trends in Genetics, 19(6): 345-351 (2003).
Barbas, et al. "Assembly of combinatorial antibody libraries on phage surfaces: the gene III site", PNAS, 88(18): 7978-7982, Abstract Only (1991).
Barker, et al. "A second type II restriction endonuclease from Thermus aquaticus with an unusual sequence specificity", Nucleic Acids Res., 12(14): 5567-5581 (1984).
Batzoglou, S. "The many faces of sequence alignment", Briefings in Bioinformatics, 6:6-22 (2005).
Baum and McCune et al. "Direct measurement of T-cell receptor repertoire diversity with AmpliCot", Nat Methods, 3(11): 895-901 (2006).
Becker-André and Hahlbrock. "Absolute mRNA quantification using the polymerase chain reaction (PCR). A novel approach by a PCR aided transcript titration assay (PATTY)", Nucleic Acids Res., 17(22): 9437-9446 (1989).
Becton-Dickinson, CD marker handbook. bdbiosciences.com/go/mousecdmarkers, p. 1-47 (2010).
Becton-Dickinson T-Cell Research Tools, "Novel multicolor flow cytometry tools for the study of CD4+ T-cell differentiation and plasticity", 16 pages (2009).
Beishuizen, et al. "Analysis of Ig and T-cell receptor genes in 40 childhood acute lymphoblastic leukemias at diagnosis and subsequent relapse: implications for the detection of minimal residual disease by polymerase chain reaction analysis", Blood, 83(8):2238-2247 (1994).
Ben-Ezra, et al. Effect of fixation on the amplification of nucleic acids from paraffin-embedded material by the polymerase chain reaction, The Journal of Histochemistry and Cytochemistry, 39(3): 351-354 (1991).
Béné and Kaeda, "How and why minimal residual disease studies are necessary in leukemia: a review from WP10 and WP12 of the European LeukaemiaNet", Haematologica, 94(8):1135-1150 (2009).
Benecke. "DNA typing in forensic medicine and in criminal investigations: a current survey", Naturwissenschaften, 84(5): 181-188 (1997).
Benichou, J. et al., "Rep-Seq: uncovering the immunological repertoire through next-generation sequencing", Immunology, 135(3): 183-191 (2011).
Benichou, J. et al., "The restricted DH gene reading frame usage in the expressed human antibody repertoire is selected based upon its amino acid content", J Immunol., 190(11): 5567-77, 29 pages (2013).
Bentley, et al. "Accurate whole human genome sequencing using reversible terminator chemistry", Nature, 456(7218) :53-59 (2008). doi: 10.1038/nature07517.
Bereczki, et al. "Optimization of PCR amplification for B- and T-cell clonality analysis on formalin-fixed and paraffin-embedded samples", Pathology Oncology Research, 13(3): 209-214 (2007). Epub Oct. 7, 2007.
Berger, et al. "The clonotypic T cell receptor is a source of tumor-associated antigens in cutaneous T cell lymphoma", Annals of the New York Academy of Sciences, 941:106-122, Abstract Only (2001).
Berget, et al. "Detection of clonality in follicular lymphoma using formalin-fixed, paraffin-embedded tissue samples and BIOMED-2 immunoglobulin primers", J Clin Pathol., 64(1):37-41 (2011). doi: 10.1136/jcp.2010.081109. Epub Oct. 28, 2010.
Bernard et al. "Color multiplexing hybridization probes using the apolipoprotein E locus as a model system for genotyping", Anal Biochem., 273(2):221-228 (1999).
Bernardin, F. et al., "Estimate of the total number of CD8+ clonal expansions in healthy adults using a new DNA heteroduplex-tracking assay for CDR3 repertoire analysis", Journal of Immunological Methods, 274(I-2):159-175 (2003).

Berquam-Vrieze, K. et al., "Cell of origin strongly influences genetic selection in a mouse model of T-ALL", Blood, 118:4646-4656 (2011).
Bertness, et al. "T-Cell Receptor Gene Rearrangements as Clinical Markers of Human T-Cell Lymphomas", The New England Journal of Medicine, 313:534-538 (1985).
Berzofsky, et al. "Progress on new vaccine strategies for the immunotherapy and prevention of cancer", J Clin Invest., 113(11): 1515-1525 (2004).
Biagi, et al. "Responses to human CD40 ligand/human interleukin-2 autologous cell vaccine in patients with B-cell chronic lymphocytic leukemia", Clin Cancer Res., 11(19 Pt 1): 6916-6923 (2005).
Biggerstaff, et al. "Enumeration of leukocyte infiltration in solid tumors by confocal laser scanning microscopy", BMC Immunol., 7:16, 13 pages (2006).
Blow, N., "PCR's next frontier," Nature Methods, 4(10):869-875 (2007).
Brochet et al. "IMGT/V-QUEST: the highly customized and integrated system for IG and TR standardized V-J and V-D-J sequence analysis", Nucleic Acids Research, vol. 36, Web Server issue W503-W508 (2008).
Bolotin, D.A. et al., "Next generation sequencing for TCR repertoire profiling: Platform-specific features and correction algorithms", Eur. J. Immunol., 42:3073-3083 (2012).
Bonarius, H.P.J. et al. "Monitoring the T-Cell Receptor Repertoire at Single-Clone Resolution", PLOS One, 1(e55):1-10 (2006).
Bonner et al. "Fluorescence activated cell sorting", Rev Sci Instrum., 43(3):404-409, Abstract Only (1972).
Boria, et al. "Primer sets for cloning the human repertoire of T cell receptor variable regions", BMC Immunology, 9:50, 9 pages (2008).
Borst, et al. "False-positive results and contamination in nucleic acid amplification assays: suggestions for a prevent and destroy strategy", Eur J Clin Microbiol Infect Dis., 23(4):289-299, Abstract Only (2004). Epub Mar. 10, 2004.
Boudinot et al. "New perspectives for large-scale repertoire analysis of immune receptors", Molecular Immunology, 45: 2437-2445 (2008).
Bousso. "Generation of MHC-peptide tetramers: a new opportunity for dissecting T-cell immune responses", Microbes Infect., 2(4):425-429, Abstract Only (2000).
Boyce, et al. "Human regulatory T-cell isolation and measurement of function", BD Biosciences, pp. 1-20 (2010).
Boyd, S.D. et al., "Individual Variation in the Germline Ig Gene Repertoire Inferred from Variable Region Gene Rearrangements", The Journal of Immunology, 184(12): 6986-6992 (2010).
Boyd, S.D. et al., "Measurement and Clinical Monitoring of Human Lymphocyte Clonality by Massively Parallel V-D-J Pyrosequencing," Science Translational Medicine, 1:12ra23, 40 pages, including Supplementary Materials (2009).
Bradfield, et al. "Graft-versus-leukemia effect in acute lymphoblastic leukemia: the importance of tumor burden and early detection", Leukemia, 18(6): 1156-1158 (2004).
Bravo and Irizarry. "Model-Based Quality Assessment and Base-Calling for Second-Generation Sequencing Data", Biometrics, 66(3): 665-674 (2010).
Brehm-Stecher and Johnson. "Single-cell microbiology: tools, technologies, and applications", Microbiology and Molecular Biology Reviews, 68(3):538-559 (2004).
Brenan, C. et al., "High throughput, nanoliter quantitative PCR," Drug Discovery Today: Technologies, 2(3):247-253 (2005).
Brenner, et al. "In vitro cloning of complex mixtures of DNA on microbeads: physical separation of differentially expressed cDNAs", PNAS, 97(4): 1665-1670 (2000).
Brentjens, et al. "CD19-targeted T cells rapidly induce molecular remissions in adults with chemotherapy-refractory acute lymphoblastic leukemia", Sci Transl Med., 5(177): 177ra38 (2013). doi: 10.1126/scitranslmed.3005930.
Brisco, et al. "Determining the repertoire of IGH gene rearrangements to develop molecular markers for minimal residual disease in B-lineage acute lymphoblastic leukemia", J Mol Diagn., 11(3):194-200 (2009).

(56) References Cited

OTHER PUBLICATIONS

Brisco, et al. "Outcome prediction in childhood acute lymphoblastic leukaemia by molecular quantification of residual disease at the end of induction", Lancet, 343:196-200 (1994).
Brockman et al, "Quality scores and SNP detection in sequencing-by-synthesis systems," Genome Research, 18: 763-770 (2008).
Brody, et al. "Active and passive immunotherapy for lymphoma: proving principles and improving results", J Clin Oncol., 29(14):1864-1875, Abstract Only (2011). doi: 10.1200/JCO.2010. 33.4623. Epub Apr. 11, 2011.
Brody, et al., "Immunotransplant for mantle cell lymphoma: Phase I/II study preliminary results", Journal of Clinical Oncology, ASCO Annual Meeting Abstracts Part 1, vol. 29, No. 15, 1 page (2011).
Brody, et al. "Lymphoma immunotherapy: vaccines, adoptive cell transfer and immunotransplant", Immunotherapy, 1(5): 809-824 (2009). doi: 10.2217/imt.09.50.
Brown, et al. "Current techniques for single-cell lysis", J. R. Soc. Interface, 5:S131-S138 (2008).
Brownie et al. "The elimination of primer-dimer accumulation in PCR", Nucleic Acids Research, 25(16): 3235-3241 (1997).
Brüggemann, et al. "Clinical significance of minimal residual disease quantification in adult patients with standard-risk acute lymphoblastic leukemia", Blood, 107(3):1116-1123 (2006). Epub Sep. 29, 2005.
Brüggemann, et al. "Rearranged T-cell receptor beta genes represent powerful targets for quantification of minimal residual disease in childhood and adult T-cell acute lymphoblastic leukemia", Leukemia, 18(4): 709-719 (2004).
Brüggemann, et al. "Standardized MRD quantification in European ALL trials: proceedings of the Second International Symposium on MRD assessment in Kiel, Germany, Sep. 18-20, 2008", Leukemia, 24(3):521-535 (2010). doi: 10.1038/leu.2009.268. Epub Dec. 24, 2009.
Buck, G.A. et al. "Design Strategies and Performance of Custom DNA Sequencing Primers", Biotechniques, 27(3):528-536 (1999).
Buccisano, et al. "Prognostic and therapeutic implications of minimal residual disease detection in acute myeloid leukemia", Blood, 119(2):332-341 (2012). doi: 10.1182/blood-2011-08-363291. Epub Oct. 28, 2011.
Buccisano, et al. "Monitoring of minimal residual disease in acute myeloid leukemia", Curr Opin Oncol., 21(6):582-588, Abstract Only (2009). doi: 10.1097/CCO.0b013e3283311856.
Butkus, B. "Hutch Team Uses ddPCR to Quantify T-Cell Response in Tumors; Adaptive Biotech Eyes Market", PCR Insider, Dec. 12, 2013, 3 pages http://www.genomeweb.com/print/1323296.
Bystrykh. "Generalized DNA Barcode Design Based on Hamming Codes", PLoS ONE, 7(5): e36852, 1-8 (2012).
Campana, D., "Progress of Minimal Residual Disease Studies in Childhood Acute Leukemia," Curr Hematol Malig Rep, 5:169-176 (2010).
Campana. "Minimal residual disease in acute lymphoblastic leukemia", Semin Hematol.,46(1):100-106 (2009).
Campana, et al. "Role of minimal residual disease monitoring in adult and pediatric acute lymphoblastic leukemia", Hematol Oncol Clin North Am., 23(5): 1083-1098 (2009). doi: 10.1016/j.hoc.2009. 07.010.
Campbell et al. "Subclonal phylogenetic structures in cancer revealed by ultra-deep sequencing," PNAS, 105(35):13081-13086 (2008).
Caporaso, J.G. et al. "Global patterns of 16S rRNA diversity at a depth of millions of sequences per sample", PNAS, 108(Suppl. 1):4516-4522 (2010).
Carlotti, et al. "Transformation of follicular lymphoma to diffuse large B-cell lymphoma may occur by divergent evolution from a common progenitor cell or by direct evolution from the follicular lymphoma clone", Blood, 113(15): 3553-3557 (2009). doi: 10.1182/blood-2008-08-174839. Epub Feb. 6, 2009.
Carlson et al. "Profiling the repertoire of TCRB usage in induced and natural Treg cells", The Journal of Immunology, 186: 62.5, Abstract (2011).
Carlson, et al. "Immune Profiling Suggests an IGH Signaling-Dependent Subtype of Aggressive B-ALL", Blood, 120: 1428, Abstract (2012).
Carlson, et al. "Deep sequencing of the human TCRγ and TCRβ repertoires provides evidence that TCRβ rearranges after αβ, γδT cell commitment". Presented at the ASHG 2011 Conference. Oct. 2011. Poster. 1 page.
Carlson, et al. "Detection of tumor tagging clones in multiple myeloma via high throughput sequencing is robust to significant levels of SHM", Presented for the 2014 ASH Annual Meeting. Poster. 1 page. Dec. 5-9, 2014.
Carlson, C.S. et al. "Using synthetic templates to design an unbiased multiplex PCR assay", Nature Communications, 4:2680, pp. 1-9 (2013).
Casali, et al. "Human monoclonals from antigen-specific selection of B lymphocytes and transformation by EBV", Science, 234(4775): 476-479, Abstract Only (1986).
Casbon et al. "A method for counting PCR template molecules with application to next-generation sequencing", Nucleic Acids Research, 39(12): e81, 8 pages. (2011).
Catherwood, M.A. et al., "Improved clonality assessment in germinal centre/post germinal centre non-Hodgkin's lymphomas with high rates of somatic hypermutation", J. Clin. Pathol., 60:524-528, Abstract (2007).
Cavé, H. et al., "Clinical Significance of minimal residual disease in childhood acute lymphoblastic leukemia," The New England Journal of Medicine, 339:591-598 (1998).
Chan et al. "Evaluation of Nanofluidics Technology for High-Throughput SNP Genotyping in a Clinical Setting", The Journal of Molecular Diagnostics, 13(3): 305-312 (2011).
Chattopadhyay, et al. "A live-cell assay to detect antigen-specific CD4+ T cells with diverse cytokine profiles", Nat Med., 11(10): 1113-1117 (2005). Epub Sep. 25, 2005.
Chen et al. "A novel approach for the analysis of T-cell reconstitution by using a T-cell receptor β-based oligonucleotide microarray in hematopoietic stem cell transplantation", Exp Hematol., 35(5):831-841 (2007).
Chen et al. "Identification of racehorse and sample contamination by novel 24-plex STR system", Forensic Science International: Genetics, 4:158-167 (2010).
Chen, et al. "Microfluidic cell sorter with integrated piezoelectric actuator", Biomed Microdevices, 11(6): 1223-1231 (2009). doi: 10.1007/s10544-009-9341-5.
Chen, Y. et al., "T-cell receptor gene expression in tumour-infiltrating lymphocytes and peripheral blood lymphocytes of patients with nasopharyngeal carcinoma", British Journal of Cancer, 72(1): 117-22 (1995).
Chen, et al. "Total Gene Synthesis: Novel Single-Step and Convergent Strategies Applied to the Construction of a 779 Base Pair Bacteriorhodopsis", Gene. J. Am. Chem Soc., 116: 8799-8800, Abstract Only (1994).
Chinese Application No. 201380042163.X, Search Report dated Apr. 12, 2016 ( English translation), 2 pages.
Chiu, et al. "Non-invasive prenatal assessment of trisomy 21 by multiplexed maternal plasma DNA sequencing: large scale validity study", BMJ, 342:c7401, 9 pages (2011). doi: 10.1136/bmj.c7401.
Choi, et al. "Relapse in children with acute lymphoblastic leukemia involving selection of a preexisting drug-resistant subclone", Blood, 110(2):632-639 (2007).
Choi, et al. "Clonal evolution in B-lineage acute lymphoblastic leukemia by contemporaneous $V_H$-$V_H$ gene replacements and $V_H$-$DJ_H$ gene rearrangements", Blood, 87(6):2506-2512 (1996).
Chothia, C. et al. "Canonical structures for the hypervariable regions of immunoglobulins," J. Mol. Biol., 196:901-917, Abstract only (1987).
Chothia, C. et al. "Conformations of immunoglobulin hypervariable regions," Nature, 342:877-883 (1989).
Churchill and Waterman. "The Accuracy of DNA Sequences: Estimating Sequence Quality", Genomics, 14:89-98 (1992).
Chute, et al. "Detection of immunoglobulin heavy chain gene rearrangements in classic Hodgkin lymphoma using commercially available BIOMED-2 primers", Diagn Mol Pathol., 17(2): 65-72 (2008). doi: 10.1097/PDM.0b013e318150d695.

(56) References Cited

OTHER PUBLICATIONS

Citri et al. "Comprehensive qPCR profiling of gene expression in single neuronal cells", Nature Protocols, 7(1): 118-127 (2012).
Ciudad, J. et al. "Detection of abnormalities in B-cell differentiation pattern is a useful tool to predict relapse in precursor-B-ALL", British Journal of Haematology, 104:695-705 (1999).
Cleary, et al. "Production of complex nucleic acid libraries using highly parallel in situ oligonucleotide synthesis", Nat Methods, 1(3): 241-248 (2004). Epub Nov. 18, 2004.
Clemente, et al. "Deep sequencing of the T-cell receptor repertoire in CD8+ T-large granular lymphocyte leukemia identifies signature landscapes", Blood, 122(25): 4077-85 (2013). doi: 10.1182/blood-2013-05-506386. Epub Oct. 22, 2013.
Cooper, et al. "BRAF inhibition is associated with increased clonality in tumorin filtrating lymphocytes", Oncoimmunology, 2(10):e26615 (2013). Epub Oct. 15, 2013.
Costabile, et al. "Molecular approaches in the diagnosis of primary immunodeficiency diseases", Human Mutation, 27(12):1163-1173 (2006).
Coustan-Smith, E. et al., "Clinical importance of minimal residual disease in childhood acute lymphoblastic leukemia," Blood, 96(8):2691-2696 (2000).
Coustan-Smith, E. et al., "Early T-cell precursor leukaemia: a subtype of very high-risk acute lymphoblastic leukaemia," Lancet Oncology, 10:147-156 (2009).
Coustan-Smith, E. et al., "Prognostic importance of measuring early clearance of leukemic cells by flow cytometry in childhood acute lymphoblastic leukemia", Blood, 100(1):52-58 (2002).
Craig et al. "Identification of genetic variants using bar-coded multiplex sequencing", Nature Methods, 5(10): 887-893 (2008) and Supplemental Materials.
Cronin, et al. "Comprehensive next-generation cancer genome sequencing in the era of targeted therapy and personalized oncology", Biomark Med., 5(3):293-305 (2011). (Abstract only). doi: 10.2217/bmm.11.37.
Cronn et al. "Multiplex sequencing of plant chloroplast genomes using Solexa sequencing-by-synthesis technology", Nucleic Acids Research, 36(19):e122, 1-11 (2008).
Curran et al. "Nucleotide sequencing of psoriatic arthritis tissue before and during methotrexate administration reveals a complex inflammatory T cell infiltrate with very few clones exhibiting features that suggest they drive the inflammatory process by recognizing autoantigens", The Journal of Immunology, 172:1935-1944 (2004).
Curran-Everett, D., "Multiple comparisons: philosophies and illustrations", Am J Physiol Regulatory Integrative Comp Physiol., 279:R1-R8 (2000).
Currier and Robinson. "Spectratype/immunoscope analysis of the expressed TCR repertoire", Current Protocols in Immunology, Supplement 38:10.28.1-10.28.24 (2000).
Dahl et al. "Multiplex amplification enabled by selective circularization of large sets of genomic DNA fragments", Nucleic Acids Res., 33(8): e71 (2005).
Damle et al. "B-cell chronic lymphocytic leukemia cells express a surface membrane phenotype of activated, antigen-experienced B lymphocytes", Blood, 99(11): 4087-93 (2002).
Dash, P. et al., "Paired analysis of TCR[alpha] and TCR[beta] chains at the single-cell level in mice", Journal of Clinical Investigation, 121(1):288-295 (2011).
Davi, et al. "Lymphocytic progenitor cell origin and clonal evolution of human B-lineage acute lymphoblastic leukemia", Blood, 88(2):609-621 (1996).
Davila, et al. Efficacy and toxicity management of 19-28z CART cell therapy in B cell acute lymphoblastic leukemia, Sci Transl Med., 6(224):224ra25 (2014). doi: 10.1126/scitranslmed.3008226.
Davis, et al. "Interrogating the repertoire: broadening the scope of peptide-MHC multimer analysis", Nat Rev Immunol., 11(8):551-558 (2011). doi: 10.1038/nri3020.

Davis, et al. "Staining of cell surface human CD4 with 2'-F-pyrimidine-containing RNA aptamers for flow cytometry", Nucleic Acids Research, 26(17):3915-3924 (1998).
De Bona et al. "Optimal spliced alignments of short sequence reads", Bioinformatics, 9(Suppl 10):O7, 2 pages (2008).
De Jonge, H.J.M., et al. "Evidence Based Selection of Housekeeping Genes," PLoS One, 9(e898):1-5 (2007).
Dean, et al. "Rapid amplification of plasmid and phage DNA using Phi 29 DNA polymerase and multiply-primed rolling circle amplification", Genome Res., 11(6): 1095-1099 (2001).
Decoste et al. "Relative and Absolute Quantitative Real-Time PCR-Based Quantifications of hcnC and phlD Gene Transcripts in Natural Soil Spiked with Pseudomonas sp. Strain LBUM300", Applied and Environmental Microbiology, 77(1): 41-47 (2011).
Dedhia, et al. "Evaluation of DNA extraction methods and real time PCR optimization on formalin-fixed paraffin-embedded tissues", Asian Pac J Cancer Prev., 8(1): 55-59 (2007).
Deiman, et al. "Characteristics and applications of nucleic acid sequence-based amplification (NASBA)", Mol Biotechnol., 20(2): 163-179, Abstract Only (2002).
DeKosky et al. "High-throughput sequencing of the paired human immunoglobulin heavy and light chain repertoire", Nature Biotechnology, 31(2): 166-169 (2013).
Delaney, et al. "Evolution and Clinical Implications of the T cell Repertoire Following Cord Blood Transplant", Biology of Blood and Marrow Transplant, vol. 19, Issue 2, S201-S202. Published Feb. 2013.
Deng et al. "Gene profiling involved in immature CD4+ T lymphocyte responsible for systemic lupus erythematosus", Molecular Immunology, 43:1497-1507 (2006).
DeNucci, C.C. et al. "Integrin function in T-cell homing to lymphoid and nonlymphoid sites: getting there and staying there," Critical Reviews in Immunology, 29(2):87-109 (2009).
Deschoolmeester, et al. "Tumor infiltrating lymphocytes: an intriguing player in the survival of colorectal cancer patients", BMC Immunology, 11:19, 12 pages (2010). doi: 10.1186/1471-2172-11-19.
Desmarais, et al. "Deep profiling of the mouse TCRβ CDR3 region in thymus and spleen". Oct. 2010. Poster. 1 page.
Desmarais, et al. High-throughput sequencing of memory and naïve T cell receptor repertoires at the RNA and DNA levels reveals differences in relative expression of expanded TCR clones. Adaptive Technologies. Seattle WA. Poster, 1 page. Presented May 5, 2012.
Desmarais and Robins. "High-throughput sequencing of memory and naïve T cell receptor repertoires at the RNA and DNA levels reveals differences in relative expression of expanded TCR clones", The Journal of Immunology, 182: 178.12 (2012).
Dheda, K., et al. "Validation of housekeeping genes for normalizing RNA expression in real-time PCR," Bio Techniques, 37:112-119 (2004).
Dictor et al. "Resolving T-cell receptor clonality in two and genotype in four multiplex polymerase chain reactions", Haematologica, 90(11): 1524-1532 (2005).
Diederichsen, et al. "Prognostic value of the CD4+/CD8+ ratio of tumour infiltrating lymphocytes in colorectal cancer and HLA-DR expression on tumour cells", Cancer Immunol Immunother., 52(7):423-428 (2003). Epub Apr. 15, 2003.
Diehl, et al. "BEAMing: single-molecule PCR on microparticles in water-in-oil emulsions", Nat Methods, 3(7):551-559, Abstract Only (2006).
Dik, W., et al. "New insights on human T cell development by quantitative T cell receptor gene rearrangement studies and gene expression profiling," JEM, 201(11):1715-1723 (2005).
Diluvio et al. "Identical TCRβ-chain rearrangements in streptococcal angina and skin lesions of patients with psoriasis vulgaris", J Immunol., 176(11 ): 7104-11 (2006).
Ding, et al. "Clonal evolution in relapsed acute myeloid leukaemia revealed by whole-genome sequencing", Nature, 481(7382):506-510 (2012). doi: 10.1038/nature10738.
Diviacco, et al. "A novel procedure for quantitative polymerase chain reaction by coamplification of competitive templates", Gene, 122(2):313-320 (1992).

(56) References Cited

OTHER PUBLICATIONS

Do and Batzoglou. "What is the expectation maximization algorithm?", *Nature Biotechnology*, 26(8): 897-899 (2008).
Dobosy, J. et al. "RNase H-dependent PCR (rhPCR): improved specificity and single nucleotide polymorphism detection using blocked cleavable primers", *BMC Biotechnology*, 11(80):1-18 (2011).
Dohm, et al. "Substantial biases in ultra-short read data sets from high throughput DNA sequencing", *Nucleic Acids Research*, 36:e105, 10 pages (2008).
Dou, et al. "Analysis of T cell receptor $V_\beta$ gene usage during the course of disease in patients with chronic hepatitis B", *Journal of Biomedical Science*, 5(6):428-434 (1998).
Dressman, et al. "Transforming single DNA molecules into fluorescent magnetic particles for detection and enumeration of genetic variations", PNAS, 100(15):8817-8822 (2003). Epub Jul. 11, 2003.
Drmanac, et al. "Human genome sequencing using unchained base reads on self-assembling DNA nanoarrays", *Science*, 327(5961):78-81 (2010). doi: 10.1126/science.1181498. Epub Nov. 5, 2009.
Droege, et al. "The Genome Sequencer FLX System—longer reads, more applications, straight forward bioinformatics and more complete data sets", *J Biotechnol.*, 136(1-2):3-10 (2008). doi: 10.1016/j.jbiotec.2008.03.021. Epub Jun. 21, 2008.
Droese, J., et al. "Validation of BIOMED-2 multiplex PCR tubes for detection of TCRB gene rearrangements in T-cell malignancies," *Leukemia*, 18:1531-1538 (2004).
Drossman, et al. "High-speed separations of DNA sequencing reactions by capillary electrophoresis", *Anal Chem.*, 62(9): 900-903 (1990).
Du et al. "TCR spectratyping revealed T lymphocytes associated with graft-versus-host disease after allogeneic hematopoietic stem cell transplantation", *Leukemia & Lymphoma*, 48(8):1618-1627 (2007).
Duby, A.D. et al., "Human T-cell receptor aberrantly rearranged beta-chain J1.5-Dx-J2.1 gene," PNAS, GenBank accession No. M13574.1, bases 1 to 100, 4 pages (1986).
Dudgeon, et al. "The evolution of thymic lymphomas in p53 knockout mice", Genes Dev., 28(23): 2613-20 (2014). doi: 10.1101/gad.252148.114.
Dunn, et al. "Focus on TILs: Prognostic significance of tumor infiltrating lymphocytes in human glioma", *Cancer Immun.*, 7:12, 16 pages (2007).
Eason et al. "Characterization of synthetic DNA bar codes in *Saccharomyces cerevisiae* gene-deletion strains," PNAS, 101(30): 11046-11051 (2004).
Edd et al. "Controlled encapsulation of single cells into monodisperse picoliter drops", *Lab Chip*, 8(8):1262-1264 (2008).
Edwards and Gibbs, "Multiplex PCR: advantages, development, and applications," Genome Research, 3:S65-S75 (1994).
Eichler, et al. "Haplotype and interspersion analysis of the FMR1 CGG repeat identifies two different mutational pathways for the origin of the fragile X syndrome", *Hum Mol Genet.*, 5(3):319-330 (1996).
Eichler, et al. "Length of uninterrupted CGG repeats determines instability in the FMR1 gene", *Nat Genet.*, 8(1):88-94, Abstract Only (1994).
Eid et al. "Real-time DNA sequencing from single polymerase molecules", *Science*, 323(5910):133-138 (2009). doi: 10.1126/science.1162986. Epub Nov. 20, 2008.
Eis, et al. "An invasive cleavage assay for direct quantitation of specific RNAs", *Nat Biotechnol.*, 19(7):673-676, Abstract Only (2001).
Eisenstein. "Personalized, sequencing-based immune profiling spurs startups", Nat Biotechnol., 31(3):184-6 (2013). doi: 10.1038/nbt0313-184b.
Elkord et al. "T regulatory cells in cancer: recent advances and therapeutic potential", *Expert Opinion on Biological Therapy*, 10(11): 1573-1586 (2010).

Elnifro, E.M., et al. "Multiplex PCR: Optimization and Application in Diagnostic Virology", *Clinical Microbiology Reviews*, 13(4):559-570 (2000).
Emerson, et al. "Correlation of TCR diversity with immune reconstitution after cord blood transplant", Presented at the American Society of Clinical Oncology's annual meeting. May 2012. Poster. 1 page.
Emerson, R.O. et al. "High-throughput sequencing of T-cell receptors reveals a homogeneous repertoire of tumour-infiltrating lymphocytes in ovarian cancer", *Journal of Pathology*, 231: 433-440 (2013).
Emerson, et al. "CD4+ and CD8+ T cell β antigen receptors have different and predictable V and J gene usage and CDR3 lengths", Presented at the Annual Meeting of the American Association of Immunologists 2012 in Boston, MA May 2012. Poster.
Emerson, et al. "Estimating the ratio of CD4+ to CD8+ T cells using high-throughput sequence data", J Immunol Methods, 391(1-2):14-21 (2013). doi: 10.1016/j.jim.2013.02.002. Epub Feb. 18, 2013.
Emerson, et al. TCR repertoire diversity assessed with immunosequencing is associated with patient mortality following cord blood transplant. Presented for the 2014 ASH Annual Meeting. Poster. 1 page. Dec. 5-9, 2014.
Estorninho, et al. "A novel approach to tracking antigen-experienced CD4 T cells into functional compartments via tandem deep and shallow TCR clonotyping", J Immunol., 191(11): 5430-40 (2013). doi: 10.4049/jimmunol.1300622. Epub Oct. 25, 2013.
Erlich, et al. "Alta-Cyclic: a self-optimizing base caller for next-generation sequencing", *Nat Methods.*, 5(8): 679-682 (2008). doi: 10.1038/nmeth.1230. Epub Jul. 6, 2008.
European Application No. 09764927.1, Notice of Opposition dated Oct. 14, 2014, Reference# 547-7.
European Application No. 09764927.1, Notice of Opposition dated Oct. 14, 2014, Reference# BR0-0001EP.
European Application No. 09764927.1, European Opposition dated Oct. 15, 2014 (in French only).
Esendagli et al. "Malignant and non-malignant lung tissue areas are differentially populated by natural killer cells and regulatory T cells in non-small cell lung cancer", *Lung Cancer*, 59(1): 32-40 (2008).
European Application No. 10732172.1, Extended European Search Report dated May 29, 2012, 5 pages.
European Patent Application No. 13195379.6, European Search Report and Opinion dated Mar. 13, 2014, 6 pages.
European Patent Application No. 11777704.5, European Search Report dated Jul. 26, 2013, 6 pages.
European Patent Application No. 13828563.0, Extended European Search Report dated Feb. 12, 2016, 10 pages.
European Patent Application No. 09764927.1, EPO's Communication of Notices of Opposition, dated Nov. 21, 2014.
European Patent Application No. 09764927.1, Patentee's Observations/Response dated May 27, 2015.
European Patent Application No. 09764927.1, Opponent's Response to Submission of the Patentee dated Nov. 23, 2015.
Ewing and Green, "Base-calling of automated sequencer traces using Phred. I. Accuracy Assessment," Genome Research, 8: 175-185 (1998).
Faham, M. et al. "Deep-sequencing approach for minimal residual disease detection in acute lymphoblastic leukemia", *Blood*, 120(26): 5173-5180 (2012).
Felsenstein, et al. "Evolutionary Trees from DNA Sequences: A Maximum Likelihood Approach", J Mol Evol, 17:368-376 (1981).
Ferradini et al. "Analysis of T Cell Receptor Variability in Tumor-infiltrating Lymphocytes from a Human Regressive Melanoma", *J. Clin. Invest.*, pp. 1183-190 (1993).
Ferrero, et al. "Multiple myeloma shows no intra-disease clustering of immunoglobulin heavy chain genes", *Haematologica*, 97(6): 849-853 (2012). doi: 10.3324/haematol.2011.052852. Epub Dec. 29, 2011.
Fisher et al. "The Relation Between the Number of Species and the Number of Individuals in a Random Sample of an Animal Population", *Journal of Animal Ecology*, 12(1): 42-58 (1943).
Flaherty et al. "Ultrasensitive detection of rare mutations using next-generation targeted resequencing", *Nucleic Acids Research*, 40(1): e2, 12 pages (2012).

(56) References Cited

OTHER PUBLICATIONS

Flicek and Birney, "Sense from sequence reads: methods for alignment and assembly," Nature Methods Supplement, 6(11s): S6-S12 (2009).
Flohr, T., et al. "Minimal residual disease-directed risk stratification using real-time quantitative PCT analysis of immunoglobulin and T-cell receptor gene rearrangements in the international multicenter trial AIEOP-BFM ALL 2000 for childhood acute lymphoblastic leukemia", Leukemia, 22:771-782 (2008).
Frampton, et al. "Development and validation of a clinical cancer genomic profiling test based on massively parallel DNA sequencing", Nat Biotechnol., 31(11): 1023-1031 (2013). doi: 10.1038/nbt.2696. Epub Oct. 20, 2013.
Frank. "BARCRAWL and BARTAB: software tools for the design and implementation of barcoded primers for highly multiplexed DNA sequencing," BMC Bioinformatics, 10: 362 (2009).
Frederiksson et al., "Multiplex amplification of all coding sequences within 10 cancer genes by Gene-Collector", Nucleic Acids Research, 35(7): e47 (2007).
Freeman, et al. "Quantitative RT-PCR: Pitfalls and Potential", Biotechniques, 6(1): 112-125 (1999).
Freeman, J.D., et al. "Profiling the T-Cell Receptor Beta-Chain Repertoire by Massively Parallel Sequencing", Genome Research, 19(10):1817-1824 (2009).
Fridman, et al. "Prognostic and predictive impact of intra- and peritumoral immune infiltrates", Cancer Research, 71(17): 5601-5605 (2011). doi: 10.1158/0008-5472.CAN-11-1316. Epub Aug. 16, 2011.
Fritz et al. "Alterations in the spinal cord T cell repertoire during relapsing experimental autoimmune encephalomyelitis," J Immunol, 164:6662-6668 (2000).
Fu et al. "Counting individual DNA molecules by the stochastic attachment of diverse labels", PNAS, 108(22): 9026-9031 and Supporting Materials, 8 pages (2011).
Fuller, et al. "The challenges of sequencing by synthesis", Nat Biotechnol., 7(11): 1013-23 (2009) (Abstract only). doi: 10.1038/nbt.1585. Epub Nov. 6, 2009.
Furmanski, et al. "Public T cell receptor β-chains are not advantaged during positive selection", The Journal of Immunology, 180(2): 1029-39 (2008).
García-Castillo and Núnez, et al. "Detection of clonal immunoglobulin and T-cell receptor gene recombination in hematological malignancies: monitoring minimal residual disease", Cardiovascular & Haematological Disorders-Drug Targets, 9:124-135 (2009).
Gauss, et al. "Mechanistic constraints on diversity in human V(D)J recombination", Mol Cell Biol., 16(1):258-269 (1996).
Gawad, et al. "Massive evolution of the immunoglobulin heavy chain locus in children with B precursor acute lymphoblastic leukemia", Blood, 120(22):4407-4417 (2012). doi: 10.1182/blood-2012-05-429811. Epub Aug. 28, 2012.
Gerlinger and Swanton. "How Darwinian models inform therapeutic failure initiated by clonal heterogeneity in cancer medicine", British Journal of Cancer, 103(8):1139-1143 (2010). doi: 10.1038/sj.bjc.6605912. Epub Sep. 28, 2010.
Gerlinger, M. et al. "Ultra deep T cell receptor sequencing reveals the complexity and intratumour heterogeneity of T cell clones in renal cell carcinomas", Journal of Pathology, 231:424-432 (2013).
Germano, et al. "Clonality profile in relapsed precursor-B-ALL children by GeneScan and sequencing analyses. Consequences on minimal residual disease monitoring", Leukemia, 17(8):1573-1582 (2003).
Giannoni, et al. Allelic exclusion and peripheral reconstitution by TCR transgenic T cells arising from transduced human hematopoietic stem/progenitor cells, Mol Ther., 21(5):1044-54 (2013). doi: 10.1038/mt.2013.8. Epub Feb. 5, 2013.
GIGA—Roche 454 FLX technology how it works. Fiche technique du Centre Interdisciplinaire de Genoproteomique Appliquee (Universite de Liege, Belgique). Accessed Oct. 15, 2014.
Gilbert, et al. "The isolation of nucleic acids from fixed, paraffin-embedded tissues—which methods are useful when?", PLoS One, 2(6):e537, 12 pages (2007).
Giuggio, et al. "Evolution of the intrahepatic T cell repertoire during chronic hepatitis C virus infection", Viral Immunology, 18(1):179-189 (2005).
Gloor et al. "Microbiome profiling by Illumina sequencing of combinatorial sequence-tagged PCR products," PLoS One, 5(10): e15406, 15 pages (2010).
Godelaine, et al. "Polyclonal CTL responses observed in melanoma patients vaccinated with dendritic cells pulsed with a MAGE-3.A1 peptide", J Immunol., 171(9):4893-4897 (2003).
Golembowski, et al. "Clonal evolution in a primary cutaneous follicle center B cell lymphoma revealed by single cell analysis in sequential biopsies", Immunobiology, 201(5):631-644 (2000).
Gomes, et al. "Single-tube nested PCR using immobilized internal primers for the identification of dengue virus serotypes", J Virol Methods., 145(1):76-9 (2007). Epub Jun. 15, 2007.
Gonzalez, et al. "Incomplete DJH rearrangements of the IgH gene are frequent in multiple myeloma patients: immunobiological characteristics and clinical implications", Leukemia, 17:1398-1403 (2003).
Gonzalez et al., "Incomplete DJH rearrangements as a novel tumor target for minimal residual disease quantitation in multiple myeloma using real-time PCR", Leukemia, 17:1051-1057 (2003).
Gonzalez, S.F., et al. "Trafficking of B Cell Antigen in Lymph Nodes", Ann. Rev. Immunol., 29: 215-233 (2011).
Gopalakrishnan, et al. "Unifying model for molecular determinants of the preselection Vβ repertoire", Proc Natl Acad Sci USA, 110(34):E3206-15 (2013). doi: 10.1073/pnas.1304048110. Epub Aug. 5, 2013.
Gorski, et al. "Circulating T cell repertoire complexity in normal individuals and bone marrow recipients analyzed by CDR3 size spectratyping. Correlation with immune status", J Immunol., 152(10):5109-5119 (1994).
Gottenberg, et al. "Markers of B-lymphocyte activation are elevated in patients with early rheumatoid arthritis and correlated with disease activity in the ESPOIR cohort", Arthritis Res Ther., 11(4): R114 (2009). doi: 10.1186/ar2773. Epub Jul. 23, 2009.
Gratama and Kern. "Flow cytometric enumeration of antigen-specific T lymphocytes", Cytometry A, 58(1): 79-86 (2004).
Gratama, et al. "Measuring antigen-specific immune responses", 2008 update. Cytometry A., 73(11): 971-974 (2008). doi: 10.1002/cyto.a.20655.
Green, et al. "Clonal diversity of Ig and T-cell-receptor gene rearrangements identifies a subset of childhood B-precursor acute lymphoblastic leukemia with increased risk of relapse", Blood, 92(3):952-958 (1998).
Greenberg, et al. "Profile of immunoglobulin heavy chain variable gene repertoires and highly selective detection of malignant clonotypes in acute lymphoblastic leukemia" J Leukoc Biol., 57(6):856-864 (1995).
Greenman, et al. "Patterns of somatic mutation in human cancer genomes", Nature, 446(7132): 153-158 (2007).
Gribben, JG. "Stem cell transplantation in chronic lymphocytic leukemia", Biol. Blood Marrow Transplant., 15(1 Suppl): 53-58 (2009). doi: 10.1016/j.bbmt.2008.10.022.
Grupp, et al. "Chimeric antigen receptor-modified T cells for acute lymphoid leukemia", N Engl J Med., 368(16):1509-18 (2013). doi: 10.1056/NEJMoa1215134. Epub Mar. 25, 2013.
Grupp, et al. "Adoptive transfer of autologous T cells improves T-cell repertoire diversity and long-term B-cell function in pediatric patients with neuroblastoma", Clin Cancer Res., 18(24):6732-41 (2012). doi: 10.1158/1078-0432.CCR-12-1432. Epub Oct. 23, 2012.
Gulliksen, et al. "Real-time nucleic acid sequence-based amplification in nanoliter volumes", Anal Chem., 76(1): 9-14, Abstract Only (2004).
Gunderson et al. "Decoding Randomly Ordered DNA Arrays", Genome Research, 14: 870-877 (2004).
Guo, et al. "Sequence changes at the V-D junction of the $V_H1$ heavy chain of anti-phosphocholine antibodies alter binding to and protection against Streptococcus pneumoniae", Int Immunol., 9(5):665-677 (1997).

(56) References Cited

OTHER PUBLICATIONS

Gupta, Pushpendra K. "Single-molecule DNA sequencing technologies for future genomics research", *Trends Biotechnol.*, 26(11): 602-611 (2008). doi: 10.1016/j.tibtech.2008.07.003. Epub Aug. 21, 2008.

Gurrieri, et al. "Chronic lymphocytic leukemia B cells can undergo somatic hypermutation and intraclonal immunoglobulin $V_H D J_H$ gene diversification", *J Exp Med.*, 196(5):629-639 (2002).

Hadrup, et al. "Parallel detection of antigen-specific T-cell responses by multidimensional encoding of MHC multimers", *Nat Methods*, 6(7): 520-526 (2009) (Abstract Only). doi: 10.1038/nmeth.1345. Epub Jun. 21, 2009.

Halldórsdóttir, et al. "Application of BIOMED-2 clonality assays to formalin-fixed paraffin embedded follicular lymphoma specimens: superior performance of the IGK assays compared to IGH for suboptimal specimens", *Leukemia & Lymphoma*, 48(7): 1338-1343 (2007).

Hamady, et al. "Error-correcting barcoded primers for pyrosequencing hundreds of samples in multiplex", *Nature Methods*, 5(3):235-237 (2008). doi: 10.1038/nmeth.1184. Epub Feb. 10, 2008.

Han et al. "Immunorepertoire analysis by multiplex PCR amplification and high throughput sequencing", *The Journal of Immunology*, 182:42.6, 1 page (2009).

Hanahan, et al. "Hallmarks of cancer: the next generation", *Cell*, 144(5): 646-674 (2011). doi: 10.1016/j.cell.2011.02.013.

Harismendy et al. "Evaluation of next generation sequencing platforms for population targeted sequencing studies", *Genome Biology*, 10:R32, 13 pages (2009).

Harris et al. "Single-Molecule DNA Sequencing of a Viral Genome", *Science*, 320: 106-109 (2008).

Hathcock, et al. "ATM influences the efficiency of TCRβ rearrangement, subsequent TCRβ-dependent T cell development, and generation of the pre-selection TCRβ CDR3 repertoire", PLoS One, 8(4):e62188 (2013). doi: 10.1371/journal.pone.0062188. Print 2013.

Hawkins, et al. "Whole genome amplification—applications and advances", *Curr Opin Biotechnol.*, 13(1): 65-67 (2002).

He, et al. "IgH gene rearrangements as plasma biomarkers in Non-Hodgkin's lymphoma patients", *Oncotarget*, 2(3): 178-185 (2011).

Heger, M. "Studies Highlight Challenges of Immune Repertoire Sequencing's Clinical Applicability", available at http://www.genomeweb.com/sequencing/studies-highlight-challenges-immune-repertoire-sequencings-clinical-applicabilit?hq_e=el&hq_m=966798&hq_l=10&hq_v=2357e2f0b3. Accessed Apr. 6, 2011.

Heger. "Roche's 454 Eyes Immune Repertoire Sequencing as Key Application for Long-Read Platform". Feb. 2, 2010. 4 pages. http://www.genomeweb.com/print/932624.

Henegariu, O. et al., "Multiplex PCR: Critical Parameters and Step-by-Step Protocol," Biotechniques, Informa HealthCare, 23(3):504-511 (1997).

Hensel et al. "Simultaneous identification of bacterial virulence genes by negative selection", *Science*, 269(5222): 400-403 (1995).

Hill, et al. "Using ecological diversity measures with bacterial communities", *FEMS Microbiol Ecol.*, 43(1):1-11 (2003). doi: 10.1111/j.1574-6941.2003.tb01040.x.

Hirohata, et al. "Regulation of human B cell function by sulfasalazine and its metabolites", *Int Immunopharmacol.*, 2(5): 631-640, Abstract Only (2002).

Hodges, E. et al. "Diagnostic role of tests for T cell receptor (TCR) genes", *J Clin Pathol.*, 56(1): 1-11 (2003).

Holder and Lewis. "Phylogeny estimation: traditional and bayesian approaches", Nat Rev Genet., 4(4): 275-84 (2009).

Holt. "Q &A: BC cancer agency's Robert Holt on sequencing the immune repertoire in immune reconstitution," *Genome Web* (www.genomeweb.com) Jun. 30, 2009.

Holt and Jones. "The new paradigm of flow cell sequencing", *Genome Research*, 18:839-846 (2008).

Hoogenboom, et al. "Multi-subunit proteins on the surface of filamentous phage: methodologies for displaying antibody (Fab) heavy and light chains", *Nucleic Acids Res.*, 19(15): 4133-4137 (1991).

Hoogendoorn, et al. "Primary allogeneic T-cell responses against mantle cell lymphoma antigen-presenting cells for adoptive immunotherapy after stem cell transplantation", *Clin Cancer Res.*, 11(14): 5310-5318 (2005).

Hoos, et al. "Improved endpoints for cancer immunotherapy trials", *J Natl Cancer Inst.*, 102(18): 1388-1397 (2010). doi: 10.1093/jnci/djq310. Epub Sep. 8, 2010.

Hoover and Lubkowski. "DNAWorks: an automated method for designing oligonucleotides for PCR-based gene synthesis", *Nucleic Acids Res.*, 30(10): e43, 7 pages (2002).

Hosono, et al. "Unbiased whole-genome amplification directly from clinical samples", *Genome Res.*, 13(5): 954-964 (2003). Epub Apr. 14, 2003.

Hoven, et al. "Detection and isolation of antigen-specific B cells by the fluorescence activated cell sorter (FACS)", *J Immunol Methods*, 117(2): 275-284, Abstract Only, 2 pages (1989).

Howe, et al. "T cell receptor clonotype analysis of T cell responses: Diagnostic application of a clonotypic database", *Blood*, 102:Abstract 3918 (2003).

Huang, et al. "Isolation of cell-free DNA from maternal plasma using manual and automated systems", *Methods Mol Biol.*, 444: 203-208, Abstract Only (2008). doi: 10.1007/978-1-59745-066-9_15.

Huh, et al. "Microfluidics for flow cytometric analysis of cells and particles", *Physiol Meas.*, 26(3): R73-98, Abstract Only (2005). Epub Feb. 1, 2005.

Huijsmans, et al. "Comparative analysis of four methods to extract DNA from paraffin-embedded tissues: effect on downstream molecular applications", *BMC Res Notes*, 3:239, 9 pages (2010). doi: 10.1186/1756-0500-3-239.

Huse, et al. "Generation of a large combinatorial library of the immunoglobulin repertoire in phage lambda", *Science*, 246(4935): 1275-1281, Abstract Only (1989).

Huse et al. "Accuracy and quality of massively parallel DNA pyrosequencing", *Genome Biology*, 8: R143 (2007).

Hwang, H.Y. et al. "Identification of a Commonly used CDR3 Region of Infiltrating T Cells Expressing Vβ13 and Vβ15 Derived from Psoriasis Patients", *The Journal of Investigative Dermatology*, 120(3):359-364 (2003).

Iancu, et al. "Profile of a serial killer: cellular and molecular approaches to study individual cytotoxic T-cells following therapeutic vaccination", *J Biomed Biotechnol.*, 2011: 452606 (2011). doi: 10.1155/2011/452606. Epub Nov. 14, 2010.

Illumina. Genome analyzer pipeline software version 1.0 user guide. Part #1004759, 176 pages (2008).

Illumina. Data Sheet: Sequencing. Genomic Sequencing. Pub. No. 770.2008-016 Reference states: "Current as of Jan. 30, 2009", 6 pages, Copyright 2010.

Illumina. Data Sheet, "TruSeq™ exome enrichment kit", 5 pages (2011).

Illumina Systems & Software, Technology Spotlight, DNA Sequencing with Solexa® Technology, Illumina, Inc., Pub. No. 770-2007-002, 4 pages (2007).

Illumina. "Technical Note: Systems and Software. Calling sequencing SNPs", 3 pages (2010).

Illumina. TruSeq Sample Preparation Kit and Data Sheet. Illumina, Inc., San Diego, CA, 4 pages (2011).

Ishii et al. "Isolation and expression profiling of genes upregulated in the peripheral blood cells of systemic lupus erythematosus patients," *DNA Research*, 12:429-439 (2005).

Jabara et al. "Accurate sampling and deep sequencing of the HIV-1 protease gene using a Primer ID", *PNAS*, 108(50): 20166-20171 (2011).

Jacobi et al. "Activated memory B cell subsets correlate with disease activity in systemic lupus erythematosus: delineation by expression of CD27, IgD, and CD95", *Arthritis & Rheumatism*, 58(6):1762-1773 (2008).

(56) References Cited

OTHER PUBLICATIONS

Jacobi et al. "Correlation between circulating CD27$^{high}$ plasma cells and disease activity in patients with systemic lupus erythematosus" *Arthritis & Rheumatism*, 48(5):1332-1342 (2003).

Jaffe, et al. "Classification of lymphoid neoplasms: the microscope as a tool for disease discovery", *Blood*, 112(12): 4384-4399 (2008). doi: 10.1182/blood-2008-07-077982.

Jalla, et al. "Enumeration of lymphocyte subsets using flow cytometry: Effect of storage before and after staining in a developing country setting", *Indian J Clin Biochem.*, 19(2): 95-99 (2004). doi: 10.1007/BF02894264.

Jena, et al. "Amplification of genes, single transcripts and cDNA libraries from one cell and direct sequence analysis of amplified products derived from one molecule", *J. Immunol. Methods*, 190:199-213 (1996).

Jochems and Schlom. "Tumor-infiltrating immune cells and prognosis: the potential link between conventional cancer therapy and immunity", *Exp Biol Med* (Maywood), 236(5): 567-579 (2011). doi: 10.1258/ebm.2011.011007. Epub Apr. 12, 2011.

Jones, et al. "Human autoimmunity after lymphocyte depletion is caused by homeostatic T-cell proliferation", Proc Natl Acad Sci USA, 110(50) :20200-5 (2013). doi: 10.1073/pnas.1313654110. Epub Nov. 26, 2013.

Jung, et al. "Unraveling V(D)J recombination; insights into gene regulation", *Cell*, 116(2): 299-311 (2004).

Jurkat, Clone 6-1 (ATCC TIB-152) Webpage retrievable from the ATCC under http:/ /www.lgcstandards-atcc.org/Products/ All MB-152. aspx#characteristics. Accessed Oct. 14, 2014.

Kalinina, O. et al. "Nanoliter scale PCR with TaqMan detection", *Nucleic Acids Research*, 25(10):1999-2004 (1997).

Kalos, M. et al. "T Cells with Chimeric Antigen Receptors Have Potent Antitumor Effects and Can Establish Memory in Patients with Advanced Leukemia", *Science Translational Medicine*, 3(95ra73): 1-11 (2011).

Kanda, et al. "Immune recovery in adult patients after myeloablative dual umbilical cord blood, matched sibling, and matched unrelated donor hematopoietic cell transplantation", Biol Blood Marrow Transplant, 18(11):1664-1676 (2012). doi: 10.1016/j.bbmt. 2012.06.005. Epub Jun. 12, 2012.

Kaplinski and Remm. "MultiPLX Automatic Grouping and Evaluation of PCR Primers", *Methods in Molecular Biology*, 402(PCR Primer Design):287-303 (2004).

Kato et al. "Analysis of accumulated T cell clonotypes in patients with systemic lupus erythematosus," *Arthritis & Rheumatism*, 43(12):2712-2721 (2000).

Katz, S.C. et al. "T Cell Infiltrate Predicts Long-Term Survival Following Resection of Colorectal Cancer Liver Metastases," Ann. Surg. Oncol., 16:2524-2530 (2009).

Kedzierska, et al. "Tracking phenotypically and functionally distinct T cell subsets via T cell repertoire diversity", *Mol Immunol.*, 45(3): 607-618 (2008). Epub Aug. 24, 2007.

Kehrl, J.H. et al. "Chemoattractant Receptor Signaling and Its Role in Lymphocyte Motility and Trafficking", *Current Topics in Microbiology and Immunology*, 334:107-127 (2009).

Kiianitsa, et al., "Development of Tools for T-Cell Repertoire Analysis (TCRB Spectratyping) for the Canine Model of Hematopoietic Cell Transplantation", *Blood*, ASH-Annual Meeting Abstracts, 110:Abstract 4873, 2 pages (2007).

Kim, et al. "An efficient and reliable DNA extraction method for preimplantation genetic diagnosis: a comparison of allele drop out and amplification rates using different single cell lysis methods", *Fertility and Sterility*, 92: 814-818 (2009).

Kim, et al. "Polony multiplex analysis of gene expression (PMAGE) in mouse hypertrophic cardiomyopathy", *Science*, 316(5830):1481-1484 (2007).

Kinde et al. "Detection and quantification of rare mutations with massively parallel sequencing," PNAS, 108(23): 9530-9535 and Supporting Information, 16 pages (2011).

Kircher, et al. "Improved base calling for the Illumina Genome Analyzer using machine learning strategies", *Genome Biol.*, 10(8): R83, 9 pages (2009). doi: 10.1186/gb-2009-10-8-r83. Epub Aug. 14, 2009.

Kirsch, et al. "Defining immunoglobulin somatic hypermutation in de novo diffuse large b-cell lymphoma patients: potential application prognosis and risk stratification", Presented for the 2014 ASH Annual Meeting. Poster. 1 page. Dec. 5-9, 2014.

Kirsch, et al. "High-throughput TCR sequencing provides added value in the diagnosis of cutaneous T-cell lymphoma", Presented for the 2014 ASH Annual meeting. Poster. 1 page. Dec. 5-9, 2014.

Kita, et al. "T cell receptor clonotypes in skin lesions from patients with systemic lupus erythematosus", *Journal of Investigative Dermatology*,110(1): 41-6 (1988).

Kivioja et al. "Counting absolute numbers of molecules using unique molecular identifiers," *Nature Methods*, 9(1): 72-76 (2012).

Klarenbeek, P.L. et al. "Human T-cell memory consists mainly of unexpanded clones", *Immunology Letters*, 133: 42-48 (2010).

Klebanoff, et al. "Therapeutic cancer vaccines: are we there yet?", *Immunol Rev.*, 239(1): 27-44 (2011). doi: 10.1111/j.1600-065X. 2010.00979.x.

Klenerman, et al. "Tracking T cells with tetramers: new tales from new tools", *Nat Rev Immunol.*, 2(4):263-272 (2002).

Kneba, M., et al. "Analysis of Rearranged T-cell Receptor β-Chain Genes by Polymerase Chain Reaction (PCR) DNA Sequencing and Automated High Resolution PCR Fragment Analysis", *Blood*, 86:3930-3937 (1995).

Kneba, et al. "Characterization of clone-specific rearrangement T-cell receptor gamma-chain genes in lymphomas and leukemias by the polymerase chain reaction and DNA sequencing", *Blood*, 84(2):574-581 (1994).

Kobari, et al. "T cells accumulating in the inflamed joints of a spontaneous murine model of rheumatoid arthritis become restricted to common clonotypes during disease progression", *Int Immunol.*, 16(1):131-138 (2004).

Koboldt et al., "VarScan: variant detection in massively parallel sequencing of individual and pooled samples", Bioinformatics, 25(17): 2283-2285 (2009).

Koch, et al. "Tumor infiltrating T lymphocytes in colorectal cancer: Tumor-selective activation and cytotoxic activity in situ," *Ann Surg.*, 244(6): 986-992; discussion 992-993 (2006).

Kojima et al. "PCR amplification from single DNA molecules on magnetic beads in emulsion: application for high-throughput screening of transcription factor targets", *Nucleic Acids Research*, 33: 17, e150, 9 pages (2005).

Kohlmann, et al. "Integration of next-generation sequencing into clinical practice: are we there yet?", *Semin Oncol.*, 39(1): 26-36, Abstract Only (2012). doi: 10.1053/j.seminoncol.2011.11.008.

Kou, et al. "T-Cell receptor Vbeta repertoire CDR3 length diversity differs within CD45RA and CD45RO T-cell subsets in healthy and human immunodeficiency virus-infected children", *Clin Diagn Lab Immunol.*, 7(6):953-9 (2000).

Krause et al. "Epitope-Specific Human Influenza Antibody Repertoires Diversify by B Cell Intraclonal Sequence Divergence and Interclonal Convergence", *The Journal of Immunology*, 187: 3704-3711 (2011).

Krueger, et al. "Large scale loss of data in low-diversity illumina sequencing libraries can be recovered by deferred cluster calling", *PLoS One*, 6(1): e16607, 7 pages (2011). doi: 10.1371/journal.pone. 0016607.

Ku, et al. "Exome sequencing: dual role as a discovery and diagnostic tool", *Ann Neurol.*, 71(1):5-14, Abstract Only (2012). doi: 10.1002/ana.22647.

Kumar, et al. "PEG-labeled nucleotides and nanopore detection for single molecule DNA sequencing by synthesis", *Sci Rep.*, 2:684, 8 pages (2012). Epub Sep. 21, 2012.

Kwak, et al. "Induction of immune responses in patients with B-cell lymphoma against the surface-immunoglobulin idiotype expressed by their tumors", N Engl J Med., 327(17):1209-1215 (1992).

Kyu et al. "Frequencies of human influenza-specific antibody secreting cells or plasmablasts post vaccination from fresh and frozen peripheral blood mononuclear cells", *Journal of Immunological Methods*, 340: 42-47 (2009).

(56) References Cited

OTHER PUBLICATIONS

Ladányi, A., et al. "Prognostic impact of B-cell density in cutaneous melanoma", *Cancer Immunol. Immunother*, 60(12): 1729-1738 (2011).

Ladetto, et al., "Next-generation sequencing and real-time quantitative PCR for minimal residual disease (MRD) detection using the immunoglobulin heavy chain variable region: A methodical comparison in acute lymphoblastic leukemia (ALL), mantle cell lymphoma (MCL) and multiple myeloma (MM)", *Blood*, vol. 120, No. 21, Abstract 788 (Conference Abstract), Entire Abstract (2012).

Ladetto, M. et al. "Real-time polymerase chain reaction in multiple myeloma: Quantitative analysis of tumor contamination of stem cell harvests", *Experimental Hematology*, 30:529-536 (2002).

Ladetto, M. et al. "Real-Time Polymerase Chain Reaction of Immunoglobulin Rearrangements for Quantitative Evaluation of Minimal Residual Disease in Multiple Myeloma", *American Society for Blood and Marrow Transplantation*, 6(3):241-253 (2000).

Landwehr-Kenzel, et al. "Novel GMP-compatible protocol employing an allogeneic B cell bank for clonal expansion of allospecific natural regulatory T cells", Am J Transplant., 14(3):594-606 (2014). doi: 10.1111/ajt.12629. Epub Jan. 27, 2014.

Langerak, et al. "Immunoglobulin/T-cell receptor clonality diagnostics", *Expert Opin. Med. Diagn.*, 1(3):451-461 (2007).

Langerak, et al. "Polymerase chain reaction-based clonality testing in tissue samples with reactive lymphoproliferations: usefulness and pitfalls. A report of the BIOMED-2 Concerted Action BMH4-CT98-3936", *Leukemia*, 21(2):222-229 (2007).

Laplaud et al. "Blood T-cell receptor β chain transcriptome in multiple sclerosis. Characterization of the T cells with altered CDR3 length distribution", *Brain*, 127:981-995 (2004).

Laplaud et al. "Serial blood T cell repertoire alterations in multiple sclerosis patients; correlation with clinical and MRI parameters", *Journal of Neuroimmunology*, 177(1-2):151-160 (2006).

Larimore, K., et al. "Shaping of Human Germline IgH Repertoires Revealed by Deep Sequencing", *The Journal of Immunology*, 189(6): 3221-3230 (2012).

Lassmann, et al. "Application of BIOMED-2 primers in fixed and decalcified bone marrow biopsies: analysis of immunoglobulin H receptor rearrangements in B-cell non-Hodgkin's lymphomas", *J Mol Diagn.*, 7(5): 582-591 (2005).

Lazareva-Ulitsky et al, "On the quality of tree-based protein classification," Bioinformatics, 21(9): 1876-1890 (2005).

Lee, et al. "Characterization of circulating T cells specific for tumor-associated antigens in melanoma patients", *Nat Med.*, 5(6): 677-685, Abstract Only (1999).

Lee, et al. "Prognostic implications of type and density of tumour-infiltrating lymphocytes in gastric cancer", *Br J Cancer*, 99(10): 1704-1711 (2008). doi: 10.1038/sj.bjc.6604738. Epub Oct. 21, 2008.

Lefranc. "IMGT, the international ImMunoGeneTics database", *Nucleic Acids Res.*, 31(1):307-310 (2003).

Leiden, J.M. et al. "The Complete Primary Structure of the T-Cell Receptor Genes From an Alloreactive Cytotoxic Human T-Lymphocyte Clone", Immunogenetics, 24(1): 17-23 (1986).

Leisner, et al. "One-pot, mix-and-read peptide-MHC tetramers", *PLoS One*, 3(2):e1678, 11 pages (2008). doi: 10.1371/journal.pone. 0001678.

Lennon, et al. "A scalable, fully automated process for construction of sequence-ready barcoded libraries for 454", *Genome Biol.*, 11(2):R15, 9 pages (2010). doi: 10.1186/gb-2010-11-2-r15. Epub Feb. 5, 2010.

Leary, et al. "Development of personalized tumor biomarkers using massively parallel sequencing", Sci Transl Med., 2(20): 20ra14 (2010). doi: 10.1126/scitranslmed.3000702.

Leone, et al. "Molecular beacon probes combined with amplification by NASBA enable homogeneous, real-time detection of RNA", *Nucleic Acids Research*, 26(9): 2150-2155 (1998).

Leproust, et al. "Synthesis of high-quality libraries of long (150mer) oligonucleotides by a novel depurination controlled process", *Nucleic Acids Res.*, 38(8): 2522-2540 (2010). doi: 10.1093/nar/gkq163. Epub Mar. 22, 2010.

Lessin, et al. "Molecular diagnosis of cutaneous T-cell lymphoma: polymerase chain reaction amplification of T-cell antigen receptor beta-chain gene rearrangements", *J Invest Dermatol.*, 96(3): 299-302 (1991).

Li, et al. "Utilization of Ig heavy chain variable, diversity, and joining gene segments in children with B-lineage acute lymphoblastic leukemia: implications for the mechanisms of VDJ recombination and for pathogenesis", *Blood*, 103(12):4602-4609 (2004).

Li, et al. "An improved one-tube RT-PCR protocol for analyzing single-cell gene expression in individual mammalian cells", *Anal. Bioanal. Chem.*, 397: 1853-1859 (2010).

Li, et al. "β cell-specific CD4+ T cell clonotypes in peripheral blood and the pancreatic islets are distinct", *J Immunol.*, 183(11): 7585-7591 (2009). doi: 10.4049/jimmunol.0901587. Epub Nov. 16, 2009.

Li, et al. "Clonal rearrangements in childhood and adult precursor B acute lymphoblastic leukemia: a comparative polymerase chain reaction study using multiple sets of primers", *Eur J Haematol.*, 63(4):211-218 (1999).

Li, et al. "Detailed clonality analysis of relapsing precursor B acute lymphoblastic leukemia: implications for minimal residual disease detection", *Leukemia Research*, 25:1033-1045 (2001).

Li et al, "Mapping short DNA sequencing reads and calling variants using mapping quality scores," Genome Research, 18: 1851-1858 (2008).

Li, et al. "Sequence analysis of clonal immunoglobulin and T-cell receptor gene rearrangements in children with acute lymphoblastic leukemia at diagnosis and at relapse: implications for pathogenesis and for the clinical utility of PCR-based methods of minimal residual disease detection", *Blood*, 102:4520-4526 (2003).

Liedtke, et al. "A comparison of methods for RNA extraction from lymphocytes for RT-PCR", *PCR Methods and Applications*, 4(3): 185-187 (1994).

Lin, et al. "Multiplex genotype determination at a large number of gene loci", *Proc Natl Acad Sci USA*, 93(6): 2582-2587 (1996).

Liu, et al. "CD127 expression inversely correlates with FoxP3 and suppressive function of human CD4+ T reg cells", *J Exp Med.*, 203(7): 1701-1711 (2006). Epub Jul. 3, 2006.

Lo, et al. "T cell immunodominance is dictated by the positively selecting self-peptide", Elife, 3:e01457 (2014). doi: 10.7554/eLife. 01457. Epub Jan. 14, 2014.

Logan, et al., "High-throughput immunoglobulin gene sequencing quantifies minimal residual disease in CLL with 10e-6 sensitivity and strongly predicts relapse after allogeneic hematopoietic cell transplantation", *Blood*, vol. 118 (21), Abstract 2542 (2011).

Logan, A.C. et al. "High-throughput VDJ sequencing for quantification of minimal residual disease in chronic lymphocytic leukemia and immune reconstitution assessment", *PNAS*, 108(52): 21194-21199 (2011).

Logan, et al., "Massively parallel immunoglobulin gene sequencing provides ultra-sensitive minimal residual disease detection and predicts post-transplant relapse in acute lymphoblastic leukemia by three to six months", *Blood*, vol. 118 (21), Abstract 4104 (2011).

Lossos, et al. "Transformation of follicular lymphoma to diffuse large-cell lymphoma: alternative patterns with increased or decreased expression of c-myc and its regulated genes", *PNAS*, 99(13): 8886-8891 (2002). Epub Jun. 19, 2002.

Lovisa, et al. "IGH and IGK gene rearrangements as PCR targets for pediatric Burkitt's lymphoma and mature B-ALL MRD analysis", *Lab Invest.*, 89(10):1182-1186 (2009).

Lowe, T., et al., "A computer program for selection of oligonucleotide primers for polymerase chain reactions," Nucleic Acids Research, 18(7):1757-1761 (1990).

Lowman, et al. "Monovalent phage display: a method for selecting variant proteins from random libraries", *Methods: A Companion to Methods in Enzymology*, 3: 205-216, Abstract Only (1991).

Lúcio, P. et al. "Flow cytometric analysis of normal B cell differentiation: a frame of reference for the detection of minimal residual disease in precursor-B-ALL", *Leukemia*, 13:419-427 (1999).

(56) References Cited

OTHER PUBLICATIONS

Lyamichev, et al. "Polymorphism identification and quantitative detection of genomic DNA by invasive cleavage of oligonucleotide probes", *Nat Biotechnol.*, 17(3): 292-396 (1999).

Luo et al. "Analysis of the interindividual conservation of T cell receptor α- and β-chain variable regions gene in the peripheral blood of patients with systemic lupus erythematosus", *Clinical & Experimental Immunology*, 154(3):316-324 (2008).

Mackay, et al. "Real-time PCR in virology", *Nucleic Acids Res.*, 30(6): 1292-305 (2002).

Mahmoud, S.M.A. et al. "Tumor-Infiltrating CD8+ Lymphocytes Predict Clinical Outcome in Breast Cancer", Journal of Clinical Oncology, 29(15): 1949-1955 (2011).

Maldonado, et al. "Intramuscular therapeutic vaccination targeting HPV16 induces T cell responses that localize in mucosal lesions", Sci Transl Med., 6(221): 221ra13 (2014). doi: 10.1126/scitranslmed.3007323.

Malyguine, et al. "ELISPOT Assay for Monitoring Cytotoxic T Lymphocytes (CTL) Activity in Cancer Vaccine Clinical Trials", *Cells*, 1(2): 111-126 (2012). doi: 10.3390/cells1020111.

Manion et al., "Reducing Error in Next Generation Sequencing Data with NextGENe Software's Condensation Tool™", Mar. 2009, pp. 1-3. XP055226038.

Manrao, et al. "Reading DNA at single-nucleotide resolution with a mutant MspA nanopore and phi29 DNA polymerase", *Nat Biotechnol.*, 30(4): 349-353 (2012). doi: 10.1038/nbt.2171.

Mar et al. "Inferring steady state single-cell gene expression distributions from analysis of mesoscopic samples", *Genome Biology*, 7(12): R119, 12 pages (2006).

Mardis. "Next-generation DNA sequencing methods", *Annu. Rev. Genomics Hum. Genet.*, 9:387-402 (2008). doi: 10.1146/annurev.genom.9.081307.164359.

Marelli-Berg, F.M., et al. "Memory T-cell trafficking: new directions for busy commuters", *Immunology*, 130:158-165 (2010).

Margulies, et al. "Genome sequencing in microfabricated high-density picolitre reactors", *Nature*, 437(7057):376-380 (2005). Epub Jul. 31, 2005.

Mariani, S. et al., "Comprehensive assessment of the TCRBV repertoire in small T-cell samples by means of an improved and convenient multiplex PCR method," *Experimental Hematology*, 37(6):728-738 (2009).

Markoulatos, P. et al., "Multiplex Polymerase Chain Reaction: A Practical Approach", Journal of Clinical Laboratory Analysis, 16:47-51 (2002).

Marrero, et al. "High-throughput sequencing of islet-infiltrating memory CD4+ T cells reveals a similar pattern of TCR Vβ usage in prediabetic and diabetic NOD mice", PLoS One, 8(10):e76546 (2013). doi: 10.1371/journal.pone.0076546. eCollection 2013.

Martin-Jimenez, et al. "Molecular characterization of heavy chain immunoglobulin gene rearrangements in Waldenström's macroglobulinemia and IgM monoclonal gammopathy of undetermined significance", *Haematologica*, 92(5): 635-642 (2007).

Mary et al. "Analysis of gene expression at the single-cell level using microdroplet-based microfluidic technology", *Biomicrofluidics*, 5: 024109-1-024109-10 (2011).

Maryanski, J.L. et al., "A quantitative, single-cell PCR analysis of an antigen-specific TCR repertoire 8 selected during an in vivo CD8 response: direct evidence for a wide range of clone sizes with uniform tissue distribution", Molecular Immunology, 36:745-753 (1999).

Maślanka, K. et al., "Molecular Analysis of T-Cell Repertoires: Spectratypes Generated by Multiplex Polymerase Chain Reaction and Evaluated by Radioactivity or Fluorescence", *Human Technology*, 44(1):28-34 (1995).

Mato et al. "Correlation of clonal T cell expansion with disease activity in systemic lupus erythematosus", *Int Immunol.*, 9(4):547-554 (1997).

Matolcsy, et al. "Clonal evolution of B cells in transformation from low- to high-grade lymphoma", *Eur. J. Immunol.*,29(4):1253-1264 (1999).

Matsubara, et al. "Microchamber array based DNA quantification and specific sequence detection from a single copy via PCR in nanoliter volumes", *Biosens Bioelectron*, 20(8): 1482-1490, Abstract Only (2005).

Matsumoto et al. "CDR3 spectratyping analysis of the TCR repertoire in Myasthenia Gravis", *The Journal of Immunology*, 176:5100-5107 (2006).

Matsumoto et al. "Complementarity-determining region 3 spectratyping analysis of the TCR repertoire in multiple sclerosis", *The Journal of Immunology*, 170:4846-4853 (2003).

Mazor et al. "Antibody internalization studied using a novel IgG binding toxin fusion", *Journal of Immunological Methods*, 321: 41-59 (2007).

Mazumder, et al., "Detection of multiple myeloma cells in peripheral blood using high-throughput sequencing assay" *Blood*, vol. 120 , No. 21, Abstract 321 (Conference Abstract), Entire Abstract (2012).

McCloskey et al. "Encoding PCR products with batch-stamps and barcodes," *Biochem. Genet.*, 45: 761-767 (2007).

McGoldrick, et al. "Cytomegalovirus-specific T cells are primed early after cord blood transplant but fail to control virus in vivo", Blood, 121(14): 2796-803 (2013). doi: 10.1182/blood-2012-09-453720. Epub Feb. 14, 2013.

Mei et al. "Blood-borne human plasma cells in steady state are derived from mucosal immune responses", *Blood*, 113(11): 2461-2469 (2009).

Meijer et al. "Isolation of Human Antibody Repertoires with Preservation of the Natural Heavy and Light Chain Pairing", *J. Mol. Biol.*, 358: 764-772 (2006).

Meier, et al. "Fractal organization of the human T cell repertoire in health and after stem cell transplantation", Biol Blood Marrow Transplant., 19(3):366-77 (2013). doi: 10.1016/j.bbmt.2012.12.004. Epub Jan. 11, 2013.

Meier et al. "Simultaneous evaluation of T-cell and B-cell clonality, t(11;14) and t(14;18), in a single reaction by a four-color multiplex polymerase chain reaction assay and automated High-Resolution fragment analysis", *American Journal of Pathology*, 159(6): 2031-2043 (2001).

Meier, et al. "The influence of different stimulation conditions on the assessment of antigen-induced CD154 expression on CD4+ T cells", *Cytometry A.*, (11):1035-1042 (2008). doi: 10.1002/cyto.a.20640.

Meleshko, et al. "Rearrangements of IgH, TCRD and TCRG genes as clonality marker of childhood acute lymphoblastic leukemia", *Experimental Oncology*, 27(4):319-324 (2005).

Menezes et al. "A public T cell clonotype within a heterogeneous autoreactive repertoire is dominant in driving EAE", *J Clin Invest*, 117(8):2176-2185 (2007).

Merriam-Webster, 2 pages, (definition of "e.g.," accessed Apr. 25, 2014).

Merriam-Webster, 4 pages (definition of "substantial," accessed Apr. 25, 2014).

Metzker, "Sequencing Technologies—The Next Generation", *Nature Reviews, Genetics*, 11:31-46 (2010).

Meyer et al. "Targeted high-throughput sequencing of tagged nucleic acid samples", *Nucleic Acids Research*, 35(15): e97, 5 pages (2007).

Miceli and Parnes. "The roles of CD4 and CD8 in T cell activation", *Seminars in Immunology*, 3(3): 133-141 (1991). Abstract only.

Michálek, et al. "Detection and long-term in vivo monitoring of individual tumor-specific T cell clones in patients with metastatic melanoma", *J Immunol.*, 178(11):6789-6795 (2007).

Michálek, et al. "Identification and monitoring of graft-versus-host specific T-cell clone in stem cell transplantation", *The Lancet*, 361(9364): 1183-1185 (2003).

Miller, et al., "Assembly algorithms for next-generation sequencing data", Genomics, 95(6): 315-327 (2010).

Miltenyi, et al. "High gradient magnetic cell separation with MACS", *Cytometry*, 11(2): 231-238 (1990).

Miner et al. "Molecular barcodes detect redundancy and contamination in hairpin-bisulfite PCR", *Nucleic Acids Research*, 32(17): e135, 4 pages (2004).

(56) References Cited

OTHER PUBLICATIONS

Miqueu, P. et al. "Statistical analysis of CDR3 length distributions for the assessment of T and B cell repertoire biases", *Molecular Immunology*, 44:1057-1064 (2007).
Mitra, et al. "Fluorescent in situ sequencing on polymerase colonies", *Anal Biochem.*, 320(1): 55-65, Abstract Only (2003).
Mittelstadl, et al. "Thymocyte responsiveness to endogenous glucocorticoids is required for immunological fitness", *J Clin Invest.*, 122(7):2384-94 (2012). doi: 10.1172/JCl63067. Epub Jun. 1, 2012.
Miyashita, et al. "N-Methyl substituted 2',4'-BNANC: a highly nuclease-resistant nucleic acid analogue with high-affinity RNA selective hybridization", *Chem Commun* (Camb), (36): 3765-3767, Abstract Only (2007). Epub Jul. 9, 2007.
Moen, et al. "Immunoglobulin G and A antibody responses to Bacteroides forsyth and Prevotella intermedia in sera and synovial fluids of arthritis patients", *Clin Diagn Lab Immunol.*, 10(6): 1043-1050 (2003).
Molloy, et al. "Soluble T cell receptors: novel immunotherapies", *Curr Opin Pharmacol.*, 5(4): 438-443 (2005) (Abstract Only).
Monod, M.Y. et al. "IMGT/JunctionAnalysis: the first tool for the analysis of the immunoglobulin and T cell receptor complex V-J and V-D-J JUNCTIONs", *Bioinformatics*, 20(Suppl 1):i379-385 (2004).
Moody, et al. "Antigen-specific B cell detection reagents: use and quality control", *Cytometry A.*, 73(11): 1086-1092 (2008). doi: 10.1002/cyto.a.20599.
Morgan, et al. "Cancer regression in patients after transfer of genetically engineered lymphocytes", *Science*, 314(5796): 126-129 (2006). Epub Aug. 31, 2006.
Morozova et al. "Applications of New Sequencing Technologies for Transcriptome Analysis", *Annu. Rev. Genomics Hum. Genet.*, 10: 135-151 (2009).
Morrissy et al. "Next-generation tag sequencing for cancer gene expression profiling", *Genome Research*, 19: 1825-1835 (2009).
Moss, et al. "The human T cell receptor in health and disease", *Annu. Rev. Immunol.*, 10:71-96 (1992).
Moura, et al. "Alterations on peripheral blood B-cell subpopulations in very early arthritis patients", *Rheumatology* (Oxford), 49(6): 1082-1092 (2010). doi: 10.1093/rheumatology/keq029. Epub Mar. 7, 2010.
Mueller, et al. "Human Treg responses allow sustained recombinant adeno-associated virus-mediated transgene expression", *J Clin Invest.*, 123(12): 5310-8 (2013). doi: 10.1172/JCI70314. Epub Nov. 15, 2013.
Muraro et al. "Molecular tracking of antigen-specific T cell clones in neurological immune-mediated disorders", *Brain*, 126(Pt 1):20-31 (2003).
Muraro, et al. "T cell repertoire following autologous stem cell transplantation for multiple sclerosis", J Clin Invest., 124(3): 1168-72 (2014). doi: 10.1172/JCI71691. Epub Feb. 17, 2014.
Murugan, et al. "Statistical inference of the generation probability of T-cell receptors from sequence repertoires", *PNAS*, 109(40): 16161-16166 (2012). doi: 10.1073/pnas.1212755109. Epub Sep. 17, 2012.
Naito, et al. "CD8+ T cells infiltrated within cancer cell nests as a prognostic factor in human colorectal cancer", *Cancer Research*, 58(16): 3491-3494 (1998).
Nakano, et al. "Single-molecule PCR using water-in-oil emulsion", *J Biotechnol.*, 102(2): 117-124, Abstract Only (2003).
Nardi, et al. "Quantitative monitoring by polymerase colony assay of known mutations resistant to ABL kinase inhibitors", *Oncogene*, 27(6):775-782 (2008). Epub Aug. 6, 2007, 1-8.
Navarrete, et al. "Upfront immunization with autologous recombinant idiotype Fab fragment without prior cytoreduction in indolent B-cell lymphoma", *Blood*, 117(5): 1483-1491 (2011). doi: 10.1182/blood-2010-06-292342. Epub Nov. 2, 2010.
Neale, et al. "Comparative analysis of flow cytometry and polymerase chain reaction for the detection of minimal residual disease in childhood acute lymphoblastic leukemia", *Leukemia*, 18(5):934-938 (2004).
Needleman and Wunsch. "A general method applicable to the search for similarities in the amino acid sequence of two proteins", *J Mol Biol.*, 48(3): 443-453 (1970).
Neller, et al. "High frequency of herpesvirus-specific clonotypes in the human T cell repertoire can remain stable over decades with minimal turnover", J Virol., 87(1): 697-700 (2013). doi: 10.1128/Nl.02180-12. Epub Oct. 17, 2012.
Nelson. "CD20+ B cells: the other tumor-infiltrating lymphocytes", *The Journal of Immunology*, 185(9): 4977-4982 (2010). doi: 10.4049/jimmunol.1001323.
Newman, et al. "Identification of an antigen-specific B cell population", *J Immunol Methods*, 272(1-2): 177-187, Abstract Only (2003).
Nguyen et al. "Identification of errors introduced during high throughput sequencing of the T cell receptor repertoire" *BMC Genomics*, 12: 106, 13 pages (2011).
Nicot, N. et al. "Housekeeping gene selection for real-time RT-PCR normalization in potato during biotic and abiotic stress", *Journal of Experimental Botany*, 56(421):2907-2914 (2005).
Nie, et al. "Optical detection of single molecules", *Annu. Rev. Biophys. Biomol. Struct.*, 26: 567-596 (1997).
Nielsen, et al. "Peptide nucleic acid (PNA). A DNA mimic with a pseudopeptide backbone", *Chem. Soc. Rev.*, 26:73-78, Abstract Only (1997).
Nolan, T. et al. "Quantification of mRNA using real-time RT-PCR", *Nature Protocols*, 1(3):1559-1582 (2006).
Nosho, et al. "Tumour-infiltrating T-cell subsets, molecular changes in colorectal cancer, and prognosis: cohort study and literature review", *J Pathol.*, 222(4): 350-366 (2010). doi: 10.1002/path.2774.
Novak, et al. "Single Cell Multiplex Gene Detection and Sequencing Using Microfluidically-Generated Agarose Emulsions", *Angew Chem Int Ed Engl.*, 50(2): 390-395, with supplemental materials (2011).
Nucleis product webpage, "Exonuclease I-Shrimp alkaline phosphatase clean up of PCR products," (Published on webpage 2013) Downloaded Dec. 15, 2015.
Oble, et al. "Focus on TILs: prognostic significance of tumor infiltrating lymphocytes in human melanoma", *Cancer Immunity*, 9: 3, 20 pages (2009).
O'Brian et al., "Sorting out mix-ups. The provenance of tissue sections may be confirmed by PCR using microsatellite markers", Am. J. Clin. Pathol., 106(6): 758-764 (1996). (Abstract Only).
Oelke, et al. "Ex vivo induction and expansion of antigen-specific cytotoxic T cells by HLA-Ig-coated artificial antigen-presenting cells", *Nat Med.*, 9(5): 619-624 (2003). Epub Apr. 21, 2003.
Ogle, et al. "Direct measurement of lymphocyte receptor diversity", *Nucleic Acids Research*, 31(22):e139, 6 pages (2003).
Ohtani. "Focus on TILs: prognostic significance of tumor infiltrating lymphocytes in human colorectal cancer", *Cancer Immunity*, 7: 4, 9 pages (2007).
Okajima et al. "Analysis of T cell receptor Vβ diversity in peripheral CD4+ and CD8+ T lymphocytes in patients with autoimmune thyroid diseases", *Clinical & Experimental Immunology*, 155:166-172 (2008).
Okello et al. "Comparison of methods in the recovery of nucleic acids from archival formalin-fixed paraffin-embedded autopsy tissues", *Anal Biochem.*, 400(1): 110-117 (2010). doi: 10.1016/j.ab. 2010.01.014. Epub Jan. 15, 2010.
Ottensmeier, et al. "Analysis of VH genes in follicular and diffuse lymphoma shows ongoing somatic mutation and multiple isotype transcripts in early disease with changes during disease progression", *Blood*, 91(11): 4292-4299 (1998).
Packer and Muraro. "Optimized clonotypic analysis of T-cell receptor repertoire in immune reconstitution", *Experimental Hematology*, 35(3):516-521 (2007).
Pagès, Franck. Tumor-associated immune parameters for personalized patient care. Sci Transl Med., 5(214):214fs42 (2013). doi: 10.1126/scitranslmed.3007942.

(56) References Cited

OTHER PUBLICATIONS

Palmowski, et al. "The use of HLA class I tetramers to design a vaccination strategy for melanoma patients", *Immunol Rev.*, 188: 155-163 (2002) (Abstract Only).
Palomaki, et al. "DNA sequencing of maternal plasma reliably identifies trisomy 18 and trisomy 13 as well as Down syndrome: an international collaborative study", *Genet Med.*, 14(3): 296-305 (2012). doi: 10.1038/gim.2011.73. Epub Feb. 2, 2012.
Pan, et al. "A new FACS approach isolates hESC derived endoderm using transcription factors", *PLoS One*, 6(3): e17536, 9 pages (2011). doi: 10.1371/journal.pone.0017536.
Panzer-Grümayer et al. "Immunogenotype changes prevail in relapses of young children with TEL-AML1-positive acute lymphoblastic leukemia and derive mainly from clonal selection", *Clin Cancer Research*, 11(21):7720-7727 (2005).
Parameswaran et al. "A pyrosequencing-tailored nucleotide barcode design unveils opportunities for large-scale sample multiplexing", *Nucleic Acids Research*, 35(19): e130, 9 pages (2007).
Parmigiani, et al. "Design and analysis issues in genome-wide somatic mutation studies of cancer", *Genomics*, 93(1): 17-21 (2009). doi: 10.1016/j.ygeno.2008.07.005. Epub Aug. 23, 2008.
Pasqual et al. "Quantitative and qualitative changes in V-J alpha rearrangements during mouse thymocytes differentiation: implication for a limited T cell receptor alpha chain repertoire", *Journal of Experimental Medicine*, 196(9): 1163-1173 (2002). XP002322207 ISSN: 0022-1007.
Paszkiewicz et al, "De novo assembly of short sequence reads," Briefings in Bioinformatics, 11(5): 457-472 (2010).
Payne, et al. "Peripheral blood mononuclear cells of patients with breast cancer can be reprogrammed to enhance anti-HER-2/neu reactivity and overcome myeloid-derived suppressor cells", Breast Cancer Res Treat., 142(1):45-57 (2013). doi: 10.1007/s10549-013-2733-5. Epub Oct. 25, 2013.
Peet. "The Measurement of Species Diversity", *Annual Review of Ecology and Systematics*, 5: 285-307, Abstract Only (1974).
Petrosino, et al. "Metagenomic pyrosequencing and microbial identification", *Clin Chem.*, 55(5): 856-866 (2009). doi: 10.1373/clinchem.2008.107565. Epub Mar. 5, 2009.
PCT/US2009/006053, International Search Report dated Jun. 15, 2010, 6 pages.
PCT/US2009/006053, Written Opinion dated Jun. 15, 2010, 4 pages.
PCT/US2009/006053, International Preliminary Report on Patentability dated May 10, 2011, 5 pages.
PCT/US2010/021264, International Search Report and Written Opinion mailed Apr. 14, 2010, 7 pages.
PCT/US2010/037477, International Search Report and Written Opinion mailed Sep. 24, 2010, 10 pages.
PCT/US2010/037477, International Preliminary Report on Patentability dated Jan. 4, 2012, 7 pages.
PCT/US2011/000791, International Search Report and Written Opinion dated Sep. 22, 2011, 13 pages.
PCT/US2011/000791, International Preliminary Report on Patentability dated Nov. 6, 2012, 10 pages.
PCT/US2011/000792, International Search Report and Written Opinion dated Oct. 19, 2011, 12 pages.
PCT/US2011/026373, International Search Report and Written Opinion mailed Oct. 20, 2011, 17 Pages.
PCT/US2011/026373, International Preliminary Report on Patentability dated Aug. 28, 2012, 11 pages.
PCT/US2011/049012, International Search Report and Written Opinion mailed Apr. 10, 2012, 9 pages.
PCT/US2011/049012, International Preliminary Report on Patentability dated Feb. 26, 2013, 5 pages.
PCT/US2013/040221, International Search Report and Written Opinion mailed Sep. 23, 2013, 15 pages.
PCT/US2013/040221, International Preliminary Report on Patentability dated Apr. 24, 2014, 41 pages.
PCT/US2013/045994, International Search Report and Written Opinion mailed Oct. 25, 2013, 15 pages.
Pekin, D. et al. "Quantitative and sensitive detection of rare mutations using droplet-based microfluidics", *Lab Chip*, 11(3): 2156-2166 (2011).
Pels et al. "Clonal evolution as pathogenetic mechanism in relapse of primary CNS lymphoma", *Neurology*, 63(1):167-169 (2004).
Perkel, J. "Overcoming the Challenges of Multiplex PCR", *Biocompare Editorial Article*, Oct. 23, 2012, 6 Pages, can be retrieved at URL:http://www.biocompare.com/Editorial-Articles/117895-Multiplex-PCR/>.
Pira et al. "Human naive CD4 T-cell clones specific for HIV envelope persist for years in vivo in the absence of antigenic challenge", *J Acquir Immune Defic Syndr.*, 40(2):132-139 (2005).
Plasilova et al. "Application of the Molecular Analysis of the T-Cell Receptor Repertoire in the Study of Immune-Mediated Hematologic Diseases", *Hematology*, 8(3): 173-181 (2003).
Pohl, G. and Shih. "Principle and applications of digital PCR", *Expert Rev. Mol. Diagn.*, 4(1):41-47 (2004).
Polstra, et al. "Development of real-time NASBA assays with molecular beacon detection to quantify mRNA coding for HHV-8 lytic and latent genes", *BMC Infect Dis.*, 2: 18 (2002). Epub Sep. 4, 2002.
Pop and Salzberg. "Bioinformatics challenges of new sequencing technology", *NIH, Trends Genet.*, 24(3): 142-149 (2008).
Pourmand, et al. "Direct electrical detection of DNA synthesis", *PNAS*, 103(17): 6466-6470 (2006). Epub Apr. 13, 2006.
Polz and Cavanaugh. "Bias in Template-to-Product Ratios in Multitemplate PCR", *Applied and Environmental Microbiology*, 64(10): 3724-3730 (1998).
Porter, et al. "Chimeric antigen receptor-modified T cells in chronic lymphoid leukemia", N Engl J Med., 365(8):725-33 (2011). doi: 10.1056/NEJMoa1103849. Epub Aug. 10, 2011.
Prabakaran et al. "454 antibody sequencing—error characterization and correction", *BMC Research Notes*, 4: 404 (2011).
Puisieux, I. et al., "Oligoclonality of Tumor-Infiltrating Lymphocytes from Human Melanomas," The Journal of Immunology, 153:2807-2818 (1994).
Putnam, et al. "Clinical grade manufacturing of human alloantigen-reactive regulatory T cells for use in transplantation", Am J Transplant., 13(11): 3010-20 (2013). doi: 10.1111/ajt.12433. Epub Sep. 18, 2013.
Qiu et al. "DNA sequence-based "bar codes" for tracking the origins of expressed sequence tags from a maize cDNA library constructed using multiple mRNA sources", *Plant Physiology*, 133(2): 475-481 (2003).
Qu et al. "Efficient frequency-based de novo short-read clustering for error trimming in next-generation sequencing", *Genome Research*, 19: 1309-1315 (2009).
Quick. SOLiD System—a next-gen DNA sequencing platform announced, Gizmag online magazine, http://www.mizmag.com/go/8248, pp. 1-5, Oct. 2007.
Quince et al. "Removing Noise From Pyrosequenced Amplicons", *BMC Informatics*, 12: 38 (2011).
Ramesh, et al. "Clonal and constricted T cell repertoire in Common Variable Immune Deficiency", Clin Immunol., pii: S1521-6616(15)00004-2 (2015). doi: 10.1016/j.clim.2015.01.002. [Epub ahead of print].
Ramsden, et al. "V(D)J recombination: Born to be wild", *Semin Cancer Biol.*, 20(4): 254-260 (2010). doi: 10.1016/j.semcancer.2010.06.002. Epub Jul. 1, 2010.
Rasmussen, T. et al. "Quantitation of minimal residual disease in multiple myeloma using an allele-specific real-time PCR assay", *Experimental Hematology*, 28:1039-1045 (2000).
Ray, et al. "Single cell multiplex PCR amplification of five dystrophin gene exons combined with gender determination", *Molecular Human Reproduction*, 7(5): 489-494 (2001).
Reddy, et al. "Monoclonal antibodies isolated without screening by analyzing the variable-gene repertoire of plasma cells", *Nature Biotechnology*, 28(9): 965-969 (2010). doi: 10.1038/nbt.1673. Epub Aug. 29, 2010.
Reddy and Georgiou. "Systems analysis of adaptive immunity by utilization of high-throughput technologies", *Current Opinion in Biotechnology*, 22(4): 584-589 (2011).

(56) References Cited

OTHER PUBLICATIONS

Reinartz et al. "Massively parallel signature sequencing (MPSS) as a tool for in-depth quantitative gene expression profiling in all organisms", *Brief Funct Genomic Proteomic.*, 1(1):95-104 (2002).
Reischl and Kochanowski. "Quantitative PCR. A Survey of the Present Technology", *Molecular Biotechnology*, 3:55-71 (1995).
Ria, et al. "Collagen-specific T-cell repertoire in blood and synovial fluid varies with disease activity in early rheumatoid arthritis", *Arthritis Res Ther.*, 10(6):R135, 18 pages (2008). Epub Nov. 17, 2008.
Rickinson and Moss. "Human cytotoxic T lymphocyte responses to Epstein-Barr virus infection", *Annu Rev Immunol.*, 15:405-431 (1997).
Rieder, et al. "A normalization procedure for removal of residual multiplex PCR amplification bias from ultra-deep sequencing of the TCR repertoire", (Program #530W). Presented at the 62nd Annual Meeting of the American Society of Human Genetics, Nov. 7, 2012 in San Francisco, California. 2 pages.
Rieder, et al. "A normalization procedure for removal of residual multiplex PCR amplification bias from ultra-deep sequencing of the TCR repertoire", Presented at the Annual Meeting of the American Society of Hematology 2012 in Atlanta, Georgia Dec. 8-11, 2012. Poster. 1 page.
Risitano et al. "In-vivo dominant immune responses in aplastic anaemia: molecular tracking of putatively pathogenetic T-cell clones by TCRβ-CDR3 sequencing", *Lancet*, 364:355-364 (2004).
Robert, et al. "CTLA4 blockade broadens the peripheral T-cell receptor repertoire", Clin Cancer Res., 20(9):2424-32 (2014). doi: 10.1158/1078-0432.CCR-13-2648. Epub Feb. 28, 2014.
Robins, H. et al. "Ultra-sensitive detection of rare T cell clones", *Journal of Immunological Methods*, 375(1-2): 14-19 (2012).
Robins, et al. "CD4+ and CD8+ T cell β antigen receptors have different and predictable V and J gene usage and CDR3 lengths", *J. Immunol.*, 188: 115.10, Abstract (2012).
Robins et al. "Detecting and monitoring lymphoma with high-throughput sequencing" *Oncotarget*, 2:287-288 (2011).
Robins, H. et al. "Digital Genomic Quantification of Tumor Infiltrating Lymphocytes", *Science Translational Medicine*, 5:214ra169, 19 pages, Supplementary Materials (2013).
Robins, H. et al. "Comprehensive assessment of T-cell receptor β-chain diversity in αβ T cells", *Blood*, 114(19):4099-4107 (and Supplemental Materials) (2009).
Robins, et al. "Effects of aging on the human adaptive immune system revealed by high-throughput DNA sequencing of T cell receptors", *J Immunol.*, 188: 47.16, Abstract (2012).
Robins, et al. "High-throughput sequencing of T-cell receptors." Sep. 2010. Poster. 1 page.
Robins, et al. "Immune profiling with high-throughput sequencing." Presented for the ASHI 2011 conference. Oct. 2011. Poster. 1 page.
Robins, et al. "Immunosequencing: applications of immune repertoire deep sequencing", *Curr Opin Immunol.*, 25(5): 646-652 (2013). doi: 10.1016/j.coi.2013.09.017. Epub Oct. 16, 2013.
Robins, H. et al. "Overlap and Effective Size of the Human CD8+ T Cell Receptor Repertoire", *Science Transitional Medicine*, 2(47, 47ra64):17 pages, Supplemental Materials (2010).
Robins, et al. "Overlap of the human CD8+ T cell receptor repertoire." Oct. 2010. Poster. 1 page.
Robins. "Overlap and effective size of the human CD8+ T cell repertoire", Keystone Symposia held Oct. 27, 2010 to Nov. 1, 2010. Immunological Mechanisms of Vaccination (Abstract). Available online Sep. 27, 2010, 1 page.
Robins, H. et al. "The Computational Detection of Functional Nucleotide Sequence Motifs in the Coding Regions of Organisms", *Exp Biol Med*, 233(6): 665-673 (2008).
Rock, E.P. et al. "CDR3 Length in Antigen-specific Immune Receptors", *J. Exp. Med.*, 179:323-328 (1994).
Ronaghi, et al. "A sequencing method based on real-time pyrophosphate", *Science*, 281(5375): 363, 365, 5 pages (1998).

Rosenberg, S.A. et al. "New Approach to the Adoptive Immunotherapy of Cancer with Tumor-Infiltrating Lymphocytes", *Science*, 233(4770): 1318-1321 (1986).
Rosenquist, et al. "Clonal evolution as judged by immunoglobulin heavy chain gene rearrangements in relapsing precursor-B acute lymphoblastic leukemia", *Eur J Haematol.*, 63(3):171-179 (1999).
Roshal, M. et al. "Immaturity Associated Antigens Are Lost During Induction for T Cell Lymphoblastic Leukemia: Implications for Minimal Residual Disease Detection", *Cytometry Part B (Clinical Cytometry)*, 78:139-146 (2010).
Rothberg, et al. "An integrated semiconductor device enabling non-optical genome sequencing", *Nature*, 475(7356): 348-352 (2011). doi: 10.1038/nature10242.
Rothberg et al. "The development and impact of 454 sequencing", *Nature Biotechnology*, 26(10): 1117-1124 (2008).
Rougemont, et al. "Probabilistic base calling of Solexa sequencing data", *BMC Bioinformatics*, 9:431, 12 pages (2008).
Rozen, S. et al. "Primer3 on the WWW for General Users and for Biologist Programmers", *Methods in Molecular Biology, Bioinformatics Methods and Protocols*, 132:365-386 (2000).
Ryan et al. "Clonal evolution of lymphoblastoid cell lines", *Laboratory Investigation*, 86(11):1193-1200 (2006). Epub Oct. 2, 2006.
Saada, R. et al. "Models for antigen receptor gene rearrangement: CDR3 length", *Immunology and Cell Biology*, 85:323-332 (2007).
Salzberg. "Mind the gaps", *Nature Methods*, 7(2): 105-106 (2010).
Sanchez-Freire et al. "Microfluidic single-cell real-time PCR for comparative analysis of gene expression patterns", *Nature Protocols*, 7(5): 829-838 (2012).
Sandberg et al. "BIOMED-2 Multiplex Immunoglobulin/T-Cell Receptor Polymerase Chain Reaction Protocols Can Reliably Replace Southern Blot Analysis in Routine Clonality Diagnostics", *J. Molecular Diagnostics*, 7(4): 495-503 (2005).
Sandberg, et al. "Capturing whole-genome characteristics in short sequences using a naïve Bayesian classifier", *Genome Res.*, 11(8): 1404-9 (2001).
Santalucia, Jr., J. "Physical Principles and Visual-OMP Software for Optimal PCR Design," *Methods in Molecular Biology*, 402(PCR Primer Design):3-33, 40 pages (2007).
Santamaria, P. et al. "Beta-Cell-Cytotoxic CD8 T Cells from Nonobese Diabetic Mice Use Highly Homologous T Cell Receptor a-Chain CDR3 Sequences", *The Journal of Immunology*, 154(5):2494-2503 (1995).
Sartorius Stedim Biotech product brochure, "Primer removal after a PCR reaction with Vivacon® 2", (2010).
Sato et al. "Intraepithelial CD8+ tumor-infiltrating lymphocytes and a high CD8+/regulatory T cell ratio are associated with favorable prognosis in ovarian cancer", *PNAS*, 102(51): 18538-18543 (2005). Epub Dec. 12, 2005.
Satoh et al. "Pretreatment with restriction enzyme or bovine serum albumin for effective PCR amplification of Epstein-Barr virus DNA in DNA extracted from paraffin-embedded gastric carcinoma tissue", *J Clin Microbiol.*, 36(11): 3423-3425 (1998).
Schaufelberger et al. "An uneven expression of T cell receptor V genes in the arterial wall and peripheral blood in giant cell arteritis", *Inflammation*, 31(6):372-383 (2008).
Schlissel, M.S. et al. "Leukemia and lymphoma: a cost of doing business for adaptive immunity", *Genes Dev.*, 20(12): 1539-1544 (2006).
Schloss, PD et al. Reducing the Effects of PCR Amplification and Sequencing Artifacts on 16S Rrna-Based Studies. PLoS One. Dec. 14, 2011, vol. 6, No. 12; e27310; DOI: 1 0.1371/journal.pone. 002731 0.
Schmitt et al. "Detection of ultra-rare mutations by next-generation sequencing," *PNAS*, 109(36): 14508-14513 and Supporting Information, 9 pages (2012).
Schøller et al. "Analysis of T cell receptor αβ variability in lymphocytes infiltrating melanoma primary tumours and metastatic lesions", *Cancer Immunol Immunother.* 39(4):239-248 (1994).
Schrappe, M. et al. "Late MRD response determines relapse risk overall and in subsets of childhood T-cell ALL: results of the AIEOP-BFM-ALL 2000 study", *Blood*, 118(8): 2077-2084 (2011).

(56) References Cited

OTHER PUBLICATIONS

Schreiber et al. "Cancer immunoediting: integrating immunity's roles in cancer suppression and promotion", *Science*, 331(6024): 1565-1570 (2011). doi: 10.1126/science.1203486.
Schwab et al. "CD8+ T-cell clones dominate brain infiltrates in Rasmussen encephalitis and persist in the periphery", *Brain*, 132:1236-1246 (2009).
Schweiger et al. "Genome-wide massively parallel sequencing of formaldehyde fixed-paraffin embedded (FFPE) tumor tissues for copy-number- and mutation-analysis", *PLoS One*, 4(5): e5548, 7 pages (2009). doi: 10.1371/journal.pone.0005548. Epub May 14, 2009.
Sebastian, E. et al., "Molecular Characterization of immunoglobulin gene rearrangements in diffuse large B-cell lymphoma", *Am. J. Pathol.*, 181: 1879-1888, Abstract (2012). (Epub: Sep. 28, 2012).
Sehouli et al. "Epigenetic quantification of tumor-infiltrating T-lymphocytes" *Epigenetics*, 6(2): 236-246 (2011). Epub Feb. 1, 2011.
Seitz, et al. "Reconstitution of paired T cell receptor α- and β-chains from microdissected single cells of human inflammatory tissues", *PNAS*, 103: 12057-12062 (2006).
Seo, et al. "Four-color DNA sequencing by synthesis on a chip using photocleavable fluorescent nucleotides", *PNAS*, 102(17): 5926-5931 (2005). Epub Apr. 13, 2005.
Sequenta and iRepertoire Join Forces on Blood Cancer Testing. Business Wire. Aug. 8, 2013. http://www.businesswire.com/news/home/20130808005363/en/SequentaiRepertoire-Join-Forces-Blo . . . #.VGTT9WdOyUk. 2 pages.
Sfanos et al. "Human Prostate-Infiltrating CD8+ T Lymphocytes are Oligoclonal and PD-1+", *The Prostate*, 69(15): 1694-1703 (2009).
Sfanos et al. "Phenotypic analysis of prostate-infiltrating lymphocytes reveals TH17 and Treg skewing", *Clinical Cancer Research*, 14(11):3254-3261 (2008). doi: 10.1158/1078-0432.CCR-07-5164.
Shen et al. "Comparing platforms for *C. elegans* mutant identification using high-throughput whole-genome sequencing", *PLoS One*, 3(12):e4012, 6 pages (2008).
Shendure, et al. "Accurate multiplex polony sequencing of an evolved bacterial genome", *Science*, 309(5741): 1728-1732, Abstract Only (2005). Epub Aug. 4, 2005.
Shendure, et al. "Advanced sequencing technologies: methods and goals", *Nat Rev Genet.*, 5(5): 335-344 (2004).
Shendure and Ji. "Next-generation DNA sequencing", *Nature Biotechnology*, 26(10):1135-1145 (2008).
Sherwood, A. et al. "Deep Sequencing of the Human TCRγ and TCRβ Repertoires Suggests that TCR β Rearranges After αβ and γδ T Cell Commitment", Science Translational Medicine, *Sci. Transl. Med.*, 3(90): 1-7 (2011).
Sherwood, et al. "New Technologies for Measurements of Tumor Infiltrating Lymphocytes", Presented Nov. 7, 2012 Moscone Center, Exhibit Halls ABC.
Sherwood, et al. "Tumor-infiltrating lymphocytes in colorectal tumors display a diversity of T cell receptor sequences that differ from the T cells in adjacent mucosal tissue", Cancer Immunol Immunother., 62(9):1453-61 (2013). doi: 10.1007/s00262-013-1446-2. Epub Jun. 16, 2013.
Shino, et al. "Usefulness of immune monitoring in lung transplantation using adenosine triphosphate production in activated lymphocytes", *The Journal of Heart and Lung Transplant*, 31: 996-1002 (2012).
Shiroguchi et al. "Digital RNA sequencing minimizes sequence-dependent bias and amplification noise with optimized single-molecule barcodes", *PNAS*, 109(4): 1347-1352 (2012).
Shoemaker et al. "Quantitative phenotypic analysis of yeast deletion mutants using a highly parallel molecular bar-coding strategy," *Nature Genetics*, 14(4): 450-456 (1996).
Shumaker, et al. "Mutation detection by solid phase primer extension", *Hum Mutat.*, 7(4): 346-354, Abstract Only (1996).
Sia, et al. "Microfluidic devices fabricated in poly(dimethylsiloxane) for biological studies", *Electrophoresis*, 24(21): 3563-3576, Abstract Only (2003).

Silver, N. et al. "Selection of housekeeping genes for gene expression studies in human reticulocytes using real-time PCR", *BMC Molecular Biology*, 7(33):1-9 (2006).
Sims, et al. "Fluorogenic DNA sequencing in PDMS microreactors", *Nat Methods*, 8(7): 575-580 (2011). doi: 10.1038/nmeth.1629.
Sims, et al. "MHC-peptide tetramers for the analysis of antigen-specific T cells", *Expert Rev Vaccines*, 9(7): 765-774 (2010). doi: 10.1586/erv.10.66.
Sing et al. "A molecular comparison of T Lymphocyte populations infiltrating the liver and circulating in the blood of patients with chronic hepatitis B: evidence for antigen-driven selection of a public complementarity-determining region 3 (CDR3) motif", *Hepatology*, 33(5):1288-1298 (2001).
Sint, D., et al. "Advances in multiplex PCR: balancing primer efficiencies and improving detection success", *Methods in Ecology and Evolution*, 3(5): 898-905 (2012).
Skulina et al. "Multiple Sclerosis: Brain-infiltrating CD8+ T cells persist as clonal expansions in the cerebrospinal fluid and blood", *PNAS*, 101(8):2428-2433 (2004).
Slightom, J.L. et al. "*Homo sapiens* germline beta T-cell receptor locus", NCBI Accession No. L36092 NCBI, 254 pages (2009) Retrieved from the Internet: <URL:http://www.ncbi.nlm.nih.gov/nuccore/L36092>.
Smith, et al. "Comparison of biosequences", *Advances in Applied Mathematics*, 2: 482-489 (1981).
Smith et al. "Rapid generation of fully human monoclonal antibodies specific to a vaccinating antigen", *Nature Protocols*, 4(3): 372-384 and CORRIGENDA (2009).
Smith et al. "Rapid whole-genome mutational profiling using next-generation sequencing technologies", *Genome Research*, 18: 1638-1642 (2008).
Smith et al. "Quantitative phenotyping via deep barcode sequencing", *Genome Research*, 19: 1836-1842 (2009).
Smith et al, "Using quality scores and longer reads improves accuracy of Solexa read mapping," BMC Bioinformatics, 9: 128 (2008).
Sobrino, et al. "SNPs in forensic genetics: a review on SNP typing methodologies", *Forensic Sci Int.*, 154(2-3): 181-194, Abstract Only (2005). Epub Jan. 11, 2005.
Spreafico, et al. "A circulating reservoir of pathogenic-like CD4+ T cells shares a genetic and phenotypic signature with the inflamed synovial micro-environment", *Ann Rheum Dis.*, 0: 1-7 (2014). doi: 10.1136/annrheumdis-2014-206226. [Epub ahead of print].
Sramkova, et al. "Detectable minimal residual disease before allogeneic hematopoietic stem cell transplantation predicts extremely poor prognosis in children with acute lymphoblastic leukemia", *Pediatr. Blood Cancer*, 48(1):93-100 (2007).
Srinivasan et al. "Effect of fixatives and tissue processing on the content and integrity of nucleic acids", *Am J Pathol.*, 161(6): 1961-1971 (2002).
Srivastava and Robins. "Palindromic nucleotide analysis in human T cell receptor rearrangements", PLoS One, 7(12):e52250 (2012). doi: 10.1371/journal.pone.0052250. Epub Dec. 21, 2012.
Standard Sequencing Primers, Max Planck Genome Center Cologne, Jan. 15, 2011, 2 pages, downloaded from https://genomecentre.mpipz.mpg.de/SeqOrderDB/export/sequencing-primers.html.
Stanley. Essentials of Immunology & Serology, Delmar, Thomson Learning, Chapter 7, T cells, p. 95 (2002).
Steenbergen, et al. "Distinct ongoing Ig heavy chain rearrangement processes in childhood B-precursor acute lymphoblastic leukemia", *Blood*, 82(2):581-589 (1993).
Steenbergen, et al. "Frequent ongoing T-cell receptor rearrangements in childhood B-precursor acute lymphoblastic leukemia: implications for monitoring minimal residual disease", *Blood*, 86(2): 692-702, Abstract Only (1995).
Stein and Nombela-Arrieta. "Chemokine control of lymphocyte trafficking: a general overview", *Immunology*, 116(10):1-12 (2005).
Steinmetz, O.M. et al. "Chemokines and B cells in renal inflammation and allograft rejection", *Frontiers in Bioscience (Schol. Ed.)*, 1:13-22 (2009).

(56) References Cited

OTHER PUBLICATIONS

Stemmer, et al. "Single-step assembly of a gene and entire plasmid from large numbers of oligodeoxyribonucleotides", *Gene*, 164(1): 49-53 (1995).
Steward et al. "A polymerase chain reaction study of the stability of Ig heavy-chain and T-cell receptor delta gene rearrangements between presentation and relapse of childhood B-lineage acute lymphoblastic leukemia", *Blood*, 83(5):1355-1362 (1994).
Stewart and Schwartz. "Immunoglobulin V regions and the B cell", *Blood*, 83(7): 1717-1730 (1994).
Stickler, et al. "An in vitro human cell-based assay to rank the relative immunogenicity of proteins", *Toxicol Sci.*, 77(2): 280-289 (2004). Epub Dec. 22, 2003.
Stiller et al. "Direct multiplex sequencing (DMPS)—a novel method for targeted high-throughput sequencing of ancient and highly degraded DNA", *Genome Research*, 19: 1843-849 (2009).
Straten, Per thor, et al. "T-cell clonotypes in cancer", *Journal of Translational Medicine*, 2(1): 11, 10 pages (2004).
Stratton. "Exploring the genomes of cancer cells: progress and promise", *Science*, 331(6024): 1553-1558 (2011). doi: 10.1126/science.1204040.
Striebich, et al. "Selective Accumulation of Related CD41 T Cell Clones in the Synovial Fluid of Patients with Rheumatoid Arthritis", *J Immunol.*, 161(8): 4428-436 (1998).
Struyk et al. "T cell receptors in rheumatoid arthritis", *Arthritis & Rheumatism*, 38(5):577-589 (1995).
Sumida et al. "T cell receptor repertoire of infiltrating T cells in lips of Sjögren's syndrome patients", *J Clin Invest.*, 89:681-685 (1992).
Sumida et al. "T cell receptor Vα repertoire of infiltrating T cells in labial salivary glands from patients with Sjögren's syndrome", *J Rheumatol.*, 21:1655-1661 (1994).
Swarup and Rajeswari. "Circulating (cell-free) nucleic acids—a promising, non-invasive tool for early detection of several human diseases", *FEBS Letters*, 581(5): 795-799 (2007). Epub Feb. 2, 2007.
Szczepanski et al. "Comparative analysis of Ig and TCR gene rearrangements at diagnosis and at relapse of childhood precursor-B-ALL provides improved strategies for selection of stable PCR targets for monitoring of minimal residual disease", *Blood*, 99(7):2315-2323 (2002).
Szczepanski, T. et al. "Minimal residual disease in leukemia patients", *Lancet Oncology*, 2:409-417 (2001).
Szczepanski et al. "Why and how to quantify minimal residual disease in acute lymphoblastic leukemia?", *Leukemia*, 21(4):622-626 (2007). Epub Feb. 15, 2007.
Tackenberg et al. "Clonal expansions of CD4+ β helper T cells in autoimmune myasthenia gravis", *European Journal of Immunology*, 37(3):849-863 (2007).
Tajiri et al. "Cell-microarray analysis of antigen-specific B-cells: single cell analysis of antigen receptor expression and specificity", *Cytometry Part A*, 71A: 961-967 (2007).
Takamatsu, et al., "A comparison between next-generation sequencing and ASO-qPCR for minimal residual disease detection in multiple myeloma", *J. Clin. Oncol.*, 31(Supplement 1): Abstract 8601 (Conference Abstract), Entire Abstract (2013).
Tanaka et al. "Single-Cell Analysis of T-Cell Receptor Repertoire of HTLV-1 Tax-Specific Cytotoxic T Cells in Allogeneic Transplant Recipients with Adult T-Cell Leukemia/Lymphoma", *Cancer Research*, 70: 6181-6192 (2010).
Taubenheim et al. "High Rate of Antibody Secretion Is not Integral to Plasma Cell Differentiation as Revealed by XBP-1 Deficiency", *The Journal of Immunology*, 189: 3328-3338 (2012).
Tautz, et al. "Cryptic simplicity in DNA is a major source of genetic variation", *Nature*, 322(6080): 652-656 (1986).
Tawfik, et al. "Man-made cell-like compartments for molecular evolution", *Nat Biotechnol.*, 16(7): 652-656, Abstract Only (1998).
ten Bosch et al. "Keeping Up With the Next Generation Massively Parallel Sequencing in Clinical Diagnostics", *Journal of Molecular Diagnostics*, 10(6): 484-492 (2008).
Tewhey, R. et al. "Corrigendum: Microdroplet-based PCR enrichment for large-scale targeted sequencing", *Nature Biotechnology*, 28(2):178, 1 page (2010).
Tewhey, R. et al. "Microdroplet-based PCR enrichment for large-scale targeted sequencing," *Nature Biotechnology*, 27(11):1025-1031 (2009).
Thiel, et al. "Antigen-specific cytometry—new tools arrived!", *Clin Immunol.*, 111(2): 155-161, Abstract Only (2004).
Thornhill et al. "A comparison of different lysis buffers to assess allele dropout from single cells for preimplantation genetic diagnosis", *Prenatal Diagnosis*, 21:490-497 (2001).
Tokimitsu et al. "Single lymphocyte analysis with a microwell array chip", *Cytometry Part A*, 71A:1003-1010 (2007).
Toriello et al. "Integrated microfluidic bioprocessor for single-cell gene expression analysis", *PNAS*, 105(51): 20173-20178 (2008).
Triebel, F. et al. "A Unique V-J-C-Rearranged Gene Encodes A y Protein Expressed on the Majority of CD3+ T Cell Receptor -a/fr Circulating Lymphocytes", *J. Exp. Med.*, 167:694-699 (1988).
Tsai et al. "Discovery of rare mutations in populations: TILLING by sequencing", Plant Physiology, 156(3): 1257-1268 (and Supplemental Data) (2011).
Tsankova, et al. "Peripheral T-cell lymphoma emerging in a patient with aggressive polymyositis: molecular evidence for neoplastic transformation of an oligo clonal T-cell infiltrate", Acta Neuropathol., 126(4):595-601 (2013). doi: 10.1007/s00401-013-1164-z. Epub Aug. 13, 2013.
Tschumper, et al. "Comprehensive assessment of potential multiple myeloma immunoglobulin heavy chain V-D-J intraclonal variation using massively parallel pyrosequencing", *Oncotarget*, 3(4): 502-513 (2012).
Turcotte and Rosenberg. "Immunotherapy for metastatic solid cancers", *Adv Surg.*, 45: 341-360 (2011).
UK combined search and examination report dated Mar. 20, 2013 for GB 1300533.5.
UK Combined Search Report and Office action dated Jun. 29, 2012 for UK application No. GB1209668.1.
UK Combined Search Report and Office action dated May 27, 2011 for UK application No. GB1105068.9.
UK Search Report and office action dated Jan. 13, 2012 for UK application No. GB1120209.0.
UK Search Report and office action dated Jul. 7, 2010 for UK application No. GB1009641.0.
Umibe et al. "Clonal expansion of T cells infiltrating in the airways of non-atopic asthmatics", *Clinical & Experimental Immunology*, 119(3):390-397 (2000).
Unrau and Deugau. "Non-cloning amplification of specific DNA fragments from whole genomic DNA digests using DNA 'indexers'", *Gene.*, 145(2): 163-169, Abstract Only, 2 pages (1994).
Uppaluri et al. "Focus on TILs: prognostic significance of tumor infiltrating lymphocytes in head and neck cancers", *Cancer Immunity*, 8:16, 10 pages (2008).
Urban, et al. "A systematic and quantitative analysis of PCR template contamination", *J Forensic Sci.*, 45(6): 1307-1311 (2000).
Urquhart, et al. "Rate-controlled delivery systems in drug and hormone research", *Annu Rev Pharmacol Toxicol.*, 24: 199-236, Abstract Only (1984).
Van Der Velden, V.H.J., et al. "Analysis of minimal residual disease by Ig/TCR gene rearrangements: guidelines for interpretation of real-time quantitative PCR data," *Leukemia*, 21:604-611 (2007).
Van Der Velden, V.H.J., et al. "Detection of minimal residual disease in hematologic malignancies by realtime quantitative PCR: principles, approaches, and laboratory aspects," *Leukemia*, 17:1013-1034 (2003).
Van Der Velden, V.H.J., et al. "Optimization of PCR-based minimal residual disease diagnostics for childhood acute lymphoblastic leukemia in a multi-center setting," *Leukemia*, 21:706-713 (2007).
Van Der Velden, V.H.J., et al. "Real-time quantitative PCR for detection of minimal residual disease before allogeneic stem cell transplantation predicts outcome in children with acute lymphoblastic leukemia", *Leukemia*, 15:1485-1487 (2001).
Van Dongen, J.J.M. et al. "Design and standardization of PCR primers and protocols for detection of clonal immunoglobulin and I-cell receptor gene recombinations in suspect lymphoprolifera-

(56) References Cited

OTHER PUBLICATIONS tions: Report of the BIOMED-2 Concerted Action BMHC-CT98-3936", *Leukemia*, 17:2257-2317 (2003).
Van Dongen, J.J.M. et al. "Prognostic value of minimal residual disease in acute lymphoblastic leukaemia in childhood", *The Lancet*, 352:1731-1738 (1998).
Vanderborght, et al. "Dynamic T cell receptor clonotype changes in synovial tissue of patients with early rheumatoid arthritis: effects of treatment with cyclosporin A (Neoral)", *J Rheumatol.*, 29(3): 416-426 (2002).
Varley and Mitra. "Nested patch PCR enables highly multiplexed mutation discovery in candidate genes", *Genome Research*, 18:1844-1850 (2008).
Venturi, et al. "A mechanism for TCR sharing between T cell subsets and individuals revealed by pyrosequencing", *J Immunol.*, 186(7): 4285-4294 (2011). doi: 10.4049/jimmunol.1003898. Epub Mar. 7, 2011.
Venturi, V. et al. "TCR β-Chain Sharing in Human CD8+ T Cell Responses to Cytomegalovirus and EBV[1]", *The Journal of Immunology*, 181:7853-7862 (2008).
Venturi, V. et al. "The molecular basis for public T-cell responses?", *Nature Reviews*, 8:231-238 (2008).
Verhagen, O.J.H.M., et al. "Application of germline IGH probes in real-time quantitative PCR for the detection of minimal residual disease in acute lymphoblastic leukemia", *Leukemia*, 14:1426-1435 (2000).
Vester, et al. "LNA (locked nucleic acid): high-affinity targeting of complementary RNA and DNA", *Biochemistry*, 43(42): 13233-13241, Abstract Only (2004).
Vlassov, et al. "Circulating nucleic acids as a potential source for cancer biomarkers", *Curr Mol Med.*, 10(2): 142-165 (2010).
Vogelstein et al. "Cancer genome landscapes", *Science*, 339(6127): 1546-1558 (2013). doi: 10.1126/science.1235122.
Vogelstein and Kinzler. "Digital PCR," *Genetics, PNAS*, 96:9236-9241 (1999).
Wälchli, et al. "A practical approach to T-cell receptor cloning and expression", *PLoS One*, 6(11): e27930, 11 pages (2011). doi: 10.1371/journal.pone.0027930. Epub Nov. 21, 2011.
Wang, et al. "Balanced-PCR amplification allows unbiased identification of genomic copy changes in minute cell and tissue samples", *Nucleic Acids Research*, 32(9): e76, 10 pages (2004).
Wang, et al. "High throughput sequencing reveals a complex pattern of dynamic interrelationships among human T cell subsets", *PNAS*, 107(4): 1518-1528 (2010).
Wang, et al. "HIV integration site selection: Analysis by massively parallel pyrosequencing reveals association with epigenetic modifications", *Genome Research*, 17(8): 1186-1194 (2007). Epub Jun. 1, 2007.
Wang et al. "Immunorepertoire analysis by multiplex PCR amplification and high throughput sequencing", Poster-Program 42.6, The 96th Annual Meeting of the America Association of Immunologists, Seattle, USA, May 8-12, 2009, 1 page.
Wang, X. et al. "Quantitative Measurement of Pathogen Specific Human Memory T Cell Repertoire Diversity using a CDR3 B-Specific Microarray", *BMC Genomics*, 8(329): 1-13 (2007).
Ward and Marelli-Berg. "Mechanisms of chemokine and antigen-dependent T-lymphocyte navigation", *Biochem. J.*, 418:13-27 (2009).
Warren et al. "Exhaustive T-cell repertoire sequencing of human peripheral blood samples reveals signatures of antigen selection and a directly measured repertoire size of at least 1 million clonotypes", *Genome Res.*, 21(5): 790-797 (2011). doi: 10.1101/gr.115428.110. Epub Feb. 24, 2011.
Warren et al. "Profiling model T-cell metagenomes with short reads", *Bioinformatics*, 25(4):458-464 (2009).
Weinstein, J.A. et al. "High-Throughput Sequencing of the Zebrafish Antibody Repertoire", *Science*, 324(5928): 807-810 (2009).
Weinstein, J.A. et al. "High-Throughput Sequencing of the Zebrafish Antibody Repertoire", *Science*, 324(5928): 807-810, Supporting/Supplementary Materials (2009).
Weiss et al. "Clonal Rearrangements of T-Cell Receptor Genes in Mycosis Fungoides and Dermatopathic Lymphadenopathy", *The New England Journal of Medicine*, 313(9):539-544 (1985).
Welch and Link. "Genomics of AML: clinical applications of next-generation sequencing", *American Society of Hematology*, 2011: 30-35 (2011). doi: 10.1182/asheducation-2011.1.30.
Wells, et al. "Rapid evolution of peptide and protein binding properties in vitro", *Curr Opin Biotechnol.*, 3(4): 355-362, Abstract Only (1992).
Wells, et al. "Strategies for preimplantation genetic diagnosis of single gene disorders by DNA amplification", *Prenatal Diagnosis*, 18(13):1389-1401 (1998).
Weng, et al. "Minimal residual disease monitoring with high-throughput sequencing of T cell receptors in cutaneous T cell lymphoma", *Sci Transl Med.*, 5(214):214ra171 (2013). doi: 10.1126/scitranslmed.3007420.
Westermann and Pabst. "Distribution of lymphocyte subsets and natural killer cells in the human body", *Clin Investig.*, 70(7): 539-544 (1992).
Wetmur and Chen. "An emulsion polymerase chain reaction-based method for molecular haplotyping", *Methods in Molecular Biology*, 410: 351-361 (1996).
Wetmur and Chen. "Linking emulsion PCR haplotype analysis", chapter 11, Park, D.J. (ed.), *PCR Protocols, Methods in Molecular Biology*, 687: 165-175 (2011).
Wetmur et al. "Molecular haplotyping by linking emulsion PCR: analysis of paraoxonase 1 haplotypes and phenotypes", *Nucleic Acids Research*, 33(8):2615-2619 (2005).
Weusten, et al. "Principles of quantitation of viral loads using nucleic acid sequence-based amplification in combination with homogeneo detection using molecular beacons", Nucleic Acids Res., 30(6): e26, 7 pages (2002).
White et al. "High-throughput microfluidic single-cell RT-qPCR", *PNAS*, 108(34): 13999-14004 (2011).
Whiteford, et al. "Swift: primary data analysis for the Illumina Solexa sequencing platform", *Bioinformatics*, 25(17): 2194-2199 (2009). doi: 10.1093/bioinformatics/btp383. Epub Jun. 23, 2009.
Williams, et al. "Amplification of complex gene libraries by emulsion PCR", *Nat Methods*, 3(7): 545-550 (2006).
Wlodarski et al. "Molecular strategies for detection and quantitation of clonal cytotoxic T-cell responses in aplastic anemia and myelodysplastic syndrome", *Blood*, 108(8):2632-2641 (2006).
Wlodarski et al. "Pathologic clonal cytotoxic T-cell responses: nonrandom nature of the T-cell-receptor restriction in large granular lymphocyte leukemia", *Blood*, 106:2769-2779 (2005).
Wolda. "Similarity Indices, Sample Size and Diversity", *Oecologia* (Berl), 50:296-302 (1981).
Wolfl, et al. "Activation-induced expression of CD137 permits detection, isolation, and expansion of the full repertoire of CD8+ T cells responding to antigen without requiring knowledge of epitope specificities", *Blood*, 110(1): 201-210 (2007). Epub Mar. 19, 2007.
Wolfl, et al. "Use of CD137 to study the full repertoire of CD8+ T cells without the need to know epitope specificities", *Cytometry A.*, 73(11): 1043-1049 (2008). doi: 10.1002/cyto.a.20594.
Wood, B. "9-Color and 10-Color Flow Cytometry in the Clinical Laboratory", *Arch Pathol Lab Med*, 130:680-690 (2006).
Wood, et al. "Using next-generation sequencing for high resolution multiplex analysis of copy number variation from nanogram quantities of DNA from formalin-fixed paraffin-embedded specimens", *Nucleic Acids Research*, 38(14): e151, 11 pages (2010). doi: 10.1093/nar/gkq510. Epub Jun. 4, 2010.
Wrammert et al. "Rapid cloning of high-affinity human monoclonal antibodies against influenza virus", *Nature*, 453: 667-672 (2008).
Wu, et al. "High-throughput sequencing detects minimal residual disease in acute T lymphoblastic leukemia", *Sci Transl Med.*, 4(134):134ra63 (2012). doi: 10.1126/scitranslmed.3003656.
Wu, et al. "High-throughput sequencing of T-cell receptor gene loci for minimal residual disease monitoring in T Lymphoblastic Leukemia", Blood, 118: 2545 (Abstr) (2011).

(56) References Cited

OTHER PUBLICATIONS

Wu, Y-C. et al. "High-throughput immunoglobulin repertoire analysis distinguishes between human IgM memory and switched memory B-cell populations", *Blood Journal*, 116(7): 1070-1078, 22 pages (2010).
Wu et al. "Focused Evolution of HIV-1 Neutralizing Antibodies Revealed by Structures and Deep Sequencing", *Science*, 333: 1593-1602 (2011).
Wu, H.D. et al. "The Lymphocytic Infiltration in Calcific Aortic Stenosis Predominantly Consists of Clonally Expanded T Cells", *The Journal of Immunology*, 178(8): 5329-5339 (2007).
Xiong, et al. "Chemical gene synthesis: strategies, softwares, error corrections, and applications", *FEMS Microbiol Rev.*, 32(3): 522-540 (2008). doi: 10.1111/j.1574-6976.2008.00109.x. Epub Apr. 2, 2008.
Xiong, et al. "Non-polymerase-cycling-assembly-based chemical gene synthesis: strategies, methods, and progress", *Biotechnol Adv.*, 26(2): 121-134, Abstract Only (2008). Epub Nov. 7, 2007.
Xu, W. et al. "A Novel Universal Primer-Multiplex-PCR Method with Sequencing Gel Electrophoresis Analysis", *PLoS One*, 7(1): e22900, 10 pages (2012).
Xu, et al. "Simultaneous isolation of DNA and RNA from the same cell population obtained by laser capture microdissection for genome and transcriptome profiling", *J Mol Diagn.*, 10(2):129-134 (2008). doi: 10.2353/jmoldx.2008.070131. Epub Feb. 7, 2008.
Yao, et al. "Analysis of the CDR3 length repertoire and the diversity of TCRα chain in human peripheral blood T Lymphocytes", *Cell Mol Immunol.*, 4(3): 215-220 (2007).
Yeh, et al. "Regulating DNA translocation through functionalized soft nanopores", *Nanoscale*, 4(8): 2685-4693, Abstract Only (2012). doi: 10.1039/c2nr30102d. Epub Mar. 15, 2012.
Yassai, M.B. et al. "A clonotype nomenclature for T cell receptors", *Immunogenetics*, 61:493-502 (2009).
Yin et al. "Antiretroviral therapy restores diversity in the T-cell receptor Vβ repertoire of CD4 T-cell subpopulations among human immunodeficiency virus type 1-infected children and adolescents", *Clinical and Vaccine Immunology*, 16(9):1293-1301 (2009).
Yon and Fried. "Precise gene fusion by PCR", *Nucleic Acids Research*, 17(12):4895, 1 page (1989).
York, et al. "Highly parallel oligonucleotide purification and functionalization using reversible chemistry", *Nucleic Acids Res.*, 40(1): e4, 7 pages (2012). doi: 10.1093/nar/gkr910. Epub Oct. 29, 2011.
Yu and Fu. "Tumor-infiltrating T lymphocytes: friends or foes?", *Lab Invest.*, 86(3): 231-245 (2006).
Zagnoni, et al. "Droplet Microfluidics for High-throughput Analysis of Cells and Particles", *Methods in Cell Biology*, Chapter 2, 102: 23-48 (2011).
Zaliova, et al. "Quantification of fusion transcript reveals a subgroup with distinct biological properties and predicts relapse in BCR/ABL-positive ALL: implications for residual disease monitoring", *Leukemia*,23(5):944-951 (2009).
Zehentner et al. "Minimal Disease Detection and Confirmation in Hematologic Malignancies: Combining Cell Sorting with Clonality Profiling", *Clinical Chemistry*, 52(3): 430-437 (2006).
Zeng et al. "High-performance single cell genetic analysis using microfluidic emulsion generator arrays", *Anal. Chem.*, 82(8):3183-3190 (2010).
Zhong, Q. et al. "Multiplex digital PCR: breaking the one target per color barrier of quantitative PCR", Lab Chip, 11:2167-2174 (2011).
Zhou et al. "High throughput analysis of TCR-β rearrangement and gene expression in single cells", *Laboratory Investigation*, 86: 314-321 (2006).
Zhou et al. "Isolation of purified and live Foxp3+ regulatory T cells using FACS sorting on scatter plot", *J Mol Cell Biol.*, 2(3): 164-169 (2010). doi: 10.1093/jmcb/mjq007. Epub Apr. 29, 2010.
Zhu, et al. "Immune surveillance by CD8αα+ skin-resident T cells in human herpes virus infection", Nature, 497(7450):494-7 and Corrigendum (2013). doi: 10.1038/nature12110. Epub May 8, 2013.
Zimmerman and Mannhalter. "Technical aspects of quantitative competitive PCR", *Biotechniques*, 21: 268-279 (1996).

SEQUENCE LISTING

<160> NUMBER OF SEQ ID NOS: 484

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: Synthetic
      TRBV2 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 1
ntcaaatttc actctgaaga tccggtccac aa                                      32

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic
      TRBV3-1 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 2
ngctcactta aatcttcaca tcaattccct gg                                      32

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      TRBV4-1 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 3
ncttaaacct tcacctacac gccctgc                                            27

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      TRBV(4-2, 4-3) sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature

```
<222> LOCATION: (1)..(1)
<223> OTHER INFORMATION: 5' end modified with universal forward primer

<400> SEQUENCE: 4
ncttattcct tcacctacac accctgc                                              27

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      TRBV5-1 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 5
ngctctgaga tgaatgtgag caccttg                                              27

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic
      TRBV5-3 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 6
ngctctgaga tgaatgtgag tgccttg                                              27

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      TRBV(5-4, 5-5, 5-6, 5-7, 5-8) sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 7
ngctctgagc tgaatgtgaa cgccttg                                              27

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      TRBV6-1 sequence
<220> FEATURE:
```

```
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 8
ntcgctcagg ctggagtcgg ctg                                           23

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      TRBV(6-2, 6-3) sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 9
ngctggggtt ggagtcggct g                                             21

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      TRBV6-4 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 10
nccctcacgt tggcgtctgc tg                                            22

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      TRBV6-5 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 11
ngctcaggct gctgtcggct g                                             21

<210> SEQ ID NO 12
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      TRBV6-6 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 12
ncgctcaggc tggagttggc tg                                           22

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      TRBV6-7 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 13
ncccctcaag ctggagtcag ctg                                          23

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      TRBV6-8 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 14
ncactcaggc tggtgtcggc tg                                           22

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      TRBV6-9 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 15
ncgctcaggc tggagtcagc tg                                           22
```

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      TRBV7-1 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 16
nccactctga agttccagcg cacac                                          25

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      TRBV7-2 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 17
ncactctgac gatccagcgc acac                                           24

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      TRBV7-3 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 18
nctctactct gaagatccag cgcacag                                        27

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      TRBV7-4 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)

<223> OTHER INFORMATION: 5' end modified with universal forward primer

<400> SEQUENCE: 19
nccactctga agatccagcg cacag    25

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      TRBV7-6 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 20
ncactctgac gatccagcgc acag    24

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      TRBV7-7 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 21
nccactctga cgattcagcg cacag    25

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      TRBV7-8 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 22
nccactctga agatccagcg cacac    25

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      TRBV7-9 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 23
ncaccttgga gatccagcgc acag                                          24

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Synthetic
      TRBV9 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 24
ngcactctga actaaacctg agctctctg                                     29

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      TRBV10-1 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 25
ncccctcact ctggagtctg ctg                                           23

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      TRBV10-2 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 26
nccccctcac tctggagtca gcta                                          24

<210> SEQ ID NO 27
<211> LENGTH: 24
<212> TYPE: DNA
<213> ORGANISM: Artificial Sequence -continued

```
<220> FEATURE:
<223> OTHER INFORMATION: Description of Artificial Sequence: Synthetic
      TRBV10-3 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 27
ncctcctcac tctggagtcc gcta                                              24

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      TRBV(11-1, 11-3) sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 28
nccactctca agatccagcc tgcag                                             25

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Synthetic
      TRBV11-2 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 29
nctccactct caagatccag cctgcaa                                           27

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      TRBV(12-3, 12-4, 12-5) sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 30
nccactctga agatccagcc ctcag                                             25
```

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence: Synthetic
   TRBV13 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 31
ncattctgaa ctgaacatga gctccttgg                                29

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: Synthetic
   TRBV14 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 32
nctactctga aggtgcagcc tgcag                                    25

<210> SEQ ID NO 33
<211> LENGTH: 29
<212> TYPE: DNA
<213> ORGANISM: Artificial Sequence
<220> FEATURE:
<223> OTHER INFORMATION: Description of Artificial Sequence: Synthetic
   TRBV15 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 33
ngataacttc caatccagga ggccgaaca                                29

<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence: Synthetic
   TRBV16 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 34
nctgtagcct tgagatccag gctacga                                              27

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Synthetic
      TRBV17 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 35
ncttccacgc tgaagatcca tcccg                                                25

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
      TRBV18 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 36
ngcatcctga ggatccagca ggtag                                                25

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      TRBV19 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 37
ncctctcact gtgacatcgg ccc                                                  23

<210> SEQ ID NO 38
<211> LENGTH: 27
<212> TYPE: DNA
<213> ORGANISM: Artificial Sequence
<220> FEATURE:
<223> OTHER INFORMATION: Description of Artificial Sequence: Synthetic
      TRBV20-1 sequence
<220> FEATURE:
<221> NAME/KEY: modified_base
<222> LOCATION: (1)..(1)

```
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 38
ncttgtccac tctgacagtg accagtg                                            27

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
      TRBV23-1 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 39
ncagcctggc aatcctgtcc tcag                                               24

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
      TRBV24-1 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 40
nctccctgtc cctagagtct gccat                                              25

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      TRBV25-1 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 41
nccctgaccc tggagtctgc ca                                                 22

<210> SEQ ID NO 42
<211> LENGTH: 22
<212> TYPE: DNA
<213> ORGANISM: Artificial Sequence
<220> FEATURE:
```

<223> OTHER INFORMATION: Description of Artificial Sequence: Synthetic
      TRBV27 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 42
nccctgatcc tggagtcgcc ca                                              22

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      TRBV28 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 43
nctccctgat tctggagtcc gcca                                            24

<210> SEQ ID NO 44
<211> LENGTH: 32
<212> TYPE: DNA
<213> ORGANISM: Artificial Sequence
<220> FEATURE:
<223> OTHER INFORMATION: Description of Artificial Sequence: Synthetic
      TRBV29-1 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 44
nctaacattc tcaactctga ctgtgagcaa ca                                   32

<210> SEQ ID NO 45
<211> LENGTH: 29
<212> TYPE: DNA
<213> ORGANISM: Artificial Sequence
<220> FEATURE:
<223> OTHER INFORMATION: Description of Artificial Sequence: Synthetic
      TRBV30 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal forward primer

<400> SEQUENCE: 45
ncggcagttc atcctgagtt ctaagaagc                                       29

```
<210> SEQ ID NO 46
<211> LENGTH: 36
<212> TYPE: DNA
<213> ORGANISM: Artificial Sequence
<220> FEATURE:
<223> OTHER INFORMATION: Description of Artificial Sequence: Synthetic
      TRBJ1-1 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal reverse primer

<400> SEQUENCE: 46
nttacctaca actgtgagtc tggtgccttg tccaaa                              36

<210> SEQ ID NO 47
<211> LENGTH: 34
<212> TYPE: DNA
<213> ORGANISM: Artificial Sequence
<220> FEATURE:
<223> OTHER INFORMATION: Description of Artificial Sequence: Synthetic
      TRBJ1-2 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal reverse primer

<400> SEQUENCE: 47
nacctacaac ggttaacctg gtccccgaac cgaa                                34

<210> SEQ ID NO 48
<211> LENGTH: 34
<212> TYPE: DNA
<213> ORGANISM: Artificial Sequence
<220> FEATURE:
<223> OTHER INFORMATION: Description of Artificial Sequence: Synthetic
      TRBJ1-3 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal reverse primer

<400> SEQUENCE: 48
nacctacaac agtgagccaa cttccctctc caaa                                34

<210> SEQ ID NO 49
<211> LENGTH: 32
<212> TYPE: DNA
<213> ORGANISM: Artificial Sequence
<220> FEATURE:
<223> OTHER INFORMATION: Description of Artificial Sequence: Synthetic
      TRBJ1-4 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal reverse primer
```

```
<400> SEQUENCE: 49
nccaagacag agagctgggt tccactgcca aa                                  32

<210> SEQ ID NO 50
<211> LENGTH: 32
<212> TYPE: DNA
<213> ORGANISM: Artificial Sequence
<220> FEATURE:
<223> OTHER INFORMATION: Description of Artificial Sequence: Synthetic
      TRBJ1-6 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal reverse primer

<400> SEQUENCE: 50
nctgtcacag tgagcctggt cccgttccca aa                                  32

<210> SEQ ID NO 51
<211> LENGTH: 26
<212> TYPE: DNA
<213> ORGANISM: Artificial Sequence
<220> FEATURE:
<223> OTHER INFORMATION: Description of Artificial Sequence: Synthetic
      TRBJ2-1 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal reverse primer

<400> SEQUENCE: 51
ncggtgagcc gtgtccctgg cccgaa                                         26

<210> SEQ ID NO 52
<211> LENGTH: 32
<212> TYPE: DNA
<213> ORGANISM: Artificial Sequence
<220> FEATURE:
<223> OTHER INFORMATION: Description of Artificial Sequence: Synthetic
      TRBJ2-2 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal reverse primer

<400> SEQUENCE: 52
nccagtacgg tcagcctaga gccttctcca aa                                  32

<210> SEQ ID NO 53
<211> LENGTH: 27
<212> TYPE: DNA
<213> ORGANISM: Artificial Sequence
<220> FEATURE:
<223> OTHER INFORMATION: Description of Artificial Sequence: Synthetic
      TRBJ2-3 sequence
<220> FEATURE:
<221> NAME/KEY: modified_base
<222> LOCATION: (1)..(1)
<223> OTHER INFORMATION: a, c, g or t
```

-continued

```
<220> FEATURE:
<221> NAME/KEY: misc_feature
<222> LOCATION: (1)..(1)
<223> OTHER INFORMATION: 5' end modified with universal reverse primer

<400> SEQUENCE: 53
nactgtcagc cgggtgcctg ggccaaa                                        27

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
      TRBJ2-4 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal reverse primer

<400> SEQUENCE: 54
nagagccggg tcccggcgcc gaa                                            23

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic
      TRBJ2-5 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal reverse primer

<400> SEQUENCE: 55
nggagccgcg tgcctggccc gaa                                            23

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence: Synthetic
      TRBJ2-6 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal reverse primer

<400> SEQUENCE: 56
ngtcagcctg ctgccggccc cgaa                                           24

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: Synthetic
```

```
      TRBJ2-7 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal reverse primer

<400> SEQUENCE: 57
ngtgagcctg gtgcccggcc cgaa                                           24

<210> SEQ ID NO 58
<211> LENGTH: 65
<212> TYPE: DNA
<213> ORGANISM: Artificial Sequence
<220> FEATURE:
<223> OTHER INFORMATION: Description of Artificial Sequence: Synthetic
      TRBV2 sequence

<400> SEQUENCE: 58
caagcagaag acggcatacg agctcttccg atcttcaaat ttcactctga agatccggtc    60
cacaa                                                                65

<210> SEQ ID NO 59
<211> LENGTH: 65
<212> TYPE: DNA
<213> ORGANISM: Artificial Sequence
<220> FEATURE:
<223> OTHER INFORMATION: Description of Artificial Sequence: Synthetic
      TRBV3-1 sequence

<400> SEQUENCE: 59
caagcagaag acggcatacg agctcttccg atctgctcac ttaaatcttc acatcaattc    60
cctgg                                                                65

<210> SEQ ID NO 60
<211> LENGTH: 60
<212> TYPE: DNA
<213> ORGANISM: Artificial Sequence
<220> FEATURE:
<223> OTHER INFORMATION: Description of Artificial Sequence: Synthetic
      TRBV4-1 sequence

<400> SEQUENCE: 60
caagcagaag acggcatacg agctcttccg atctcttaaa ccttcaccta cacgccctgc    60

<210> SEQ ID NO 61
<211> LENGTH: 60
<212> TYPE: DNA
<213> ORGANISM: Artificial Sequence
<220> FEATURE:
<223> OTHER INFORMATION: Description of Artificial Sequence: Synthetic
      TRBV(4-2, 4-3) sequence

<400> SEQUENCE: 61
caagcagaag acggcatacg agctcttccg atctcttatt ccttcaccta cacccctgc     60

<210> SEQ ID NO 62
<211> LENGTH: 60
<212> TYPE: DNA
<213> ORGANISM: Artificial Sequence
<220> FEATURE:
<223> OTHER INFORMATION: Description of Artificial Sequence: Synthetic
      TRBV5-1 sequence
```

<400> SEQUENCE: 62
caagcagaag acggcatacg agctcttccg atctgctctg agatgaatgt gagcaccttg    60

<210> SEQ ID NO 63
<211> LENGTH: 60
<212> TYPE: DNA
<213> ORGANISM: Artificial Sequence
<220> FEATURE:
<223> OTHER INFORMATION: Description of Artificial Sequence: Synthetic
      TRBV5-3 sequence

<400> SEQUENCE: 63
caagcagaag acggcatacg agctcttccg atctgctctg agatgaatgt gagtgccttg    60

<210> SEQ ID NO 64
<211> LENGTH: 60
<212> TYPE: DNA
<213> ORGANISM: Artificial Sequence
<220> FEATURE:
<223> OTHER INFORMATION: Description of Artificial Sequence: Synthetic
      TRBV(5-4, 5-5, 5-6, 5-7, 5-8) sequence

<400> SEQUENCE: 64
caagcagaag acggcatacg agctcttccg atctgctctg agctgaatgt gaacgccttg    60

<210> SEQ ID NO 65
<211> LENGTH: 56
<212> TYPE: DNA
<213> ORGANISM: Artificial Sequence
<220> FEATURE:
<223> OTHER INFORMATION: Description of Artificial Sequence: Synthetic
      TRBV6-1 sequence

<400> SEQUENCE: 65
caagcagaag acggcatacg agctcttccg atcttcgctc aggctggagt cggctg        56

<210> SEQ ID NO 66
<211> LENGTH: 54
<212> TYPE: DNA
<213> ORGANISM: Artificial Sequence
<220> FEATURE:
<223> OTHER INFORMATION: Description of Artificial Sequence: Synthetic
      TRBV(6-2, 6-3) sequence

<400> SEQUENCE: 66
caagcagaag acggcatacg agctcttccg atctgctggg gttggagtcg gctg          54

<210> SEQ ID NO 67
<211> LENGTH: 55
<212> TYPE: DNA
<213> ORGANISM: Artificial Sequence
<220> FEATURE:
<223> OTHER INFORMATION: Description of Artificial Sequence: Synthetic
      TRBV6-4 sequence

<400> SEQUENCE: 67
caagcagaag acggcatacg agctcttccg atctccctca cgttggcgtc tgctg         55

<210> SEQ ID NO 68
<211> LENGTH: 54
<212> TYPE: DNA
<213> ORGANISM: Artificial Sequence
<220> FEATURE:
<223> OTHER INFORMATION: Description of Artificial Sequence: Synthetic
      TRBV6-5 sequence

<400> SEQUENCE: 68

```
caagcagaag acggcatacg agctcttccg atctgctcag gctgctgtcg gctg        54
```

<210> SEQ ID NO 69
<211> LENGTH: 55
<212> TYPE: DNA
<213> ORGANISM: Artificial Sequence
<220> FEATURE:
<223> OTHER INFORMATION: Description of Artificial Sequence: Synthetic
      TRBV6-6 sequence

<400> SEQUENCE: 69

```
caagcagaag acggcatacg agctcttccg atctcgctca ggctggagtt ggctg       55
```

<210> SEQ ID NO 70
<211> LENGTH: 56
<212> TYPE: DNA
<213> ORGANISM: Artificial Sequence
<220> FEATURE:
<223> OTHER INFORMATION: Description of Artificial Sequence: Synthetic
      TRBV6-7 sequence

<400> SEQUENCE: 70

```
caagcagaag acggcatacg agctcttccg atctcccctc aagctggagt cagctg      56
```

<210> SEQ ID NO 71
<211> LENGTH: 55
<212> TYPE: DNA
<213> ORGANISM: Artificial Sequence
<220> FEATURE:
<223> OTHER INFORMATION: Description of Artificial Sequence: Synthetic
      TRBV6-8 sequence

<400> SEQUENCE: 71

```
caagcagaag acggcatacg agctcttccg atctcactca ggctggtgtc ggctg       55
```

<210> SEQ ID NO 72
<211> LENGTH: 55
<212> TYPE: DNA
<213> ORGANISM: Artificial Sequence
<220> FEATURE:
<223> OTHER INFORMATION: Description of Artificial Sequence: Synthetic
      TRBV6-9 sequence

<400> SEQUENCE: 72

```
caagcagaag acggcatacg agctcttccg atctcgctca ggctggagtc agctg       55
```

<210> SEQ ID NO 73
<211> LENGTH: 58
<212> TYPE: DNA
<213> ORGANISM: Artificial Sequence
<220> FEATURE:
<223> OTHER INFORMATION: Description of Artificial Sequence: Synthetic
      TRBV7-1 sequence

<400> SEQUENCE: 73

```
caagcagaag acggcatacg agctcttccg atctccactc tgaagttcca gcgcacac   58
```

<210> SEQ ID NO 74
<211> LENGTH: 57
<212> TYPE: DNA
<213> ORGANISM: Artificial Sequence
<220> FEATURE:
<223> OTHER INFORMATION: Description of Artificial Sequence: Synthetic
      TRBV7-2 sequence

<400> SEQUENCE: 74

```
caagcagaag acggcatacg agctcttccg atctcactct gacgatccag cgcacac      57
```

<210> SEQ ID NO 75
<211> LENGTH: 60
<212> TYPE: DNA
<213> ORGANISM: Artificial Sequence
<220> FEATURE:
<223> OTHER INFORMATION: Description of Artificial Sequence: Synthetic
      TRBV7-3 sequence

<400> SEQUENCE: 75

```
caagcagaag acggcatacg agctcttccg atctctctac tctgaagatc cagcgcacag   60
```

<210> SEQ ID NO 76
<211> LENGTH: 58
<212> TYPE: DNA
<213> ORGANISM: Artificial Sequence
<220> FEATURE:
<223> OTHER INFORMATION: Description of Artificial Sequence: Synthetic
      TRBV7-4 sequence

<400> SEQUENCE: 76

```
caagcagaag acggcatacg agctcttccg atctccactc tgaagatcca gcgcacag     58
```

<210> SEQ ID NO 77
<211> LENGTH: 57
<212> TYPE: DNA
<213> ORGANISM: Artificial Sequence
<220> FEATURE:
<223> OTHER INFORMATION: Description of Artificial Sequence: Synthetic
      TRBV7-6 sequence

<400> SEQUENCE: 77

```
caagcagaag acggcatacg agctcttccg atctcactct gacgatccag cgcacag      57
```

<210> SEQ ID NO 78
<211> LENGTH: 58
<212> TYPE: DNA
<213> ORGANISM: Artificial Sequence
<220> FEATURE:
<223> OTHER INFORMATION: Description of Artificial Sequence: Synthetic
      TRBV7-7 sequence

<400> SEQUENCE: 78

```
caagcagaag acggcatacg agctcttccg atctccactc tgacgattca gcgcacag     58
```

<210> SEQ ID NO 79
<211> LENGTH: 58
<212> TYPE: DNA
<213> ORGANISM: Artificial Sequence
<220> FEATURE:
<223> OTHER INFORMATION: Description of Artificial Sequence: Synthetic
      TRBV7-8 sequence

<400> SEQUENCE: 79

```
caagcagaag acggcatacg agctcttccg atctccactc tgaagatcca gcgcacac     58
```

<210> SEQ ID NO 80
<211> LENGTH: 57
<212> TYPE: DNA
<213> ORGANISM: Artificial Sequence
<220> FEATURE:
<223> OTHER INFORMATION: Description of Artificial Sequence: Synthetic
      TRBV7-9 sequence

<400> SEQUENCE: 80

```
caagcagaag acggcatacg agctcttccg atctcacctt ggagatccag cgcacag      57
```

<210> SEQ ID NO 81
<211> LENGTH: 62
<212> TYPE: DNA
<213> ORGANISM: Artificial Sequence
<220> FEATURE:
<223> OTHER INFORMATION: Description of Artificial Sequence: Synthetic
      TRBV9 sequence

<400> SEQUENCE: 81
caagcagaag acggcatacg agctcttccg atctgcactc tgaactaaac ctgagctctc    60
tg                                                                   62

<210> SEQ ID NO 82
<211> LENGTH: 56
<212> TYPE: DNA
<213> ORGANISM: Artificial Sequence
<220> FEATURE:
<223> OTHER INFORMATION: Description of Artificial Sequence: Synthetic
      TRBV10-1 sequence

<400> SEQUENCE: 82
caagcagaag acggcatacg agctcttccg atctcccctc actctggagt ctgctg        56

<210> SEQ ID NO 83
<211> LENGTH: 57
<212> TYPE: DNA
<213> ORGANISM: Artificial Sequence
<220> FEATURE:
<223> OTHER INFORMATION: Description of Artificial Sequence: Synthetic
      TRBV10-2 sequence

<400> SEQUENCE: 83
caagcagaag acggcatacg agctcttccg atctcccccT cactctggag tcagcta       57

<210> SEQ ID NO 84
<211> LENGTH: 57
<212> TYPE: DNA
<213> ORGANISM: Artificial Sequence
<220> FEATURE:
<223> OTHER INFORMATION: Description of Artificial Sequence: Synthetic
      TRBV10-3 sequence

<400> SEQUENCE: 84
caagcagaag acggcatacg agctcttccg atctcctcct cactctggag tccgcta       57

<210> SEQ ID NO 85
<211> LENGTH: 58
<212> TYPE: DNA
<213> ORGANISM: Artificial Sequence
<220> FEATURE:
<223> OTHER INFORMATION: Description of Artificial Sequence: Synthetic
      TRBV(11-1, 11-3) sequence

<400> SEQUENCE: 85
caagcagaag acggcatacg agctcttccg atctccactc tcaagatcca gcctgcag      58

<210> SEQ ID NO 86
<211> LENGTH: 60
<212> TYPE: DNA
<213> ORGANISM: Artificial Sequence
<220> FEATURE:
<223> OTHER INFORMATION: Description of Artificial Sequence: Synthetic
      TRBV11-2 sequence

<400> SEQUENCE: 86
caagcagaag acggcatacg agctcttccg atctctccac tctcaagatc cagcctgcaa     60

<210> SEQ ID NO 87
<211> LENGTH: 58
<212> TYPE: DNA
<213> ORGANISM: Artificial Sequence
<220> FEATURE:
<223> OTHER INFORMATION: Description of Artificial Sequence: Synthetic
      TRBV(12-3, 12-4, 12-5) sequence

<400> SEQUENCE: 87
caagcagaag acggcatacg agctcttccg atctccactc tgaagatcca gccctcag     58

<210> SEQ ID NO 88
<211> LENGTH: 62
<212> TYPE: DNA
<213> ORGANISM: Artificial Sequence
<220> FEATURE:
<223> OTHER INFORMATION: Description of Artificial Sequence: Synthetic
      TRBV13 sequence

<400> SEQUENCE: 88
caagcagaag acggcatacg agctcttccg atctcattct gaactgaaca tgagctcctt     60
gg                                                                    62

<210> SEQ ID NO 89
<211> LENGTH: 58
<212> TYPE: DNA
<213> ORGANISM: Artificial Sequence
<220> FEATURE:
<223> OTHER INFORMATION: Description of Artificial Sequence: Synthetic
      TRBV14 sequence

<400> SEQUENCE: 89
caagcagaag acggcatacg agctcttccg atctctactc tgaaggtgca gcctgcag     58

<210> SEQ ID NO 90
<211> LENGTH: 62
<212> TYPE: DNA
<213> ORGANISM: Artificial Sequence
<220> FEATURE:
<223> OTHER INFORMATION: Description of Artificial Sequence: Synthetic
      TRBV15 sequence

<400> SEQUENCE: 90
caagcagaag acggcatacg agctcttccg atctgataac ttccaatcca ggaggccgaa     60
ca                                                                    62

<210> SEQ ID NO 91
<211> LENGTH: 60
<212> TYPE: DNA
<213> ORGANISM: Artificial Sequence
<220> FEATURE:
<223> OTHER INFORMATION: Description of Artificial Sequence: Synthetic
      TRBV16 sequence

<400> SEQUENCE: 91
caagcagaag acggcatacg agctcttccg atctctgtag ccttgagatc caggctacga     60

<210> SEQ ID NO 92
<211> LENGTH: 58
<212> TYPE: DNA
<213> ORGANISM: Artificial Sequence
<220> FEATURE:
<223> OTHER INFORMATION: Description of Artificial Sequence: Synthetic
      TRBV17 sequence

<400> SEQUENCE: 92
caagcagaag acggcatacg agctcttccg atctcttcca cgctgaagat ccatcccg      58

<210> SEQ ID NO 93
<211> LENGTH: 58
<212> TYPE: DNA
<213> ORGANISM: Artificial Sequence
<220> FEATURE:
<223> OTHER INFORMATION: Description of Artificial Sequence: Synthetic
      TRBV18 sequence

<400> SEQUENCE: 93
caagcagaag acggcatacg agctcttccg atctgcatcc tgaggatcca gcaggtag      58

<210> SEQ ID NO 94
<211> LENGTH: 56
<212> TYPE: DNA
<213> ORGANISM: Artificial Sequence
<220> FEATURE:
<223> OTHER INFORMATION: Description of Artificial Sequence: Synthetic
      TRBV19 sequence

<400> SEQUENCE: 94
caagcagaag acggcatacg agctcttccg atctcctctc actgtgacat cggccc        56

<210> SEQ ID NO 95
<211> LENGTH: 60
<212> TYPE: DNA
<213> ORGANISM: Artificial Sequence
<220> FEATURE:
<223> OTHER INFORMATION: Description of Artificial Sequence: Synthetic
      TRBV20-1 sequence

<400> SEQUENCE: 95
caagcagaag acggcatacg agctcttccg atctcttgtc cactctgaca gtgaccagtg    60

<210> SEQ ID NO 96
<211> LENGTH: 57
<212> TYPE: DNA
<213> ORGANISM: Artificial Sequence
<220> FEATURE:
<223> OTHER INFORMATION: Description of Artificial Sequence: Synthetic
      TRBV23-1 sequence

<400> SEQUENCE: 96
caagcagaag acggcatacg agctcttccg atctcagcct ggcaatcctg tcctcag       57

<210> SEQ ID NO 97
<211> LENGTH: 58
<212> TYPE: DNA
<213> ORGANISM: Artificial Sequence
<220> FEATURE:
<223> OTHER INFORMATION: Description of Artificial Sequence: Synthetic
      TRBV24-1 sequence

<400> SEQUENCE: 97
caagcagaag acggcatacg agctcttccg atctctccct gtccctagag tctgccat      58

<210> SEQ ID NO 98
<211> LENGTH: 55
<212> TYPE: DNA
<213> ORGANISM: Artificial Sequence
<220> FEATURE:
<223> OTHER INFORMATION: Description of Artificial Sequence: Synthetic
      TRBV25-1 sequence

<400> SEQUENCE: 98
caagcagaag acggcatacg agctcttccg atctccctga ccctggagtc tgcca        55

<210> SEQ ID NO 99
<211> LENGTH: 55
<212> TYPE: DNA
<213> ORGANISM: Artificial Sequence
<220> FEATURE:
<223> OTHER INFORMATION: Description of Artificial Sequence: Synthetic
      TRBV27 sequence

<400> SEQUENCE: 99
caagcagaag acggcatacg agctcttccg atctccctga tcctggagtc gccca        55

<210> SEQ ID NO 100
<211> LENGTH: 57
<212> TYPE: DNA
<213> ORGANISM: Artificial Sequence
<220> FEATURE:
<223> OTHER INFORMATION: Description of Artificial Sequence: Synthetic
      TRBV28 sequence

<400> SEQUENCE: 100
caagcagaag acggcatacg agctcttccg atctctccct gattctggag tccgcca      57

<210> SEQ ID NO 101
<211> LENGTH: 65
<212> TYPE: DNA
<213> ORGANISM: Artificial Sequence
<220> FEATURE:
<223> OTHER INFORMATION: Description of Artificial Sequence: Synthetic
      TRBV29-1 sequence

<400> SEQUENCE: 101
caagcagaag acggcatacg agctcttccg atctctaaca ttctcaactc tgactgtgag   60
caaca                                                               65

<210> SEQ ID NO 102
<211> LENGTH: 62
<212> TYPE: DNA
<213> ORGANISM: Artificial Sequence
<220> FEATURE:
<223> OTHER INFORMATION: Description of Artificial Sequence: Synthetic
      TRBV30 sequence

<400> SEQUENCE: 102
caagcagaag acggcatacg agctcttccg atctcggcag ttcatcctga gttctaagaa   60
gc                                                                  62

<210> SEQ ID NO 103
<211> LENGTH: 60
<212> TYPE: DNA
<213> ORGANISM: Artificial Sequence
<220> FEATURE:
<223> OTHER INFORMATION: Description of Artificial Sequence: Synthetic
      TRBJ1-1 sequence

<400> SEQUENCE: 103
aatgatacgg cgaccaccga gatctttacc tacaactgtg agtctggtgc cttgtccaaa   60

<210> SEQ ID NO 104
<211> LENGTH: 58
<212> TYPE: DNA
<213> ORGANISM: Artificial Sequence
<220> FEATURE:

<223> OTHER INFORMATION: Description of Artificial Sequence: Synthetic
      TRBJ1-3 sequence

<400> SEQUENCE: 104
aatgatacgg cgaccaccga gatctaccta caacagtgag ccaacttccc tctccaaa    58

<210> SEQ ID NO 105
<211> LENGTH: 56
<212> TYPE: DNA
<213> ORGANISM: Artificial Sequence
<220> FEATURE:
<223> OTHER INFORMATION: Description of Artificial Sequence: Synthetic
      TRBJ1-4 sequence

<400> SEQUENCE: 105
aatgatacgg cgaccaccga gatctccaag acagagagct gggttccact gccaaa    56

<210> SEQ ID NO 106
<211> LENGTH: 56
<212> TYPE: DNA
<213> ORGANISM: Artificial Sequence
<220> FEATURE:
<223> OTHER INFORMATION: Description of Artificial Sequence: Synthetic
      TRBJ1-6 sequence

<400> SEQUENCE: 106
aatgatacgg cgaccaccga gatctctgtc acagtgagcc tggtcccgtt cccaaa    56

<210> SEQ ID NO 107
<211> LENGTH: 50
<212> TYPE: DNA
<213> ORGANISM: Artificial Sequence
<220> FEATURE:
<223> OTHER INFORMATION: Description of Artificial Sequence: Synthetic
      TRBJ2-1 sequence

<400> SEQUENCE: 107
aatgatacgg cgaccaccga gatctcggtg agccgtgtcc ctggcccgaa    50

<210> SEQ ID NO 108
<211> LENGTH: 56
<212> TYPE: DNA
<213> ORGANISM: Artificial Sequence
<220> FEATURE:
<223> OTHER INFORMATION: Description of Artificial Sequence: Synthetic
      TRBJ2-2 sequence

<400> SEQUENCE: 108
aatgatacgg cgaccaccga gatctccagt acggtcagcc tagagccttc tccaaa    56

<210> SEQ ID NO 109
<211> LENGTH: 51
<212> TYPE: DNA
<213> ORGANISM: Artificial Sequence
<220> FEATURE:
<223> OTHER INFORMATION: Description of Artificial Sequence: Synthetic
      TRBJ2-3 sequence

<400> SEQUENCE: 109
aatgatacgg cgaccaccga gatctactgt cagccgggtg cctgggccaa a    51

<210> SEQ ID NO 110
<211> LENGTH: 47
<212> TYPE: DNA
<213> ORGANISM: Artificial Sequence
<220> FEATURE:
<223> OTHER INFORMATION: Description of Artificial Sequence: Synthetic TRBJ2-4 sequence

<400> SEQUENCE: 110
aatgatacgg cgaccaccga gatctagagc cgggtcccgg cgccgaa         47

<210> SEQ ID NO 111
<211> LENGTH: 47
<212> TYPE: DNA
<213> ORGANISM: Artificial Sequence
<220> FEATURE:
<223> OTHER INFORMATION: Description of Artificial Sequence: Synthetic
      TRBJ2-5 sequence

<400> SEQUENCE: 111
aatgatacgg cgaccaccga gatctggagc cgcgtgcctg gcccgaa         47

<210> SEQ ID NO 112
<211> LENGTH: 48
<212> TYPE: DNA
<213> ORGANISM: Artificial Sequence
<220> FEATURE:
<223> OTHER INFORMATION: Description of Artificial Sequence: Synthetic
      TRBJ2-6 sequence

<400> SEQUENCE: 112
aatgatacgg cgaccaccga gatctgtcag cctgctgccg gccccgaa        48

<210> SEQ ID NO 113
<211> LENGTH: 48
<212> TYPE: DNA
<213> ORGANISM: Artificial Sequence
<220> FEATURE:
<223> OTHER INFORMATION: Description of Artificial Sequence: Synthetic
      TRBJ2-7 sequence

<400> SEQUENCE: 113
aatgatacgg cgaccaccga gatctgtgag cctggtgccc ggcccgaa        48

<210> SEQ ID NO 114
<211> LENGTH: 284
<212> TYPE: DNA
<213> ORGANISM: Artificial Sequence
<220> FEATURE:
<223> OTHER INFORMATION: Description of Artificial Sequence: Synthetic
      TRBV1*01 sequence

<400> SEQUENCE: 114
gatactggaa ttacccagac accaaaatac ctggtcacag caatggggag taaaaggaca      60
atgaaacgtg agcatctggg acatgattct atgtattggt acagacagaa agctaagaaa     120
tccctggagt tcatgtttta ctacaactgt aaggaattca ttgaaaacaa gactgtgcca     180
aatcacttca cacctgaatg ccctgacagc tctcgcttat accttcatgt ggtcgcactg     240
cagcaagaag actcagctgc gtatctctgc accagcagcc aaga                      284

<210> SEQ ID NO 115
<211> LENGTH: 290
<212> TYPE: DNA
<213> ORGANISM: Artificial Sequence
<220> FEATURE:
<223> OTHER INFORMATION: Description of Artificial Sequence: Synthetic
      TRBV2*01 sequence

<400> SEQUENCE: 115
gaacctgaag tcacccagac tcccagccat caggtcacac agatgggaca ggaagtgatc      60

```
ttgcgctgtg tccccatctc taatcactta tacttctatt ggtacagaca aatcttgggg      120
cagaaagtcg agtttctggt ttccttttat aataatgaaa tctcagagaa gtctgaaata      180
ttcgatgatc aattctcagt tgaaaggcct gatggatcaa atttcactct gaagatccgg      240
tccacaaagc tggaggactc agccatgtac ttctgtgcca gcagtgaagc                 290
```

<210> SEQ ID NO 116
<211> LENGTH: 288
<212> TYPE: DNA
<213> ORGANISM: Artificial Sequence
<220> FEATURE:
<223> OTHER INFORMATION: Description of Artificial Sequence: Synthetic TRBV2*03 sequence

<400> SEQUENCE: 116

```
gaacctgaag tcacccagac tcccagccat caggtcacac agatgggaca ggaagtgatc       60
ttgcgctgtg tccccatctc taatcactta tacttctatt ggtacagaca aatcttgggg      120
cagaaagtcg agtttctggt ttccttttat aataatgaaa tctcagagaa gtctgaaata      180
ttcgatgatc aattctcagt tgagaggcct gatggatcaa atttcactct gaagatccgg      240
tccacaaagc tggaggactc agccatgtac ttctgtgcca gcagtgaa                   288
```

<210> SEQ ID NO 117
<211> LENGTH: 287
<212> TYPE: DNA
<213> ORGANISM: Artificial Sequence
<220> FEATURE:
<223> OTHER INFORMATION: Description of Artificial Sequence: Synthetic TRBV3-1*01 sequence

<400> SEQUENCE: 117

```
gacacagctg tttcccagac tccaaaatac ctggtcacac agatgggaaa cgacaagtcc       60
attaaatgtg aacaaaatct gggccatgat actatgtatt ggtataaaca ggactctaag      120
aaatttctga agataatgtt tagctacaat aataaggagc tcattataaa tgaaacagtt      180
ccaaatcgct tctcacctaa atctccagac aaagctcact taaatcttca catcaattcc      240
ctggagcttg gtgactctgc tgtgtatttc tgtgccagca gccaaga                    287
```

<210> SEQ ID NO 118
<211> LENGTH: 279
<212> TYPE: DNA
<213> ORGANISM: Artificial Sequence
<220> FEATURE:
<223> OTHER INFORMATION: Description of Artificial Sequence: Synthetic TRBV3-1*02 sequence

<400> SEQUENCE: 118

```
gacacagctg tttcccagac tccaaaatac ctggtcacac agatgggaaa cgacaagtcc       60
attaaatgtg aacaaaatct gggccatgat actatgtatt ggtataaaca ggactctaag      120
aaatttctga agataatgtt tagctacaat aacaaggaga tcattataaa tgaaacagtt      180
ccaaatcgat tctcacctaa atctccagac aaagctaaat taaatcttca catcaattcc      240
ctggagcttg gtgactctgc tgtgtatttc tgtgccagc                             279
```

<210> SEQ ID NO 119
<211> LENGTH: 287
<212> TYPE: DNA
<213> ORGANISM: Artificial Sequence
<220> FEATURE:
<223> OTHER INFORMATION: Description of Artificial Sequence: Synthetic TRBV3-2*01 sequence -continued

<400> SEQUENCE: 119

```
gacacagccg tttcccagac tccaaaatac ctggtcacac agatgggaaa aaaggagtct    60
cttaaatgag aacaaaatct gggccataat gctatgtatt ggtataaaca ggactctaag   120
aaatttctga agacaatgtt tatctacagt aacaaggagc aattttaaa tgaaacagtt    180
ccaaatcgct tctcacctga ctctccagac aaagctcatt taaatcttca catcaattcc   240
ctggagcttg gtgactctgc tgtgtatttc tgtgccagca gccaaga              287
```

<210> SEQ ID NO 120
<211> LENGTH: 287
<212> TYPE: DNA
<213> ORGANISM: Artificial Sequence
<220> FEATURE:
<223> OTHER INFORMATION: Description of Artificial Sequence: Synthetic
      TRBV3-2*02 sequence

<400> SEQUENCE: 120

```
gacacagccg tttcccagac tccaaaatac ctggtcacac agatgggaaa aaaggagtct    60
cttaaatgag aacaaaatct gggccataat gctatgtatt ggtataaaca ggactctaag   120
aaatttctga agacaatgtt tatctacagt aacaaggagc aattttaaa tgaaacagtt    180
ccaaatcgct tctcacctga ctctccagac aaagttcatt taaatcttca catcaattcc   240
ctggagcttg gtgactctgc tgtgtatttc tgtgccagca gccaaga              287
```

<210> SEQ ID NO 121
<211> LENGTH: 285
<212> TYPE: DNA
<213> ORGANISM: Artificial Sequence
<220> FEATURE:
<223> OTHER INFORMATION: Description of Artificial Sequence: Synthetic
      TRBV3-2*03 sequence

<400> SEQUENCE: 121

```
gacacagccg tttcccagac tccaaaatac ctggtcacac agacgggaaa aaaggagtct    60
cttaaatgag aacaaaatct gggccataat gctatgtatt ggtataaaca ggactctaag   120
aaatttctga agacaatgtt tatctacagt aacaaggagc aattttaaa tgaaacagtt    180
ccaaatcgct tctcacctga ctctccagac aaagttcatt taaatcttca catcaattcc   240
ctggagcttg gtgactctgc tgtgtatttc tgtgccagca gccaa                 285
```

<210> SEQ ID NO 122
<211> LENGTH: 287
<212> TYPE: DNA
<213> ORGANISM: Artificial Sequence
<220> FEATURE:
<223> OTHER INFORMATION: Description of Artificial Sequence: Synthetic
      TRBV4-1*01 sequence

<400> SEQUENCE: 122

```
gacactgaag ttacccagac accaaaacac ctggtcatgg gaatgacaaa taagaagtct    60
ttgaaatgtg aacaacatat ggggcacagg gctatgtatt ggtacaagca gaaagctaag   120
aagccaccgg agctcatgtt tgtctacagc tatgagaaac tctctataaa tgaaagtgtg   180
ccaagtcgct tctcacctga atgccccaac agctctctct taaaccttca cctacacgcc   240
ctgcagccag aagactcagc cctgtatctc tgcgccagca gccaaga              287
```

<210> SEQ ID NO 123
<211> LENGTH: 258

<212> TYPE: DNA
<213> ORGANISM: Artificial Sequence
<220> FEATURE:
<223> OTHER INFORMATION: Description of Artificial Sequence: Synthetic
      TRBV4-1*02 sequence

<400> SEQUENCE: 123
cacctggtca tgggaatgac aaataagaag tctttgaaat gtgaacaaca tatggggcac    60
agggcaatgt attggtacaa gcagaaagct aagaagccac cggagctcat gtttgtctac   120
agctatgaga aactctctat aaatgaaagt gtgccaagtc gcttctcacc tgaatgcccc   180
aacagctctc tcttaaacct tcacctacac gccctgcagc cagaagactc agccctgtat   240
ctctgcgcca gcagccaa                                                 258

<210> SEQ ID NO 124
<211> LENGTH: 287
<212> TYPE: DNA
<213> ORGANISM: Artificial Sequence
<220> FEATURE:
<223> OTHER INFORMATION: Description of Artificial Sequence: Synthetic
      TRBV4-2*01 sequence

<400> SEQUENCE: 124
gaaacgggag ttacgcagac accaagacac ctggtcatgg gaatgacaaa taagaagtct    60
ttgaaatgtg aacaacatct ggggcataac gctatgtatt ggtacaagca aagtgctaag   120
aagccactgg agctcatgtt tgtctacaac tttaaagaac agactgaaaa caacagtgtg   180
ccaagtcgct tctcacctga atgccccaac agctctcact tattccttca cctacacacc   240
ctgcagccag aagactcggc cctgtatctc tgtgccagca gccaaga                 287

<210> SEQ ID NO 125
<211> LENGTH: 282
<212> TYPE: DNA
<213> ORGANISM: Artificial Sequence
<220> FEATURE:
<223> OTHER INFORMATION: Description of Artificial Sequence: Synthetic
      TRBV4-2*02 sequence

<400> SEQUENCE: 125
gaaacgggag ttacgcagac accaagacac ctggtcatgg gaatgacaaa taagaagtct    60
ttgaaatgtg aacaacatct ggggcataac gctatgtatt ggtacaagca aagtgctaag   120
aagccactgg agctcatgtt tgtctacaac tttaaagaac agactgaaaa caacagtgtg   180
ccaagtcgct tctcacctga atgccccaac agctctcact tatgccttca cctacacacc   240
ctgcagccag aagactcggc cctgtatctc tgtgccagca cc                      282

<210> SEQ ID NO 126
<211> LENGTH: 287
<212> TYPE: DNA
<213> ORGANISM: Artificial Sequence
<220> FEATURE:
<223> OTHER INFORMATION: Description of Artificial Sequence: Synthetic
      TRBV4-3*01 sequence

<400> SEQUENCE: 126
gaaacgggag ttacgcagac accaagacac ctggtcatgg gaatgacaaa taagaagtct    60
ttgaaatgtg aacaacatct gggtcataac gctatgtatt ggtacaagca aagtgctaag   120
aagccactgg agctcatgtt tgtctacagt cttgaagaac gggttgaaaa caacagtgtg   180
ccaagtcgct tctcacctga atgccccaac agctctcact tattccttca cctacacacc   240

```
ctgcagccag aagactcggc cctgtatctc tgcgccagca gccaaga          287
```

<210> SEQ ID NO 127
<211> LENGTH: 282
<212> TYPE: DNA
<213> ORGANISM: Artificial Sequence
<220> FEATURE:
<223> OTHER INFORMATION: Description of Artificial Sequence: Synthetic
      TRBV4-3*02 sequence

<400> SEQUENCE: 127

```
gaaacgggag ttacgcagac accaagacac ctggtcatgg gaatgacaaa taagaagtct    60
ttgaaatgtg aacaacatct gggtcataac gctatgtatt ggtacaagca aagtgctaag   120
aagccactgg agctcatgtt tgtctacagt cttgaagaac gggttgaaaa caacagtgtg   180
ccaagtcgct ctcacctga atgccccaac agctctcact tatcccttca cctacacacc    240
ctgcagccag aagactcggc cctgtatctc tgcgccagca gc                      282
```

<210> SEQ ID NO 128
<211> LENGTH: 282
<212> TYPE: DNA
<213> ORGANISM: Artificial Sequence
<220> FEATURE:
<223> OTHER INFORMATION: Description of Artificial Sequence: Synthetic
      TRBV4-3*03 sequence

<400> SEQUENCE: 128

```
gaaacgggag ttacgcagac accaagacac ctggtcatgg gaatgacaaa taagaagtct    60
ttgaaatgtg aacaacatct gggtcataac gctatgtatt ggtacaagca aagtgctaag   120
aagccactgg agctcatgtt tgtctacagt cttgaagaac gtgttgaaaa caacagtgtg   180
ccaagtcgct ctcacctga atgccccaac agctctcact tattccttca cctacacacc    240
ctgcagccag aagactcggc cctgtatctc tgcgccagca gc                      282
```

<210> SEQ ID NO 129
<211> LENGTH: 231
<212> TYPE: DNA
<213> ORGANISM: Artificial Sequence
<220> FEATURE:
<223> OTHER INFORMATION: Description of Artificial Sequence: Synthetic
      TRBV4-3*04 sequence

<400> SEQUENCE: 129

```
aagaagtctt tgaaatgtga acaacatctg ggcataacg ctatgtattg gtacaagcaa    60
agtgctaaga agccactgga gctcatgttt gtctacagtc ttgaagaacg ggttgaaaac   120
aacagtgtgc caagtcgctt ctcacctgaa tgccccaaca gctctcactt attccttcac   180
ctacacaccc tgcagccaga agactcggcc ctgtatctct gcgccagcag c            231
```

<210> SEQ ID NO 130
<211> LENGTH: 286
<212> TYPE: DNA
<213> ORGANISM: Artificial Sequence
<220> FEATURE:
<223> OTHER INFORMATION: Description of Artificial Sequence: Synthetic
      TRBV5-1*01 sequence

<400> SEQUENCE: 130

```
aaggctggag tcactcaaac tccaagatat ctgatcaaaa cgagaggaca gcaagtgaca    60
ctgagctgct cccctatctc tgggcatagg agtgtatcct ggtaccaaca gaccccagga   120
cagggccttc agttcctctt tgaatacttc agtgagacac agagaaacaa aggaaacttc   180
```

```
cctggtcgat tctcagggcg ccagttctct aactctcgct ctgagatgaa tgtgagcacc      240
ttggagctgg gggactcggc cctttatctt tgcgccagca gcttgg                    286

<210> SEQ ID NO 131
<211> LENGTH: 285
<212> TYPE: DNA
<213> ORGANISM: Artificial Sequence
<220> FEATURE:
<223> OTHER INFORMATION: Description of Artificial Sequence: Synthetic
      TRBV5-1*02 sequence

<400> SEQUENCE: 131
agggctgggg tcactcaaac tccaagacat ctgatcaaaa cgagaggaca gcaagtgaca      60
ctgggctgct cccctatctc tgggcatagg agtgtatcct ggtaccaaca gaccctagga     120
cagggccttc agttcctctt tgaatacttc agtgagacac agaaaacaa aggaaacttc      180 cttggtcgat tctcagggcg ccagttctct aactctcgct ctgagatgaa tgtgagcacc    240
ttggagctgg gggactcggc cctttatctt tgcgccagcg cttgc                    285

<210> SEQ ID NO 132
<211> LENGTH: 286
<212> TYPE: DNA
<213> ORGANISM: Artificial Sequence
<220> FEATURE:
<223> OTHER INFORMATION: Description of Artificial Sequence: Synthetic
      TRBV5-3*01 sequence

<400> SEQUENCE: 132
gaggctggag tcacccaaag tcccacacac ctgatcaaaa cgagaggaca gcaagtgact      60
ctgagatgct ctcctatctc tgggcacagc agtgtgtcct ggtaccaaca ggccccgggt     120
caggggcccc agtttatctt tgaatatgct aatgagttaa ggagatcaga aggaaacttc    180
cctaatcgat tctcagggcg ccagttccat gactgttgct ctgagatgaa tgtgagtgcc    240
ttggagctgg gggactcggc cctgtatctc tgtgccagaa gcttgg                    286

<210> SEQ ID NO 133
<211> LENGTH: 286
<212> TYPE: DNA
<213> ORGANISM: Artificial Sequence
<220> FEATURE:
<223> OTHER INFORMATION: Description of Artificial Sequence: Synthetic
      TRBV5-3*02 sequence

<400> SEQUENCE: 133
gaggctggag tcacccaaag tcccacacac ctgatcaaaa cgagaggaca gcaagtgact      60
ctgagatgct ctcctatctc tgggcacagc agtgtgtcct ggtaccaaca ggccccgggt     120
caggggcccc agtttatctt tgaatatgct aatgagttaa ggagatcaga aggaaacttc    180
cctaatcgat tctcagggcg ccagttccat gactattgct ctgagatgaa tgtgagtgcc    240
ttggagctgg gggactcggc cctgtatctc tgtgccagaa gcttgg                    286

<210> SEQ ID NO 134
<211> LENGTH: 286
<212> TYPE: DNA
<213> ORGANISM: Artificial Sequence
<220> FEATURE:
<223> OTHER INFORMATION: Description of Artificial Sequence: Synthetic
      TRBV5-4*01 sequence

<400> SEQUENCE: 134
```

```
gagactggag tcacccaaag tcccacacac ctgatcaaaa cgagaggaca gcaagtgact    60
ctgagatgct cttctcagtc tgggcacaac actgtgtcct ggtaccaaca ggccctgggt   120
caggggcccc agtttatctt tcagtattat agggaggaag agaatggcag aggaaacttc   180
cctcctagat tctcaggtct ccagttccct aattatagct ctgagctgaa tgtgaacgcc   240
ttggagctgg acgactcggc cctgtatctc tgtgccagca gcttgg                 286

<210> SEQ ID NO 135
<211> LENGTH: 282
<212> TYPE: DNA
<213> ORGANISM: Artificial Sequence
<220> FEATURE:
<223> OTHER INFORMATION: Description of Artificial Sequence: Synthetic
      TRBV5-4*02 sequence

<400> SEQUENCE: 135
gagactggag tcacccaaag tcccacacac ctgatcaaaa cgagaggaca gcaagtgact    60
ctgagatgct cttctcagtc tgggcacaac actgtgtcct ggtaccaaca ggccctgggt   120
caggggcccc agtttatctt tcagtattat agggaggaag agaatggcag aggaaacttc   180
cctcctagat tctcaggtct ccagttccct aattataact ctgagctgaa tgtgaacgcc   240
ttggagctgg acgactcggc cctgtatctc tgtgccagca gc                     282

<210> SEQ ID NO 136
<211> LENGTH: 234
<212> TYPE: DNA
<213> ORGANISM: Artificial Sequence
<220> FEATURE:
<223> OTHER INFORMATION: Description of Artificial Sequence: Synthetic
      TRBV5-4*03 sequence

<400> SEQUENCE: 136
cagcaagtga cactgagatg ctcttctcag tctgggcaca acactgtgtc ctggtaccaa    60
caggccctgg gtcaggggcc ccagtttatc tttcagtatt atagggagga agagaatggc   120
agaggaaact ccctcctag attctcaggt ctccagttcc ctaattatag ctctgagctg   180
aatgtgaacg ccttggagct ggacgactcg gccctgtatc tctgtgccag cagc         234

<210> SEQ ID NO 137
<211> LENGTH: 192
<212> TYPE: DNA
<213> ORGANISM: Artificial Sequence
<220> FEATURE:
<223> OTHER INFORMATION: Description of Artificial Sequence: Synthetic
      TRBV5-4*04 sequence

<400> SEQUENCE: 137
actgtgtcct ggtaccaaca ggccctgggt caggggcccc agtttatctt tcagtattat    60
agggaggaag agaatggcag aggaaactcc ctcctagat tctcaggtct ccagttccct   120
aattatagct ctgagctgaa tgtgaacgcc ttggagctgg acgactcggc cctgtatctc   180
tgtgccagca gc                                                      192

<210> SEQ ID NO 138
<211> LENGTH: 286
<212> TYPE: DNA
<213> ORGANISM: Artificial Sequence
<220> FEATURE:
<223> OTHER INFORMATION: Description of Artificial Sequence: Synthetic
      TRBV5-5*01 sequence

<400> SEQUENCE: 138
```

```
gacgctggag tcacccaaag tcccacacac ctgatcaaaa cgagaggaca gcaagtgact    60
ctgagatgct ctcctatctc tgggcacaag agtgtgtcct ggtaccaaca ggtcctgggt   120
caggggcccc agtttatctt tcagtattat gagaaagaag agagaggaag aggaaacttc   180
cctgatcgat tctcagctcg ccagttccct aactatagct ctgagctgaa tgtgaacgcc   240
ttgttgctgg gggactcggc cctgtatctc tgtgccagca gcttgg                  286
```

<210> SEQ ID NO 139
<211> LENGTH: 282
<212> TYPE: DNA
<213> ORGANISM: Artificial Sequence
<220> FEATURE:
<223> OTHER INFORMATION: Description of Artificial Sequence: Synthetic
      TRBV5-5*02 sequence

<400> SEQUENCE: 139

```
gacgctggag tcacccaaag tcccacacac ctgatcaaaa cgagaggaca gcacgtgact    60
ctgagatgct ctcctatctc tgggcacaag agtgtgtcct ggtaccaaca ggtcctgggt   120
caggggcccc agtttatctt tcagtattat gagaaagaag agagaggaag aggaaacttc   180
cctgatcgat tctcagctcg ccagttccct aactatagct ctgagctgaa tgtgaacgcc   240
ttgttgctgg gggactcggc cctgtatctc tgtgccagca gc                      282
```

<210> SEQ ID NO 140
<211> LENGTH: 282
<212> TYPE: DNA
<213> ORGANISM: Artificial Sequence
<220> FEATURE:
<223> OTHER INFORMATION: Description of Artificial Sequence: Synthetic
      TRBV5-5*03 sequence

<400> SEQUENCE: 140

```
gacgctggag tcacccaaag tcccacacac ctgatcaaaa cgagaggaca gcaagtgact    60
ctgagatgct ctcctatctc tgagcacaag agtgtgtcct ggtaccaaca ggtcctgggt   120
caggggcccc agtttatctt tcagtattat gagaaagaag agagaggaag aggaaacttc   180
cctgatcgat tctcagctcg ccagttccct aactatagct ctgagctgaa tgtgaacgcc   240
ttgttgctgg gggactcggc cctgtatctc tgtgccagca gc                      282
```

<210> SEQ ID NO 141
<211> LENGTH: 286
<212> TYPE: DNA
<213> ORGANISM: Artificial Sequence
<220> FEATURE:
<223> OTHER INFORMATION: Description of Artificial Sequence: Synthetic
      TRBV5-6*01 sequence

<400> SEQUENCE: 141

```
gacgctggag tcacccaaag tcccacacac ctgatcaaaa cgagaggaca gcaagtgact    60
ctgagatgct ctcctaagtc tgggcatgac actgtgtcct ggtaccaaca ggccctgggt   120
caggggcccc agtttatctt tcagtattat gaggaggaag agagacagag aggcaacttc   180
cctgatcgat tctcaggtca ccagttccct aactatagct ctgagctgaa tgtgaacgcc   240
ttgttgctgg gggactcggc cctctatctc tgtgccagca gcttgg                  286
```

<210> SEQ ID NO 142
<211> LENGTH: 286
<212> TYPE: DNA
<213> ORGANISM: Artificial Sequence
<220> FEATURE:
<223> OTHER INFORMATION: Description of Artificial Sequence: Synthetic
      TRBV5-7*01 sequence

<400> SEQUENCE: 142
gacgctggag tcacccaaag tcccacacac ctgatcaaaa cgagaggaca gcacgtgact      60
ctgagatgct ctcctatctc tgggcacacc agtgtgtcct cgtaccaaca ggccctgggt     120
caggggcccc agtttatctt tcagtattat gagaaagaag agagaggaag aggaaacttc    180
cctgatcaat tctcaggtca ccagttccct aactatagct ctgagctgaa tgtgaacgcc    240
ttgttgctag gggactcggc cctctatctc tgtgccagca gcttgg                   286

<210> SEQ ID NO 143
<211> LENGTH: 286
<212> TYPE: DNA
<213> ORGANISM: Artificial Sequence
<220> FEATURE:
<223> OTHER INFORMATION: Description of Artificial Sequence: Synthetic
      TRBV5-8*01 sequence

<400> SEQUENCE: 143
gaggctggag tcacacaaag tcccacacac ctgatcaaaa cgagaggaca gcaagcgact     60
ctgagatgct ctcctatctc tgggcacacc agtgtgtact ggtaccaaca ggccctgggt    120
ctgggcctcc agttcctcct ttggtatgac gagggtgaag agagaaacag aggaaacttc    180
cctcctagat tttcaggtcg ccagttccct aattatagct ctgagctgaa tgtgaacgcc    240
ttggagctgg aggactcggc cctgtatctc tgtgccagca gcttgg                   286

<210> SEQ ID NO 144
<211> LENGTH: 238
<212> TYPE: DNA
<213> ORGANISM: Artificial Sequence
<220> FEATURE:
<223> OTHER INFORMATION: Description of Artificial Sequence: Synthetic
      TRBV5-8*02 sequence

<400> SEQUENCE: 144
aggacagcaa gcgactctga gatgctctcc tatctctggg cacaccagtg tgtactggta     60
ccaacaggcc ctgggtctgg gcctccagct cctcctttgg tatgacgagg gtgaagagag    120
aaacagagga aacttccctc ctagattttc aggtcgccag ttccctaatt atagctctga    180
gctgaatgtg aacgccttgg agctggagga ctcggccctg tatctctgtg ccagcagc     238

<210> SEQ ID NO 145
<211> LENGTH: 287
<212> TYPE: DNA
<213> ORGANISM: Artificial Sequence
<220> FEATURE:
<223> OTHER INFORMATION: Description of Artificial Sequence: Synthetic
      TRBV6-1*01 sequence

<400> SEQUENCE: 145
aatgctggtg tcactcagac cccaaaattc caggtcctga agacaggaca gagcatgaca     60
ctgcagtgtg cccaggatat gaaccataac tccatgtact ggtatcgaca agacccaggc    120
atgggactga ggctgattta ttactcagct tctgagggta ccactgacaa aggagaagtc    180
cccaatggct acaatgtctc cagattaaac aaacgggagt ctcgctcag gctggagtcg     240 gctgctccct cccagacatc tgtgtacttc tgtgccagca gtgaagc                  287

<210> SEQ ID NO 146

```
<211> LENGTH: 287
<212> TYPE: DNA
<213> ORGANISM: Artificial Sequence
<220> FEATURE:
<223> OTHER INFORMATION: Description of Artificial Sequence: Synthetic
      TRBV6-2*01 sequence

<400> SEQUENCE: 146
aatgctggtg tcactcagac cccaaaattc cgggtcctga agacaggaca gagcatgaca    60
ctgctgtgtg cccaggatat gaaccatgaa tacatgtact ggtatcgaca agacccaggc   120
atggggctga ggctgattca ttactcagtt ggtgagggta caactgccaa aggagaggtc   180
cctgatggct acaatgtctc cagattaaaa aaacagaatt cctgctgggg gttggagtcg   240
gctgctccct cccaaacatc tgtgtacttc tgtgccagca gttactc                287

<210> SEQ ID NO 147
<211> LENGTH: 287
<212> TYPE: DNA
<213> ORGANISM: Artificial Sequence
<220> FEATURE:
<223> OTHER INFORMATION: Description of Artificial Sequence: Synthetic
      TRBV6-3*01 sequence

<400> SEQUENCE: 147
aatgctggtg tcactcagac cccaaaattc cgggtcctga agacaggaca gagcatgaca    60
ctgctgtgtg cccaggatat gaaccatgaa tacatgtact ggtatcgaca agacccaggc   120
atggggctga ggctgattca ttactcagtt ggtgagggta caactgccaa aggagaggtc   180
cctgatggct acaatgtctc cagattaaaa aaacagaatt cctgctgggg gttggagtcg   240
gctgctccct cccaaacatc tgtgtacttc tgtgccagca gttactc                287

<210> SEQ ID NO 148
<211> LENGTH: 287
<212> TYPE: DNA
<213> ORGANISM: Artificial Sequence
<220> FEATURE:
<223> OTHER INFORMATION: Description of Artificial Sequence: Synthetic
      TRBV6-4*01 sequence

<400> SEQUENCE: 148
attgctggga tcacccaggc accaacatct cagatcctgg cagcaggacg gcgcatgaca    60
ctgagatgta cccaggatat gagacataat gccatgtact ggtatagaca agatctagga   120
ctggggctaa ggctcatcca ttattcaaat actgcaggta ccactggcaa aggagaagtc   180
cctgatggtt atagtgtctc cagagcaaac acagatgatt tcccctcac gttggcgtct   240 gctgtaccct ctcagacatc tgtgtacttc tgtgccagca gtgactc                287

<210> SEQ ID NO 149
<211> LENGTH: 287
<212> TYPE: DNA
<213> ORGANISM: Artificial Sequence
<220> FEATURE:
<223> OTHER INFORMATION: Description of Artificial Sequence: Synthetic
      TRBV6-4*02 sequence

<400> SEQUENCE: 149
actgctggga tcacccaggc accaacatct cagatcctgg cagcaggacg gagcatgaca    60
ctgagatgta cccaggatat gagacataat gccatgtact ggtatagaca agatctagga   120
ctggggctaa ggctcatcca ttattcaaat actgcaggta ccactggcaa aggagaagtc   180
cctgatggtt atagtgtctc cagagcaaac acagatgatt tcccctcac gttggcgtct   240
```

```
gctgtaccct ctcagacatc tgtgtacttc tgtgccagca gtgactc        287
```

<210> SEQ ID NO 150
<211> LENGTH: 287
<212> TYPE: DNA
<213> ORGANISM: Artificial Sequence
<220> FEATURE:
<223> OTHER INFORMATION: Description of Artificial Sequence: Synthetic
      TRBV6-5*01 sequence

<400> SEQUENCE: 150

```
aatgctggtg tcactcagac cccaaaattc caggtcctga agacaggaca gagcatgaca    60
ctgcagtgtg cccaggatat gaaccatgaa tacatgtcct ggtatcgaca agacccaggc   120
atggggctga ggctgattca ttactcagtt ggtgctggta tcactgacca aggagaagtc   180
cccaatggct acaatgtctc cagatcaacc acagaggatt cccgctcag gctgctgtcg    240 gctgctccct cccagacatc tgtgtacttc tgtgccagca gttactc        287
```

<210> SEQ ID NO 151
<211> LENGTH: 287
<212> TYPE: DNA
<213> ORGANISM: Artificial Sequence
<220> FEATURE:
<223> OTHER INFORMATION: Description of Artificial Sequence: Synthetic
      TRBV6-6*01 sequence

<400> SEQUENCE: 151

```
aatgctggtg tcactcagac cccaaaattc cgcatcctga agataggaca gagcatgaca    60
ctgcagtgta cccaggatat gaaccataac tacatgtact ggtatcgaca agacccaggc   120
atggggctga agctgattta ttattcagtt ggtgctggta tcactgataa aggagaagtc   180
ccgaatggct acaacgtctc cagatcaacc acagaggatt cccgctcag gctggagttg    240 gctgctccct cccagacatc tgtgtacttc tgtgccagca gttactc        287
```

<210> SEQ ID NO 152
<211> LENGTH: 282
<212> TYPE: DNA
<213> ORGANISM: Artificial Sequence
<220> FEATURE:
<223> OTHER INFORMATION: Description of Artificial Sequence: Synthetic
      TRBV6-6*02 sequence

<400> SEQUENCE: 152

```
aatgctggtg tcactcagac cccaaaattc cgcatcctga agataggaca gagcatgaca    60
ctgcagtgtg cccaggatat gaaccataac tacatgtact ggtatcgaca agacccaggc   120
atggggctga agctgattta ttattcagtt ggtgctggta tcactgacaa aggagaagtc   180
ccgaatggct acaacgtctc cagatcaacc acagaggatt cccgctcag gctggagttg    240 gctgctccct cccagacatc tgtgtacttc tgtgccagca gt              282
```

<210> SEQ ID NO 153
<211> LENGTH: 282
<212> TYPE: DNA
<213> ORGANISM: Artificial Sequence
<220> FEATURE:
<223> OTHER INFORMATION: Description of Artificial Sequence: Synthetic
      TRBV6-6*03 sequence

<400> SEQUENCE: 153

```
aatgctggtg tcactcagac cccaaaattc cgcatcctga agataggaca gagcatgaca    60
```

```
ctgcagtgtg cccaggatat gaaccataac tacatgtact ggtatcgaca agacccaggc    120
atggggctga agctgattta ttattcagtt ggtgctggta tcactgataa aggagaagtc    180
ccgaatggct acaacgtctc cagatcaacc acagaggatt tcccgctcag ctggagttg     240 gctgctccct cccagacatc tgtgtacttc tgtgccagca gt                       282
```

<210> SEQ ID NO 154  
<211> LENGTH: 285  
<212> TYPE: DNA  
<213> ORGANISM: Artificial Sequence  
<220> FEATURE:  
<223> OTHER INFORMATION: Description of Artificial Sequence: Synthetic TRBV6-6*04 sequence

<400> SEQUENCE: 154

```
aatgctggtg tcactcagac cccaaaattc cgcatcctga agataggaca gagcatgaca    60
ctgcagtgta cccaggatat gaaccatgaa tacatgtact ggtatcgaca agacccaggc    120
atggggctga agctgattta ttattcagtt ggtgctggta tcactgataa aggagaagtc    180
ccgaatggct acaatgtctc cagatcaacc acagaggatt tcccgctcag ctggagttg     240 gctgctccct cccagacatc tgtgtacttc tgtgccagca gtcga                    285
```

<210> SEQ ID NO 155  
<211> LENGTH: 282  
<212> TYPE: DNA  
<213> ORGANISM: Artificial Sequence  
<220> FEATURE:  
<223> OTHER INFORMATION: Description of Artificial Sequence: Synthetic TRBV6-6*05 sequence

<400> SEQUENCE: 155

```
aatgctggtg tcactcagac cccaaaattc cgcatcctga agataggaca gagcatgaca    60
ctgcagtgtg cccaggatat gaaccataac tacatgtact ggtatcgaca agacccaggc    120
atggggctga agctgattta ttattcagtt ggtgctggta tcactgacaa aggagaagtc    180
ccgaatggct acaacgtctc cagatcaacc acagaggatt tcccgctcag ctggagttg     240 gctgctgcct cccagacatc tgtgtacttc tgtgccagca gc                       282
```

<210> SEQ ID NO 156  
<211> LENGTH: 287  
<212> TYPE: DNA  
<213> ORGANISM: Artificial Sequence  
<220> FEATURE:  
<223> OTHER INFORMATION: Description of Artificial Sequence: Synthetic TRBV6-7*01 sequence

<400> SEQUENCE: 156

```
aatgctggtg tcactcagac cccaaaattc cacgtcctga agacaggaca gagcatgact    60
ctgctgtgtg cccaggatat gaaccatgaa tacatgtatc ggtatcgaca agacccaggc    120
aaggggctga ggctgattta ctactcagtt gctgctgctc tcactgacaa aggagaagtt    180
cccaatggct acaatgtctc cagatcaaac acagaggatt tccccctcaa gctggagtca    240
gctgctccct ctcagacttc tgtttacttc tgtgccagca gttactc                  287
```

<210> SEQ ID NO 157  
<211> LENGTH: 284  
<212> TYPE: DNA  
<213> ORGANISM: Artificial Sequence  
<220> FEATURE:  
<223> OTHER INFORMATION: Description of Artificial Sequence: Synthetic TRBV6-8*01 sequence

<400> SEQUENCE: 157

```
aatgctggtg tcactcagac cccaaaattc cacatcctga agacaggaca gagcatgaca    60
ctgcagtgtg cccaggatat gaaccatgga tacatgtcct ggtatcgaca agacccaggc   120
atggggctga gactgattta ctactcagct gctgctggta ctactgacaa agaagtcccc   180
aatggctaca atgtctctag attaaacaca gaggatttcc cactcaggct ggtgtcggct   240
gctccctccc agacatctgt gtacttgtgt gccagcagtt actc                    284
```

<210> SEQ ID NO 158
<211> LENGTH: 287
<212> TYPE: DNA
<213> ORGANISM: Artificial Sequence
<220> FEATURE:
<223> OTHER INFORMATION: Description of Artificial Sequence: Synthetic
      TRBV6-9*01 sequence

<400> SEQUENCE: 158

```
aatgctggtg tcactcagac cccaaaattc cacatcctga agacaggaca gagcatgaca    60
ctgcagtgtg cccaggatat gaaccatgga tacttgtcct ggtatcgaca agacccaggc   120
atggggctga ggcgcattca ttactcagtt gctgctggta tcactgacaa aggagaagtc   180
cccgatggct acaatgtatc cagatcaaac acagaggatt tcccgctcag gctggagtca   240
gctgctccct cccagacatc tgtatacttc tgtgccagca gttattc                 287
```

<210> SEQ ID NO 159
<211> LENGTH: 290
<212> TYPE: DNA
<213> ORGANISM: Artificial Sequence
<220> FEATURE:
<223> OTHER INFORMATION: Description of Artificial Sequence: Synthetic
      TRBV7-1*01 sequence

<400> SEQUENCE: 159

```
ggtgctggag tctcccagtc cctgagacac aaggtagcaa agaagggaaa ggatgtagct    60
ctcagatatg atccaatttc aggtcataat gcccttttatt ggtaccgaca gagcctgggg   120
cagggcctgg agtttccaat ttacttccaa ggcaaggatg cagcagacaa atcgggggctt   180 ccccgtgatc ggttctctgc acagaggtct gagggatcca tctccactct gaagttccag   240
cgcacacagc aggggggactt ggctgtgtat ctctgtgcca gcagctcagc                290
```

<210> SEQ ID NO 160
<211> LENGTH: 290
<212> TYPE: DNA
<213> ORGANISM: Artificial Sequence
<220> FEATURE:
<223> OTHER INFORMATION: Description of Artificial Sequence: Synthetic
      TRBV7-2*01 sequence

<400> SEQUENCE: 160

```
ggagctggag tctcccagtc ccccagtaac aaggtcacag agaagggaaa ggatgtagag    60
ctcaggtgtg atccaatttc aggtcatact gccctttact ggtaccgaca gagcctgggg   120
cagggcctgg agttttttaat ttacttccaa ggcaacagtg caccagacaa atcagggctg   180
cccagtgatc gcttctctgc agagaggact gggggatccg tctccactct gacgatccag   240
cgcacacagc aggaggactc ggccgtgtat ctctgtgcca gcagcttagc                290
```

<210> SEQ ID NO 161
<211> LENGTH: 290

<210> SEQ ID NO 161
<211> LENGTH: 290
<212> TYPE: DNA
<213> ORGANISM: Artificial Sequence
<220> FEATURE:
<223> OTHER INFORMATION: Description of Artificial Sequence: Synthetic
      TRBV7-2*02 sequence

<400> SEQUENCE: 161

```
ggagctggag tctcccagtc ccccagtaac aaggtcacag agaagggaaa ggatgtagag      60
ctcaggtgtg atccaatttc aggtcatact gcccttact ggtaccgaca gaggctgggg     120
cagggcctgg agttttttaat ttacttccaa ggcaacagtg caccagacaa atcagggctg    180
cccagtgatc gcttctctgc agagaggact ggggaatccg tctccactct gacgatccag    240
cgcacacagc aggaggactc ggccgtgtat ctctgtgcca gcagcttagc                 290
```

<210> SEQ ID NO 162
<211> LENGTH: 290
<212> TYPE: DNA
<213> ORGANISM: Artificial Sequence
<220> FEATURE:
<223> OTHER INFORMATION: Description of Artificial Sequence: Synthetic
      TRBV7-2*03 sequence

<400> SEQUENCE: 162

```
ggagctggag tctcccagtc ccccagtaac aaggtcacag agaagggaaa ggatgtagag      60
ctcaggtgtg atccaatttc aggtcatact gcccttact ggtaccgaca gaggctgggg     120
cagggcctgg agttttttaat ttacttccaa ggcaacagtg caccagacaa atcagggctg    180
cccagtgatc gcttctctgc agagaggact ggggaatccg tctccactct gacgatccag    240
cgcacacagc aggaggactc ggccgtgtat ctctgtacca gcagcttagc                 290
```

<210> SEQ ID NO 163
<211> LENGTH: 288
<212> TYPE: DNA
<213> ORGANISM: Artificial Sequence
<220> FEATURE:
<223> OTHER INFORMATION: Description of Artificial Sequence: Synthetic
      TRBV7-2*04 sequence

<400> SEQUENCE: 163

```
ggagctggag tttcccagtc ccccagtaac aaggtcacag agaagggaaa ggatgtagag      60
ctcaggtgtg atccaatttc aggtcatact gcccttact ggtaccgaca gagcctgggg     120
cagggcctgg agttttttaat ttacttccaa ggcaacagtg caccagacaa atcagggctg    180
cccagtgatc gcttctctgc agagaggact gggggatccg tctccactct gacgatccag    240
cgcacacagc aggaggactc ggccgtgtat ctctgtgcca gcagctta                   288
```

<210> SEQ ID NO 164
<211> LENGTH: 290
<212> TYPE: DNA
<213> ORGANISM: Artificial Sequence
<220> FEATURE:
<223> OTHER INFORMATION: Description of Artificial Sequence: Synthetic
      TRBV7-3*01 sequence

<400> SEQUENCE: 164

```
ggtgctggag tctcccagac ccccagtaac aaggtcacag agaagggaaa atatgtagag      60
ctcaggtgtg atccaatttc aggtcatact gcccttact ggtaccgaca aagcctgggg     120
cagggcccag agtttctaat ttacttccaa ggcacgggtg cggcagatga ctcagggctg    180
cccaacgatc ggttctttgc agtcaggcct gagggatccg tctctactct gaagatccag    240
```
cgcacagagc gggggggactc agccgtgtat ctctgtgcca gcagcttaac                290

<210> SEQ ID NO 165
<211> LENGTH: 290
<212> TYPE: DNA
<213> ORGANISM: Artificial Sequence
<220> FEATURE:
<223> OTHER INFORMATION: Description of Artificial Sequence: Synthetic
      TRBV7-3*02 sequence

<400> SEQUENCE: 165
ggtgctggag tctcccagac ccccagtaac aaggtcacag agaagggaaa agatgtagag    60
ctcaggtgtg atccaatttc aggtcatact gcccttact ggtaccgaca aagcctgggg     120
cagggcccag agtttctaat ttacttccaa ggcacgggtg cggcagatga ctcagggctg    180
cccaaagatc ggttctttgc agtcaggcct gagggatccg tctctactct gaagatccag   240
cgcacagagc aggggggactc agccgtgtat ctccgtgcca gcagcttaac                290

<210> SEQ ID NO 166
<211> LENGTH: 288
<212> TYPE: DNA
<213> ORGANISM: Artificial Sequence
<220> FEATURE:
<223> OTHER INFORMATION: Description of Artificial Sequence: Synthetic
      TRBV7-3*03 sequence

<400> SEQUENCE: 166
ggtgctggag tctcccagac ccccagtaac aaggtcacag agaagggaaa agatgtagag    60
ctcaggtgtg atccaatttc aggtcatact gcccttact ggtaccgaca aagcctgggg     120
cagggcccag agtttctaat ttacttccaa ggcacgggtg cggcagatga ctcagggctg    180
cccaaagatc ggttctttgc agtcaggcct gagggatccg tctctactct gaagatccag   240
cgcacagagc aggggggactc agccgcgtat ctccgtgcca gcagctta                  288

<210> SEQ ID NO 167
<211> LENGTH: 285
<212> TYPE: DNA
<213> ORGANISM: Artificial Sequence
<220> FEATURE:
<223> OTHER INFORMATION: Description of Artificial Sequence: Synthetic
      TRBV7-3*04 sequence

<400> SEQUENCE: 167
ggtgctggag tctcccagac ccccagtaac aaggtcacag agaagggaaa atatgtagag    60
ctcaggtgtg atccaatttc aggtcatact gcccttact ggtaccgaca aagcctgggg     120
cagggcccag agtttctaat ttacttccaa ggcacgggtg cggcagatga ctcagggctg    180
cccaacgatc ggttctttgc agtcaggcct gagggatccg tctctactct gaagatccag   240
cgcacagagc gggggggactc tgccgtgtat ctctgtgcca gcagc                     285

<210> SEQ ID NO 168
<211> LENGTH: 231
<212> TYPE: DNA
<213> ORGANISM: Artificial Sequence
<220> FEATURE:
<223> OTHER INFORMATION: Description of Artificial Sequence: Synthetic
      TRBV7-3*05 sequence

<400> SEQUENCE: 168
tgggagctca ggtgtgatcc aatttcaggt catactgccc tttactggta ccgacaaagc    60
ctggggcagg gcccagagct tctaatttac ttccaaggca cgggtgcggc agatgactca   120

```
gggctgccca acgatcggtt ctttgcagtc aggcctgagg gatccgtctc tactctgaag    180
atccagcgca cagagcgggg ggactcagcc gtgtatctct gtgccagcag c            231
```

<210> SEQ ID NO 169
<211> LENGTH: 290
<212> TYPE: DNA
<213> ORGANISM: Artificial Sequence
<220> FEATURE:
<223> OTHER INFORMATION: Description of Artificial Sequence: Synthetic
      TRBV7-4*01 sequence

<400> SEQUENCE: 169

```
ggtgctggag tctcccagtc cccaaggtac aaagtcgcaa agaggggacg ggatgtagct     60
ctcaggtgtg attcaatttc gggtcatgta acccttt att ggtaccgaca gaccctgggg    120
cagggctcag aggttctgac ttactcccag agtgatgctc aacgagacaa atcagggcgg    180
cccagtggtc ggttctctgc agagaggcct gagagatccg tctccactct gaagatccag    240
cgcacagagc aggggactc agctgtgtat ctctgtgcca gcagcttagc                290
```

<210> SEQ ID NO 170
<211> LENGTH: 288
<212> TYPE: DNA
<213> ORGANISM: Artificial Sequence
<220> FEATURE:
<223> OTHER INFORMATION: Description of Artificial Sequence: Synthetic
      TRBV7-5*01 sequence

<400> SEQUENCE: 170

```
ggtgctggag tctcccagtc cccaaggtac gaagtcacac agaggggaca ggatgtagct     60
cccaggtgtg atccaatttc gggtcaggta accctttatt ggtaccgaca gaccctgggg    120
cagggccaag agtttctgac ttccttccag gatgaaactc aacaagataa atcagggctg    180
ctcagtgatc aattctccac agagaggtct gaggatcttt ctccacctga agatccagcg    240
cacagagcaa gggcgactcg gctgtgtatc tctgtgccag aagcttag                288
```

<210> SEQ ID NO 171
<211> LENGTH: 289
<212> TYPE: DNA
<213> ORGANISM: Artificial Sequence
<220> FEATURE:
<223> OTHER INFORMATION: Description of Artificial Sequence: Synthetic
      TRBV7-5*02 sequence

<400> SEQUENCE: 171

```
ggtgctggag tctcccagtc cccaaggtac gaagtcacac agaggggaca ggatgtagct     60
cccaggtgtg atccaatttc gggtcaggta accctttatt ggtaccgaca gaccctgggg    120
cagggccaag agtttctgac ttccttccag gatgaaactc aacaagataa atcagggctg    180
ctcagtgatc aattctccac agagaggtct gaggatcttt ctccacctga agatccagcg    240
cacagagcaa gggcgactcg gctgtgtatc tctgtgtcag aagcttagc                289
```

<210> SEQ ID NO 172
<211> LENGTH: 290
<212> TYPE: DNA
<213> ORGANISM: Artificial Sequence
<220> FEATURE:
<223> OTHER INFORMATION: Description of Artificial Sequence: Synthetic
      TRBV7-6*01 sequence

<400> SEQUENCE: 172

```
ggtgctggag tctcccagtc tcccaggtac aaagtcacaa agaggggaca ggatgtagct    60
ctcaggtgtg atccaatttc gggtcatgta tccctttatt ggtaccgaca ggccctgggg   120
cagggcccag agtttctgac ttacttcaat tatgaagccc aacaagacaa atcagggctg   180
cccaatgatc ggttctctgc agagaggcct gagggatcca tctccactct gacgatccag   240
cgcacagagc agcgggactc ggccatgtat cgctgtgcca gcagcttagc                290
```

<210> SEQ ID NO 173
<211> LENGTH: 285
<212> TYPE: DNA
<213> ORGANISM: Artificial Sequence
<220> FEATURE:
<223> OTHER INFORMATION: Description of Artificial Sequence: Synthetic
      TRBV7-6*02 sequence

<400> SEQUENCE: 173

```
ggtgctggag tctcccagtc tcccaggtac aaagtcacaa agaggggaca ggatgtagct    60
ctcaggtgtg atccaatctc gggtcatgta tccctttatt ggtaccgaca ggccctgggg   120
cagggcccag agtttctgac ttacttcaat tatgaagccc aacaagacaa atcagggctg   180
cccaatgatc ggttctctgc agagaggcct gagggatcca tctccactct gacgatccag   240
cgcacagagc agcgggactc ggccatgtat cgctgtgcca gcagc                    285
```

<210> SEQ ID NO 174
<211> LENGTH: 290
<212> TYPE: DNA
<213> ORGANISM: Artificial Sequence
<220> FEATURE:
<223> OTHER INFORMATION: Description of Artificial Sequence: Synthetic
      TRBV7-7*01 sequence

<400> SEQUENCE: 174

```
ggtgctggag tctcccagtc tcccaggtac aaagtcacaa agaggggaca ggatgtaact    60
ctcaggtgtg atccaatttc gagtcatgca acccttta tt ggtatcaaca ggccctgggg   120
cagggcccag agtttctgac ttacttcaat tatgaagctc aaccagacaa atcagggctg   180
cccagtgatc ggttctctgc agagaggcct gagggatcca tctccactct gacgattcag   240
cgcacagagc agcgggactc agccatgtat cgctgtgcca gcagcttagc                290
```

<210> SEQ ID NO 175
<211> LENGTH: 285
<212> TYPE: DNA
<213> ORGANISM: Artificial Sequence
<220> FEATURE:
<223> OTHER INFORMATION: Description of Artificial Sequence: Synthetic
      TRBV7-7*02 sequence

<400> SEQUENCE: 175

```
ggtgctggag tctcccagtc tcccaggtac aaagtcacaa agaggggaca ggatgtaact    60
ctcaggtgtg atccaatttc gagtcatgta acccttta tt ggtatcaaca ggccctgggg   120
cagggcccag agtttctgac ttacttcaat tatgaagctc aaccagacaa atcagggctg   180
cccagtgatc ggttctctgc agagaggcct gagggatcca tctccactct gacgattcag   240
cgcacagagc agcgggactc agccatgtat cgctgtgcca gcagc                    285
```

<210> SEQ ID NO 176
<211> LENGTH: 290
<212> TYPE: DNA
<213> ORGANISM: Artificial Sequence
<220> FEATURE:

<223> OTHER INFORMATION: Description of Artificial Sequence: Synthetic
      TRBV7-8*01 sequence

<400> SEQUENCE: 176

| ggtgctggag tctcccagtc ccctaggtac aaagtcgcaa agagaggaca ggatgtagct | 60 |
| ctcaggtgtg atccaatttc gggtcatgta tccctttttt ggtaccaaca ggccctgggg | 120 |
| caggggccag agtttctgac ttatttccag aatgaagctc aactagacaa atcggggctg | 180 |
| cccagtgatc gcttctttgc agaaaggcct gagggatccg tctccactct gaagatccag | 240 |
| cgcacacagc aggaggactc cgccgtgtat ctctgtgcca gcagcttagc | 290 |

<210> SEQ ID NO 177
<211> LENGTH: 290
<212> TYPE: DNA
<213> ORGANISM: Artificial Sequence
<220> FEATURE:
<223> OTHER INFORMATION: Description of Artificial Sequence: Synthetic
      TRBV7-8*02 sequence

<400> SEQUENCE: 177

| ggtgctggag tctcccagtc ccctaggtac aaagtcgcaa agagaggaca ggatgtagct | 60 |
| ctcaggtgtg atccaatttc gggtcatgta tccctttttt ggtaccaaca ggccctgggg | 120 |
| caggggccag agtttctgac ttatttccag aatgaagctc aactagacaa atcggggctg | 180 |
| cccagtgatc gcttctttgc agaaaggcct gagggatccg tctccactct gaagatccag | 240 |
| cgcacacaga aggaggactc cgccgtgtat ctctgtgcca gcagcttagc | 290 |

<210> SEQ ID NO 178
<211> LENGTH: 288
<212> TYPE: DNA
<213> ORGANISM: Artificial Sequence
<220> FEATURE:
<223> OTHER INFORMATION: Description of Artificial Sequence: Synthetic
      TRBV7-8*03 sequence

<400> SEQUENCE: 178

| ggtgctggag tctcccagtc ccctaggtac aaagtcgcaa agagaggaca ggatgtagct | 60 |
| ctcaggtgtg atccaatttc gggtcatgta tccctttttt ggtaccaaca ggccctcggg | 120 |
| caggggccag agtttctgac ttatttccag aatgaagctc aactagacaa atcggggctg | 180 |
| cccagtgatc gcttctttgc agaaaggcct gagggatccg tctccactct gaagatccag | 240 |
| cgcacacagc aggaggactc cgccgtgtat ctctgtgcca gcagccga | 288 |

<210> SEQ ID NO 179
<211> LENGTH: 288
<212> TYPE: DNA
<213> ORGANISM: Artificial Sequence
<220> FEATURE:
<223> OTHER INFORMATION: Description of Artificial Sequence: Synthetic
      TRBV7-9*05 sequence

<400> SEQUENCE: 179

| gatactggag tctcccagaa ccccagacac aagatcacaa agaggggaca gaatgtaact | 60 |
| ttcaggtgtg atccaatttc tgaacacaac cgcctttatt ggtaccgaca gacccctggg | 120 |
| cagggcccag agtttctgac ttacttccag aatgaagctc aactagaaaa atcaaggctg | 180 |
| ctcagtgatc ggttctctgc agagaggcct aagggatctc tctccacctt ggagatccag | 240 |
| cgcacagagc aggggggactc ggccatgtat ctctgtgcca gcaccaaa | 288 |

<210> SEQ ID NO 180
<211> LENGTH: 288
<212> TYPE: DNA
<213> ORGANISM: Artificial Sequence
<220> FEATURE:
<223> OTHER INFORMATION: Description of Artificial Sequence: Synthetic
      TRBV7-9*06 sequence

<400> SEQUENCE: 180
gatactggag tctcccagaa ccccagacac aagatcacaa agaggggaca gaatgtaact      60
ttcaggtgtg atccaatttc tgaacacaac cgcctttatt ggtaccgaca gaccctgggg     120
cagggcccag agtttctgac ttacttccag aatgaagctc aactagaaaa atcaaggctg     180
ctcagtgatc ggttctctgc agagaggcct aagggatctc tttccacctt ggagatccag     240
cgcacagagc aggggggactc ggccatgtat ctctgtgcca gcacgttg                 288

<210> SEQ ID NO 181
<211> LENGTH: 285
<212> TYPE: DNA
<213> ORGANISM: Artificial Sequence
<220> FEATURE:
<223> OTHER INFORMATION: Description of Artificial Sequence: Synthetic
      TRBV7-9*03 sequence

<400> SEQUENCE: 181
gatactggag tctcccagga ccccagacac aagatcacaa agaggggaca gaatgtaact      60
ttcaggtgtg atccaatttc tgaacacaac cgcctttatt ggtaccgaca gaccctgggg     120
cagggcccag agtttctgac ttacttccag aatgaagctc aactagaaaa atcaaggctg     180
ctcagtgatc ggttctctgc agagaggcct aagggatctt tctccacctt ggagatccag     240
cgcacagagc aggggggactc ggccatgtat ctctgtgcca gcagc                    285

<210> SEQ ID NO 182
<211> LENGTH: 290
<212> TYPE: DNA
<213> ORGANISM: Artificial Sequence
<220> FEATURE:
<223> OTHER INFORMATION: Description of Artificial Sequence: Synthetic
      TRBV7-9*01 sequence

<400> SEQUENCE: 182
gatactggag tctcccagaa ccccagacac aagatcacaa agaggggaca gaatgtaact      60
ttcaggtgtg atccaatttc tgaacacaac cgcctttatt ggtaccgaca gaccctgggg     120
cagggcccag agtttctgac ttacttccag aatgaagctc aactagaaaa atcaaggctg     180
ctcagtgatc ggttctctgc agagaggcct aagggatctt tctccacctt ggagatccag     240
cgcacagagc aggggggactc ggccatgtat ctctgtgcca gcagcttagc               290

<210> SEQ ID NO 183
<211> LENGTH: 288
<212> TYPE: DNA
<213> ORGANISM: Artificial Sequence
<220> FEATURE:
<223> OTHER INFORMATION: Description of Artificial Sequence: Synthetic
      TRBV7-9*02 sequence

<400> SEQUENCE: 183
gatactggag tctcccagaa ccccagacac aacatcacaa agaggggaca gaatgtaact      60
ttcaggtgtg atccaatttc tgaacacaac cgcctttatt ggtaccgaca gaccctgggg     120
cagggcccag agtttctgac ttacttccag aatgaagctc aactagaaaa atcaaggctg     180

```
ctcagtgatc ggttctctgc agagaggcct aagggatctt tctccacctt ggagatccag    240
cgcacagagc aggggactc ggccatgtat ctctgtgcca gcagctta                   288
```

```
<210> SEQ ID NO 184
<211> LENGTH: 207
<212> TYPE: DNA
<213> ORGANISM: Artificial Sequence
<220> FEATURE:
<223> OTHER INFORMATION: Description of Artificial Sequence: Synthetic
      TRBV7-9*07 sequence

<400> SEQUENCE: 184
cacaaccgcc tttattggta ccgacagacc ctggggcagg gcccagagtt tctgacttac    60
ttccagaatg aagctcaact agaaaaatca aggctgctca gtgatcggtt ctctgcagag   120
aggcctaagg gatctttctc caccttggag atccagcgca cagaggaggg ggactcggcc   180
atgtatctct gtgccagcag cagcagt                                        207
```

```
<210> SEQ ID NO 185
<211> LENGTH: 288
<212> TYPE: DNA
<213> ORGANISM: Artificial Sequence
<220> FEATURE:
<223> OTHER INFORMATION: Description of Artificial Sequence: Synthetic
      TRBV7-9*04 sequence

<400> SEQUENCE: 185
atatctggag tctcccacaa ccccagacac aagatcacaa agaggggaca gaatgtaact    60
ttcaggtgtg atccaatttc tgaacacaac cgcctttatt ggtaccgaca gaaccctggg   120
cagggcccag agtttctgac ttacttccag aatgaagctc aactggaaaa atcagggctg   180
ctcagtgatc ggatctctgc agagaggcct aagggatctt tctccacctt ggagatccag   240
cgcacagagc aggggactc ggccatgtat ctctgtgcca gcagctct                 288
```

```
<210> SEQ ID NO 186
<211> LENGTH: 279
<212> TYPE: DNA
<213> ORGANISM: Artificial Sequence
<220> FEATURE:
<223> OTHER INFORMATION: Description of Artificial Sequence: Synthetic
      TRBV8-1*01 sequence

<400> SEQUENCE: 186
gaggcaggga tcagccagat accaagatat cacagacaca cagggaaaaa gatcatcctg    60
aaatatgctc agattaggaa ccattattca gtgttctgtt atcaataaga ccaagaatag   120
gggctgaggc tgatccatta ttcaggtagt attggcagca tgaccaaagg cggtgccaag   180
gaagggtaca atgtctctgg aaacaagctc aagcattttc cctcaaccct ggagtctact   240
agcaccagcc agacctctgt acctctgtgg cagtgcatc                           279
```

```
<210> SEQ ID NO 187
<211> LENGTH: 271
<212> TYPE: DNA
<213> ORGANISM: Artificial Sequence
<220> FEATURE:
<223> OTHER INFORMATION: Description of Artificial Sequence: Synthetic
      TRBV8-2*01 sequence

<400> SEQUENCE: 187
gatgctggga tcacccagat gccaagatat cacattgtac agaagaaaga gatgatcctg    60
gaatgtgctc aggttaggaa cagtgttctg atatcgacag gacccaagac gggggctgaa   120
```

```
gcttatccac tattcaggca gtggtcacag caggaccaaa gttgatgtca cagagggta      180 ctgtgtttct tgaaacaagc ttgagcattt ccccaatcct ggcatccacc agcaccagcc      240
agacctatct gtaccactgt ggcagcacat c                                     271
```

<210> SEQ ID NO 188
<211> LENGTH: 286
<212> TYPE: DNA
<213> ORGANISM: Artificial Sequence
<220> FEATURE:
<223> OTHER INFORMATION: Description of Artificial Sequence: Synthetic
      TRBV9*01 sequence

<400> SEQUENCE: 188

```
gattctggag tcacacaaac cccaaagcac ctgatcacag caactggaca gcgagtgacg      60
ctgagatgct cccctaggtc tggagacctc tctgtgtact ggtaccaaca gagcctggac     120
cagggcctcc agttcctcat tcagtattat aatggagaag agagagcaaa aggaaacatt     180
cttgaacgat tctccgcaca acagttccct gacttgcact ctgaactaaa cctgagctct     240
ctggagctgg gggactcagc tttgtatttc tgtgccagca gcgtag                    286
```

<210> SEQ ID NO 189
<211> LENGTH: 282
<212> TYPE: DNA
<213> ORGANISM: Artificial Sequence
<220> FEATURE:
<223> OTHER INFORMATION: Description of Artificial Sequence: Synthetic
      TRBV9*03 sequence

<400> SEQUENCE: 189

```
gattctggag tcacacaaac cccaaagcac ctgatcacag caactggaca gcgagtgacg      60
ctgagatgct cccctaggtc tggagacctc tctgtgtact ggtaccaaca gagcctggac     120
cagggcctcc agttcctcat tcaatattat aatggagaag agagagcaaa aggaaacatt     180
cttgaacgat tctccgcaca acagttccct gacttgcact ctgaactaaa cctgagctct     240
ctggagctgg gggactcagc tttgtatttc tgtgccagca gc                        282
```

<210> SEQ ID NO 190
<211> LENGTH: 286
<212> TYPE: DNA
<213> ORGANISM: Artificial Sequence
<220> FEATURE:
<223> OTHER INFORMATION: Description of Artificial Sequence: Synthetic
      TRBV9*02 sequence

<400> SEQUENCE: 190

```
gattctggag tcacacaaac cccaaagcac ctgatcacag caactggaca gcgagtgacg      60
ctgagatgct cccctaggtc tggagacctc tctgtgtact ggtaccaaca gagcctggac     120
cagggcctcc agttcctcat tcactattat aatggagaag agagagcaaa aggaaacatt     180
cttgaacgat tctccgcaca acagttccct gacttgcact ctgaactaaa cctgagctct     240
ctggagctgg gggactcagc tttgtatttc tgtgccagca gcgtag                    286
```

<210> SEQ ID NO 191
<211> LENGTH: 287
<212> TYPE: DNA
<213> ORGANISM: Artificial Sequence
<220> FEATURE:
<223> OTHER INFORMATION: Description of Artificial Sequence: Synthetic
      TRBV10-1*01 sequence

<400> SEQUENCE: 191

```
gatgctgaaa tcacccagag cccaagacac aagatcacag agacaggaag gcaggtgacc      60
ttggcgtgtc accagacttg gaaccacaac aatatgttct ggtatcgaca agacctggga     120
catgggctga ggctgatcca ttactctat ggtgttcaag acactaacaa aggagaagtc     180
tcagatggct acagtgtctc tagatcaaac acagaggacc tcccctcac tctggagtct     240
gctgcctcct cccagacatc tgtatatttc tgcgccagca gtgagtc                  287
```

<210> SEQ ID NO 192
<211> LENGTH: 282
<212> TYPE: DNA
<213> ORGANISM: Artificial Sequence
<220> FEATURE:
<223> OTHER INFORMATION: Description of Artificial Sequence: Synthetic
      TRBV10-1*02 sequence

<400> SEQUENCE: 192

```
gatgctgaaa tcacccagag cccaagacac aagatcacag agacaggaag gcaggtgacc      60
ttggcgtgtc accagacttg gaaccacaac aatatgttct ggtatcgaca agacctggga     120
catgggctga ggctgatcca ttactctat ggtgttcacg acactaacaa aggagaagtc     180
tcagatggct acagtgtctc tagatcaaac acagaggacc tcccctcac tctggagtct     240
gctgcctcct cccagacatc tgtatatttc tgcgccagca gt                        282
```

<210> SEQ ID NO 193
<211> LENGTH: 287
<212> TYPE: DNA
<213> ORGANISM: Artificial Sequence
<220> FEATURE:
<223> OTHER INFORMATION: Description of Artificial Sequence: Synthetic
      TRBV10-2*01 sequence

<400> SEQUENCE: 193

```
gatgctggaa tcacccagag cccaagatac aagatcacag agacaggaag gcaggtgacc      60
ttgatgtgtc accagacttg gagccacagc tatatgttct ggtatcgaca agacctggga     120
catgggctga ggctgatcta ttactcagca gctgctgata ttacagataa aggagaagtc     180
cccgatggct atgttgtctc cagatccaag acagagaatt tcccctcac tctggagtca     240
gctacccgct cccagacatc tgtgtatttc tgcgccagca gtgagtc                  287
```

<210> SEQ ID NO 194
<211> LENGTH: 217
<212> TYPE: DNA
<213> ORGANISM: Artificial Sequence
<220> FEATURE:
<223> OTHER INFORMATION: Description of Artificial Sequence: Synthetic
      TRBV10-2*02 sequence

<400> SEQUENCE: 194

```
aaggcaggtg accttgatgt gtcaccagac ttggagccac agctatatgt tctggtatcg      60
acaagacctg ggacatgggc tgaggctgat ctattactca gcagctgctg atattacaga     120
taaaggagaa gtccccgatg gctacgttgt ctccagatcc aagacagaga atttccccct     180
cactctggag tcagctaccc gctcccagac atctgtg                              217
```

<210> SEQ ID NO 195
<211> LENGTH: 273
<212> TYPE: DNA
<213> ORGANISM: Artificial Sequence
<220> FEATURE:

<223> OTHER INFORMATION: Description of Artificial Sequence: Synthetic
      TRBV10-3*03 sequence

<400> SEQUENCE: 195

```
gatgctggaa tcacccagag cccaagacac aaggtcacag agacaggaac accagtgact     60
ctgagatgtc accagactga gaaccaccgc tacatgtact ggtatcgaca agacccgggg    120
catgggctga ggctaatcca ttactcatat ggtgttaaag atactgacaa aggagaagtc    180
tcagatggct atagtgtctc tagatcaaag acagaggatt cctcctcac tctggagtcc     240
gctaccagct cccagacatc tgtgtacttc tgt                                 273
```

<210> SEQ ID NO 196
<211> LENGTH: 273
<212> TYPE: DNA
<213> ORGANISM: Artificial Sequence
<220> FEATURE:
<223> OTHER INFORMATION: Description of Artificial Sequence: Synthetic
      TRBV10-3*04 sequence

<400> SEQUENCE: 196

```
gatgctggaa tcacccagag cccaagacac aaggtcacag agacaggaac accagtgact     60
ctgagatgtc accagactga gaaccaccgc tacatgtact ggtatcgaca agacccgggg    120
catgggctga ggctgatcca ttactcatat ggtgttaaag atactgacaa aggagaagtc    180
tcagatggct atagtgtctc tagatcaaag acagaggatt cctcctcac tctggagtcc     240
gctaccagct cccagacatc tgtgtacttc tgt                                 273
```

<210> SEQ ID NO 197
<211> LENGTH: 287
<212> TYPE: DNA
<213> ORGANISM: Artificial Sequence
<220> FEATURE:
<223> OTHER INFORMATION: Description of Artificial Sequence: Synthetic
      TRBV10-3*01 sequence

<400> SEQUENCE: 197

```
gatgctggaa tcacccagag cccaagacac aaggtcacag agacaggaac accagtgact     60
ctgagatgtc accagactga gaaccaccgc tatatgtact ggtatcgaca agacccgggg    120
catgggctga ggctgatcca ttactcatat ggtgttaaag atactgacaa aggagaagtc    180
tcagatggct atagtgtctc tagatcaaag acagaggatt cctcctcac tctggagtcc     240
gctaccagct cccagacatc tgtgtacttc tgtgccatca gtgagtc                  287
```

<210> SEQ ID NO 198
<211> LENGTH: 287
<212> TYPE: DNA
<213> ORGANISM: Artificial Sequence
<220> FEATURE:
<223> OTHER INFORMATION: Description of Artificial Sequence: Synthetic
      TRBV10-3*02 sequence

<400> SEQUENCE: 198

```
gatgctggaa tcacccagag cccaagacac aaggtcacag agacaggaac accagtgact     60
ctgagatgtc atcagactga gaaccaccgc tatatgtact ggtatcgaca agacccgggg    120
catgggctga ggctgatcca ttactcatat ggtgttaaag atactgacaa aggagaagtc    180
tcagatggct atagtgtctc tagatcaaag acagaggatt cctcctcac tctggagtcc     240
gctaccagct cccagacatc tgtgtacttc tgtgccatca gtgagtc                  287
```

```
<210> SEQ ID NO 199
<211> LENGTH: 290
<212> TYPE: DNA
<213> ORGANISM: Artificial Sequence
<220> FEATURE:
<223> OTHER INFORMATION: Description of Artificial Sequence: Synthetic
      TRBV11-1*01 sequence

<400> SEQUENCE: 199
gaagctgaag ttgcccagtc ccccagatat aagattacag agaaaagcca ggctgtggct      60
ttttggtgtg atcctatttc tggccatgct acccttact ggtaccggca gatcctggga     120
cagggcccgg agcttctggt tcaatttcag gatgagagtg tagtagatga ttcacagttg     180
cctaaggatc gattttctgc agagaggctc aaaggagtag actccactct caagatccag     240
cctgcagagc ttggggactc ggccatgtat ctctgtgcca gcagcttagc                290

<210> SEQ ID NO 200
<211> LENGTH: 290
<212> TYPE: DNA
<213> ORGANISM: Artificial Sequence
<220> FEATURE:
<223> OTHER INFORMATION: Description of Artificial Sequence: Synthetic
      TRBV11-3*01 sequence

<400> SEQUENCE: 200
gaagctggag tggttcagtc tcccagatat aagattatag agaaaaaaca gcctgtggct      60
ttttggtgca atcctatttc tggccacaat acccttact ggtacctgca gaacttggga     120
cagggcccgg agcttctgat tcgatatgag aatgaggaag cagtagacga ttcacagttg     180
cctaaggatc gattttctgc agagaggctc aaaggagtag actccactct caagatccag     240
cctgcagagc ttggggactc ggccgtgtat ctctgtgcca gcagcttaga                290

<210> SEQ ID NO 201
<211> LENGTH: 285
<212> TYPE: DNA
<213> ORGANISM: Artificial Sequence
<220> FEATURE:
<223> OTHER INFORMATION: Description of Artificial Sequence: Synthetic
      TRBV11-3*02 sequence

<400> SEQUENCE: 201
gaagctggag tggttcagtc tcccagatat aagattatag agaaaaagca gcctgtggct      60
ttttggtgca atcctatttc tggccacaat acccttact ggtaccggca gaacttggga     120
cagggcccgg agcttctgat tcgatatgag aatgaggaag cagtagacga ttcacagttg     180
cctaaggatc gattttctgc agagaggctc aaaggagtag actccactct caagatccag     240
cctgcagagc ttggggactc ggccgtgtat ctctgtgcca gcagc                     285

<210> SEQ ID NO 202
<211> LENGTH: 269
<212> TYPE: DNA
<213> ORGANISM: Artificial Sequence
<220> FEATURE:
<223> OTHER INFORMATION: Description of Artificial Sequence: Synthetic
      TRBV11-3*03 sequence

<400> SEQUENCE: 202
ggtctcccag atataagatt atagagaaga acagcctgt ggcttttttgg tgcaatccaa      60 tttctggcca caatacccctt tactggtacc tgcagaactt gggacagggc ccggagcttc    120
tgattcgata tgagaatgag gaagcagtag acgattcaca gttgcctaag gatcgatttt    180
```

```
ctgcagagag gctcaaagga gtagactcca ctctcaagat ccagccagca gagcttgggg      240
actcggccat gtatctctgt gccagcagc                                        269
```

<210> SEQ ID NO 203
<211> LENGTH: 290
<212> TYPE: DNA
<213> ORGANISM: Artificial Sequence
<220> FEATURE:
<223> OTHER INFORMATION: Description of Artificial Sequence: Synthetic
      TRBV11-2*01 sequence

<400> SEQUENCE: 203

```
gaagctggag ttgcccagtc tcccagatat aagattatag agaaaaggca gagtgtggct      60
ttttggtgca atcctatatc tggccatgct acccttact ggtaccagca gatcctggga       120
cagggcccaa agcttctgat tcagtttcag aataacggtg tagtggatga ttcacagttg      180
cctaaggatc gattttctgc agagaggctc aaaggagtag actccactct caagatccag      240
cctgcaaagc ttgaggactc ggccgtgtat ctctgtgcca gcagcttaga                 290
```

<210> SEQ ID NO 204
<211> LENGTH: 285
<212> TYPE: DNA
<213> ORGANISM: Artificial Sequence
<220> FEATURE:
<223> OTHER INFORMATION: Description of Artificial Sequence: Synthetic
      TRBV11-2*03 sequence

<400> SEQUENCE: 204

```
gaagctggag ttgcccagtc tcccagatat aagattatag agaaaaggca gagtgtggct      60
ttttggtgca atcctatatc tggccatgct acccttact ggtaccagca gatcctggga       120
cagggcccaa agcttctgat tcagtttcag aataacggtg tagtggatga ttcacagttg      180
cctaaggatc gattttctgc agagaggctc aaaggagtag actccactct caagatccaa      240
cctgcaaagc ttgaggactc ggccgtgtat ctctgtgcca gcagc                      285
```

<210> SEQ ID NO 205
<211> LENGTH: 285
<212> TYPE: DNA
<213> ORGANISM: Artificial Sequence
<220> FEATURE:
<223> OTHER INFORMATION: Description of Artificial Sequence: Synthetic
      TRBV11-2*02 sequence

<400> SEQUENCE: 205

```
gaagctggag ttgcccagtc tcccagatat aagattatag agaaaaggca gagtgtggct      60
ttttggtgca atcctatatc tggccatgct acccttact ggtaccagca gatcctggga       120
cagggcccaa agcttctgat tcagtttcag aataacggtg tagtggatga ttcacagttg      180
cctaaggatc gattttctgc agagaggctc aaaggagtag actccactct caagatccag      240
cctgcaaagc ttgagaactc ggccgtgtat ctctgtgcca gcagt                      285
```

<210> SEQ ID NO 206
<211> LENGTH: 290
<212> TYPE: DNA
<213> ORGANISM: Artificial Sequence
<220> FEATURE:
<223> OTHER INFORMATION: Description of Artificial Sequence: Synthetic
      TRBV12-1*01 sequence

<400> SEQUENCE: 206

```
gatgctggtg ttatccagtc acccaggcac aaagtgacag agatgggaca atcagtaact      60
```

```
ctgagatgcg aaccaatttc aggccacaat gatcttctct ggtacagaca gacctttgtg      120
cagggactgg aattgctgaa ttacttctgc agctggaccc tcgtagatga ctcaggagtg      180
tccaaggatt gattctcagc acagatgcct gatgtatcat tctccactct gaggatccag      240
cccatggaac ccagggactt gggcctatat ttctgtgcca gcagctttgc                 290

<210> SEQ ID NO 207
<211> LENGTH: 290
<212> TYPE: DNA
<213> ORGANISM: Artificial Sequence
<220> FEATURE:
<223> OTHER INFORMATION: Description of Artificial Sequence: Synthetic
      TRBV12-2*01 sequence

<400> SEQUENCE: 207
gatgctggca ttatccagtc acccaagcat gaggtgacag aaatgggaca acagtgact       60 ctgagatgtg agccaatttt tggccacaat ttccttttct ggtacagaga taccttcgtg     120
cagggactgg aattgctgag ttacttccgg agctgatcta ttatagataa tgcaggtatg     180
cccacagagc gattctcagc tgagaggcct gatggatcat tctctactct gaagatccag     240
cctgcagagc aggggactc ggccgtgtat gtctgtgcaa gtcgcttagc                  290

<210> SEQ ID NO 208
<211> LENGTH: 290
<212> TYPE: DNA
<213> ORGANISM: Artificial Sequence
<220> FEATURE:
<223> OTHER INFORMATION: Description of Artificial Sequence: Synthetic
      TRBV12-4*01 sequence

<400> SEQUENCE: 208
gatgctggag ttatccagtc accccggcac gaggtgacag agatgggaca agaagtgact      60
ctgagatgta aaccaatttc aggacacgac taccttttct ggtacagaca gaccatgatg     120
cggggactgg agttgctcat ttactttaac aacaacgttc cgatagatga ttcagggatg     180
cccgaggatc gattctcagc taagatgcct aatgcatcat tctccactct gaagatccag     240
ccctcagaac ccagggactc agctgtgtac ttctgtgcca gcagtttagc                 290

<210> SEQ ID NO 209
<211> LENGTH: 288
<212> TYPE: DNA
<213> ORGANISM: Artificial Sequence
<220> FEATURE:
<223> OTHER INFORMATION: Description of Artificial Sequence: Synthetic
      TRBV12-4*02 sequence

<400> SEQUENCE: 209
gatgctggag ttatccagtc accccggcac gaggtgacag agatgggaca agaagtgact      60
ctgagatgta aaccaatttc aggacatgac taccttttct ggtacagaca gaccatgatg     120
cggggactgg agttgctcat ttactttaac aacaacgttc cgatagatga ttcagggatg     180
cccgaggatc gattctcagc taagatgcct aatgcatcat tctccactct gaggatccag     240
ccctcagaac ccagggactc agctgtgtac ttctgtgcca gcagttta                   288

<210> SEQ ID NO 210
<211> LENGTH: 290
<212> TYPE: DNA
<213> ORGANISM: Artificial Sequence
<220> FEATURE:
<223> OTHER INFORMATION: Description of Artificial Sequence: Synthetic
```

-continued

TRBV12-3*01 sequence

<400> SEQUENCE: 210
gatgctggag ttatccagtc accccgccat gaggtgacag agatgggaca agaagtgact    60
ctgagatgta aaccaatttc aggccacaac tccctttctt ggtacagaca gaccatgatg   120
cggggactgg agttgctcat ttactttaac aacaacgttc cgatagatga ttcaggatg    180 cccgaggatc gattctcagc taagatgcct aatgcatcat tctccactct gaagatccag   240
ccctcagaac ccagggactc agctgtgtac ttctgtgcca gcagtttagc              290

<210> SEQ ID NO 211
<211> LENGTH: 290
<212> TYPE: DNA
<213> ORGANISM: Artificial Sequence
<220> FEATURE:
<223> OTHER INFORMATION: Description of Artificial Sequence: Synthetic
      TRBV12-5*01 sequence

<400> SEQUENCE: 211
gatgctagag tcacccagac accaaggcac aaggtgacag agatgggaca agaagtaaca    60
atgagatgtc agccaatttt aggccacaat actgttttct ggtacagaca gaccatgatg   120
caaggactgg agttgctggc ttacttccgc aaccgggctc ctctagatga ttcggggatg   180
ccgaaggatc gattctcagc agagatgcct gatgcaactt tagccactct gaagatccag   240
ccctcagaac ccagggactc agctgtgtat ttttgtgcta gtggtttggt              290

<210> SEQ ID NO 212
<211> LENGTH: 287
<212> TYPE: DNA
<213> ORGANISM: Artificial Sequence
<220> FEATURE:
<223> OTHER INFORMATION: Description of Artificial Sequence: Synthetic
      TRBV13*01 sequence

<400> SEQUENCE: 212
gctgctggag tcatccagtc cccaagacat ctgatcaaag aaaagaggga aacagccact    60
ctgaaatgct atcctatccc tagacacgac actgtcctact ggtaccagca gggtccaggt   120
caggaccccc agttcctcat ttcgttttat gaaaagatgc agagcgataa aggaagcatc   180
cctgatcgat tctcagctca acagttcagt gactatcatt ctgaactgaa catgagctcc   240
ttggagctgg gggactcagc cctgtacttc tgtgccagca gcttagg                 287

<210> SEQ ID NO 213
<211> LENGTH: 282
<212> TYPE: DNA
<213> ORGANISM: Artificial Sequence
<220> FEATURE:
<223> OTHER INFORMATION: Description of Artificial Sequence: Synthetic
      TRBV13*02 sequence

<400> SEQUENCE: 213
gctgctggag tcatccagtc cccaagacat ctgatcagag aaaagaggga aacagccact    60
ctgaaatgct atcctatccc tagacacgac actgtcctact ggtaccagca gggcccaggt   120
caggaccccc agttcttcat ttcgttttat gaaaagatgc agagcgataa aggaagcatc   180
cctgatcgat tctcagctca acagttcagt gactatcatt ctgaactgaa catgagctcc   240
ttggagctgg gggactcagc cctgtacttc tgtgccagca gc                      282

<210> SEQ ID NO 214

<211> LENGTH: 290
<212> TYPE: DNA
<213> ORGANISM: Artificial Sequence
<220> FEATURE:
<223> OTHER INFORMATION: Description of Artificial Sequence: Synthetic
      TRBV14*01 sequence

<400> SEQUENCE: 214
gaagctggag ttactcagtt ccccagccac agcgtaatag agaagggcca gactgtgact     60
ctgagatgtg acccaatttc tggacatgat aatctttatt ggtatcgacg tgttatggga    120
aaagaaataa aatttctgtt acattttgtg aaagagtcta acaggatga gtccggtatg     180 cccaacaatc gattcttagc tgaaaggact ggagggacgt attctactct gaaggtgcag    240
cctgcagaac tggaggattc tggagtttat ttctgtgcca gcagccaaga              290

<210> SEQ ID NO 215
<211> LENGTH: 285
<212> TYPE: DNA
<213> ORGANISM: Artificial Sequence
<220> FEATURE:
<223> OTHER INFORMATION: Description of Artificial Sequence: Synthetic
      TRBV14*02 sequence

<400> SEQUENCE: 215
gaagctggag ttactcagtt ccccagccac agcgtaatag agaagggcca gactgtgact     60
ctgagatgtg acccaatttc tggacatgat aatctttatt ggtatcgacg tgttatggga    120
aaagaaataa aatttctgtt acattttgtg aaagagtcta acaggatga atccggtatg     180 cccaacaatc gattcttagc tgaaaggact ggagggacgt attctactct gaaggtgcag    240
cctgcagaac tggaggattc tggagtttat ttctgtgcca gcagc                   285

<210> SEQ ID NO 216
<211> LENGTH: 287
<212> TYPE: DNA
<213> ORGANISM: Artificial Sequence
<220> FEATURE:
<223> OTHER INFORMATION: Description of Artificial Sequence: Synthetic
      TRBV15*01 sequence

<400> SEQUENCE: 216
gatgccatgg tcatccagaa cccaagatac caggttaccc agtttggaaa gccagtgacc     60
ctgagttgtt ctcagacttt gaaccataac gtcatgtact ggtaccagca gaagtcaagt    120
caggccccaa agctgctgtt ccactactat gacaaagatt ttaacaatga agcagacacc    180
cctgataact tccaatccag gaggccgaac acttctttct gctttcttga catccgctca    240
ccaggcctgg gggacacagc catgtacctg tgtgccacca gcagaga                 287

<210> SEQ ID NO 217
<211> LENGTH: 282
<212> TYPE: DNA
<213> ORGANISM: Artificial Sequence
<220> FEATURE:
<223> OTHER INFORMATION: Description of Artificial Sequence: Synthetic
      TRBV15*03 sequence

<400> SEQUENCE: 217
gatgccatgg tcatccagaa cccaagatac cgggttaccc agtttggaaa gccagtgacc     60
ctgagttgtt ctcagacttt gaaccataac gtcatgtact ggtaccagca gaagtcaagt    120
caggccccaa agctgctgtt ccactactat aacaaagatt ttaacaatga agcagacacc    180
cctgataact tccaatccag gaggccgaac acttctttct gctttctaga catccgctca    240

```
ccaggcctgg gggacgcagc catgtaccag tgtgccacca gc              282
```

<210> SEQ ID NO 218
<211> LENGTH: 282
<212> TYPE: DNA
<213> ORGANISM: Artificial Sequence
<220> FEATURE:
<223> OTHER INFORMATION: Description of Artificial Sequence: Synthetic
      TRBV15*02 sequence

<400> SEQUENCE: 218

```
gatgccatgg tcatccagaa cccaagatac caggttaccc agtttggaaa gccagtgacc   60
ctgagttgtt ctcagacttt gaaccataac gtcatgtact ggtaccagca gaagtcaagt  120
caggccccaa agctgctgtt ccactactat gacaaagatt ttaacaatga agcagacacc  180
cctgataact tccaatccag gaggccgaac acttctttct gctttcttga catccgctca  240
ccaggcctgg gggacgcagc catgtacctg tgtgccacca gc                     282
```

<210> SEQ ID NO 219
<211> LENGTH: 290
<212> TYPE: DNA
<213> ORGANISM: Artificial Sequence
<220> FEATURE:
<223> OTHER INFORMATION: Description of Artificial Sequence: Synthetic
      TRBV16*01 sequence

<400> SEQUENCE: 219

```
ggtgaagaag tcgcccagac tccaaaacat cttgtcagag gggaaggaca gaaagcaaaa   60
ttatattgtg ccccaataaa aggacacagt tatgtttttt ggtaccaaca ggtcctgaaa  120
aacgagttca gttcttgat ttccttccag aatgaaaatg tctttgatga aacaggtatg   180
cccaaggaaa gattttcagc taagtgcctc ccaaattcac cctgtagcct tgagatccag  240
gctacgaagc ttgaggattc agcagtgtat ttttgtgcca gcagccaatc               290
```

<210> SEQ ID NO 220
<211> LENGTH: 290
<212> TYPE: DNA
<213> ORGANISM: Artificial Sequence
<220> FEATURE:
<223> OTHER INFORMATION: Description of Artificial Sequence: Synthetic
      TRBV16*02 sequence

<400> SEQUENCE: 220

```
ggtgaagaag tcgcccagac tccaaaacat cttgtcagag gggaaggaca gaaagcaaaa   60
ttatattgtg ccccaataaa aggacacagt taggtttttt ggtaccaaca ggtcctgaaa  120
aacgagttca gttcttgat ttccttccag aatgaaaatg tctttgatga aacaggtatg   180
cccaaggaaa gattttcagc taagtgcctc ccaaattcac cctgtagcct tgagatccag  240
gctacgaagc ttgaggattc agcagtgtat ttttgtgcca gcagccaatc               290
```

<210> SEQ ID NO 221
<211> LENGTH: 285
<212> TYPE: DNA
<213> ORGANISM: Artificial Sequence
<220> FEATURE:
<223> OTHER INFORMATION: Description of Artificial Sequence: Synthetic
      TRBV16*03 sequence

<400> SEQUENCE: 221

```
ggtgaagaag tcgcccagac tccaaaacat cttgtcagag gggaaggaca gaaagcaaaa   60
```

```
ttatattgtg ccccaataaa aggacacagt tatgtttttt ggtaccaaca ggtcctgaaa      120
aacgagttca agttcttggt ttccttccag aatgaaaatg tctttgatga aacaggtatg      180
cccaaggaaa gattttcagc taagtgcctc ccaaattcac cctgtagcct tgagatccag      240
gctacgaagc ttgaggattc agcagtgtat ttttgtgcca gcagc                     285
```

<210> SEQ ID NO 222
<211> LENGTH: 287
<212> TYPE: DNA
<213> ORGANISM: Artificial Sequence
<220> FEATURE:
<223> OTHER INFORMATION: Description of Artificial Sequence: Synthetic
      TRBV17*01 sequence

<400> SEQUENCE: 222

```
gagcctggag tcagccagac ccccagacac aaggtcacca acatgggaca ggaggtgatt      60
ctgaggtgcg atccatcttc tggtcacatg tttgttcact ggtaccgaca gaatctgagg     120
caagaaatga agttgctgat tccttccag taccaaaaca ttgcagttga ttcagggatg       180
cccaaggaac gattcacagc tgaaagacct aacggaacgt cttccacgct gaagatccat     240
cccgcagagc cgagggactc agccgtgtat ctctacagta gcggtgg                   287
```

<210> SEQ ID NO 223
<211> LENGTH: 290
<212> TYPE: DNA
<213> ORGANISM: Artificial Sequence
<220> FEATURE:
<223> OTHER INFORMATION: Description of Artificial Sequence: Synthetic
      TRBV18*01 sequence

<400> SEQUENCE: 223

```
aatgccggcg tcatgcagaa cccaagacac ctggtcagga ggaggggaca ggaggcaaga      60
ctgagatgca gcccaatgaa aggacacagt catgtttact ggtatcggca gctcccagag     120
gaaggtctga aattcatggt ttatctccag aaagaaaata tcatagatga gtcaggaatg     180
ccaaaggaac gatttctgc tgaatttccc aaagagggcc ccagcatcct gaggatccag       240
caggtagtgc gaggagattc ggcagcttat ttctgtgcca gctcaccacc                290
```

<210> SEQ ID NO 224
<211> LENGTH: 287
<212> TYPE: DNA
<213> ORGANISM: Artificial Sequence
<220> FEATURE:
<223> OTHER INFORMATION: Description of Artificial Sequence: Synthetic
      TRBV19*01 sequence

<400> SEQUENCE: 224

```
gatggtggaa tcactcagtc cccaaagtac ctgttcagaa aggaaggaca gaatgtgacc      60
ctgagttgtg aacagaattt gaaccacgat gccatgtact ggtaccgaca ggacccaggg     120
caagggctga gattgatcta ctactcacag atagtaaatg actttcagaa aggagatata     180
gctgaagggt acagcgtctc tcgggagaag aaggaatcct ttcctctcac tgtgacatcg     240
gcccaaaaga acccgacagc tttctatctc tgtgccagta gtataga                  287
```

<210> SEQ ID NO 225
<211> LENGTH: 287
<212> TYPE: DNA
<213> ORGANISM: Artificial Sequence
<220> FEATURE:
<223> OTHER INFORMATION: Description of Artificial Sequence: Synthetic
      TRBV19*02 sequence

<400> SEQUENCE: 225

```
gatggtggaa tcactcagtc cccaaagtac ctgttcagaa aggaaggaca gaatgtgacc      60
ctgagttgtg aacagaattt gaaccacgat gccatgtact ggtaccgaca ggtcccaggg     120
caagggctga gattgatcta ctactcacac atagtaaatg actttcagaa aggagatata    180
gctgaagggt acagcgtctc tcgggagaag aaggaatcct ttcctctcac tgtgacatcg    240
gcccaaaaga acccgacagc tttctatctc tgtgccagta gtataga                  287
```

<210> SEQ ID NO 226
<211> LENGTH: 282
<212> TYPE: DNA
<213> ORGANISM: Artificial Sequence
<220> FEATURE:
<223> OTHER INFORMATION: Description of Artificial Sequence: Synthetic
TRBV19*03 sequence

<400> SEQUENCE: 226

```
gatggtggaa tcactcagtc cccaaagtac ctgttcagaa aggaaggaca gaatgtgacc      60
ctgagttgtg aacagaattt gaaccacgat gccatgtact ggtaccgaca ggacccaggg     120
caagggctga gattgatcta ctactcacac atagtaaatg actttcagaa aggagatata    180
gctgaagggt acagcgtctc tcgggagaag aaggaatcct ttcctctcac tgtgacatcg    240
gcccaaaaga acccgacagc tttctatctc tgtgccagta gc                       282
```

<210> SEQ ID NO 227
<211> LENGTH: 291
<212> TYPE: DNA
<213> ORGANISM: Artificial Sequence
<220> FEATURE:
<223> OTHER INFORMATION: Description of Artificial Sequence: Synthetic
TRBV20-1*05 sequence

<400> SEQUENCE: 227

```
ggtgctgtcg tctctcaaca tccgagcagg gttatctgta agagtggaac ctctgtgaag      60
atcgagtgcc gttccctgga ctttcaggcc acaactatgt tttggtatcg tcagttcccg     120
aaaaagagtc tcatgctgat ggcaacttcc aatgagggct ccaaggccac atacgagcaa    180
ggcgtcgaga aggacaagtt tctcatcaac catgcaagcc tgaccttgtc cactctgaca    240
gtgaccagtg cccatcctga agacagcagc ttctacatct gcagtgctag a             291
```

<210> SEQ ID NO 228
<211> LENGTH: 291
<212> TYPE: DNA
<213> ORGANISM: Artificial Sequence
<220> FEATURE:
<223> OTHER INFORMATION: Description of Artificial Sequence: Synthetic
TRBV20-1*07 sequence

<400> SEQUENCE: 228

```
ggtgctgtcg tctctcaaca tccgagcagg gttatctgta agagtggaac ctctgtgaag      60
atcgagtgcc gttccctgga ctttcaggcc acaactatgt tttggtatcg tcagttcccg     120
aaaaagagtc tcatgcagat cgcaacttcc aatgagggct ccaaggccac atacgagcaa    180
ggcgtcgaga aggacaagtt tctcatcaac catgcaagcc tgaccttgtc cactctgaca    240
gtgaccagtg cccatcctga agacagcagc ttctacatct gcagtgctag a             291
```

<210> SEQ ID NO 229
<211> LENGTH: 291

```
<212> TYPE: DNA
<213> ORGANISM: Artificial Sequence
<220> FEATURE:
<223> OTHER INFORMATION: Description of Artificial Sequence: Synthetic
      TRBV20-1*04 sequence

<400> SEQUENCE: 229
ggtgctgtcg tctctcaaca tccgagcagg gttatctgta agagtggaac ctctgtgaag    60
atcgagtgcc gttccttgga ctttcaggcc acaactatgt tttggtatcg tcagttcccg   120
aaaaagagtc tcatgctgat ggcaacttcc aatgagggct ccaaggccac atacgagcaa   180
ggcgtcgaga aggacaagtt tctcatcaac catgcaagcc tgaccttgtc cactctgaca   240
gtgaccagtg cccatcctga agacagcagc ttctacatct gcagtgctag t            291

<210> SEQ ID NO 230
<211> LENGTH: 288
<212> TYPE: DNA
<213> ORGANISM: Artificial Sequence
<220> FEATURE:
<223> OTHER INFORMATION: Description of Artificial Sequence: Synthetic
      TRBV20-1*06 sequence

<400> SEQUENCE: 230
ggtgctgtcg tctctcaaca tccgagtagg gttatctgta agagtggaac ctctgtgaag    60
atcgagtgcc gttccctgga ctttcaggcc acaactatgt tttggtatcg tcagttcccg   120
aaaaagagtc tcatgctgat ggcaacttcc aatgagggct ccaaggccac atacgagcaa   180
ggcgtcgaga aggacaagtt tctcatcaac catgcaagcc tgaccttgtc cactctgaca   240
gtgaccagtg cccatcctga agacagcagc ttctacatct gcagtgct                288

<210> SEQ ID NO 231
<211> LENGTH: 288
<212> TYPE: DNA
<213> ORGANISM: Artificial Sequence
<220> FEATURE:
<223> OTHER INFORMATION: Description of Artificial Sequence: Synthetic
      TRBV20-1*02 sequence

<400> SEQUENCE: 231
ggtgctgtcg tctctcaaca tccgagcagg gttatctgta agagtggaac ctctgtgaag    60
atcgagtgcc gttccctgga ctttcaggcc acaactatgt tttggtatcg tcagttcccg   120
aaacagagtc tcatgctgat ggcaacttcc aatgagggct ccaaggccac atacgagcaa   180
ggcgtcgaga aggacaagtt tctcatcaac catgcaagcc tgaccttgtc cactctgaca   240
gtgaccagtg cccatcctga agacagcagc ttctacatct gcagtgct                288

<210> SEQ ID NO 232
<211> LENGTH: 293
<212> TYPE: DNA
<213> ORGANISM: Artificial Sequence
<220> FEATURE:
<223> OTHER INFORMATION: Description of Artificial Sequence: Synthetic
      TRBV20-1*01 sequence

<400> SEQUENCE: 232
ggtgctgtcg tctctcaaca tccgagctgg gttatctgta agagtggaac ctctgtgaag    60
atcgagtgcc gttccctgga ctttcaggcc acaactatgt tttggtatcg tcagttcccg   120
aaacagagtc tcatgctgat ggcaacttcc aatgagggct ccaaggccac atacgagcaa   180
ggcgtcgaga aggacaagtt tctcatcaac catgcaagcc tgaccttgtc cactctgaca   240
```

```
gtgaccagtg cccatcctga agacagcagc ttctacatct gcagtgctag aga          293
```

<210> SEQ ID NO 233
<211> LENGTH: 288
<212> TYPE: DNA
<213> ORGANISM: Artificial Sequence
<220> FEATURE:
<223> OTHER INFORMATION: Description of Artificial Sequence: Synthetic
      TRBV20-1*03 sequence

<400> SEQUENCE: 233

```
ggtgctgtcg tctctcaaca tccgagctgg gttatctgta agagtggaac ctctgtgaag    60
atcgagtgcc gttccctgga ctttcaggcc acaactatgt tttggtatcg tcagttcccg   120
aaacagagtc tcatgctgat ggcaacttcc aatgagggct gcaaggccac atacgagcaa   180
ggcgtcgaga aggacaagtt tctcatcaac catgcaagcc tgaccttgtc cactctgaca   240
gtgaccagtg cccatcctga agacagcagc ttctacatct gcagtgct               288
```

<210> SEQ ID NO 234
<211> LENGTH: 290
<212> TYPE: DNA
<213> ORGANISM: Artificial Sequence
<220> FEATURE:
<223> OTHER INFORMATION: Description of Artificial Sequence: Synthetic
      TRBV21-1*01 sequence

<400> SEQUENCE: 234

```
gacaccaagg tcacccagag acctagactt ctggtcaaag caagtgaaca gaaagcaaag    60
atggattgtg ttcctataaa agcacatagt tatgtttact ggtatcgtaa gaagctggaa   120
gaagagctca gttttttggt ttactttcag aatgaagaac ttattcagaa agcagaaata   180
atcaatgagc gattttagc ccaatgctcc aaaaactcat cctgtacctt ggagatccag   240
tccacggagt cagggacaca agcactgtat ttctgtgcca gcagcaaagc               290
```

<210> SEQ ID NO 235
<211> LENGTH: 288
<212> TYPE: DNA
<213> ORGANISM: Artificial Sequence
<220> FEATURE:
<223> OTHER INFORMATION: Description of Artificial Sequence: Synthetic
      TRBV22-1*01 sequence

<400> SEQUENCE: 235

```
gatgctgaca tctatcagat gccattccag ctcactgggg ctggatggga tgtgactctg    60
gagtggaaac ggaatttgag acacaatgac atgtactgct actggtactg gcaggaccca   120
aagcaaaatc tgagactgat ctattactca agggttgaaa aggatattca gagaggagat   180
ctaactgaag gctacgtgtc tgccaagagg agaaggggac atttcttctc agggtgaagt   240
tggcccacac cagccaaaca gctttgtact tctgtcctgg gagcgcac                288
```

<210> SEQ ID NO 236
<211> LENGTH: 290
<212> TYPE: DNA
<213> ORGANISM: Artificial Sequence
<220> FEATURE:
<223> OTHER INFORMATION: Description of Artificial Sequence: Synthetic
      TRBV23-1*01 sequence

<400> SEQUENCE: 236

```
catgccaaag tcacacagac tccaggacat ttggtcaaag gaaaaggaca gaaaacaaag    60
atggattgta cccccgaaaa aggacatact tttgtttatt ggtatcaaca gaatcagaat   120
```

```
aaagagttta tgcttttgat ttcctttcag aatgaacaag ttcttcaaga aacggagatg    180
cacaagaagc gattctcatc tcaatgcccc aagaacgcac cctgcagcct ggcaatcctg    240
tcctcagaac cgggagacac ggcactgtat ctctgcgcca gcagtcaatc                290
```

<210> SEQ ID NO 237
<211> LENGTH: 288
<212> TYPE: DNA
<213> ORGANISM: Artificial Sequence
<220> FEATURE:
<223> OTHER INFORMATION: Description of Artificial Sequence: Synthetic
      TRBV24-1*01 sequence

<400> SEQUENCE: 237

```
gatgctgatg ttacccagac cccaaggaat aggatcacaa agacaggaaa gaggattatg     60
ctggaatgtt ctcagactaa gggtcatgat agaatgtact ggtatcgaca agacccagga    120
ctgggcctac ggttgatcta ttactccttt gatgtcaaag atataaacaa aggagagatc    180
tctgatggat acagtgtctc tcgacaggca caggctaaat tctccctgtc cctagagtct    240 gccatccccca accagacagc tctttacttc tgtgccacca gtgatttg                288
```

<210> SEQ ID NO 238
<211> LENGTH: 287
<212> TYPE: DNA
<213> ORGANISM: Artificial Sequence
<220> FEATURE:
<223> OTHER INFORMATION: Description of Artificial Sequence: Synthetic
      TRBV25-1*01 sequence

<400> SEQUENCE: 238

```
gaagctgaca tctaccagac cccaagatac cttgttatag ggacaggaaa gaagatcact     60
ctggaatgtt ctcaaaccat gggccatgac aaaatgtact ggtatcaaca agatccagga    120
atggaactac acctcatcca ctattcctat ggagttaatt ccacagagaa gggagatctt    180
tcctctgagt caacagtctc cagaataagg acggagcatt ttcccctgac cctggagtct    240
gccaggccct cacatacctc tcagtacctc tgtgccagca gtgaata                  287
```

<210> SEQ ID NO 239
<211> LENGTH: 287
<212> TYPE: DNA
<213> ORGANISM: Artificial Sequence
<220> FEATURE:
<223> OTHER INFORMATION: Description of Artificial Sequence: Synthetic
      TRBV26*01 sequence

<400> SEQUENCE: 239

```
gatgctgtag ttacacaatt cccaagacac agaatcattg gacaggaaa ggaattcatt      60 ctacagtgtt cccagaatat gaatcatgtt acaatgtact ggtatcgaca ggacccagga    120
cttggactga agctggtcta ttattcacct ggcactggga gcactgaaaa aggagatatc    180
tctgaggggt atcatgtttc ttgaaatact atagcatctt ttcccctgac cctgaagtct    240
gccagcacca accagacatc tgtgtatctc tatgccagca gttcatc                  287
```

<210> SEQ ID NO 240
<211> LENGTH: 287
<212> TYPE: DNA
<213> ORGANISM: Artificial Sequence
<220> FEATURE:
<223> OTHER INFORMATION: Description of Artificial Sequence: Synthetic
      TRBV27*01 sequence

<400> SEQUENCE: 240
gaagcccaag tgacccagaa cccaagatac ctcatcacag tgactggaaa gaagttaaca    60
gtgacttgtt ctcagaatat gaaccatgag tatatgtcct ggtatcgaca agacccaggg   120
ctgggcttaa ggcagatcta ctattcaatg aatgttgagg tgactgataa gggagatgtt   180
cctgaagggt acaaagtctc tcgaaaagag aagaggaatt tcccctgat cctggagtcg    240 cccagcccca accagacctc tctgtacttc tgtgccagca gtttatc                 287

<210> SEQ ID NO 241
<211> LENGTH: 287
<212> TYPE: DNA
<213> ORGANISM: Artificial Sequence
<220> FEATURE:
<223> OTHER INFORMATION: Description of Artificial Sequence: Synthetic
      TRBV28*01 sequence

<400> SEQUENCE: 241
gatgtgaaag taacccagag ctcgagatat ctagtcaaaa ggacgggaga gaaagttttt    60
ctggaatgtg tccaggatat ggaccatgaa atatgttct ggtatcgaca agacccaggt    120
ctggggctac ggctgatcta tttctcatat gatgttaaaa tgaaagaaaa aggagatatt   180 cctgagggt acagtgtctc tagagagaag aaggagcgct ctcccctgat tctggagtcc   240
gccagcacca accagacatc tatgtacctc tgtgccagca gtttatg                 287

<210> SEQ ID NO 242
<211> LENGTH: 290
<212> TYPE: DNA
<213> ORGANISM: Artificial Sequence
<220> FEATURE:
<223> OTHER INFORMATION: Description of Artificial Sequence: Synthetic
      TRBV29-1*01 sequence

<400> SEQUENCE: 242
agtgctgtca tctctcaaaa gccaagcagg gatatctgtc aacgtggaac ctccctgacg    60
atccagtgtc aagtcgatag ccaagtcacc atgatgttct ggtaccgtca gcaacctgga   120
cagagcctga cactgatcgc aactgcaaat cagggctctg aggccacata tgagagtgga   180
tttgtcattg acaagtttcc catcagccgc ccaaacctaa cattctcaac tctgactgtg   240
agcaacatga gccctgaaga cagcagcata tatctctgca gcgttgaaga              290

<210> SEQ ID NO 243
<211> LENGTH: 288
<212> TYPE: DNA
<213> ORGANISM: Artificial Sequence
<220> FEATURE:
<223> OTHER INFORMATION: Description of Artificial Sequence: Synthetic
      TRBV29-1*02 sequence

<400> SEQUENCE: 243
agtgctgtca tctctcaaaa gccaagcagg gatatctgtc aacgtggaac ctccctgacg    60
atccagtgtc aagtcgatag ccaagtcacc atgatgttct ggtaccgtca gcaacctgga   120
cagagcctga cactgatcgc aactgcaaat cagggctctg aggccacata tgagagtgga   180
tttgtcattg acaagtttcc catcagccgc ccaaacctaa cattctcaag tctgactgtg   240
agcaacatga gccctgaaga cagcagcata tatctctgca gcgttgaa                288

<210> SEQ ID NO 244
<211> LENGTH: 231
<212> TYPE: DNA

<213> ORGANISM: Artificial Sequence
<220> FEATURE:
<223> OTHER INFORMATION: Description of Artificial Sequence: Synthetic
      TRBV29-1*03 sequence

<400> SEQUENCE: 244

```
acgatccagt gtcaagtcga tagccaagtc accatgatat tctggtaccg tcagcaacct    60
ggacagagcc tgacactgat cgcaactgca aatcagggct ctgaggccac atatgagagt   120
ggatttgtca ttgacaagtt tcccatcagc cgcccaaacc taacattctc aactctgact   180
gtgagcaaca tgagccctga agacagcagc atatatctct gcagcgcggg c            231
```

<210> SEQ ID NO 245
<211> LENGTH: 284
<212> TYPE: DNA
<213> ORGANISM: Artificial Sequence
<220> FEATURE:
<223> OTHER INFORMATION: Description of Artificial Sequence: Synthetic
      TRBV30*02 sequence

<400> SEQUENCE: 245

```
tctcagacta ttcatcaatg gccagcgacc ctggtgcagc ctgtgggcag cccgctctct    60
ctggagtgca ctgtggaggg aacatcaaac cccaacctat actggtaccg acaggctgca   120
ggcaggggcc tccagctgct cttctactcc gttggtattg gccagatcag ctctgaggtg   180
ccccagaatc tctcagcctc cagaccccag gaccggcagt tcatcctgag ttctaagaag   240
ctcctcctca gtgactctgg cttctatctc tgtgcctgga gtgt                     284
```

<210> SEQ ID NO 246
<211> LENGTH: 282
<212> TYPE: DNA
<213> ORGANISM: Artificial Sequence
<220> FEATURE:
<223> OTHER INFORMATION: Description of Artificial Sequence: Synthetic
      TRBV30*05 sequence

<400> SEQUENCE: 246

```
tctcagacta ttcatcaatg gccagcgacc ctggtgcagc ctgtgggcag cccgctctcc    60
ctggagtgca ctgtggaggg aacatcaaac cccaacctat actggtaccg acaggctgca   120
ggacggggcc tccagctgct cttctactcc gttggtattg gccagatcag ctctgaggtg   180
ccccagaatc tctcagcctc cagaccccag gaccggcagt tcatcctgag ttctaagaag   240
ctccttctca gtgactctgg cttctatctc tgtgcctggg ga                       282
```

<210> SEQ ID NO 247
<211> LENGTH: 284
<212> TYPE: DNA
<213> ORGANISM: Artificial Sequence
<220> FEATURE:
<223> OTHER INFORMATION: Description of Artificial Sequence: Synthetic
      TRBV30*01 sequence

<400> SEQUENCE: 247

```
tctcagacta ttcatcaatg gccagcgacc ctggtgcagc ctgtgggcag cccgctctct    60
ctggagtgca ctgtggaggg aacatcaaac cccaacctat actggtaccg acaggctgca   120
ggcaggggcc tccagctgct cttctactcc gttggtattg gccagatcag ctctgaggtg   180
ccccagaatc tctcagcctc cagaccccag gaccggcagt tcatcctgag ttctaagaag   240
ctccttctca gtgactctgg cttctatctc tgtgcctgga gtgt                     284
```

<210> SEQ ID NO 248
<211> LENGTH: 276
<212> TYPE: DNA
<213> ORGANISM: Artificial Sequence
<220> FEATURE:
<223> OTHER INFORMATION: Description of Artificial Sequence: Synthetic
      TRBV30*04 sequence

<400> SEQUENCE: 248
actattcatc aatggccagc gaccctggtg cagcctgtgg gcagcccgct ctctctggag      60
tgcactgtgg agggaacatc aaaccccaac ctatactggt accgacaggc tgcaggcagg     120
ggcctccagc tgctcttcta ctccattggt attgaccaga tcagctctga ggtgccccag     180
aatctctcag cctccagacc ccaggaccgg cagttcattc tgagttctaa gaagctcctc     240
ctcagtgact ctggcttcta tctctgtgcc tggagt                               276

<210> SEQ ID NO 249
<211> LENGTH: 448
<212> TYPE: DNA
<213> ORGANISM: Artificial Sequence
<220> FEATURE:
<223> OTHER INFORMATION: Description of Artificial Sequence: Synthetic
      TCRBJ1S1 sequence

<400> SEQUENCE: 249
ttgaaaaagg aacctaggac cctgtggatg gactctgtca ttctccatgg tcctaaaaag      60
caaaagtcaa agtgttcttc tgtgtaatac ccataaagca caggaggaga tttcttagct     120
cactgtcctc catcctagcc agggccctct cccctctcta tgccttcaat gtgattttca     180
ccttgacccc tgtcactgtg tgaacactga agctttcttt ggacaaggca ccagactcac     240
agttgtaggt aagacatttt tcaggttctt ttgcagatcc gtcacaggga aaagtgggtc     300
cacagtgtcc cttttagagt ggctatattc ttatgtgcta actatggcta caccttcggt     360
tcggggacca ggttaaccgt tgtaggtaag ctgggggtc tctaggaggg gtgcgatgag      420
ggaggactct gtcctgggaa atgtcaaa                                        448

<210> SEQ ID NO 250
<211> LENGTH: 448
<212> TYPE: DNA
<213> ORGANISM: Artificial Sequence
<220> FEATURE:
<223> OTHER INFORMATION: Description of Artificial Sequence: Synthetic
      TCRBJ1S2 sequence

<400> SEQUENCE: 250
gccagggccc tctcccctct ctatgccttc aatgtgattt tcaccttgac ccctgtcact      60
gtgtgaacac tgaagctttc tttggacaag gcaccagact cacagttgta ggtaagacat     120
ttttcaggtt cttttgcaga tccgtcacag ggaaaagtgg gtccacagtg tccctttag      180 agtggctata ttcttatgtg ctaactatgg ctacaccttc ggttcgggga ccaggttaac     240
cgttgtaggt aaggctgggg gtctctagga ggggtgcgat gagggaggac tctgtcctgg     300
gaaatgtcaa agagaacaga gatcccagct cccggagcca gactgaggga gacgtcatgt     360
catgtcccgg gattgagttc aggggaggct ccctgtgagg gcgaatccac ccaggcttcc     420
cagaggctct gagcagtcac agctgagc                                        448

<210> SEQ ID NO 251
<211> LENGTH: 450
<212> TYPE: DNA
<213> ORGANISM: Artificial Sequence

```
<220> FEATURE:
<223> OTHER INFORMATION: Description of Artificial Sequence: Synthetic
      TCRBJ1S3 sequence

<400> SEQUENCE: 251
gattttatag gaggccactc tgtgtctctt tttgtcacct gcctgagtct tgggcaagct      60
ctggaaggga acacagagta ctggaagcag agctgctgtc cctgtgaggg aagagttccc     120
atgaactccc aacctctgcc tgaatcccag ctgtgctcag cagagactgg ggggttttga    180
agtggccctg ggaggctgtg ctctggaaac accatatatt ttggagaggg aagttggctc    240
actgttgtag gtgagtaagt caaggctgga cagctgggaa cttgcaaaaa ggggctggaa    300
tccagacgga gcctttgtct ctagtgctta ggtgaaagtg tattttttgtc aggaaggcct   360 atgaggcaga tgaggagggg atagcctccc tctcctctcg actattttgt agactgcctg    420
tgccaagtta ggttcccta ctgagagatg                                      450

<210> SEQ ID NO 252
<211> LENGTH: 451
<212> TYPE: DNA
<213> ORGANISM: Artificial Sequence
<220> FEATURE:
<223> OTHER INFORMATION: Description of Artificial Sequence: Synthetic
      TCRBJ1S4 sequence

<400> SEQUENCE: 252
cagaagaggg aacttggggg atcacacggg gcctaattgg tctgctgacc accgcatttt     60
gggttgtacc attgtctacc cctctaccca ccagggttaa aattctacta aggaacagga    120
gaggacctgg caggtggact tggggaggca ggagtggaag gcagcaggtc gcggttttcc    180
ttccagtctt taatgttgtg caactaatga aaaactgttt tttggcagtg aacccagct    240 ctctgtcttg ggtatgtaaa agacttcttt cgggatagtg tatcataagg tcggagttcc   300
aggaggaccc cttgcgggag ggcagaaact gagaacacag ccaagaaaag ctcataaaat    360
gtgggtcagt ggagtgtgtg gtggggcccc aagagttctg tgtgtaagca gcttctggaa    420
ggaagggccc acaccagctc ctctggggtt t                                   451

<210> SEQ ID NO 253
<211> LENGTH: 450
<212> TYPE: DNA
<213> ORGANISM: Artificial Sequence
<220> FEATURE:
<223> OTHER INFORMATION: Description of Artificial Sequence: Synthetic
      TCRBJ1S5 sequence

<400> SEQUENCE: 253
gatagtgtat cataaggtcg gagttccagg aggacccctt gcgggagggc agaaactgag     60
aacacagcca agaaaagctc ataaaatgtg gtcagtgga gtgtgtggtg gggccccaag    120
agttctgtgt gtaagcagct tctggaagga agggcccaca ccagctcctc tggggttgc    180 cacactcatg atgcactgtg tagcaatcag ccccagcatt ttggtgatgg gactcgactc   240
tccatcctag gtaagttgca gaatcagggt ggtatggcca ttgtcccttg aaggcagagt    300
tctctgcttc tcctcccggt gctggtgagg cagattgagt aaaatctctt acccatggg    360 gtaagagctg tgcctgtgcc tgcgttccct ttggtgtgtc ttggttgact cctctatttc    420
tcttctctaa gtcttcagtc cataatctgc                                     450

<210> SEQ ID NO 254
<211> LENGTH: 453
```

```
<212> TYPE: DNA
<213> ORGANISM: Artificial Sequence
<220> FEATURE:
<223> OTHER INFORMATION: Description of Artificial Sequence: Synthetic
      TCRBJ1S6 sequence

<400> SEQUENCE: 254
atggctctgc ctctcctaag cctcttcctc ttgcgcctta tgctgcacag tatgcttagg      60 ccttttcct  aacagaatcc ctttggtcca gagccatgaa tccaggcaga gaaaggcagc     120
catcctgctg tcagggagct aagacttgcc ctctgactgg agatcgccgg gtgggtttta    180
tctaagcctc tgcagctgtg ctcctataat tcaccctcc  actttgggaa cgggaccagg    240
ctcactgtga caggtatggg ggctccactc ttgactcggg ggtgcctggg tttgactgca    300
atgatcagtt gctgggaagg gaattgagtg taagaacgga ggtcagggtc acccttctt    360 acctggagca ctgtgccctc tcctcccctc cctggagctc ttccagcttg ttgctctgct    420
gtgttgcctg cagttcctca gctgtagagc tcc                                 453

<210> SEQ ID NO 255
<211> LENGTH: 449
<212> TYPE: DNA
<213> ORGANISM: Artificial Sequence
<220> FEATURE:
<223> OTHER INFORMATION: Description of Artificial Sequence: Synthetic
      TCRBJ2S1 sequence

<400> SEQUENCE: 255
aatccactgt gttgtccccc agccaagtgg attctcctct gcaaattggt ggtggcctca     60
tgcaagatcc agttaccgtg tccagctaac tcgagacagg aaaagatagg ctcaggaaag    120
agaggaaggg tgtgccctct gtctgtgcta agggaggtgg ggaaggagaa ggaattctgg    180 gcagccccctt cccactgtgc tcctacaatg agcagttctt cgggccaggg acacggctca   240
ccgtgctagg taagaagggg gctccaggtg ggagagaggg tgagcagccc agcctgcacg    300
accccagaac cctgttctta ggggagtgga cactgggcaa tccagggccc tcctcgaggg    360 aagcgggggtt tgcgccaggg tccccagggc tgtgcgaaca ccggggagct gttttttgga   420
gaaggctcta ggctgaccgt actgggtaa                                      449

<210> SEQ ID NO 256
<211> LENGTH: 451
<212> TYPE: DNA
<213> ORGANISM: Artificial Sequence
<220> FEATURE:
<223> OTHER INFORMATION: Description of Artificial Sequence: Synthetic
      TCRBJ2S2 sequence

<400> SEQUENCE: 256
ctgtgctcct acaatgagca gttcttcggg ccagggacac ggctcaccgt gctaggtaag     60 aaggggctc  caggtgggag agagggtgag cagcccagcc tgcacgaccc cagaaccctg    120
ttcttagggg agtggacact gggcaatcca gggcctcct  cgaggaagc  ggggtttgcg    180 ccagggtccc cagggctgtg cgaacaccgg ggagctgttt tttggagaag gctctaggct    240
gaccgtactg gtaaggagg cggttgggc  tccggagagc tccgagaggg cgggatgggc     300
agaggtaagc agctgcccca ctctgagagg ggctgtgctg agaggcgctg ctgggcgtct    360 ggcggagga  ctcctggttc tgggtgctgg gagagcgatg gggctctcag cggtgggaag    420
gacccgagct gagtctggga cagcagagcg g                                   451
```

```
<210> SEQ ID NO 257
<211> LENGTH: 449
<212> TYPE: DNA
<213> ORGANISM: Artificial Sequence
<220> FEATURE:
<223> OTHER INFORMATION: Description of Artificial Sequence: Synthetic
      TCRBJ2S3 sequence

<400> SEQUENCE: 257
gggcgggatg ggcagaggta agcagctgcc ccactctgag aggggctgtg ctgagaggcg      60
ctgctgggcg tctgggcgga ggactcctgg ttctgggtgc tgggagagcg atggggctct     120
cagcggtggg aaggacccga gctgagtctg ggacagcaga gcgggcagca ccggttttg      180 tcctgggcct ccaggctgtg agcacagata cgcagtattt tggcccaggc acccggctga     240
cagtgctcgg taagcggggg ctcccgctga agccccggaa ctggggaggg gcgccccgg      300 gacgccgggg gcgtcgcagg gccagtttct gtgccgcgtc tcggggctgt gagccaaaaa     360
cattcagtac ttcggcgccg gaccccggct ctcagtgctg ggtaagctgg ggccgccggg     420
ggaccgggga cgagactgcg ctcgggttt                                       449

<210> SEQ ID NO 258
<211> LENGTH: 450
<212> TYPE: DNA
<213> ORGANISM: Artificial Sequence
<220> FEATURE:
<223> OTHER INFORMATION: Description of Artificial Sequence: Synthetic
      TCRBJ2S4 sequence

<400> SEQUENCE: 258
gacagcagag cgggcagcac cggttttgt cctgggcctc aggctgtga gcacagatac       60 gcagtatttt ggcccaggca cccggctgac agtgctcggt aagcggggc tcccgctgaa     120 gccccggaac tggggagggg cgccccggg acgccggggg cgtcgcaggg ccagtttctg     180
tgccgcgtct cggggctgtg agccaaaaac attcagtact tcggcgccgg accccggctc    240
tcagtgctgg gtaagctggg gccgccgggg gaccggggac gagactgcgc tcgggttttt    300
gtgcggggct cggggccgt gaccaagaga cccagtactt cgggccaggc acgcggctcc     360
tggtgctcgg tgagcgcggg ctgctggggc gcggcgcgg gcggcttggg tctggttttt     420
gcggggagtc cccgggctgt gctctggggc                                     450

<210> SEQ ID NO 259
<211> LENGTH: 448
<212> TYPE: DNA
<213> ORGANISM: Artificial Sequence
<220> FEATURE:
<223> OTHER INFORMATION: Description of Artificial Sequence: Synthetic
      TCRBJ2S5 sequence

<400> SEQUENCE: 259
ccccggaact ggggaggggg cgccccggga cgcggggggc gtcgcagggc cagtttctgt      60
gccgcgtctc ggggctgtga gccaaaaaca ttcagtactt cggcgccggg acccggctct    120
cagtgctggg taagctgggg ccgccgggg accggggacg agactgcgct cgggttttg      180 tgcgggctc gggggccgtg accaagagac ccagtacttc gggccaggca cgcggctcct    240
ggtgctcggt gagcgcgggc tgctggggcg cggcgcggg cggcttgggt ctggttttg      300 cggggagtcc ccgggctgtg ctctggggcc aacgtcctga ctttcggggc cggcagcagg    360
ctgaccgtgc tgggtgagtt ttcgcggac caccccgggcg gcgggattca ggtggaaggc    420
ggcggctgct tcgcggcacc cggtccgg                                       448
```

<210> SEQ ID NO 260
<211> LENGTH: 453
<212> TYPE: DNA
<213> ORGANISM: Artificial Sequence
<220> FEATURE:
<223> OTHER INFORMATION: Description of Artificial Sequence: Synthetic
      TCRBJ2S6 sequence

<400> SEQUENCE: 260
cagtgctggg taagctgggg ccgccggggg accggggacg agactgcgct cgggttttg      60 tgcgggctc gggggccgtg accaagagac ccagtacttc gggccaggca cgcggctcct    120
ggtgctcggt gagcgcgggc tgctggggcg cgggcgcggg cggcttgggt ctggttttg    180 cggggagtcc ccgggctgtg ctctgggcc aacgtcctga ctttcggggc cggcagcagg    240
ctgaccgtgc tgggtgagtt ttcgcgggac cacccgggcg gcgggattca ggtggaaggc    300
ggcggctgct tcgcggcacc cggtccggcc ctgtgctggg agacctgggc tgggtcccca    360
gggtgggcag gagctcgggg agccttagag gtttgcatgc ggggtgcac ctccgtgctc    420 ctacgagcag tacttcgggc cgggcaccag gct                                 453

<210> SEQ ID NO 261
<211> LENGTH: 447
<212> TYPE: DNA
<213> ORGANISM: Artificial Sequence
<220> FEATURE:
<223> OTHER INFORMATION: Description of Artificial Sequence: Synthetic
      TCRBJ2S7 sequence

<400> SEQUENCE: 261
tgactttcgg ggccggcagc aggctgaccg tgctgggtga gttttcgcgg gaccacccgg     60
gcggcgggat tcaggtggaa ggcggcggct gcttcgcggc acccggtccg gccctgtgct    120
gggagacctg gctgggtcc ccaggtgggg caggagctcg gggagccta gaggtttgca    180 tgcggggtg caccctccgtg ctcctacgag cagtacttcg gccgggcac caggctcacg    240 gtcacaggtg agattcgggc gtctccccac cttccagccc ctcggtcccc ggagtcggag    300
ggtggaccgg agctggagga gctgggtgtc cggggtcagc tctgcaaggt cacctccccg    360
ctcctgggga aagactgggg aagagggagg gggtggggag gtgctcagag tccggaaagc    420
tgagcagagg gcgaggccac tttaat                                         447

<210> SEQ ID NO 262
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV1-46*02 sequence

<400> SEQUENCE: 262
caggtgcagc tggtgcagtc tggggctgag gtgaagaagc ctggggcctc agtgaaggtt     60
tcctgcaagg catctggata caccttcaac agctactata tgcactgggt gcgacaggcc    120
cctggacaag gcttgagtg gatgggaata atcaacccta gtggtggtag cacaagctac    180
gcacagaagt tccagggcag agtcaccatg accagggaca cgtccacgag cacagtctac    240
atggagctga gcagcctgag atctgaggac acggccgtgt attactgtgc gagaga        296

<210> SEQ ID NO 263
<211> LENGTH: 260

```
<212> TYPE: DNA
<213> ORGANISM: Artificial Sequence
<220> FEATURE:
<223> OTHER INFORMATION: Description of Artificial Sequence: Synthetic
      IGHV1/OR15-5*01 sequence

<400> SEQUENCE: 263
agaagcctgg ggcctcagtg aaggtctcct gcaaggcttc tggatacacc ttcaccagct     60
actgtatgca ctgggtgcac caggtccatg cacaagggct tgagtggatg ggattggtgt    120
gccctagtga tggcagcaca agctatgcac agaagttcca ggccagagtc accataacca    180
gggacacatc catgagcaca gcctacatgg agctaagcag tctgagatct gaggacacgg    240
ccatgtatta ctgtgtgaga                                                260

<210> SEQ ID NO 264
<211> LENGTH: 294
<212> TYPE: DNA
<213> ORGANISM: Artificial Sequence
<220> FEATURE:
<223> OTHER INFORMATION: Description of Artificial Sequence: Synthetic
      IGHV1/OR15-5*03 sequence

<400> SEQUENCE: 264
caggtacagc tggtgcagtc tggggctgag gtgaagaagc ctggggcctc agtgaaggtc     60
tcctgcaagg cttctggata caccttcacc aactactgta tgcactgggt gcgccaggtc    120
catgcacaag ggcttgagtg gatgggattg gtgtgcccta gtgatggcag cacaagctat    180
gcacaaaagt tccaggccag agtcaccata accaggaca catccatgag cacagcctac    240
atggagctaa gcagtctgag atctgaggac acggccatgt attactgtgt gaga           294

<210> SEQ ID NO 265
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV1/OR15-9*01 sequence

<400> SEQUENCE: 265
caggtacagc tgatgcagtc tggggctgag gtgaagaagc ctggggcctc agtgaggatc     60
tcctgcaagg cttctggata caccttcacc agctactgta tgcactgggt gtgccaggcc    120
catgcacaag ggcttgagtg gatgggattg gtgtgcccta gtgatggcag cacaagctat    180
gcacagaagt tccagggcag agtcaccata accaggaca catccatggg cacagcctac    240
atggagctaa gcagcctgag atctgaggac acggccatgt attactgtgt gagaga         296

<210> SEQ ID NO 266
<211> LENGTH: 260
<212> TYPE: DNA
<213> ORGANISM: Artificial Sequence
<220> FEATURE:
<223> OTHER INFORMATION: Description of Artificial Sequence: Synthetic
      IGHV1-c*01 sequence

<400> SEQUENCE: 266
ggaagtctgg ggcctcagtg aaagtctcct gtagtttttc tgggtttacc atcaccagct     60
acggtataca ttgggtgcaa cagtccctg gacaagggct tgagtggatg ggatggatca    120
accctggcaa tggtagccca agctatgcca agaagtttca ggcagattc accatgacca    180 gggacatgtc cacaaccaca gcctacacag acctgagcag cctgacatct gaggacatgg    240
```
ctgtgtatta ctatgcaaga                                                  260

<210> SEQ ID NO 267
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV1-NL1*01 sequence
<220> FEATURE:
<221> NAME/KEY: modified_base
<222> LOCATION: (136)..(136)
<223> OTHER INFORMATION: a, c, g or t
<220> FEATURE:
<221> NAME/KEY: modified_base
<222> LOCATION: (253)..(253)
<223> OTHER INFORMATION: a, c, g or t

<400> SEQUENCE: 267
caggttcagc tgttgcagcc tggggtccag gtgaagaagc ctgggtcctc agtgaaggtc      60
tcctgctagg cttccagata caccttcacc aaatacttta cacggtgggt gtgacaaagc     120
cctggacaag ggcatnagtg gatgggatga atcaacccct acaacgataa cacacactac     180
gcacagacgt tctggggcag agtcaccatt accagtgaca ggtccatgag cacagcctac     240
atggagctga gcngcctgag atccgaagac atggtcgtgt attactgtgt gagaga         296

<210> SEQ ID NO 268
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV1-58*01 sequence

<400> SEQUENCE: 268
caaatgcagc tggtgcagtc tgggcctgag gtgaagaagc ctgggacctc agtgaaggtc      60
tcctgcaagg cttctggatt cacctttact agctctgctg tgcagtgggt gcgacaggct     120
cgtggacaac gccttgagtg gataggatgg atcgtcgttg gcagtggtaa cacaaactac     180
gcacagaagt tccaggaaag agtcaccatt accaggaca tgtccacaag cacagcctac      240
atggagctga gcagcctgag atccgaggac acggccgtgt attactgtgc ggcaga         296

<210> SEQ ID NO 269
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV1-58*02 sequence

<400> SEQUENCE: 269
caaatgcagc tggtgcagtc tgggcctgag gtgaagaagc ctgggacctc agtgaaggtc      60
tcctgcaagg cttctggatt cacctttact agctctgcta tgcagtgggt gcgacaggct     120
cgtggacaac gccttgagtg gataggatgg atcgtcgttg gcagtggtaa cacaaactac     180
gcacagaagt tccaggaaag agtcaccatt accaggaca tgtccacaag cacagcctac      240
atggagctga gcagcctgag atccgaggac acggccgtgt attactgtgc ggcaga         296

<210> SEQ ID NO 270
<211> LENGTH: 275
<212> TYPE: DNA
<213> ORGANISM: Artificial Sequence
<220> FEATURE:

<223> OTHER INFORMATION: Description of Artificial Sequence: Synthetic
      IGHV1-69*03 sequence

<400> SEQUENCE: 270
caggtgcagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaggg atcatcccta tctttggtac agcaaactac     180
gcacagaagt tccagggcag agtcacgatt accgcggacg aatccacgag cacagcctac     240
atggagctga gcagcctgag atctgatgac acggc                                275

<210> SEQ ID NO 271
<211> LENGTH: 233
<212> TYPE: DNA
<213> ORGANISM: Artificial Sequence
<220> FEATURE:
<223> OTHER INFORMATION: Description of Artificial Sequence: Synthetic
      IGHV1-69*07 sequence

<400> SEQUENCE: 271
agaagcctgg gtcctcggtg aaggtctcct gcaaggcttc tggaggcacc ttcagcagct      60
atgctatcag ctgggtgcga caggcccctg gacaagggct tgagtggatg gaaggatca     120 tccctatctt tggtacagca aactacgcac agaagttcca gggcagagtc acgattaccg     180
cggacgaatc cacgagcaca gcctacatgg agctgagcag cctgagatct gag           233

<210> SEQ ID NO 272
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV1-69*12 sequence

<400> SEQUENCE: 272
caggtccagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaggg atcatcccta tctttggtac agcaaactac     180
gcacagaagt tccagggcag agtcacgatt accgcggacg aatccacgag cacagcctac     240
atggagctga gcagcctgag atctgaggac acggccgtgt attactgtgc gagaga        296

<210> SEQ ID NO 273
<211> LENGTH: 294
<212> TYPE: DNA
<213> ORGANISM: Artificial Sequence
<220> FEATURE:
<223> OTHER INFORMATION: Description of Artificial Sequence: Synthetic
      IGHV1-69*05 sequence

<400> SEQUENCE: 273
caggtccagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaggg atcatcccta tctttggtac agcaaactac     180
gcacagaagt tccagggcag agtcacgatt accacggacg aatccacgag cacagcctac     240
atggagctga gcagcctgag atctgaggac acggccgtgt attactgtgc gaga          294

<210> SEQ ID NO 274
<211> LENGTH: 296

```
<212> TYPE: DNA
<213> ORGANISM: Artificial Sequence
<220> FEATURE:
<223> OTHER INFORMATION: Description of Artificial Sequence: Synthetic
      IGHV1-69*13 sequence

<400> SEQUENCE: 274
caggtccagc tggtgcagtc tggggctgag gtgaagaagc ctgggtcctc agtgaaggtc     60
tcctgcaagg cttctggagg caccttcagc agctatgcta tcagctgggt gcgacaggcc    120
cctggacaag ggcttgagtg gatgggaggg atcatccota tctttggtac agcaaactac    180
gcacagaagt tccagggcag agtcacgatt accgcggacg aatccacgag cacagcctac    240
atggagctga gcagcctgag atctgaggac acggccgtgt attactgtgc gagaga        296

<210> SEQ ID NO 275
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV1-69*01 sequence

<400> SEQUENCE: 275
caggtgcagc tggtgcagtc tggggctgag gtgaagaagc ctgggtcctc ggtgaaggtc     60
tcctgcaagg cttctggagg caccttcagc agctatgcta tcagctgggt gcgacaggcc    120
cctggacaag ggcttgagtg gatgggaggg atcatccota tctttggtac agcaaactac    180
gcacagaagt tccagggcag agtcacgatt accgcggacg aatccacgag cacagcctac    240
atggagctga gcagcctgag atctgaggac acggccgtgt attactgtgc gagaga        296

<210> SEQ ID NO 276
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV1-69*06 sequence

<400> SEQUENCE: 276
caggtgcagc tggtgcagtc tggggctgag gtgaagaagc ctgggtcctc ggtgaaggtc     60
tcctgcaagg cttctggagg caccttcagc agctatgcta tcagctgggt gcgacaggcc    120
cctggacaag ggcttgagtg gatgggaggg atcatccota tctttggtac agcaaactac    180
gcacagaagt tccagggcag agtcacgatt accgcggaca aatccacgag cacagcctac    240
atggagctga gcagcctgag atctgaggac acggccgtgt attactgtgc gagaga        296

<210> SEQ ID NO 277
<211> LENGTH: 294
<212> TYPE: DNA
<213> ORGANISM: Artificial Sequence
<220> FEATURE:
<223> OTHER INFORMATION: Description of Artificial Sequence: Synthetic
      IGHV1-69*02 sequence

<400> SEQUENCE: 277
caggtccagc tggtgcaatc tggggctgag gtgaagaagc ctgggtcctc ggtgaaggtc     60
tcctgcaagg cttctggagg caccttcagc agctatacta tcagctgggt gcgacaggcc    120
cctggacaag ggcttgagtg gatgggaagg atcatccota tccttggtat agcaaactac    180
gcacagaagt tccagggcag agtcacgatt accgcggaca aatccacgag cacagcctac    240
```

```
atggagctga gcagcctgag atctgaggac acggccgtgt attactgtgc gaga      294

<210> SEQ ID NO 278
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV1-69*08 sequence

<400> SEQUENCE: 278
caggtccagc tggtgcaatc tggggctgag gtgaagaagc ctgggtcctc ggtgaaggtc    60
tcctgcaagg cttctggagg caccttcagc agctatacta tcagctgggt gcgacaggcc   120
cctggacaag ggcttgagtg gatgggaagg atcatcccta tccttggtac agcaaactac   180
gcacagaagt tccagggcag agtcacgatt accgcggaca atccacgag cacagcctac    240 atggagctga gcagcctgag atctgaggac acggccgtgt attactgtgc gagaga       296

<210> SEQ ID NO 279
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV1-69*04 sequence

<400> SEQUENCE: 279
caggtccagc tggtgcagtc tggggctgag gtgaagaagc ctgggtcctc ggtgaaggtc    60
tcctgcaagg cttctggagg caccttcagc agctatgcta tcagctgggt gcgacaggcc   120
cctggacaag ggcttgagtg gatgggaagg atcatcccta tccttggtat agcaaactac   180
gcacagaagt tccagggcag agtcacgatt accgcggaca atccacgag cacagcctac    240 atggagctga gcagcctgag atctgaggac acggccgtgt attactgtgc gagaga       296

<210> SEQ ID NO 280
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV1-69*11 sequence

<400> SEQUENCE: 280
caggtccagc tggtgcagtc tggggctgag gtgaagaagc ctgggtcctc ggtgaaggtc    60
tcctgcaagg cttctggagg caccttcagc agctatgcta tcagctgggt gcgacaggcc   120
cctggacaag ggcttgagtg gatgggaagg atcatcccta tccttggtac agcaaactac   180
gcacagaagt tccagggcag agtcacgatt accgcggacg aatccacgag cacagcctac   240
atggagctga gcagcctgag atctgaggac acggccgtgt attactgtgc gagaga       296

<210> SEQ ID NO 281
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV1-69*09 sequence

<400> SEQUENCE: 281
caggtgcagc tggtgcagtc tggggctgag gtgaagaagc ctgggtcctc ggtgaaggtc    60
tcctgcaagg cttctggagg caccttcagc agctatgcta tcagctgggt gcgacaggcc   120
```

```
cctggacaag ggcttgagtg gatgggaagg atcatccta tccttggtat agcaaactac    180
gcacagaagt tccagggcag agtcacgatt accgcggaca aatccacgag cacagcctac    240
atggagctga gcagcctgag atctgaggac acggccgtgt attactgtgc gagaga        296
```

<210> SEQ ID NO 282
<211> LENGTH: 296
<212> TYPE: DNA
<213> ORGANISM: Artificial Sequence
<220> FEATURE:
<223> OTHER INFORMATION: Description of Artificial Sequence: Synthetic IGHV1-69*10 sequence

<400> SEQUENCE: 282

```
caggtccagc tggtgcagtc tggggctgag gtgaagaagc ctgggtcctc agtgaaggtc    60
tcctgcaagg cttctggagg caccttcagc agctatgcta tcagctgggt gcgacaggcc    120
cctggacaag ggcttgagtg gatgggaggg atcatccta tccttggtat agcaaactac    180
gcacagaagt tccagggcag agtcacgatt accgcggaca aatccacgag cacagcctac    240
atggagctga gcagcctgag atctgaggac acggccgtgt attactgtgc gagaga        296
```

<210> SEQ ID NO 283
<211> LENGTH: 294
<212> TYPE: DNA
<213> ORGANISM: Artificial Sequence
<220> FEATURE:
<223> OTHER INFORMATION: Description of Artificial Sequence: Synthetic IGHV1-f*01 sequence

<400> SEQUENCE: 283

```
gaggtccagc tggtacagtc tggggctgag gtgaagaagc ctggggctac agtgaaaatc    60
tcctgcaagg tttctggata caccttcacc gactactaca tgcactgggt gcaacaggcc    120
cctggaaaag ggcttgagtg gatgggactt gttgatcctg aagatggtga aacaatatac    180
gcagagaagt tccagggcag agtcaccata accgcggaca cgtctacaga cacagcctac    240
atggagctga gcagcctgag atctgaggac acggccgtgt attactgtgc aaca           294
```

<210> SEQ ID NO 284
<211> LENGTH: 233
<212> TYPE: DNA
<213> ORGANISM: Artificial Sequence
<220> FEATURE:
<223> OTHER INFORMATION: Description of Artificial Sequence: Synthetic IGHV1-f*02 sequence

<400> SEQUENCE: 284

```
agaagcctgg ggctacagtg aaaatctcct gcaaggtttc tggatacacc ttcaccgact    60
actacatgca ctgggtgcaa caggcccctg gaaaagggct tgagtggatg ggacttgttg    120
atcctgaaga tggtgaaaca atatatgcag agaagttcca gggcagagtc accataaccg    180
cggacacgtc tacagacaca gcctacatgg agctgagcag cctgagatct gag           233
```

<210> SEQ ID NO 285
<211> LENGTH: 296
<212> TYPE: DNA
<213> ORGANISM: Artificial Sequence
<220> FEATURE:
<223> OTHER INFORMATION: Description of Artificial Sequence: Synthetic IGHV1-24*01 sequence

<400> SEQUENCE: 285

```
caggtccagc tggtacagtc tggggctgag gtgaagaagc ctggggcctc agtgaaggtc      60
tcctgcaagg tttccggata caccctcact gaattatcca tgcactgggt gcgacaggct     120
cctgaaaaag ggcttgagtg gatgggaggt tttgatcctg aagatggtga acaatctac     180 gcacagaagt tccagggcag agtcaccatg accgaggaca catctacaga cacagcctac     240
atggagctga gcagcctgag atctgaggac acggccgtgt attactgtgc aacaga          296
```

<210> SEQ ID NO 286
<211> LENGTH: 294
<212> TYPE: DNA
<213> ORGANISM: Artificial Sequence
<220> FEATURE:
<223> OTHER INFORMATION: Description of Artificial Sequence: Synthetic
      IGHV7-4-1*01 sequence

<400> SEQUENCE: 286

```
caggtgcagc tggtgcaatc tgggtctgag ttgaagaagc ctggggcctc agtgaaggtt      60
tcctgcaagg cttctggata caccttcact agctatgcta tgaattgggt gcgacaggcc     120
cctggacaag ggcttgagtg gatgggatgg atcaacacca cactgggaa cccaacgtat      180 gcccagggct tcacaggacg gtttgtcttc tccttggaca cctctgtcag cacggcatat     240
ctgcagatct gcagcctaaa ggctgaggac actgccgtgt attactgtgc gaga            294
```

<210> SEQ ID NO 287
<211> LENGTH: 274
<212> TYPE: DNA
<213> ORGANISM: Artificial Sequence
<220> FEATURE:
<223> OTHER INFORMATION: Description of Artificial Sequence: Synthetic
      IGHV7-4-1*03 sequence

<400> SEQUENCE: 287

```
caggtgcagc tggtgcaatc tgggtctgag ttgaagaagc ctggggcctc agtgaaggtt      60
tcctgcaagg cttctggata caccttcact agctatgcta tgaattgggt gcgacaggcc     120
cctggacaag ggcttgagtg gatgggatgg atcaacacca cactgggaa cccaacgtat      180 gcccagggct tcacaggacg gtttgtcttc tccttggaca cctctgtcag cacggcatat     240
ctgcagatca gcacgctaaa ggctgaggac actg                                  274
```

<210> SEQ ID NO 288
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV7-4-1*02 sequence

<400> SEQUENCE: 288

```
caggtgcagc tggtgcaatc tgggtctgag ttgaagaagc ctggggcctc agtgaaggtt      60
tcctgcaagg cttctggata caccttcact agctatgcta tgaattgggt gcgacaggcc     120
cctggacaag ggcttgagtg gatgggatgg atcaacacca cactgggaa cccaacgtat      180 gcccagggct tcacaggacg gtttgtcttc tccttggaca cctctgtcag cacggcatat     240
ctgcagatca gcagcctaaa ggctgaggac actgccgtgt attactgtgc gagaga          296
```

<210> SEQ ID NO 289
<211> LENGTH: 296
<212> TYPE: DNA
<213> ORGANISM: Artificial Sequence
<220> FEATURE:

<223> OTHER INFORMATION: Description of Artificial Sequence: Synthetic
      IGHV7-81*01 sequence

<400> SEQUENCE: 289

```
caggtgcagc tggtgcagtc tggccatgag gtgaagcagc ctggggcctc agtgaaggtc     60
tcctgcaagg cttctggtta cagtttcacc acctatggta tgaattgggt gccacaggcc    120
cctggacaag ggcttgagtg gatgggatgg ttcaacacct acactgggaa cccaacatat    180
gcccagggct tcacaggacg gtttgtcttc tccatggaca cctctgccag cacagcatac    240
ctgcagatca gcagcctaaa ggctgaggac atggccatgt attactgtgc gagata       296
```

<210> SEQ ID NO 290
<211> LENGTH: 289
<212> TYPE: DNA
<213> ORGANISM: Artificial Sequence
<220> FEATURE:
<223> OTHER INFORMATION: Description of Artificial Sequence: Synthetic
      IGHV7-40*03 sequence

<400> SEQUENCE: 290

```
ctgcagctgg tgcagtctgg gcctgaggtg aagaagcctg ggcctcagt gaaggtctcc      60 tataagtctt ctggttacac cttcaccatc tatggtatga attgggtatg atagacccct   120
ggacagggct tgagtggat gtgatggatc atcacctaca ctgggaaccc aacgtatacc    180
cacggcttca caggatggtt tgtcttctcc atggacacgt ctgtcagcac ggcgtgtctt    240
cagatcagca gcctaaaggc tgaggacacg gccgagtatt actgtgcga               289
```

<210> SEQ ID NO 291
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV5-51*01 sequence

<400> SEQUENCE: 291

```
gaggtgcagc tggtgcagtc tggagcagag gtgaaaaagc ccggggagtc tctgaagatc     60
tcctgtaagg gttctggata cagctttacc agctactgga tcggctgggt gcgccagatg    120
cccgggaaag gcctggagtg gatggggatc atctatcctg gtgactctga taccagatac    180
agcccgtcct tccaaggcca ggtcaccatc tcagccgaca gtccatcag caccgcctac    240 ctgcagtgga gcagcctgaa ggcctcggac accgccatgt attactgtgc gagaca       296
```

<210> SEQ ID NO 292
<211> LENGTH: 245
<212> TYPE: DNA
<213> ORGANISM: Artificial Sequence
<220> FEATURE:
<223> OTHER INFORMATION: Description of Artificial Sequence: Synthetic
      IGHV5-51*05 sequence

<400> SEQUENCE: 292

```
aaaagcccgg ggagtctctg aagatctcct gtaagggttc tggatacagc tttaccagct     60
actggatcgg ctgggtgcgc cagatgccca ggaaaggcct ggagtggatg gggatcatct    120
atcctggtga ctctgatacc agatacagcc cgtccttcca aggccaggtc accatctcag    180
ccgacaagtc catcagcacc gcctacctgc agtggagcag cctgaaggcc tcggacaccg    240
ccatg                                                               245
```

```
<210> SEQ ID NO 293
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV5-51*02 sequence

<400> SEQUENCE: 293
gaggtgcagc tggtgcagtc tggagcagag gtgaaaaagc ccggggagtc tctgaagatc      60
tcctgtaagg gttctggata cagctttacc agctactgga ccggctgggt gcgccagatg     120
cccgggaaag gcttggagtg gatggggatc atctatcctg gtgactctga taccagatac     180
agcccgtcct tccaaggcca ggtcaccatc tcagccgaca agtccatcag caccgcctac     240
ctgcagtgga gcagcctgaa ggcctcggac accgccatgt attactgtgc gagaca         296

<210> SEQ ID NO 294
<211> LENGTH: 294
<212> TYPE: DNA
<213> ORGANISM: Artificial Sequence
<220> FEATURE:
<223> OTHER INFORMATION: Description of Artificial Sequence: Synthetic
      IGHV5-51*03 sequence

<400> SEQUENCE: 294
gaggtgcagc tggtgcagtc tggagcagag gtgaaaaagc cggggagtc tctgaagatc       60 tcctgtaagg gttctggata cagctttacc agctactgga tcggctgggt gcgccagatg     120
cccgggaaag gcctggagtg gatggggatc atctatcctg gtgactctga taccagatac     180
agcccgtcct tccaaggcca ggtcaccatc tcagccgaca agtccatcag caccgcctac     240
ctgcagtgga gcagcctgaa ggcctcggac accgccatgt attactgtgc gaga           294

<210> SEQ ID NO 295
<211> LENGTH: 294
<212> TYPE: DNA
<213> ORGANISM: Artificial Sequence
<220> FEATURE:
<223> OTHER INFORMATION: Description of Artificial Sequence: Synthetic
      IGHV5-51*04 sequence

<400> SEQUENCE: 295
gaggtgcagc tggtgcagtc tggagcagag gtgaaaaagc cggggagtc tctgaagatc       60 tcctgtaagg gttctggata cagctttacc agctactgga tcggctgggt gcgccagatg     120
cccgggaaag gcctggagtg gatggggatc atctatcctg gtgactctga taccagatac     180
agcccgtcct tccaaggcca ggtcaccatc tcagccgaca agcccatcag caccgcctac     240
ctgcagtgga gcagcctgaa ggcctcggac accgccatgt attactgtgc gaga           294

<210> SEQ ID NO 296
<211> LENGTH: 294
<212> TYPE: DNA
<213> ORGANISM: Artificial Sequence
<220> FEATURE:
<223> OTHER INFORMATION: Description of Artificial Sequence: Synthetic
      IGHV5-a*01 sequence

<400> SEQUENCE: 296
gaagtgcagc tggtgcagtc tggagcagag gtgaaaaagc ccggggagtc tctgaggatc      60
tcctgtaagg gttctggata cagctttacc agctactgga tcagctgggt gcgccagatg     120
cccgggaaag gcctggagtg gatggggagg attgatccta gtgactctta taccaactac     180
```

```
agcccgtcct tccaaggcca cgtcaccatc tcagctgaca agtccatcag cactgcctac      240
ctgcagtgga gcagcctgaa ggcctcggac accgccatgt attactgtgc gaga            294
```

<210> SEQ ID NO 297
<211> LENGTH: 294
<212> TYPE: DNA
<213> ORGANISM: Artificial Sequence
<220> FEATURE:
<223> OTHER INFORMATION: Description of Artificial Sequence: Synthetic
      IGHV5-a*03 sequence

<400> SEQUENCE: 297

```
gaagtgcagc tggtgcagtc cggagcagag gtgaaaaagc ccggggagtc tctgaggatc      60
tcctgtaagg gttctggata cagctttacc agctactgga tcagctgggt gcgccagatg     120
cccgggaaag gcctggagtg gatggggagg attgatccta gtgactctta taccaactac     180
agcccgtcct tccaaggcca cgtcaccatc tcagctgaca agtccatcag cactgcctac     240
ctgcagtgga gcagcctgaa ggcctcggac accgccatgt attactgtgc gaga            294
```

<210> SEQ ID NO 298
<211> LENGTH: 294
<212> TYPE: DNA
<213> ORGANISM: Artificial Sequence
<220> FEATURE:
<223> OTHER INFORMATION: Description of Artificial Sequence: Synthetic
      IGHV5-a*04 sequence

<400> SEQUENCE: 298

```
gaagtgcagc tggtgcagtc tggagcagag gtgaaaaagc ccggggagtc tctgaggatc      60
tcctgtaagg gttctggata cagctttacc agctactgga tcagctgggt gcgccagatg     120
cccgggaaag gcctggagtg gatggggagg attgatccta gtgactctta taccaactac     180
agcccgtcct tccaaggcca ggtcaccatc tcagctgaca agtccatcag cactgcctac     240
ctgcagtgga gcagcctgaa ggcctcggac accgccatgt attactgtgc gaga            294
```

<210> SEQ ID NO 299
<211> LENGTH: 295
<212> TYPE: DNA
<213> ORGANISM: Artificial Sequence
<220> FEATURE:
<223> OTHER INFORMATION: Description of Artificial Sequence: Synthetic
      IGHV5-a*02 sequence

<400> SEQUENCE: 299

```
gaagtgcagc tggtgcagtc tggagcagag gtgaaaaagc ccggggagtc tctgaggatc      60
tcctgtaagg gttctggata cagctttacc agctactgga tcagctgggt gcgccagatg     120
cccgggaaag gcttggagtg gatggggagg attgatccta gtgactctta taccaactac     180
agcccgtcct tccaaggcca cgtcaccatc tcagctgaca agtccatcag cactgcctac     240
ctgcagtgga gcagcctgaa ggctcggaca ccgccatgta ttactgtgcg agaca          295
```

<210> SEQ ID NO 300
<211> LENGTH: 294
<212> TYPE: DNA
<213> ORGANISM: Artificial Sequence
<220> FEATURE:
<223> OTHER INFORMATION: Description of Artificial Sequence: Synthetic
      IGHV5-78*01 sequence

<400> SEQUENCE: 300

```
gaggtgcagc tgttgcagtc tgcagcagag gtgaaaagac ccggggagtc tctgaggatc      60
```

```
tcctgtaaga cttctggata cagctttacc agctactgga tccactgggt gcgccagatg      120
cccgggaaag aactggagtg gatggggagc atctatcctg ggaactctga taccagatac      180
agcccatcct tccaaggcca cgtcaccatc tcagccgaca gctccagcag caccgcctac      240
ctgcagtgga gcagcctgaa ggcctcggac gccgccatgt attattgtgt gaga            294
```

<210> SEQ ID NO 301
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV3-11*01 sequence

<400> SEQUENCE: 301

```
caggtgcagc tggtggagtc tgggggaggc ttggtcaagc ctggagggtc cctgagactc      60
tcctgtgcag cctctggatt caccttcagt gactactaca tgagctggat ccgccaggct     120
ccagggaagg ggctggagtg ggtttcatac attagtagta gtggtagtac catatactac     180
gcagactctg tgaagggccg attcaccatc tccagggaca cgccaagaa ctcactgtat      240 ctgcaaatga acagcctgag agccgaggac acggccgtgt attactgtgc gagaga         296
```

<210> SEQ ID NO 302
<211> LENGTH: 294
<212> TYPE: DNA
<213> ORGANISM: Artificial Sequence
<220> FEATURE:
<223> OTHER INFORMATION: Description of Artificial Sequence: Synthetic
      IGHV3-11*03 sequence

<400> SEQUENCE: 302

```
caggtgcagc tgttggagtc tgggggaggc ttggtcaagc ctggagggtc cctgagactc      60
tcctgtgcag cctctggatt caccttcagt gactactaca tgagctggat ccgccaggct     120
ccagggaagg ggctggagtg ggtttcatac attagtagta gtagtagtta cacaaactac     180
gcagactctg tgaagggccg attcaccatc tccagagaca cgccaagaa ctcactgtat      240 ctgcaaatga acagcctgag agccgaggac acggccgtgt attactgtgc gaga           294
```

<210> SEQ ID NO 303
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV3-21*01 sequence

<400> SEQUENCE: 303

```
gaggtgcagc tggtggagtc tgggggaggc ctggtcaagc ctgggggtc cctgagactc       60 tcctgtgcag cctctggatt caccttcagt agctatagca tgaactgggt ccgccaggct     120
ccagggaagg ggctggagtg ggtctcatcc attagtagta gtagtagtta catatactac     180
gcagactcag tgaagggccg attcaccatc tccagagaca cgccaagaa ctcactgtat      240 ctgcaaatga acagcctgag agccgaggac acggctgtgt attactgtgc gagaga         296
```

<210> SEQ ID NO 304
<211> LENGTH: 296
<212> TYPE: DNA
<213> ORGANISM: Artificial Sequence
<220> FEATURE:
<223> OTHER INFORMATION: Description of Artificial Sequence: Synthetic IGHV3-21*02 sequence

<400> SEQUENCE: 304
gaggtgcaac tggtggagtc tgggggaggc ctggtcaagc ctggggggtc cctgagactc    60
tcctgtgcag cctctggatt caccttcagt agctatagca tgaactgggt ccgccaggct   120
ccagggaagg ggctggagtg ggtctcatcc attagtagta gtagtagtta catatactac   180
gcagactcag tgaagggccg attcaccatc tccagagaca cgccaagaa ctcactgtat   240 ctgcaaatga acagcctgag agccgaggac acggctgtgt attactgtgc gagaga       296

<210> SEQ ID NO 305
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV3-48*01 sequence

<400> SEQUENCE: 305
gaggtgcagc tggtggagtc tgggggaggc ttggtacagc ctggggggtc cctgagactc    60
tcctgtgcag cctctggatt caccttcagt agctatagca tgaactgggt ccgccaggct   120
ccagggaagg ggctggagtg ggtttcatac attagtagta gtagtagtac catatactac   180
gcagactctg tgaagggccg attcaccatc tccagagaca tgccaagaa ctcactgtat   240 ctgcaaatga acagcctgag agccgaggac acggctgtgt attactgtgc gagaga       296

<210> SEQ ID NO 306
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV3-48*02 sequence

<400> SEQUENCE: 306
gaggtgcagc tggtggagtc tgggggaggc ttggtacagc ctggggggtc cctgagactc    60
tcctgtgcag cctctggatt caccttcagt agctatagca tgaactgggt ccgccaggct   120
ccagggaagg ggctggagtg ggtttcatac attagtagta gtagtagtac catatactac   180
gcagactctg tgaagggccg attcaccatc tccagagaca tgccaagaa ctcactgtat   240 ctgcaaatga acagcctgag agacgaggac acggctgtgt attactgtgc gagaga       296

<210> SEQ ID NO 307
<211> LENGTH: 293
<212> TYPE: DNA
<213> ORGANISM: Artificial Sequence
<220> FEATURE:
<223> OTHER INFORMATION: Description of Artificial Sequence: Synthetic
      IGHV3-h*01 sequence

<400> SEQUENCE: 307
gaggtgcagc tggtggagtc tgggggaggc ttggtaaagc ctggggggtc cctgagactc    60
tcctgtgcag cctctggatt caccttcagt gactactaca tgaactgggt ccgccaggct   120
ccagggaagg ggctggagtg ggtctcatcc attagtagta gtagtaccat atactacgca   180
gactctgtga agggccgatt caccatctcc agagacaacg ccaagaactc actgtatctg   240
caaatgaaca gcctgagagc cgaggacacg gctgtgtatt actgtgcgag aga          293

<210> SEQ ID NO 308

```
<211> LENGTH: 293
<212> TYPE: DNA
<213> ORGANISM: Artificial Sequence
<220> FEATURE:
<223> OTHER INFORMATION: Description of Artificial Sequence: Synthetic
      IGHV3-h*02 sequence

<400> SEQUENCE: 308
gaggtgcagc tggtggagtc tgggggaggc ttggtaaagc ctggggggtc cctgagactc     60
tcctgtgcag cctctggatt caccttcagt gactactaca tgaactgggt ccgccaggct    120
ccagggaagg ggctggagtg ggtctcatcc attagtagta gtagtaccat atactacgca    180
gactctgtga agggccgatt caccatctcc agagacaacg ccaagaactc actgtatctg    240
caaatgaaca gcctgagagc cgaggacacg gctgtttatt actgtgcgag aga           293

<210> SEQ ID NO 309
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV3-48*03 sequence

<400> SEQUENCE: 309
gaggtgcagc tggtggagtc tgggggaggc ttggtacagc ctggagggtc cctgagactc     60
tcctgtgcag cctctggatt caccttcagt agttatgaaa tgaactgggt ccgccaggct    120
ccagggaagg ggctggagtg ggtttcatac attagtagta gtggtagtac catatactac    180
gcagactctg tgaagggccg attcaccatc tccagagaca acgccaagaa ctcactgtat    240
ctgcaaatga acagcctgag agccgaggac acggctgttt attactgtgc gagaga        296

<210> SEQ ID NO 310
<211> LENGTH: 292
<212> TYPE: DNA
<213> ORGANISM: Artificial Sequence
<220> FEATURE:
<223> OTHER INFORMATION: Description of Artificial Sequence: Synthetic
      IGHV3/OR16-8*01 sequence

<400> SEQUENCE: 310
gaggtgcagc tggtggagtc tgggggaggc ttggtacagc ctgggggtc cctgagactg      60 tcctgtccag cctctggatt caccttcagt aaccactaca tgagctgggt ccgccaggct    120
ccagggaagg gactggagtg ggtttcatac attagtggtg atagtggtta cacaaactac    180
gcagactctg tgaagggccg attcaccatc tccagggaca cgccaataa ctcaccgtat     240 ctgcaaatga acagcctgag agctgaggac acggctgtgt attactgtgt ga            292

<210> SEQ ID NO 311
<211> LENGTH: 292
<212> TYPE: DNA
<213> ORGANISM: Artificial Sequence
<220> FEATURE:
<223> OTHER INFORMATION: Description of Artificial Sequence: Synthetic
      IGHV3/OR16-9*01 sequence

<400> SEQUENCE: 311
gaggtgcagc tggtggagtc tggaggaggc ttggtacagc ctgggggtc cctgagactc      60 tcctgtgcag cctctggatt caccttcagt aaccactaca cgagctgggt ccgccaggct    120
ccagggaagg gactggagtg ggtttcatac agtagtggta atagtggtta cacaaactac    180
gcagactctg tgaaggccg attcaccatc tccagggaca acgccaagaa ctcactgtat     240
```
ctgcaaatga acagcctgag agccgaggac acggctgtgt attactgtgt ga      292

<210> SEQ ID NO 312
<211> LENGTH: 293
<212> TYPE: DNA
<213> ORGANISM: Artificial Sequence
<220> FEATURE:
<223> OTHER INFORMATION: Description of Artificial Sequence: Synthetic
      IGHV3-13*01 sequence

<400> SEQUENCE: 312
gaggtgcagc tggtggagtc tgggggaggc ttggtacagc ctgggggtc cctgagactc     60 tcctgtgcag cctctggatt caccttcagt agctacgaca tgcactgggt ccgccaagct   120
acaggaaaag gtctggagtg ggtctcagct attggtactg ctggtgacac atactatcca   180
ggctccgtga agggccgatt caccatctcc agagaaaatg ccaagaactc cttgtatctt   240
caaatgaaca gcctgagagc cggggacacg gctgtgtatt actgtgcaag aga          293

<210> SEQ ID NO 313
<211> LENGTH: 291
<212> TYPE: DNA
<213> ORGANISM: Artificial Sequence
<220> FEATURE:
<223> OTHER INFORMATION: Description of Artificial Sequence: Synthetic
      IGHV3-13*03 sequence

<400> SEQUENCE: 313
gaggtgcagc tggtggagtc tgggggaggc ttggtacagc ctgggggtc cctgagactc     60 tcctgtgcag cctgtggatt caccttcagt agctacgaca tgcactgggt ccgccaagct   120
acaggaaaag gtctggagtg ggtctcagct attggtactg ctggtgacac atactatcca   180
ggctccgtga agggccaatt caccatctcc agagaaaatg ccaagaactc cttgtatctt   240
caaatgaaca gcctgagagc cggggacacg gctgtgtatt actgtgcaag a            291

<210> SEQ ID NO 314
<211> LENGTH: 293
<212> TYPE: DNA
<213> ORGANISM: Artificial Sequence
<220> FEATURE:
<223> OTHER INFORMATION: Description of Artificial Sequence: Synthetic
      IGHV3-13*02 sequence

<400> SEQUENCE: 314
gaggtgcatc tggtggagtc tgggggaggc ttggtacagc ctggggggggc cctgagactc    60 tcctgtgcag cctctggatt caccttcagt aactacgaca tgcactgggt ccgccaagct   120
acaggaaaag gtctggagtg ggtctcagcc aatggtactg ctggtgacac atactatcca   180
ggctccgtga aggggcgatt caccatctcc agagaaaatg ccaagaactc cttgtatctt   240
caaatgaaca gcctgagagc cggggacacg gctgtgtatt actgtgcaag aga          293

<210> SEQ ID NO 315
<211> LENGTH: 123
<212> TYPE: DNA
<213> ORGANISM: Artificial Sequence
<220> FEATURE:
<223> OTHER INFORMATION: Description of Artificial Sequence: Synthetic
      IGHV3-47*02 sequence

<400> SEQUENCE: 315
atactatgca gactccgtga tgggccgatt caccatctcc agagacaacg ccaagaagtc    60
cttgtatctt caaatgaaca gcctgatagc tgaggacatg gctgtgtatt attgtgcaag    120
aga                                                                  123

<210> SEQ ID NO 316
<211> LENGTH: 282
<212> TYPE: DNA
<213> ORGANISM: Artificial Sequence
<220> FEATURE:
<223> OTHER INFORMATION: Description of Artificial Sequence: Synthetic
      IGHV3-47*03 sequence

<400> SEQUENCE: 316
gaggatcagc tggtggagtc tgggggaggc ttggtacagc ctgggggttc cctgagaccc    60
tcctgtgcag cctctggatt cgccttcagt agctatgttc tgcactgggt tcgccgggct    120
ccagggaagg gtccggagtg gtatcagct attggtactg gtggtgatac atactatgca    180
gactccgtga tgggccgatt caccatctcc agagacaacg ccaagaagtc cttgtatctc    240
aaatgaacag cctgatagct gaggacatgg ctgtgtatta tg                       282

<210> SEQ ID NO 317
<211> LENGTH: 291
<212> TYPE: DNA
<213> ORGANISM: Artificial Sequence
<220> FEATURE:
<223> OTHER INFORMATION: Description of Artificial Sequence: Synthetic
      IGHV3-47*01 sequence

<400> SEQUENCE: 317
gaggatcagc tggtggagtc tgggggaggc ttggtacagc ctgggggtc cctgcgaccc     60 tcctgtgcag cctctggatt cgccttcagt agctatgctc tgcactgggt tcgccgggct    120
ccagggaagg gtctggagtg gtatcagct attggtactg gtggtgatac atactatgca    180
gactccgtga tgggccgatt caccatctcc agagacaacg ccaagaagtc cttgtatctt    240
catatgaaca gcctgatagc tgaggacatg gctgtgtatt attgtgcaag a             291

<210> SEQ ID NO 318
<211> LENGTH: 291
<212> TYPE: DNA
<213> ORGANISM: Artificial Sequence
<220> FEATURE:
<223> OTHER INFORMATION: Description of Artificial Sequence: Synthetic
      IGHV3/OR16-10*01 sequence

<400> SEQUENCE: 318
gaggttcagc tggtgcagtc tgggggaggc ttggtacatc ctgggggtc cctgagactc     60 tcctgtgcag gctctggatt caccttcagt agctatgcta tgcactgggt tcgccaggct    120
ccaggaaaag gtctggagtg gtatcagct attggtactg gtggtggcac atactatgca    180
gactccgtga agggccgatt caccatctcc agagacaatg ccaagaactc cttgtatctt    240
caaatgaaca gcctgagagc cgaggacatg gctgtgtatt actgtgcaag a             291

<210> SEQ ID NO 319
<211> LENGTH: 291
<212> TYPE: DNA
<213> ORGANISM: Artificial Sequence
<220> FEATURE:
<223> OTHER INFORMATION: Description of Artificial Sequence: Synthetic
      IGHV3/OR16-10*02 sequence

<400> SEQUENCE: 319
gaggttcagc tggtgcagtc tgggggaggc ttggtacagc ctgggggtc cctgagactc     60

```
tcctgtgcag gctctggatt caccttcagt agctatgcta tgcactgggt tcgccaggct    120
ccaggaaaag gtctggagtg ggtatcagct attggtactg gtggtggcac atactatgca    180
gactccgtga agggccgatt caccatctcc agagacaatg ccaagaactc cttgtatctt    240
caaatgaaca gcctgagagc cgaggacatg gctgtgtatt actgtgcaag a             291

<210> SEQ ID NO 320
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV3-62*01 sequence

<400> SEQUENCE: 320
gaggtgcagc tggtggagtc tggggaaggc ttggtccagc ctggggggtc cctgagactc    60
tcctgtgcag cctctggatt caccttcagt agctctgcta tgcactgggt ccgccaggct    120
ccaagaaagg gtttgtagtg ggtctcagtt attagtacaa gtggtgatac cgtactctac    180
acagactctg tgaagggccg attcaccatc tccagagaca atgcccagaa ttcactgtct    240
ctgcaaatga cagcctgaga gccgagggca cagttgtgt actactgtgt gaaaga         296

<210> SEQ ID NO 321
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV3-64*01 sequence

<400> SEQUENCE: 321
gaggtgcagc tggtggagtc tgggggaggc ttggtccagc ctggggggtc cctgagactc    60
tcctgtgcag cctctggatt caccttcagt agctatgcta tgcactgggt ccgccaggct    120
ccagggaagg gactggaata tgtttcagct attagtagta atgggggtag cacatattat    180
gcaaactctg tgaagggcag attcaccatc tccagagaca attccaagaa cacgctgtat    240
cttcaaatgg gcagcctgag agctgaggac atggctgtgt attactgtgc gagaga        296

<210> SEQ ID NO 322
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV3-64*02 sequence

<400> SEQUENCE: 322
gaggtgcagc tggtggagtc tggggaaggc ttggtccagc ctggggggtc cctgagactc    60
tcctgtgcag cctctggatt caccttcagt agctatgcta tgcactgggt ccgccaggct    120
ccagggaagg gactggaata tgtttcagct attagtagta atgggggtag cacatattat    180
gcagactctg tgaagggcag attcaccatc tccagagaca attccaagaa cacgctgtat    240
cttcaaatgg gcagcctgag agctgaggac atggctgtgt attactgtgc gagaga        296

<210> SEQ ID NO 323
<211> LENGTH: 296
<212> TYPE: DNA
<213> ORGANISM: Artificial Sequence
<220> FEATURE:
<223> OTHER INFORMATION: Description of Artificial Sequence: Synthetic
```

IGHV3-64*03 sequence

<400> SEQUENCE: 323

| | | | | |
|---|---|---|---|---|
| gaggtgcagc | tggtggagtc | tgggggaggc | ttggtccagc | ctggggggtc cctgagactc | 60 |
| tcctgttcag | cctctggatt | caccttcagt | agctatgcta | tgcactgggt ccgccaggct | 120 |
| ccagggaagg | gactggaata | tgtttcagct | attagtagta | atgggggtag cacatactac | 180 |
| gcagactcag | tgaagggcag | attcaccatc | tccagagaca | attccaagaa cacgctgtat | 240 |
| gtccaaatga | gcagtctgag | agctgaggac | acggctgtgt | attactgtgt gaaaga | 296 |

<210> SEQ ID NO 324
<211> LENGTH: 296
<212> TYPE: DNA
<213> ORGANISM: Artificial Sequence
<220> FEATURE:
<223> OTHER INFORMATION: Description of Artificial Sequence: Synthetic
    IGHV3-64*05 sequence

<400> SEQUENCE: 324

| | | | | |
|---|---|---|---|---|
| gaggtgcagc | tggtggagtc | tgggggaggc | ttggtccagc | ctggggggtc cctgagactc | 60 |
| tcctgttcag | cctctggatt | caccttcagt | agctatgcta | tgcactgggt ccgccaggct | 120 |
| ccagggaagg | gactggaata | tgtttcagct | attagtagta | atgggggtag cacatactac | 180 |
| gcagactcag | tgaagggcag | attcaccatc | tccagagaca | attccaagaa cacgctgtat | 240 |
| gttcaaatga | gcagtctgag | agctgaggac | acggctgtgt | attactgtgt gaaaga | 296 |

<210> SEQ ID NO 325
<211> LENGTH: 296
<212> TYPE: DNA
<213> ORGANISM: Artificial Sequence
<220> FEATURE:
<223> OTHER INFORMATION: Description of Artificial Sequence: Synthetic
    IGHV3-64*04 sequence

<400> SEQUENCE: 325

| | | | | |
|---|---|---|---|---|
| caggtgcagc | tggtggagtc | tgggggaggc | ttggtccagc | ctggggggtc cctgagactc | 60 |
| tcctgttcag | cctctggatt | caccttcagt | agctatgcta | tgcactgggt ccgccaggct | 120 |
| ccagggaagg | gactggaata | tgtttcagct | attagtagta | atgggggtag cacatactac | 180 |
| gcagactcag | tgaagggcag | attcaccatc | tccagagaca | attccaagaa cacgctgtat | 240 |
| ctgcaaatga | acagcctgag | agctgaggac | acggctgtgt | attactgtgc gagaga | 296 |

<210> SEQ ID NO 326
<211> LENGTH: 296
<212> TYPE: DNA
<213> ORGANISM: Artificial Sequence
<220> FEATURE:
<223> OTHER INFORMATION: Description of Artificial Sequence: Synthetic
    IGHV3-16*01 sequence

<400> SEQUENCE: 326

| | | | | |
|---|---|---|---|---|
| gaggtacaac | tggtggagtc | tgggggaggc | ttggtacagc | ctggggggtc cctgagactc | 60 |
| tcctgtgcag | cctctggatt | caccttcagt | aacagtgaca | tgaactgggc ccgcaaggct | 120 |
| ccaggaaagg | ggctggagtg | ggtatcgggt | gttagttgga | atggcagtag gacgcactat | 180 |
| gtggactccg | tgaagcgccg | attcatcatc | tccagagaca | attccaggaa ctccctgtat | 240 |
| ctgcaaaaga | acagacggag | agccgaggac | atggctgtgt | attactgtgt gagaaa | 296 |

<210> SEQ ID NO 327

```
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV3-16*02 sequence

<400> SEQUENCE: 327
gaggtgcagc tggtggagtc tgggggaggc ttggtacagc ctggggggtc cctgagactc    60
tcctgtgcag cctctggatt caccttcagt aacagtgaca tgaactgggc ccgcaaggct   120
ccaggaaagg ggctggagtg ggtatcgggt gttagttgga atggcagtag gacgcactat   180
gtggactccg tgaagcgccg attcatcatc tccagagaca attccaggaa ctccctgtat   240
ctgcaaaaga acagacggag agccgaggac atggctgtgt attactgtgt gagaaa       296

<210> SEQ ID NO 328
<211> LENGTH: 294
<212> TYPE: DNA
<213> ORGANISM: Artificial Sequence
<220> FEATURE:
<223> OTHER INFORMATION: Description of Artificial Sequence: Synthetic
      IGHV3/OR16-15*02 sequence

<400> SEQUENCE: 328
gaggtgcagc tggtggagtc tgggggaggc ttggtccagc ctggggggtc cctgagacac    60
tcctgtgcag cctctggatt caccttcagt aacagtgaca tgaactgggt cctctaggct   120
ccaggaaagg ggctggagtg ggtctcgggt attagttgga atggcggtaa gacgcactat   180
gtggactccg tgaagggcca atttaccatc tccagagaca attccagcaa gtccctgtat   240
ctgcaaaaga acagacagag agccaaagac atggccgtgt attactgtgt gaga          294

<210> SEQ ID NO 329
<211> LENGTH: 294
<212> TYPE: DNA
<213> ORGANISM: Artificial Sequence
<220> FEATURE:
<223> OTHER INFORMATION: Description of Artificial Sequence: Synthetic
      IGHV3/OR16-16*01 sequence

<400> SEQUENCE: 329
gaggtgcagc tggtggagtc tgggggaggc ttggtccagc ctggggggtc cctgagacac    60
tcctgtgcag cctctggatt caccttcagt aacagtgaca tgaactgggt cctctaggct   120
ccaggaaagg ggctggagtg ggtctcggat attagttgga atggcggtaa gacgcactat   180
gtggactccg tgaagggcca atttaccatc tccagagaca attccagcaa gtccctgtat   240
ctgcaaaaga acagacagag agccaaggac atggccgtgt attactgtgt gaga          294

<210> SEQ ID NO 330
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV3/OR16-15*01 sequence

<400> SEQUENCE: 330
gaagtgcagc tggtggagtc tgggggaggc ttggtccagc ctggggggtc cctgagactc    60
tcctgtgcag cctctgtatt caccttcagt aacagtgaca taaactgggt cctctaggct   120
ccaggaaagg ggctggagtg ggtctcgggt attagttgga atggcggtaa gacgcactat   180
gtggactccg tgaagggcca attttccatc tccagagaca attccagcaa gtccctgtat   240
```

```
ctgcaaaaga acagacagag agccaaggac atggccgtgt attactgtgt gagaaa        296
```

<210> SEQ ID NO 331
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV3-19*01 sequence

<400> SEQUENCE: 331

```
acagtgcagc tggtggagtc tgggggaggc ttggtagagc ctgggggatc cctgagactc      60
tcctgtgcag cctctggatt caccttcagt aacagtgaca tgaactgggt ccgccaggct     120
ccaggaaagg ggctggagtg ggtatcgggt gttagttgga atggcagtag gacgcactat     180
gcagactctg tgaagggccg attcatcatc tccagagaca attccaggaa cttcctgtat     240
cagcaaatga acagcctgag gcccgaggac atggctgtgt attactgtgt gagaaa        296
```

<210> SEQ ID NO 332
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV3-35*01 sequence

<400> SEQUENCE: 332

```
gaggtgcagc tggtggagtc tgggggaggc ttggtacagc ctgggggatc cctgagactc      60
tcctgtgcag cctctggatt caccttcagt aacagtgaca tgaactgggt ccatcaggct     120
ccaggaaagg ggctggagtg ggtatcgggt gttagttgga atggcagtag gacgcactat     180
gcagactctg tgaagggccg attcatcatc tccagagaca attccaggaa caccctgtat     240
ctgcaaacga atagcctgag ggccgaggac acggctgtgt attactgtgt gagaaa        296
```

<210> SEQ ID NO 333
<211> LENGTH: 298
<212> TYPE: DNA
<213> ORGANISM: Artificial Sequence
<220> FEATURE:
<223> OTHER INFORMATION: Description of Artificial Sequence: Synthetic
      IGHV3-43*01 sequence

<400> SEQUENCE: 333

```
gaagtgcagc tggtggagtc tgggggagtc gtggtacagc ctgggggtc cctgagactc      60 tcctgtgcag cctctggatt cacctttgat gattatacca tgcactgggt ccgtcaagct    120
ccggggaagg gtctggagtg ggtctctctt attagttggg atggtggtag cacatactat    180
gcagactctg tgaagggccg attcaccatc tccagagaca acagcaaaaa ctccctgtat    240
ctgcaaatga acagtctgag aactgaggac accgccttgt attactgtgc aaaagata     298
```

<210> SEQ ID NO 334
<211> LENGTH: 294
<212> TYPE: DNA
<213> ORGANISM: Artificial Sequence
<220> FEATURE:
<223> OTHER INFORMATION: Description of Artificial Sequence: Synthetic
      IGHV3-43*02 sequence

<400> SEQUENCE: 334

```
gaagtgcagc tggtggagtc tgggggaggc gtggtacagc ctgggggtc cctgagactc      60
```

```
tcctgtgcag cctctggatt cacctttgat gattatgcca tgcactgggt ccgtcaagct    120
ccagggaagg gtctggagtg ggtctctctt attagtgggg atggtggtag cacatactat    180
gcagactctg tgaagggccg attcaccatc tccagagaca acagcaaaaa ctccctgtat    240
ctgcaaatga acagtctgag aactgaggac accgccttgt attactgtgc aaaa          294
```

<210> SEQ ID NO 335
<211> LENGTH: 298
<212> TYPE: DNA
<213> ORGANISM: Artificial Sequence
<220> FEATURE:
<223> OTHER INFORMATION: Description of Artificial Sequence: Synthetic
      IGHV3-9*01 sequence

<400> SEQUENCE: 335

```
gaagtgcagc tggtggagtc tgggggaggc ttggtacagc ctggcaggtc cctgagactc    60
tcctgtgcag cctctggatt cacctttgat gattatgcca tgcactgggt ccggcaagct    120
ccagggaagg gcctggagtg ggtctcaggt attagttgga atagtggtag cataggctat    180
gcggactctg tgaagggccg attcaccatc tccagagaca acgccaagaa ctccctgtat    240
ctgcaaatga acagtctgag agctgaggac acggccttgt attactgtgc aaaagata     298
```

<210> SEQ ID NO 336
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV3-20*01 sequence

<400> SEQUENCE: 336

```
gaggtgcagc tggtggagtc tgggggaggt gtggtacggc ctgggggtc cctgagactc    60 tcctgtgcag cctctggatt cacctttgat gattatggca tgagctgggt ccgccaagct    120
ccagggaagg ggctggagtg ggtctctggt attaattgga atggtggtag cacaggttat    180
gcagactctg tgaagggccg attcaccatc tccagagaca acgccaagaa ctccctgtat    240
ctgcaaatga acagtctgag agccgaggac acggccttgt atcactgtgc gagaga       296
```

<210> SEQ ID NO 337
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV3-74*01 sequence

<400> SEQUENCE: 337

```
gaggtgcagc tggtggagtc cgggggaggc ttagttcagc ctgggggtc cctgagactc    60 tcctgtgcag cctctggatt caccttcagt agctactgga tgcactgggt ccgccaagct    120
ccagggaagg ggctggtgtg gtctcacgt attaatagtg atgggagtag cacaagctac    180
gcggactccg tgaagggccg attcaccatc tccagagaca acgccaagaa cacgctgtat    240
ctgcaaatga acagtctgag agccgaggac acggctgtgt attactgtgc aagaga       296
```

<210> SEQ ID NO 338
<211> LENGTH: 294
<212> TYPE: DNA
<213> ORGANISM: Artificial Sequence
<220> FEATURE:
<223> OTHER INFORMATION: Description of Artificial Sequence: Synthetic
      IGHV3-74*02 sequence

<400> SEQUENCE: 338

```
gaggtgcagc tggtggagtc tgggggaggc ttagttcagc ctgggggtc cctgagactc      60 tcctgtgcag cctctggatt caccttcagt agctactgga tgcactgggt ccgccaagct    120
ccagggaagg ggctggtgtg gtctcacgt attaatagtg atgggagtag cacaagctac     180
gcggactccg tgaagggccg attcaccatc tccagagaca acgccaagaa cacgctgtat    240
ctgcaaatga acagtctgag agccgaggac acggctgtgt attactgtgc aaga          294
```

<210> SEQ ID NO 339
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV3-74*03 sequence

<400> SEQUENCE: 339

```
gaggtgcagc tggtggagtc cggggaggc ttagttcagc ctgggggtc cctgagactc      60 tcctgtgcag cctctggatt caccttcagt agctactgga tgcactgggt ccgccaagct    120
ccagggaagg ggctggtgtg gtctcacgt attaatagtg atgggagtag cacaacgtac     180
gcggactccg tgaagggccg attcaccatc tccagagaca acgccaagaa cacgctgtat    240
ctgcaaatga acagtctgag agccgaggac acggctgtgt attactgtgc aagaga        296
```

<210> SEQ ID NO 340
<211> LENGTH: 294
<212> TYPE: DNA
<213> ORGANISM: Artificial Sequence
<220> FEATURE:
<223> OTHER INFORMATION: Description of Artificial Sequence: Synthetic
      IGHV3/OR16-13*01 sequence

<400> SEQUENCE: 340

```
gaggtgcagc tggtggagtc tgggggaggc ttagtacagc ctggagggtc cctgagactc    60
tcctgtgcag cctctggatt caccttcagt agctactgga tgcactgggt ccgccaagct   120
ccagggaagg ggctggtgtg gtctcacgt attaatagtg atgggagtag cacaagctac    180
gcagactcca tgaagggcca attcaccatc tccagagaca atgctaagaa cacgctgtat   240
ctgcaaatga acagtctgag agctgaggac atggctgtgt attactgtac taga          294
```

<210> SEQ ID NO 341
<211> LENGTH: 294
<212> TYPE: DNA
<213> ORGANISM: Artificial Sequence
<220> FEATURE:
<223> OTHER INFORMATION: Description of Artificial Sequence: Synthetic
      IGHV3/OR16-14*01 sequence

<400> SEQUENCE: 341

```
gaggtgcagc tggaggagtc tgggggaggc ttagtacagc ctggagggtc cctgagactc    60
tcctgtgcag cctctggatt caccttcagt agctactgga tgcactgggt ccgccaatct   120
ccagggaagg ggctggtgtg agtctcacgt attaatagtg atgggagtag cacaagctac   180
gcagactcct tgaagggcca attcaccatc tccagagaca atgctaagaa cacgctgtat   240
ctgcaaatga acagtctgag agctgaggac atggctgtgt attactgtac taga          294
```

<210> SEQ ID NO 342
<211> LENGTH: 296

```
<212> TYPE: DNA
<213> ORGANISM: Artificial Sequence
<220> FEATURE:
<223> OTHER INFORMATION: Description of Artificial Sequence: Synthetic
      IGHV3-30*01 sequence

<400> SEQUENCE: 342
caggtgcagc tggtggagtc tgggggaggc gtggtccagc ctggggaggtc cctgagactc      60 tcctgtgcag cctctggatt caccttcagt agctatgcta tgcactgggt ccgccaggct     120
ccaggcaagg ggctagagtg ggtggcagtt atatcatatg atggaagtaa taaatactac     180
gcagactccg tgaagggccg attcaccatc tccagagaca attccaagaa cacgctgtat     240
ctgcaaatga acagcctgag agctgaggac acggctgtgt attactgtgc gagaga         296

<210> SEQ ID NO 343
<211> LENGTH: 294
<212> TYPE: DNA
<213> ORGANISM: Artificial Sequence
<220> FEATURE:
<223> OTHER INFORMATION: Description of Artificial Sequence: Synthetic
      IGHV3-30*08 sequence

<400> SEQUENCE: 343
caggtgcagc tggtggactc tgggggaggc gtggtccagc ctggggaggtc cctgagactc      60 tcctgtgcag cctctgcatt caccttcagt agctatgcta tgcactgggt ccgccaggct     120
ccaggcaagg ggctagagtg ggtggcagtt atatcatatg atggaagtaa taaatactac     180
gcagactccg tgaagggccg attcaccatc tccagagaca attccaagaa cacgctgtat     240
ctgcaaatga acagcctgag agctgaggac acggctgtgt attactgtgc gaga           294

<210> SEQ ID NO 344
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV3-30*17 sequence

<400> SEQUENCE: 344
caggtgcagc tggtggagtc tgggggaggc gtggtccagc ctggggaggtc cctgagactc      60 tcctgtgcag cctctggatt caccttcagt agctatgcta tgcactgggt ccgccaggct     120
ccgggcaagg ggctagagtg ggtggcagtt atatcatatg atggaagtaa taaatactac     180
gcagactccg tgaagggccg attcaccatc tccagagaca attccaagaa cacgctgtat     240
ctgcaaatga acagcctgag agctgaggac acggctgtgt attactgtgc gagaga         296

<210> SEQ ID NO 345
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV3-30*11 sequence

<400> SEQUENCE: 345
caggtgcagc tggtggagtc tgggggaggc gtggtccagc ctggggaggtc cctgagactc      60 tcctgtgcag cgtctggatt caccttcagt agctatgcta tgcactgggt ccgccaggct     120
ccaggcaagg ggctagagtg ggtggcagtt atatcatatg atggaagtaa taaatactac     180
gcagactccg tgaagggccg attcaccatc tccagagaca attccaagaa cacgctgtat     240
```
ctgcaaatga acagcctgag agctgaggac acggctgtgt attactgtgc gagaga      296

<210> SEQ ID NO 346
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV3-30*10 sequence

<400> SEQUENCE: 346
caggtgcagc tggtggagtc tgggggaggc gtggtccagc ctgggaggtc cctgagactc      60
tcctgtgcag cctctggatt caccttcagt agctatgcta tgcactgggt ccgccaggct     120
ccaggcaagg ggctagagtg ggtggcagtt atatcatatg atggaagtaa taaatactac     180
acagactccg tgaagggccg attcaccatc tccagagaca attccaagaa cacgctgtat     240
ctgcaaatga acagcctgag agctgaggac acggctgtgt attactgtgc gagaga          296

<210> SEQ ID NO 347
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV3-30*16 sequence

<400> SEQUENCE: 347
caggtgcagc tggtggagtc tgggggaggc gtggtccagc ctgggaggtc cctgagactc      60
tcctgtgcag cctctggatt caccttcagt agctatgcta tgcactgggt ccgccaggcc     120
ccaggcaagg ggctagagtg ggtggcagtt atatcatatg atggaagtaa taaatactac     180
gcagactccg tgaagggccg attcaccatc tccagagaca attccaagaa cacgctgtat     240
ctgcaaatga acagcctgag agctgaggac acggctgtgt attactgtgc gagaga          296

<210> SEQ ID NO 348
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV3-30*15 sequence

<400> SEQUENCE: 348
caggtgcagc tggtggagtc tgggggaggc gtggtccagc ctgggaggtc cctgagactc      60
tcctgtgcag cctctggatt caccttcagt agctatgcta tgcactgggt ccgccaggct     120
ccaggcaagg ggctagagtg ggtggcagtt atatcatatg atggaagtaa taaatactac     180
gcagactccg tgaagggccg attcaccatc tccagagaca attccaagaa cacgctgtat     240
ctgcaaatga gcagcctgag agctgaggac acggctgtgt attactgtgc gagaga          296

<210> SEQ ID NO 349
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV3-30*07 sequence

<400> SEQUENCE: 349
caggtgcagc tggtggagtc tgggggaggc gtggtccagc ctgggaggtc cctgagactc      60
tcctgtgcag cctctggatt caccttcagt agctatgcta tgcactgggt ccgccaggct     120

```
ccaggcaagg ggctagagtg ggtggcagtt atatcatatg atggaagtaa taaatactac      180
gcagactccg tgaagggccg attcaccatc tccagagaca attccaagaa cacgctgtat      240
ctgcaaatga acagcctgag agccgaggac acggctgtgt attactgtgc gagaga          296
```

<210> SEQ ID NO 350
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV3-30*04 sequence

<400> SEQUENCE: 350

```
caggtgcagc tggtggagtc tgggggaggc gtggtccagc ctgggaggtc cctgagactc      60
tcctgtgcag cctctggatt caccttcagt agctatgcta tgcactgggt ccgccaggct      120
ccaggcaagg ggctggagtg ggtggcagtt atatcatatg atggaagtaa taaatactac      180
gcagactccg tgaagggccg attcaccatc tccagagaca attccaagaa cacgctgtat      240
ctgcaaatga acagcctgag agctgaggac acggctgtgt attactgtgc gagaga          296
```

<210> SEQ ID NO 351
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV3-30*09 sequence

<400> SEQUENCE: 351

```
caggtgcagc tggtggagtc tgggggaggc gtggtccagc ctgggaggtc cctgagactc      60
tcctgtgcag cctctggatt caccttcagt agctatgcta tgcactgggt ccgccaggct      120
ccaggcaagg ggctggagtg ggtggcagtt atatcatatg atggaagtaa taaatactac      180
gcagactccg tgaagggccg attcgccatc tccagagaca attccaagaa cacgctgtat      240
ctgcaaatga acagcctgag agctgaggac acggctgtgt attactgtgc gagaga          296
```

<210> SEQ ID NO 352
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV3-30*14 sequence

<400> SEQUENCE: 352

```
caggtgcagc tggtggagtc tgggggaggc gtggtccagc ctgggaggtc cctgagactc      60
tcctgtgcag cctctggatt caccttcagt agctatgcta tgcactgggt ccgccaggct      120
ccaggcaagg ggctggagtg ggtggcagtt atatcatatg atggaagtaa taaatactac      180
gcagactccg tgaagggccg attcaccatc tccagagaca attccaagaa cacgctgtat      240
cttcaaatga acagcctgag agctgaggac acggctgtgt attactgtgc gagaga          296
```

<210> SEQ ID NO 353
<211> LENGTH: 294
<212> TYPE: DNA
<213> ORGANISM: Artificial Sequence
<220> FEATURE:
<223> OTHER INFORMATION: Description of Artificial Sequence: Synthetic
      IGHV3-30-3*01 sequence

<400> SEQUENCE: 353

```
caggtgcagc tggtggagtc tgggggaggc gtggtccagc ctgggaggtc cctgagactc    60
tcctgtgcag cctctggatt caccttcagt agctatgcta tgcactgggt ccgccaggct   120
ccaggcaagg ggctggagtg ggtggcagtt atatcatatg atggaagcaa taaatactac   180
gcagactccg tgaagggccg attcaccatc tccagagaca attccaagaa cacgctgtat   240
ctgcaaatga acagcctgag agctgaggac acggctgtgt attactgtgc gaga         294
```

<210> SEQ ID NO 354
<211> LENGTH: 296
<212> TYPE: DNA
<213> ORGANISM: Artificial Sequence
<220> FEATURE:
<223> OTHER INFORMATION: Description of Artificial Sequence: Synthetic IGHV3-30-3*02 sequence

<400> SEQUENCE: 354

```
caggtgcagc tggtggagtc tgggggaggc gtggtccagc ctgggaggtc cctgagactc    60
tcctgtgcag cgtctggatt caccttcagt agctatgcta tgcactgggt ccgccaggct   120
ccaggcaagg ggctggagtg ggtggcagtt atatcatatg atggaagcaa taaatactac   180
gcagactccg tgaagggccg attcaccatc tccagagaca attccaagaa cacgctgtat   240
ctgcaaatga acagcctgag agctgaggac acggctgtgt attactgtgc gaaaga       296
```

<210> SEQ ID NO 355
<211> LENGTH: 296
<212> TYPE: DNA
<213> ORGANISM: Artificial Sequence
<220> FEATURE:
<223> OTHER INFORMATION: Description of Artificial Sequence: Synthetic IGHV3-30*03 sequence

<400> SEQUENCE: 355

```
caggtgcagc tggtggagtc tgggggaggc gtggtccagc ctgggaggtc cctgagactc    60
tcctgtgcag cctctggatt caccttcagt agctatggca tgcactgggt ccgccaggct   120
ccaggcaagg ggctggagtg ggtggcagtt atatcatatg atggaagtaa taaatactat   180
gcagactccg tgaagggccg attcaccatc tccagagaca attccaagaa cacgctgtat   240
ctgcaaatga acagcctgag agctgaggac acggctgtgt attactgtgc gagaga       296
```

<210> SEQ ID NO 356
<211> LENGTH: 296
<212> TYPE: DNA
<213> ORGANISM: Artificial Sequence
<220> FEATURE:
<223> OTHER INFORMATION: Description of Artificial Sequence: Synthetic IGHV3-30*18 sequence

<400> SEQUENCE: 356

```
caggtgcagc tggtggagtc tgggggaggc gtggtccagc ctgggaggtc cctgagactc    60
tcctgtgcag cctctggatt caccttcagt agctatggca tgcactgggt ccgccaggct   120
ccaggcaagg ggctggagtg ggtggcagtt atatcatatg atggaagtaa taaatactat   180
gcagactccg tgaagggccg attcaccatc tccagagaca attccaagaa cacgctgtat   240
ctgcaaatga acagcctgag agctgaggac acggctgtgt attactgtgc gaaaga       296
```

<210> SEQ ID NO 357
<211> LENGTH: 296
<212> TYPE: DNA

<213> ORGANISM: Artificial Sequence
<220> FEATURE:
<223> OTHER INFORMATION: Description of Artificial Sequence: Synthetic
IGHV3-30*06 sequence

<400> SEQUENCE: 357

```
caggtgcagc tggtggagtc tgggggaggc gtggtccagc ctggagggtc cctgagactc      60
tcctgtgcag cgtctggatt caccttcagt agctatggca tgcactgggt ccgccaggct     120
ccaggcaagg ggctagagtg ggtggcagtt atatcatatg atggaagtaa taaatactac    180
gcagactccg tgaagggccg attcaccatc tccagagaca attccaagaa cacgctgtat   240
ctgcaaatga acagcctgag agctgaggac acggctgtgt attactgtgc gagaga        296
```

<210> SEQ ID NO 358
<211> LENGTH: 296
<212> TYPE: DNA
<213> ORGANISM: Artificial Sequence
<220> FEATURE:
<223> OTHER INFORMATION: Description of Artificial Sequence: Synthetic
IGHV3-30*12 sequence

<400> SEQUENCE: 358

```
caggtgcagc tggtggagtc tggggggggc gtggtccagc ctggagggtc cctgagactc      60
tcctgtgcag cgtctggatt caccttcagt agctatggca tgcactgggt ccgccaggct     120
ccaggcaagg ggctagagtg ggtggcagtt atatcatatg atggaagtaa taaatactac    180
gcagactccg tgaagggccg attcaccatc tccagagaca attccaagaa cacgctgtat   240
ctgcaaatga acagcctgag agccgaggac acggctgtgt attactgtgc gagaga        296
```

<210> SEQ ID NO 359
<211> LENGTH: 296
<212> TYPE: DNA
<213> ORGANISM: Artificial Sequence
<220> FEATURE:
<223> OTHER INFORMATION: Description of Artificial Sequence: Synthetic
IGHV3-30*19 sequence

<400> SEQUENCE: 359

```
caggtgcagc tggtggagtc tgggggaggc gtggtccagc ctggagggtc cctgagactc      60
tcctgtgcag cgtctggatt caccttcagt agctatggca tgcactgggt ccgccaggct    120
ccaggcaagg ggctggagtg ggtggcagtt atatcatatg atggaagtaa taaatactac   180
gcagactccg tgaagggccg attcaccatc tccagagaca attccaagaa cacgctgtat   240
ctgcaaatga acagcctgag agctgaggac acggctgtgt attactgtgc gagaga        296
```

<210> SEQ ID NO 360
<211> LENGTH: 296
<212> TYPE: DNA
<213> ORGANISM: Artificial Sequence
<220> FEATURE:
<223> OTHER INFORMATION: Description of Artificial Sequence: Synthetic
IGHV3-33*05 sequence

<400> SEQUENCE: 360

```
caggtgcagc tggtggagtc tgggggaggc gtggtccagc ctggagggtc cctgagactc     60
tcctgtgcag cgtctggatt caccttcagt agctatggca tgcactgggt ccgccaggct   120
ccaggcaagg ggctggagtg ggtggcagtt atatcatatg atggaagtaa taaatactat  180
gcagactccg tgaagggccg attcaccatc tccagagaca attccaagaa cacgctgtat  240
ctgcaaatga acagcctgag agccgaggac acggctgtgt attactgtgc gagaga       296
```

-continued

<210> SEQ ID NO 361
<211> LENGTH: 296
<212> TYPE: DNA
<213> ORGANISM: Artificial Sequence
<220> FEATURE:
<223> OTHER INFORMATION: Description of Artificial Sequence: Synthetic
    IGHV3-30*05 sequence

<400> SEQUENCE: 361
caggtgcagc tggtggagtc tgggggaggc gtggtccagc ctggagggtc cctgagactc    60
tcctgtgcag cctctggatt caccttcagt agctatggca tgcactgggt ccgccaggct   120
ccaggcaagg ggctagagtg ggtggcagtt atatcatatg atggaagtaa taaatactac   180
gcagactccg tgaagggccg attcaccatc tccagagaca attccaagaa cacgctgtat   240
ctgcaaatga acagcctgag agctgagggc acggctgtgt attactgtgc gagaga       296

<210> SEQ ID NO 362
<211> LENGTH: 296
<212> TYPE: DNA
<213> ORGANISM: Artificial Sequence
<220> FEATURE:
<223> OTHER INFORMATION: Description of Artificial Sequence: Synthetic
    IGHV3-30*13 sequence

<400> SEQUENCE: 362
caggtgcagc tggtggagtc tgggggaggc gtggtccagc ctggagggtc cctgagactc    60
tcctgtgcag cctctggatt caccttcagt agctatggca tgcactgggt ccgccaggct   120
ccaggcaagg ggctagagtg ggtggcagtt atatcatatg atggaagtaa taaatactac   180
gcagactccg tgaagggccg attcaccatc tccagagaca attccaagaa caggctgtat   240
ctgcaaatga acagcctgag agctgaggac acggctgtgt attactgtgc gagaga       296

<210> SEQ ID NO 363
<211> LENGTH: 296
<212> TYPE: DNA
<213> ORGANISM: Artificial Sequence
<220> FEATURE:
<223> OTHER INFORMATION: Description of Artificial Sequence: Synthetic
    IGHV3-33*01 sequence

<400> SEQUENCE: 363
caggtgcagc tggtggagtc tgggggaggc gtggtccagc ctggagggtc cctgagactc    60
tcctgtgcag cgtctggatt caccttcagt agctatggca tgcactgggt ccgccaggct   120
ccaggcaagg ggctggagtg ggtggcagtt atatggtatg atggaagtaa taaatactat   180
gcagactccg tgaagggccg attcaccatc tccagagaca attccaagaa cacgctgtat   240
ctgcaaatga acagcctgag agccgaggac acggctgtgt attactgtgc gagaga       296

<210> SEQ ID NO 364
<211> LENGTH: 296
<212> TYPE: DNA
<213> ORGANISM: Artificial Sequence
<220> FEATURE:
<223> OTHER INFORMATION: Description of Artificial Sequence: Synthetic
    IGHV3-33*04 sequence

<400> SEQUENCE: 364
caggtgcagc tggtggagtc tgggggaggc gtggtccagc ctggagggtc cctgagactc    60
tcctgtgcag cgtctggatt caccttcagt agctatggca tgcactgggt ccgccaggct   120

```
ccaggcaagg ggctagagtg ggtggcagtt atatggtatg acggaagtaa taaatactat    180
gcagactccg tgaagggccg attcaccatc tccagagaca attccaagaa cacgctgtat    240
ctgcaaatga acagcctgag agccgaggac acggctgtgt attactgtgc gagaga        296
```

<210> SEQ ID NO 365
<211> LENGTH: 296
<212> TYPE: DNA
<213> ORGANISM: Artificial Sequence
<220> FEATURE:
<223> OTHER INFORMATION: Description of Artificial Sequence: Synthetic
    IGHV3-33*02 sequence

<400> SEQUENCE: 365

```
caggtacagc tggtggagtc tgggggaggc gtggtccagc ctgggaggtc cctgagactc    60
tcctgtgcag cgtctggatt caccttcagt agctatggca tgcactgggt ccgccaggct    120
ccaggcaagg ggctggagtg ggtggcagtt atatggtatg atggaagtaa taaatactat    180
gcagactccg cgaagggccg attcaccatc tccagagaca attccacgaa cacgctgttt    240
ctgcaaatga acagcctgag agccgaggac acggctgtgt attactgtgc gagaga        296
```

<210> SEQ ID NO 366
<211> LENGTH: 296
<212> TYPE: DNA
<213> ORGANISM: Artificial Sequence
<220> FEATURE:
<223> OTHER INFORMATION: Description of Artificial Sequence: Synthetic
    IGHV3-33*03 sequence

<400> SEQUENCE: 366

```
caggtgcagc tggtggagtc tgggggaggc gtggtccagc ctgggaggtc cctgagactc    60
tcctgtgcag cgtctggatt caccttcagt agctatggca tgcactgggt ccgccaggct    120
ccaggcaagg ggctggagtg ggtggcagtt atatggtatg atggaagtaa taaatactat    180
gcagactccg tgaagggccg attcaccatc tccagagaca actccaagaa cacgctgtat    240
ctgcaaatga acagcctgag agccgaggac acggctgtgt attactgtgc gaaaga        296
```

<210> SEQ ID NO 367
<211> LENGTH: 296
<212> TYPE: DNA
<213> ORGANISM: Artificial Sequence
<220> FEATURE:
<223> OTHER INFORMATION: Description of Artificial Sequence: Synthetic
    IGHV3-30*02 sequence

<400> SEQUENCE: 367

```
caggtgcagc tggtggagtc tgggggaggc gtggtccagc ctgggggtc cctgagactc     60 tcctgtgcag cgtctggatt caccttcagt agctatggca tgcactgggt ccgccaggct    120
ccaggcaagg ggctggagtg ggtggcatttt atacggtatg atggaagtaa taaatactat   180
gcagactccg tgaagggccg attcaccatc tccagagaca attccaagaa cacgctgtat    240
ctgcaaatga acagcctgag agctgaggac acggctgtgt attactgtgc gaaaga        296
```

<210> SEQ ID NO 368
<211> LENGTH: 296
<212> TYPE: DNA
<213> ORGANISM: Artificial Sequence
<220> FEATURE:
<223> OTHER INFORMATION: Description of Artificial Sequence: Synthetic
    IGHV3-52*01 sequence

<400> SEQUENCE: 368

```
gaggtgcagc tggtggagtc tgggtgaggc ttggtacagc ctggagggtc cctgagactc      60
tcctgtgcag cctctggatt caccttcagt agctcctgga tgcactgggt ctgccaggct     120
ccggagaagg ggctggagtg ggtggccgac ataaagtgtg acggaagtga gaaatactat     180
gtagactctg tgaagggccg attgaccatc tccagagaca tgccaagaa ctccctctat      240 ctgcaagtga acagcctgag agctgaggac atgaccgtgt attactgtgt gagagg        296
```

<210> SEQ ID NO 369
<211> LENGTH: 294
<212> TYPE: DNA
<213> ORGANISM: Artificial Sequence
<220> FEATURE:
<223> OTHER INFORMATION: Description of Artificial Sequence: Synthetic IGHV3-52*02 sequence

<400> SEQUENCE: 369

```
gaggtgcagc tggtggagtc tgggtgaggc ttggtacagc ctggagggtc cctgagactc      60
tcctgtgcag cctctggatt caccttcagt agctcctgga tgcactgggt ctgccaggct     120
ccggagaagg ggcaggagtg ggtggccgac ataaagtgtg acggaagtga gaaatactat     180
gtagactctg tgaagggccg attgaccatc tccagagaca tgccaagaa ctccctctat      240 ctgcaagtga acagcctgag agctgaggac atgaccgtgt attactgtgt gaga           294
```

<210> SEQ ID NO 370
<211> LENGTH: 294
<212> TYPE: DNA
<213> ORGANISM: Artificial Sequence
<220> FEATURE:
<223> OTHER INFORMATION: Description of Artificial Sequence: Synthetic IGHV3-52*03 sequence

<400> SEQUENCE: 370

```
gaggtgcagc tggtcgagtc tgggtgaggc ttggtacagc ctggagggtc cctgagactc      60
tcctgtgcag cctctggatt caccttcagt agctcctgga tgcactgggt ctgccaggct     120
ccggagaagg ggctggagtg ggtggccgac ataaagtgtg acggaagtga gaaatactat     180
gtagactctg tgaagggccg attgaccatc tccagagaca tgccaagaa ctccctctat      240 ctgcaagtga acagcctgag agctgaggac atgaccgtgt attactgtgt gaga           294
```

<210> SEQ ID NO 371
<211> LENGTH: 296
<212> TYPE: DNA
<213> ORGANISM: Artificial Sequence
<220> FEATURE:
<223> OTHER INFORMATION: Description of Artificial Sequence: Synthetic IGHV3-7*01 sequence

<400> SEQUENCE: 371

```
gaggtgcagc tggtggagtc tggggagggc ttggtccagc ctgggggtc cctgagactc       60 tcctgtgcag cctctggatt cacctttagt agctattgga tgagctgggt ccgccaggct     120
ccagggaagg ggctggagtg ggtggccaac ataaagcaag atggaagtga gaaatactat     180
gtggactctg tgaagggccg attcaccatc tccagagaca acgccaagaa ctcactgtat    240
ctgcaaatga acagcctgag agccgaggac acggctgtgt attactgtgc gagaga        296
```

<210> SEQ ID NO 372
<211> LENGTH: 294
<212> TYPE: DNA
<213> ORGANISM: Artificial Sequence -continued

```
<220> FEATURE:
<223> OTHER INFORMATION: Description of Artificial Sequence: Synthetic
      IGHV3-7*02 sequence

<400> SEQUENCE: 372
gaggtgcagc tggtggagtc tgggggaggc ttggtccagc ctgggggtc cctgagactc    60 tcctgtgcag cctctggatt cacctttagt agctattgga tgagctgggt ccgccaggct   120
ccagggaaag gctggagtg gtggccaac ataaagcaag atggaagtga aaatactat      180 gtggactctg tgaagggccg attcaccatc tccagagaca cgccaagaa ctcactgtat    240 ctgcaaatga acagcctgag agccgaggac acggctgtgt attactgtgc gaga          294

<210> SEQ ID NO 373
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV3-23*01 sequence

<400> SEQUENCE: 373
gaggtgcagc tgttggagtc tgggggaggc ttggtacagc ctgggggtc cctgagactc    60 tcctgtgcag cctctggatt cacctttagc agctatgcca tgagctgggt ccgccaggct   120
ccagggaagg gctggagtg gtctcagct attagtggta gtggtggtag cacatactac     180
gcagactccg tgaagggccg gttcaccatc tccagagaca attccaagaa cacgctgtat   240
ctgcaaatga acagcctgag agccgaggac acggccgtat attactgtgc gaaaga        296

<210> SEQ ID NO 374
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV3-23*04 sequence

<400> SEQUENCE: 374
gaggtgcagc tggtggagtc tgggggaggc ttggtacagc ctgggggtc cctgagactc    60 tcctgtgcag cctctggatt cacctttagc agctatgcca tgagctgggt ccgccaggct   120
ccagggaagg gctggagtg gtctcagct attagtggta gtggtggtag cacatactac     180
gcagactccg tgaagggccg gttcaccatc tccagagaca attccaagaa cacgctgtat   240
ctgcaaatga acagcctgag agccgaggac acggccgtat attactgtgc gaaaga        296

<210> SEQ ID NO 375
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV3-23*02 sequence

<400> SEQUENCE: 375
gaggtgcagc tgttggagtc tgggggaggc ttggtacagc ctgggggtc cctgagactc    60 tcctgtgcag cctctggatt cacctttagc agctatgcca tgagctgggt ccgccaggct   120
ccagggaagg gctggagtg gtctcagct attagtggta gtggtggtag cacatactac     180
ggagactccg tgaagggccg gttcaccatc tcaagagaca attccaagaa cacgctgtat   240
ctgcaaatga acagcctgag agccgaggac acggccgtat attactgtgc gaaaga        296
```

<210> SEQ ID NO 376
<211> LENGTH: 294
<212> TYPE: DNA
<213> ORGANISM: Artificial Sequence
<220> FEATURE:
<223> OTHER INFORMATION: Description of Artificial Sequence: Synthetic
    IGHV3-23*03 sequence

<400> SEQUENCE: 376

```
gaggtgcagc tgttggagtc tgggggaggc ttggtacagc ctggggggtc cctgagactc    60
tcctgtgcag cctctggatt cacctttagc agctatgcca tgagctgggt ccgccaggct   120
ccagggaagg ggctggagtg ggtctcagtt atttatagcg gtggtagtag cacatactat   180
gcagactccg tgaagggccg gttcaccatc tccagagata attccaagaa cacgctgtat   240
ctgcaaatga acagcctgag agccgaggac acggccgtat attactgtgc gaaa         294
```

<210> SEQ ID NO 377
<211> LENGTH: 294
<212> TYPE: DNA
<213> ORGANISM: Artificial Sequence
<220> FEATURE:
<223> OTHER INFORMATION: Description of Artificial Sequence: Synthetic
    IGHV3-23*05 sequence

<400> SEQUENCE: 377

```
gaggtgcagc tgttggagtc tgggggaggc ttggtacagc ctggggggtc cctgagactc    60
tcctgtgcag cctctggatt cacctttagc agctatgcca tgagctgggt ccgccaggct   120
ccagggaagg ggctggagtg ggtctcagct atttatagca gtggtagtag cacatactat   180
gcagactccg tgaagggccg gttcaccatc tccagagaca attccaagaa cacgctgtat   240
ctgcaaatga acagcctgag agccgaggac acggccgtat attactgtgc gaaa         294
```

<210> SEQ ID NO 378
<211> LENGTH: 293
<212> TYPE: DNA
<213> ORGANISM: Artificial Sequence
<220> FEATURE:
<223> OTHER INFORMATION: Description of Artificial Sequence: Synthetic
    IGHV3-53*01 sequence

<400> SEQUENCE: 378

```
gaggtgcagc tggtggagtc tgaggaggc ttgatccagc ctggggggtc cctgagactc     60
tcctgtgcag cctctgggtt caccgtcagt agcaactaca tgagctgggt ccgccaggct   120
ccagggaagg ggctggagtg ggtctcagtt atttatagcg gtggtagcac atactacgca   180
gactccgtga agggccgatt caccatctcc agagacaatt ccaagaacac gctgtatctt   240
caaatgaaca gcctgagagc cgaggacacg gccgtgtatt actgtgcgag aga          293
```

<210> SEQ ID NO 379
<211> LENGTH: 291
<212> TYPE: DNA
<213> ORGANISM: Artificial Sequence
<220> FEATURE:
<223> OTHER INFORMATION: Description of Artificial Sequence: Synthetic
    IGHV3-53*02 sequence

<400> SEQUENCE: 379

```
gaggtgcagc tggtggagac tgaggaggc ttgatccagc ctggggggtc cctgagactc     60
tcctgtgcag cctctgggtt caccgtcagt agcaactaca tgagctgggt ccgccaggct   120
ccagggaagg ggctggagtg ggtctcagtt atttatagcg gtggtagcac atactacgca   180
```

```
gactccgtga agggccgatt caccatctcc agagacaatt ccaagaacac gctgtatctt    240
caaatgaaca gcctgagagc cgaggacacg gccgtgtatt actgtgcgag a             291
```

<210> SEQ ID NO 380
<211> LENGTH: 293
<212> TYPE: DNA
<213> ORGANISM: Artificial Sequence
<220> FEATURE:
<223> OTHER INFORMATION: Description of Artificial Sequence: Synthetic
      IGHV3-66*03 sequence

<400> SEQUENCE: 380

```
gaggtgcagc tggtggagtc tggaggaggc ttgatccagc ctggggggtc cctgagactc    60
tcctgtgcag cctctgggtt caccgtcagt agcaactaca tgagctgggt ccgccaggct    120
ccagggaagg ggctggagtg ggtctcagtt atttatagct gtggtagcac atactacgca    180
gactccgtga agggccgatt caccatctcc agagacaatt ccaagaacac gctgtatctt    240
caaatgaaca gcctgagagc tgaggacacg gctgtgtatt actgtgcgag aga           293
```

<210> SEQ ID NO 381
<211> LENGTH: 293
<212> TYPE: DNA
<213> ORGANISM: Artificial Sequence
<220> FEATURE:
<223> OTHER INFORMATION: Description of Artificial Sequence: Synthetic
      IGHV3-53*03 sequence

<400> SEQUENCE: 381

```
gaggtgcagc tggtggagtc tggaggaggc ttgatccagc ctggggggtc cctgagactc    60
tcctgtgcag cctctgggtt caccgtcagt agcaactaca tgagctgggt ccgccagcct    120
ccagggaagg ggctggagtg ggtctcagtt atttatagcg gtggtagcac atactacgca    180
gactctgtga agggccgatt caccatctcc agagacaatt ccaagaacac gctgtatctt    240
caaatgaaca gcctgagagc cgaggacacg gccgtgtatt actgtgctag gga           293
```

<210> SEQ ID NO 382
<211> LENGTH: 293
<212> TYPE: DNA
<213> ORGANISM: Artificial Sequence
<220> FEATURE:
<223> OTHER INFORMATION: Description of Artificial Sequence: Synthetic
      IGHV3-66*01 sequence

<400> SEQUENCE: 382

```
gaggtgcagc tggtggagtc tgggggaggc ttggtccagc ctggggggtc cctgagactc    60
tcctgtgcag cctctggatt caccgtcagt agcaactaca tgagctgggt ccgccaggct    120
ccagggaagg ggctggagtg ggtctcagtt atttatagcg gtggtagcac atactacgca    180
gactccgtga agggcagatt caccatctcc agagacaatt ccaagaacac gctgtatctt    240
caaatgaaca gcctgagagc cgaggacacg gctgtgtatt actgtgcgag aga           293
```

<210> SEQ ID NO 383
<211> LENGTH: 293
<212> TYPE: DNA
<213> ORGANISM: Artificial Sequence
<220> FEATURE:
<223> OTHER INFORMATION: Description of Artificial Sequence: Synthetic
      IGHV3-66*04 sequence

<400> SEQUENCE: 383

```
gaggtgcagc tggtggagtc tgggggaggc ttggtccagc ctggggggtc cctgagactc    60
tcctgtgcag cctctggatt caccgtcagt agcaactaca tgagctgggt ccgccaggct   120
ccagggaagg ggctggagtg ggtctcagtt atttatagcg gtggtagcac atactacgca   180
gactccgtga agggcagatt caccatctcc agagacaatt ccaagaacac gctgtatctt   240
caaatgaaca gcctgagagc cgaggacacg gctgtgtatt actgtgcgag aca           293
```

<210> SEQ ID NO 384
<211> LENGTH: 291
<212> TYPE: DNA
<213> ORGANISM: Artificial Sequence
<220> FEATURE:
<223> OTHER INFORMATION: Description of Artificial Sequence: Synthetic
      IGHV3-66*02 sequence

<400> SEQUENCE: 384

```
gaggtgcagc tggtggagtc tgggggaggc ttggtccagc ctggggggtc cctgagactc    60
tcctgtgcag cctctggatt caccgtcagt agcaactaca tgagctgggt ccgccaggct   120
ccagggaagg ggctggagtg ggtctcagtt atttatagcg gtggtagcac atactacgca   180
gactccgtga agggccgatt caccatctcc agagacaatt ccaagaacac gctgtatctt   240
caaatgaaca gcctgagagc tgaggacacg gctgtgtatt actgtgcgag a             291
```

<210> SEQ ID NO 385
<211> LENGTH: 292
<212> TYPE: DNA
<213> ORGANISM: Artificial Sequence
<220> FEATURE:
<223> OTHER INFORMATION: Description of Artificial Sequence: Synthetic
      IGHV3-38*01 sequence

<400> SEQUENCE: 385

```
gaggtgcagc tggtggagtc tgggggaggc ttggtacagc ctaggggggtc cctgagactc    60 tcctgtgcag cctctggatt caccgtcagt agcaatgaga tgagctggat ccgccaggct   120
ccagggaagg ggctggagtg ggtctcatcc attagtggtg gtagcacata ctacgcagac   180
tccaggaagg gcagattcac catctccaga gacaattcca agaacacgct gtatcttcaa   240
atgaacaacc tgagagctga gggcacggcc gcgtattact gtgccagata ta            292
```

<210> SEQ ID NO 386
<211> LENGTH: 292
<212> TYPE: DNA
<213> ORGANISM: Artificial Sequence
<220> FEATURE:
<223> OTHER INFORMATION: Description of Artificial Sequence: Synthetic
      IGHV3-38*02 sequence

<400> SEQUENCE: 386

```
gaggtgcagc tggtggagtc tgggggaggc ttggtacagc ctaggggggtc cctgagactc    60 tcctgtgcag cctctggatt caccgtcagt agcaatgaga tgagctggat ccgccaggct   120
ccagggaagg ggctggagtg ggtctcatcc attagtggtg gtagcacata ctacgcagac   180
tccaggaagg gcagattcac catctccaga gacaattcca agaacacgct gtatcttcaa   240
atgaacaacc tgagagctga gggcacggcc gtgtattact gtgccagata ta            292
```

<210> SEQ ID NO 387
<211> LENGTH: 288
<212> TYPE: DNA
<213> ORGANISM: Artificial Sequence
<220> FEATURE:

<223> OTHER INFORMATION: Description of Artificial Sequence: Synthetic
     IGHV3-d*01 sequence

<400> SEQUENCE: 387

```
gaggtgcagc tggtggagtc tcggggagtc ttggtacagc ctgggggggtc cctgagactc      60
tcctgtgcag cctctggatt caccgtcagt agcaatgaga tgagctgggt ccgccaggct     120
ccagggaagg gtctggagtg ggtctcatcc attagtggtg gtagcacata ctacgcagac     180
tccaggaagg gcagattcac catctccaga gacaattcca gaacacgct gcatcttcaa      240
atgaacagcc tgagagctga ggacacggct gtgtattact gtaagaaa                  288
```

<210> SEQ ID NO 388
<211> LENGTH: 294
<212> TYPE: DNA
<213> ORGANISM: Artificial Sequence
<220> FEATURE:
<223> OTHER INFORMATION: Description of Artificial Sequence: Synthetic
     IGHV3/OR16-12*01 sequence

<400> SEQUENCE: 388

```
gaggtgcagc tggtagagtc tgggagaggc ttggcccagc ctgggggggta cctaaaactc      60
tccggtgcag cctctggatt caccgtcggt agctggtaca tgagctggat ccaccaggct     120
ccagggaagg gtctggagtg ggtctcatac attagtagta gtggttgtag cacaaactac     180
gcagactctg tgaagggcag attcaccatc tccacagaca actcaaagaa cacgctctac    240
ctgcaaatga acagcctgag agtggaggac acggccgtgt attactgtgc aaga           294
```

<210> SEQ ID NO 389
<211> LENGTH: 302
<212> TYPE: DNA
<213> ORGANISM: Artificial Sequence
<220> FEATURE:
<223> OTHER INFORMATION: Description of Artificial Sequence: Synthetic
     IGHV3-15*01 sequence

<400> SEQUENCE: 389

```
gaggtgcagc tggtggagtc tgggggaggc ttggtaaagc ctgggggggtc ccttagactc      60
tcctgtgcag cctctggatt cactttcagt aacgcctgga tgagctgggt ccgccaggct     120
ccagggaagg ggctggagtg ggttggccgt attaaaagca aaactgatgg tgggacaaca    180
gactacgctg cacccgtgaa aggcagattc accatctcaa gagatgattc aaaaaacacg    240
ctgtatctgc aaatgaacag cctgaaaacc gaggacacag ccgtgtatta ctgtaccaca    300
ga                                                                   302
```

<210> SEQ ID NO 390
<211> LENGTH: 302
<212> TYPE: DNA
<213> ORGANISM: Artificial Sequence
<220> FEATURE:
<223> OTHER INFORMATION: Description of Artificial Sequence: Synthetic
     IGHV3-15*02 sequence

<400> SEQUENCE: 390

```
gaggtgcagc tggtggagtc tgggggagcc ttggtaaagc ctgggggggtc ccttagactc      60
tcctgtgcag cctctggatt cactttcagt aacgcctgga tgagctgggt ccgccaggct     120
ccagggaagg ggctggagtg ggttggccgt attaaaagca aaactgatgg tgggacaaca    180
gactacgctg cacccgtgaa aggcagattc accatctcaa gagatgattc aaaaaacacg    240
ctgtatctgc aaatgaacag cctgaaaacc gaggacacag ccgtgtatta ctgtaccaca    300
``` ga                                                                    302

<210> SEQ ID NO 391
<211> LENGTH: 302
<212> TYPE: DNA
<213> ORGANISM: Artificial Sequence
<220> FEATURE:
<223> OTHER INFORMATION: Description of Artificial Sequence: Synthetic
      IGHV3-15*04 sequence

<400> SEQUENCE: 391
gaggtgcagc tggtggagtc tgggggaggc ttggtaaagc ctgggggtc ccttagactc      60 tcctgtgcag cctctggatt cactttcagt aacgcctgga tgagctgggt ccgccaggct    120
ccagggaagg gctggagtg gttggccgt attgaaagca aaactgatgg tgggacaaca      180
gactacgctg cacccgtgaa aggcagattc accatctcaa gagatgattc aaaaaacacg    240
ctgtatctgc aaatgaacag cctgaaaacc gaggacacag ccgtgtatta ctgtaccaca    300
ga                                                                    302

<210> SEQ ID NO 392
<211> LENGTH: 302
<212> TYPE: DNA
<213> ORGANISM: Artificial Sequence
<220> FEATURE:
<223> OTHER INFORMATION: Description of Artificial Sequence: Synthetic
      IGHV3-15*05 sequence

<400> SEQUENCE: 392
gaggtgcagc tggtggagtc tgggggaggc ttggtaaagc ctgggggtc ccttagactc      60 tcctgtgcag cctctggatt cactttcagt aacgcctgga tgagctgggt ccgccaggct    120
ccagggaagg gctggagtg gttggccgt attaaaagca aaactgatgg tgggacaaca      180
gactacgctg cacccgtgaa aggcagattc accatctcaa gagatgattc aaaaaacacg    240
ctgtatctgc aaatgaacag tctgaaaacc gaggacacag ccgtgtatta ctgtaccaca    300
ga                                                                    302

<210> SEQ ID NO 393
<211> LENGTH: 302
<212> TYPE: DNA
<213> ORGANISM: Artificial Sequence
<220> FEATURE:
<223> OTHER INFORMATION: Description of Artificial Sequence: Synthetic
      IGHV3-15*06 sequence

<400> SEQUENCE: 393
gaggtgcagc tggtggagtc tgggggaggc ttggtaaagc ctgggggtc ccttagactc      60 tcctgtgcag cctctggatt cactttcagt aacgcctgga tgagctgggt ccgccaggct    120
ccagggaagg gctggagtg ggtcggccgt attaaaagca aaactgatgg tgggacaaca     180
aactacgctg cacccgtgaa aggcagattc accatctcaa gagatgattc aaaaaacacg    240
ctgtatctgc aaatgaacag cctgaaaacc gaggacacag ccgtgtatta ctgtaccaca    300
ga                                                                    302

<210> SEQ ID NO 394
<211> LENGTH: 302
<212> TYPE: DNA
<213> ORGANISM: Artificial Sequence
<220> FEATURE:
<223> OTHER INFORMATION: Description of Artificial Sequence: Synthetic -continued IGHV3-15*07 sequence

<400> SEQUENCE: 394
gaggtgcagc tggtggagtc tgggggaggc ttggtaaagc ctggggggtc ccttagactc    60
tcctgtgcag cctctggttt cactttcagt aacgcctgga tgaactgggt ccgccaggct   120
ccagggaagg ggctggagtg ggtcggccgt attaaaagca aaactgatgg tgggacaaca   180
gactacgctg cacccgtgaa aggcagattc accatctcaa gagatgattc aaaaaacacg   240
ctgtatctgc aaatgaacag cctgaaaacc gaggacacag ccgtgtatta ctgtaccaca   300
ga                                                                 302

<210> SEQ ID NO 395
<211> LENGTH: 302
<212> TYPE: DNA
<213> ORGANISM: Artificial Sequence
<220> FEATURE:
<223> OTHER INFORMATION: Description of Artificial Sequence: Synthetic
      IGHV3-15*03 sequence

<400> SEQUENCE: 395
gaggtgcagc tggtggagtc tgccggagcc ttggtacagc ctggggggtc ccttagactc    60
tcctgtgcag cctctggatt cacttgcagt aacgcctgga tgagctgggt ccgccaggct   120
ccagggaagg ggctggagtg ggttggccgt attaaaagca aagctaatgg tgggacaaca   180
gactacgctg cacctgtgaa aggcagattc accatctcaa gagttgattc aaaaaacacg   240
ctgtatctgc aaatgaacag cctgaaaacc gaggacacag ccgtgtatta ctgtaccaca   300
ga                                                                 302

<210> SEQ ID NO 396
<211> LENGTH: 302
<212> TYPE: DNA
<213> ORGANISM: Artificial Sequence
<220> FEATURE:
<223> OTHER INFORMATION: Description of Artificial Sequence: Synthetic
      IGHV3-15*08 sequence

<400> SEQUENCE: 396
gaggtgcagc tggtggagtc tgcgggaggc ttggtacagc ctggggggtc ccttagactc    60
tcctgtgcag cctctggatt cacttgcagt aacgcctgga tgagctgggt ccgccaggct   120
ccagggaagg ggctggagtg ggttggctgt attaaaagca aagctaatgg tgggacaaca   180
gactacgctg cacctgtgaa aggcagattc accatctcaa gagatgattc aaaaaacacg   240
ctgtatctgc aaatgatcag cctgaaaacc gaggacacgg ccgtgtatta ctgtaccaca   300
gg                                                                 302

<210> SEQ ID NO 397
<211> LENGTH: 302
<212> TYPE: DNA
<213> ORGANISM: Artificial Sequence
<220> FEATURE:
<223> OTHER INFORMATION: Description of Artificial Sequence: Synthetic
      IGHV3-72*01 sequence

<400> SEQUENCE: 397
gaggtgcagc tggtggagtc tgggggaggc ttggtccagc ctggagggtc cctgagactc    60
tcctgtgcag cctctggatt caccttcagt gaccactaca tggactgggt ccgccaggct   120
ccagggaagg ggctggagtg ggttggccgt actagaaaca agctaacag ttacaccaca   180

```
gaatacgccg cgtctgtgaa aggcagattc accatctcaa gagatgattc aaagaactca    240
ctgtatctgc aaatgaacag cctgaaaacc gaggacacgg ccgtgtatta ctgtgctaga    300
ga                                                                   302

<210> SEQ ID NO 398
<211> LENGTH: 165
<212> TYPE: DNA
<213> ORGANISM: Artificial Sequence
<220> FEATURE:
<223> OTHER INFORMATION: Description of Artificial Sequence: Synthetic
      IGHV3-72*02 sequence

<400> SEQUENCE: 398
accttcagtg accactacat ggactgggtc cgccaggctc cagggaaggg gctggagtgg    60
gttggccgta ctagaaacaa agctaacagc tacaccacag aatacgccgc gtctgtgaaa    120
ggcagattca ccatctcaag agatgattca aagaactcac tgtat                    165

<210> SEQ ID NO 399
<211> LENGTH: 300
<212> TYPE: DNA
<213> ORGANISM: Artificial Sequence
<220> FEATURE:
<223> OTHER INFORMATION: Description of Artificial Sequence: Synthetic
      IGHV3/OR15-7*01 sequence

<400> SEQUENCE: 399
gaggtgcagc tggtggagtc tgggggaggc ttggtccagc ctgggggttc tctgagactc    60
tcatgtgcag cctctggatt caccttcagt gaccactaca tgagctgggt ccgccaggct    120
caagggaaag ggctagagtt ggtaggttta ataagaaaca agctaacag ttacacgaca    180 gaatatgctg cgtctgtgaa aggcagactt accatctcaa gagaggattc aaagaacacg    240
atgtatctgc aaatgagcaa cctgaaaacc gaggacttgg ccgtgtatta ctgtgctaga    300

<210> SEQ ID NO 400
<211> LENGTH: 300
<212> TYPE: DNA
<213> ORGANISM: Artificial Sequence
<220> FEATURE:
<223> OTHER INFORMATION: Description of Artificial Sequence: Synthetic
      IGHV3/OR15-7*03 sequence

<400> SEQUENCE: 400
gaggtgcagc tggtggagtc tgggggaggc ttggtccagc ctgggggttc tctgagactc    60
tcatgtgcag cctctggatt caccttcagt gaccactaca tgagctgggt ccgccaggct    120
caagggaaag ggctagagtt ggtaggttta ataagaaaca agctaacag ttacacgaca    180 gaatatgctg cgtctgtgaa aggcagactt accatctcaa gagaggattc aaagaacacg    240
ctgtatctgc aaatgagcag cctgaaaacc gaggacttgg ccgtgtatta ctgtgctaga    300

<210> SEQ ID NO 401
<211> LENGTH: 300
<212> TYPE: DNA
<213> ORGANISM: Artificial Sequence
<220> FEATURE:
<223> OTHER INFORMATION: Description of Artificial Sequence: Synthetic
      IGHV3/OR15-7*02 sequence

<400> SEQUENCE: 401
gaggtgcagc tgttggagtc tgggggaggc ttggtccagc ctgggggttc tctgagactc    60
tcatgtgctg cctctggatt caccttcagt gaccactaca tgagctgggt ccgccaggct    120
```

```
caagggaaag ggctagagtt ggtaggttta ataagaaaca aagctaacag ttacacgaca      180
gaatatgctg cgtctgtgaa aggcagactt accatctcaa gagaggattc aaagaacacg      240
ctgtatctgc aaatgagcag cctgaaaacc gaggacttgg ccgtgtatta ctgtgctaga      300
```

<210> SEQ ID NO 402
<211> LENGTH: 302
<212> TYPE: DNA
<213> ORGANISM: Artificial Sequence
<220> FEATURE:
<223> OTHER INFORMATION: Description of Artificial Sequence: Synthetic
      IGHV3-73*01 sequence

<400> SEQUENCE: 402

```
gaggtgcagc tggtggagtc tgggggaggc ttggtccagc ctgggggtc cctgaaactc       60 tcctgtgcag cctctgggtt caccttcagt ggctctgcta tgcactgggt ccgccaggct     120
tccgggaaag gctggagtg gttggccgt attagaagca aagctaacag ttacgcgaca       180
gcatatgctg cgtcggtgaa aggcaggttc accatctcca gagatgattc aaagaacacg     240
gcgtatctgc aaatgaacag cctgaaaacc gaggacacgg ccgtgtatta ctgtactaga     300
ca                                                                    302
```

<210> SEQ ID NO 403
<211> LENGTH: 302
<212> TYPE: DNA
<213> ORGANISM: Artificial Sequence
<220> FEATURE:
<223> OTHER INFORMATION: Description of Artificial Sequence: Synthetic
      IGHV3-73*02 sequence

<400> SEQUENCE: 403

```
gaggtgcagc tggtggagtc cggggaggc ttggtccagc ctgggggtc cctgaaactc        60 tcctgtgcag cctctgggtt caccttcagt ggctctgcta tgcactgggt ccgccaggct     120
tccgggaaag gctggagtg gttggccgt attagaagca aagctaacag ttacgcgaca       180
gcatatgctg cgtcggtgaa aggcaggttc accatctcca gagatgattc aaagaacacg     240
gcgtatctgc aaatgaacag cctgaaaacc gaggacacgg ccgtgtatta ctgtactaga     300
ca                                                                    302
```

<210> SEQ ID NO 404
<211> LENGTH: 302
<212> TYPE: DNA
<213> ORGANISM: Artificial Sequence
<220> FEATURE:
<223> OTHER INFORMATION: Description of Artificial Sequence: Synthetic
      IGHV3-22*01 sequence

<400> SEQUENCE: 404

```
gaggtgcatc tggtggagtc tgggggagcc ttggtacagc ctgggggtc cctgagactc       60 tcctgtgcag cctctggatt caccttcagt tactactaca tgagcgggt ccgccaggct     120 cccgggaagg gctggaatg gtaggttc attagaaaca aagctaatgg tgggacaaca        180
gaatagacca cgtctgtgaa aggcagattc acaatctcaa gagatgattc caaaagcatc     240
acctatctgc aaatgaagag cctgaaaacc gaggacacgg ccgtgtatta ctgttccaga     300
ga                                                                    302
```

<210> SEQ ID NO 405
<211> LENGTH: 302

```
<212> TYPE: DNA
<213> ORGANISM: Artificial Sequence
<220> FEATURE:
<223> OTHER INFORMATION: Description of Artificial Sequence: Synthetic
      IGHV3-22*02 sequence

<400> SEQUENCE: 405
gaggtgcagc tggtggagtc tgggggaggc ttggtacagc ctggggggtc cctgagactc    60
tcctgtgcag cctctggatt caccttcagt tactactaca tgagcggggt ccgccaggct   120
cccgggaagg ggctggaatg ggtaggtttc attagaaaca agctaatgg tgggacaaca    180 gaatagacca cgtctgtgaa aggcagattc acaatctcaa gagatgattc caaaagcatc   240
acctatctgc aaatgaagag cctgaaaacc gaggacacgg ccgtgtatta ctgttccaga   300
ga                                                                   302

<210> SEQ ID NO 406
<211> LENGTH: 302
<212> TYPE: DNA
<213> ORGANISM: Artificial Sequence
<220> FEATURE:
<223> OTHER INFORMATION: Description of Artificial Sequence: Synthetic
      IGHV3-71*01 sequence

<400> SEQUENCE: 406
gaggtgcagc tggtggagtc cgggggaggc ttggtccagc ctggggggtc cctgagactc    60
tcctgtgcag cctctggatt caccttcagt gactactaca tgagctgggt ccgccaggct   120
cccgggaagg ggctggagtg ggtaggtttc attagaaaca agctaatgg tgggacaaca    180 gaatagacca cgtctgtgaa aggcagattc acaatctcaa gagatgattc caaaagcatc   240
acctatctgc aaatgaacag cctgagagcc gaggacacgg ccgtgtatta ctgtgcgaga   300
ga                                                                   302

<210> SEQ ID NO 407
<211> LENGTH: 302
<212> TYPE: DNA
<213> ORGANISM: Artificial Sequence
<220> FEATURE:
<223> OTHER INFORMATION: Description of Artificial Sequence: Synthetic
      IGHV3-49*03 sequence

<400> SEQUENCE: 407
gaggtgcagc tggtggagtc tgggggaggc ttggtacagc cagggcggtc cctgagactc    60
tcctgtacag cttctggatt cacctttggt gattatgcta tgagctggtt ccgccaggct   120
ccagggaagg ggctggagtg ggtaggtttc attagaagca agcttatgg tgggacaaca    180 gaatacgccg cgtctgtgaa aggcagattc accatctcaa gagatgattc caaaagcatc   240
gcctatctgc aaatgaacag cctgaaaacc gaggacacag ccgtgtatta ctgtactaga   300
ga                                                                   302

<210> SEQ ID NO 408
<211> LENGTH: 302
<212> TYPE: DNA
<213> ORGANISM: Artificial Sequence
<220> FEATURE:
<223> OTHER INFORMATION: Description of Artificial Sequence: Synthetic
      IGHV3-49*05 sequence

<400> SEQUENCE: 408
gaggtgcagc tggtggagtc tgggggaggc ttggtaaagc cagggcggtc cctgagactc    60
```

```
tcctgtacag cttctggatt cacctttggt gattatgcta tgagctggtt ccgccaggct    120
ccagggaagg ggctggagtg ggtaggtttc attagaagca aagcttatgg tgggacaaca    180
gaatacgccg cgtctgtgaa aggcagattc accatctcaa gagatgattc caaaagcatc    240
gcctatctgc aaatgaacag cctgaaaacc gaggacacag ccgtgtatta ctgtactaga    300
ga                                                                  302

<210> SEQ ID NO 409
<211> LENGTH: 302
<212> TYPE: DNA
<213> ORGANISM: Artificial Sequence
<220> FEATURE:
<223> OTHER INFORMATION: Description of Artificial Sequence: Synthetic
      HV3-49*01 sequence

<400> SEQUENCE: 409
gaggtgcagc tggtggagtc tgggggaggc ttggtacagc cagggcggtc cctgagactc    60
tcctgtacag cttctggatt cacctttggt gattatgcta tgagctggtt ccgccaggct    120
ccagggaagg ggctggagtg ggtaggtttc attagaagca aagcttatgg tgggacaaca    180
gaatacaccg cgtctgtgaa aggcagattc accatctcaa gagatggttc caaaagcatc    240
gcctatctgc aaatgaacag cctgaaaacc gaggacacag ccgtgtatta ctgtactaga    300
ga                                                                  302

<210> SEQ ID NO 410
<211> LENGTH: 302
<212> TYPE: DNA
<213> ORGANISM: Artificial Sequence
<220> FEATURE:
<223> OTHER INFORMATION: Description of Artificial Sequence: Synthetic
      IGHV3-49*04 sequence

<400> SEQUENCE: 410
gaggtgcagc tggtggagtc tgggggaggc ttggtacagc cagggcggtc cctgagactc    60
tcctgtacag cttctggatt cacctttggt gattatgcta tgagctgggt ccgccaggct    120
ccagggaagg ggctggagtg ggtaggtttc attagaagca aagcttatgg tgggacaaca    180
gaatacgccg cgtctgtgaa aggcagattc accatctcaa gagatgattc caaaagcatc    240
gcctatctgc aaatgaacag cctgaaaacc gaggacacag ccgtgtatta ctgtactaga    300
ga                                                                  302

<210> SEQ ID NO 411
<211> LENGTH: 302
<212> TYPE: DNA
<213> ORGANISM: Artificial Sequence
<220> FEATURE:
<223> OTHER INFORMATION: Description of Artificial Sequence: Synthetic
      IGHV3-49*02 sequence

<400> SEQUENCE: 411
gaggtgcagc tggtggagtc tgggggaggc ttggtacagc cagggccgtc cctgagactc    60
tcctgtacag cttctggatt cacctttggg tattatccta tgagctgggt ccgccaggct    120
ccagggaagg ggctggagtg ggtaggtttc attagaagca aagcttatgg tgggacaaca    180
gaatacgccg cgtctgtgaa aggcagattc accatctcaa gagatgattc caaaagcatc    240
gcctatctgc aaatgaacag cctgaaaacc gaggacacag ccgtgtatta ctgtactaga    300
ga                                                                  302
```

<210> SEQ ID NO 412
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV3-25*01 sequence

<400> SEQUENCE: 412
gagatgcagc tggtggagtc tggggaggc ttgcaaaagc ctgcgtggtc cccgagactc      60
tcctgtgcag cctctcaatt caccttcagt agctactaca tgaactgtgt ccgccaggct     120
ccagggaatg ggctggagtt ggtttgacaa gttaatccta atgggggtag cacataccct    180
atagactccg gtaaggaccg attcaatacc tccagagata cgccaagaa cacacttcat     240 ctgcaaatga acagcctgaa aaccgaggac acggccctct attagtgtac cagaga         296

<210> SEQ ID NO 413
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV3-25*02 sequence

<400> SEQUENCE: 413
gagatgcagc tggtggagtc tggggaggc ttggcaaagc ctgcgtggtc cccgagactc      60
tcctgtgcag cctctcaatt caccttcagt agctactaca tgaactgtgt ccgccaggct     120
ccagggaatg ggctggagtt ggtttgacaa gttaatccta atgggggtag cacataccct    180
atagactccg gtaaggaccg attcaatacc tccagagata cgccaagaa cacacttcat     240 ctgcaaatga acagcctgaa aaccgaggac acggccctct attagtgtac cagaga         296

<210> SEQ ID NO 414
<211> LENGTH: 294
<212> TYPE: DNA
<213> ORGANISM: Artificial Sequence
<220> FEATURE:
<223> OTHER INFORMATION: Description of Artificial Sequence: Synthetic
      IGHV3-25*03 sequence

<400> SEQUENCE: 414
gagatgcagc tggtggagtc tggggaggc ttggcaaagc ctgcgtggtc cccgagactc      60
tcctgtgcag cctctcaatt caccttcagt agctactaca tgaactgtgt ccgccaggct     120
ccagggaatg ggctggagtt ggttggacaa gttaatccta atgggggtag cacataccct    180
atagactccg gtaaggaccg attcaatacc tccagagata cgccaagaa cacacttcat     240 ctgcaaatga acagcctgaa aaccgaggac acggccctgt attagtgtac caga           294

<210> SEQ ID NO 415
<211> LENGTH: 298
<212> TYPE: DNA
<213> ORGANISM: Artificial Sequence
<220> FEATURE:
<223> OTHER INFORMATION: Description of Artificial Sequence: Synthetic
      IGHV3-63*01 sequence

<400> SEQUENCE: 415
gaggtggagc tgatagagtc catagagggc ctgagacaac ttgggaagtt cctgagactc     60
tcctgtgtag cctctggatt caccttcagt agctactgaa tgagctgggt caatgagact    120
ctagggaagg ggctggaggg agtaatagat gtaaatatg atggaagtca gatataccat     180

```
gcagactctg tgaagggcag attcaccatc tccaaagaca atgctaagaa ctcaccgtat    240
ctccaaacga acagtctgag agctgaggac atgaccatgc atggctgtac ataaggtt     298

<210> SEQ ID NO 416
<211> LENGTH: 294
<212> TYPE: DNA
<213> ORGANISM: Artificial Sequence
<220> FEATURE:
<223> OTHER INFORMATION: Description of Artificial Sequence: Synthetic
      IGHV3-63*02 sequence

<400> SEQUENCE: 416
gaggtggagc tgatagagtc catagagggc ctgagacaac ttgggaagtt cctgagactc    60
tcctgtgtag cctctggatt caccttcagt agctactgaa tgagctgggt caatgagact   120
ctagggaagg ggctggaggg agtaatagat gtaaaatatg atggaagtca gatataccat   180
gcagactctg tgaagggcag attcaccatc tccaaagaca atgctaagaa ctcaccgtat   240
ctgcaaacga acagtctgag agctgaggac atgaccatgc atggctgtac ataa         294

<210> SEQ ID NO 417
<211> LENGTH: 298
<212> TYPE: DNA
<213> ORGANISM: Artificial Sequence
<220> FEATURE:
<223> OTHER INFORMATION: Description of Artificial Sequence: Synthetic
      IGHV3-32*01 sequence

<400> SEQUENCE: 417
gaggtggagc tgatagagtc catagaggac ctgagacaac ctgggaagtt cctgagactc    60
tcctgtgtag cctctagatt cgccttcagt agcttctgaa tgagccgagt tcaccagtct   120
ccaggcaagg ggctggagtg agtaatagat ataaagatg atggaagtca gatacaccat    180
gcagactctg tgaagggcag attctccatc tccaaagaca atgctaagaa ctctctgtat   240
ctgcaaatga acactcagag agctgaggac gtggccgtgt atggctatac ataaggtc     298

<210> SEQ ID NO 418
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV3-54*01 sequence

<400> SEQUENCE: 418
gaggtacagc tggtggagtc tgaagaaaac caaagacaac ttgggggatc cctgagactc    60
tcctgtgcag actctggatt aaccttcagt agctactgaa tgagctcaga ttcccaagct   120
ccagggaagg ggctggagtg agtagtagat atatagtagg atagaagtca gctatgttat   180
gcacaatctg tgaagagcag attcaccatc tccaaagaaa atgccaagaa ctcactctgt   240
ttgcaaatga acagtctgag agcagagggc acggccgtgt attactgtat gtgagy       296

<210> SEQ ID NO 419
<211> LENGTH: 296
<212> TYPE: DNA
<213> ORGANISM: Artificial Sequence
<220> FEATURE:
<223> OTHER INFORMATION: Description of Artificial Sequence: Synthetic
      IGHV3-54*04 sequence

<400> SEQUENCE: 419
```

```
gaggtacagc tggtggagtc tgaagaaaac caaagacaac ttgggggatc cctgagactc    60
tcctgtgcag actctggatt aaccttcagt agctactgaa tgagctcaga ttcccaggct   120
ccagggaagg ggctggagtg agtagtagat atatagtagg atagaagtca gctatgttat   180
gcacaatctg tgaagagcag attcaccatc tccaaagaaa atgccaagaa ctcactctgt   240
ttgcaaatga acagtctgag agcagagggc acggccgtgt attactgtat gtgagt        296
```

<210> SEQ ID NO 420
<211> LENGTH: 207
<212> TYPE: DNA
<213> ORGANISM: Artificial Sequence
<220> FEATURE:
<223> OTHER INFORMATION: Description of Artificial Sequence: Synthetic
    IGHV3-54*02 sequence

<400> SEQUENCE: 420

```
tagctactga atgagctcag attcccaggc tccagggaag gggctggagt gagtagtaga    60
tatatagtac gatagaagtc agatatgtta tgcacaatct gtgaagagca gattcaccat   120
ctccaaagaa aatgccaaga actcactccg tttgcaaatg aacagtctga gagcagaggg   180
cacggccgtg tattactgta tgtgagg                                        207
```

<210> SEQ ID NO 421
<211> LENGTH: 31
<212> TYPE: DNA
<213> ORGANISM: Artificial Sequence
<220> FEATURE:
<223> OTHER INFORMATION: Description of Artificial Sequence: Synthetic
    >IGHJ4_1 sequence

<400> SEQUENCE: 421

```
tgaggagacg gtgaccaggg ttccttggcc c                                    31
```

<210> SEQ ID NO 422
<211> LENGTH: 31
<212> TYPE: DNA
<213> ORGANISM: Artificial Sequence
<220> FEATURE:
<223> OTHER INFORMATION: Description of Artificial Sequence: Synthetic
    >IGHJ4_3 sequence

<400> SEQUENCE: 422

```
tgaggagacg gtgaccaggg tcccttggcc c                                    31
```

<210> SEQ ID NO 423
<211> LENGTH: 31
<212> TYPE: DNA
<213> ORGANISM: Artificial Sequence
<220> FEATURE:
<223> OTHER INFORMATION: Description of Artificial Sequence: Synthetic
    >IGHJ4_2 sequence

<400> SEQUENCE: 423

```
tgaggagacg gtgaccaggg ttccctggcc c                                    31
```

<210> SEQ ID NO 424
<211> LENGTH: 32
<212> TYPE: DNA
<213> ORGANISM: Artificial Sequence
<220> FEATURE:
<223> OTHER INFORMATION: Description of Artificial Sequence: Synthetic
    >IGHJ3_12 sequence

<400> SEQUENCE: 424

```
ctgaagagac ggtgaccatt gtcccttggc cc                                 32
```

<210> SEQ ID NO 425
<211> LENGTH: 32
<212> TYPE: DNA
<213> ORGANISM: Artificial Sequence
<220> FEATURE:
<223> OTHER INFORMATION: Description of Artificial Sequence: Synthetic
      >IGHJ6_1 sequence

<400> SEQUENCE: 425

```
ctgaggagac ggtgaccgtg gtcccttgcc cc                                 32
```

<210> SEQ ID NO 426
<211> LENGTH: 31
<212> TYPE: DNA
<213> ORGANISM: Artificial Sequence
<220> FEATURE:
<223> OTHER INFORMATION: Description of Artificial Sequence: Synthetic
      >IGHJ6_2 sequence

<400> SEQUENCE: 426

```
tgaggagacg gtgaccgtgg tcccttggcc c                                  31
```

<210> SEQ ID NO 427
<211> LENGTH: 32
<212> TYPE: DNA
<213> ORGANISM: Artificial Sequence
<220> FEATURE:
<223> OTHER INFORMATION: Description of Artificial Sequence: Synthetic
      >IGHJ6_34 sequence

<400> SEQUENCE: 427

```
ctgaggagac ggtgaccgtg gtccctttgc cc                                 32
```

<210> SEQ ID NO 428
<211> LENGTH: 32
<212> TYPE: DNA
<213> ORGANISM: Artificial Sequence
<220> FEATURE:
<223> OTHER INFORMATION: Description of Artificial Sequence: Synthetic
      >IGHJ2_1 sequence

<400> SEQUENCE: 428

```
ctgaggagac agtgaccagg gtgccacggc cc                                 32
```

<210> SEQ ID NO 429
<211> LENGTH: 32
<212> TYPE: DNA
<213> ORGANISM: Artificial Sequence
<220> FEATURE:
<223> OTHER INFORMATION: Description of Artificial Sequence: Synthetic
      >IGHJ5_1 sequence

<400> SEQUENCE: 429

```
ctgaggagac ggtgaccagg gttccttggc cc                                 32
```

<210> SEQ ID NO 430
<211> LENGTH: 32
<212> TYPE: DNA
<213> ORGANISM: Artificial Sequence
<220> FEATURE:
<223> OTHER INFORMATION: Description of Artificial Sequence: Synthetic
      >IGHJ5_2 sequence

<400> SEQUENCE: 430

```
ctgaggagac ggtgaccagg gttccctggc cc                                 32
```

<210> SEQ ID NO 431
<211> LENGTH: 32
<212> TYPE: DNA
<213> ORGANISM: Artificial Sequence
<220> FEATURE:
<223> OTHER INFORMATION: Description of Artificial Sequence: Synthetic
>IGHJ1_1 sequence

<400> SEQUENCE: 431
ctgaggagac ggtgaccagg gtgccctggc cc                                32

<210> SEQ ID NO 432
<211> LENGTH: 34
<212> TYPE: DNA
<213> ORGANISM: Artificial Sequence
<220> FEATURE:
<223> OTHER INFORMATION: Description of Artificial Sequence: Synthetic
>IGHJSEQ4_1 sequence

<400> SEQUENCE: 432
tgaggagacg gtgaccaggg ttccttggcc ccag                              34

<210> SEQ ID NO 433
<211> LENGTH: 34
<212> TYPE: DNA
<213> ORGANISM: Artificial Sequence
<220> FEATURE:
<223> OTHER INFORMATION: Description of Artificial Sequence: Synthetic
>IGHJSEQ4_3 sequence

<400> SEQUENCE: 433
tgaggagacg gtgaccaggg tcccttggcc ccag                              34

<210> SEQ ID NO 434
<211> LENGTH: 34
<212> TYPE: DNA
<213> ORGANISM: Artificial Sequence
<220> FEATURE:
<223> OTHER INFORMATION: Description of Artificial Sequence: Synthetic
>IGHJSEQ4_2 sequence

<400> SEQUENCE: 434
tgaggagacg gtgaccaggg ttccctggcc ccag                              34

<210> SEQ ID NO 435
<211> LENGTH: 35
<212> TYPE: DNA
<213> ORGANISM: Artificial Sequence
<220> FEATURE:
<223> OTHER INFORMATION: Description of Artificial Sequence: Synthetic
>IGHJSEQ3_12 sequence

<400> SEQUENCE: 435
ctgaagagac ggtgaccatt gtcccttggc cccag                             35

<210> SEQ ID NO 436
<211> LENGTH: 35
<212> TYPE: DNA
<213> ORGANISM: Artificial Sequence
<220> FEATURE:
<223> OTHER INFORMATION: Description of Artificial Sequence: Synthetic
>IGHJSEQ6_1 sequence

<400> SEQUENCE: 436
ctgaggagac ggtgaccgtg gtcccttgcc cccag                             35

<210> SEQ ID NO 437
<211> LENGTH: 34
<212> TYPE: DNA
<213> ORGANISM: Artificial Sequence
<220> FEATURE:
<223> OTHER INFORMATION: Description of Artificial Sequence: Synthetic
      >IGHJSEQ6_2 sequence

<400> SEQUENCE: 437
tgaggagacg gtgaccgtgg tcccttggcc ccag                                34

<210> SEQ ID NO 438
<211> LENGTH: 35
<212> TYPE: DNA
<213> ORGANISM: Artificial Sequence
<220> FEATURE:
<223> OTHER INFORMATION: Description of Artificial Sequence: Synthetic
      >IGHJSEQ6_34 sequence

<400> SEQUENCE: 438
ctgaggagac ggtgaccgtg gtccctttgc cccag                               35

<210> SEQ ID NO 439
<211> LENGTH: 35
<212> TYPE: DNA
<213> ORGANISM: Artificial Sequence
<220> FEATURE:
<223> OTHER INFORMATION: Description of Artificial Sequence: Synthetic
      >IGHJSEQ2_1 sequence

<400> SEQUENCE: 439
ctgaggagac agtgaccagg gtgccacggc cccag                               35

<210> SEQ ID NO 440
<211> LENGTH: 35
<212> TYPE: DNA
<213> ORGANISM: Artificial Sequence
<220> FEATURE:
<223> OTHER INFORMATION: Description of Artificial Sequence: Synthetic
      >IGHJSEQ5_1 sequence

<400> SEQUENCE: 440
ctgaggagac ggtgaccagg gttccttggc cccag                               35

<210> SEQ ID NO 441
<211> LENGTH: 35
<212> TYPE: DNA
<213> ORGANISM: Artificial Sequence
<220> FEATURE:
<223> OTHER INFORMATION: Description of Artificial Sequence: Synthetic
      >IGHJSEQ5_2 sequence

<400> SEQUENCE: 441
ctgaggagac ggtgaccagg gttccctggc cccag                               35

<210> SEQ ID NO 442
<211> LENGTH: 35
<212> TYPE: DNA
<213> ORGANISM: Artificial Sequence
<220> FEATURE:
<223> OTHER INFORMATION: Description of Artificial Sequence: Synthetic
      >IGHJSEQ1_1 sequence

<400> SEQUENCE: 442
ctgaggagac ggtgaccagg gtgccctggc cccag                               35

```
<210> SEQ ID NO 443
<211> LENGTH: 36
<212> TYPE: DNA
<213> ORGANISM: Artificial Sequence
<220> FEATURE:
<223> OTHER INFORMATION: Description of Artificial Sequence: Synthetic
      >IGHV1 sequence
<220> FEATURE:
<221> NAME/KEY: modified_base
<222> LOCATION: (18)..(18)
<223> OTHER INFORMATION: a, c, g or t
<220> FEATURE:
<221> NAME/KEY: modified_base
<222> LOCATION: (20)..(20)
<223> OTHER INFORMATION: a, c, g or t

<400> SEQUENCE: 443
tgggtgcacc aggtccangn acaagggctt gagtgg                                36

<210> SEQ ID NO 444
<211> LENGTH: 36
<212> TYPE: DNA
<213> ORGANISM: Artificial Sequence
<220> FEATURE:
<223> OTHER INFORMATION: Description of Artificial Sequence: Synthetic
      >IGHV2 sequence
<220> FEATURE:
<221> NAME/KEY: modified_base
<222> LOCATION: (18)..(18)
<223> OTHER INFORMATION: a, c, g or t
<220> FEATURE:
<221> NAME/KEY: modified_base
<222> LOCATION: (20)..(20)
<223> OTHER INFORMATION: a, c, g or t

<400> SEQUENCE: 444
tgggtgcgac aggctcgngn acaacgcctt gagtgg                                36

<210> SEQ ID NO 445
<211> LENGTH: 36
<212> TYPE: DNA
<213> ORGANISM: Artificial Sequence
<220> FEATURE:
<223> OTHER INFORMATION: Description of Artificial Sequence: Synthetic
      >IGHV3 sequence
<220> FEATURE:
<221> NAME/KEY: modified_base
<222> LOCATION: (18)..(18)
<223> OTHER INFORMATION: a, c, g or t
<220> FEATURE:
<221> NAME/KEY: modified_base
<222> LOCATION: (20)..(20)
<223> OTHER INFORMATION: a, c, g or t

<400> SEQUENCE: 445
tgggtgcgcc agatgccngn gaaaggcctg gagtgg                                36

<210> SEQ ID NO 446
<211> LENGTH: 36
<212> TYPE: DNA
<213> ORGANISM: Artificial Sequence
<220> FEATURE:
<223> OTHER INFORMATION: Description of Artificial Sequence: Synthetic
      >IGHV4 sequence
<220> FEATURE:
<221> NAME/KEY: modified_base
<222> LOCATION: (18)..(18)
<223> OTHER INFORMATION: a, c, g or t
<220> FEATURE:
<221> NAME/KEY: modified_base
<222> LOCATION: (20)..(20)
<223> OTHER INFORMATION: a, c, g or t
```

```
<400> SEQUENCE: 446
tgggtccgcc agscyccngn gaagggggctg gagtgg                36
```

```
<210> SEQ ID NO 447
<211> LENGTH: 36
<212> TYPE: DNA
<213> ORGANISM: Artificial Sequence
<220> FEATURE:
<223> OTHER INFORMATION: Description of Artificial Sequence: Synthetic
      >IGHV5 sequence
<220> FEATURE:
<221> NAME/KEY: modified_base
<222> LOCATION: (18)..(18)
<223> OTHER INFORMATION: a, c, g or t
<220> FEATURE:
<221> NAME/KEY: modified_base
<222> LOCATION: (20)..(20)
<223> OTHER INFORMATION: a, c, g or t

<400> SEQUENCE: 447
tgggtccgcc aggctccngn aaagggggctg gagtgg                36
```

```
<210> SEQ ID NO 448
<211> LENGTH: 36
<212> TYPE: DNA
<213> ORGANISM: Artificial Sequence
<220> FEATURE:
<223> OTHER INFORMATION: Description of Artificial Sequence: Synthetic
      >IGHV6 sequence
<220> FEATURE:
<221> NAME/KEY: modified_base
<222> LOCATION: (18)..(18)
<223> OTHER INFORMATION: a, c, g or t
<220> FEATURE:
<221> NAME/KEY: modified_base
<222> LOCATION: (20)..(20)
<223> OTHER INFORMATION: a, c, g or t

<400> SEQUENCE: 448
tgggtctgcc aggctccngn gaagggggcag gagtgg                36
```

```
<210> SEQ ID NO 449
<211> LENGTH: 37
<212> TYPE: DNA
<213> ORGANISM: Artificial Sequence
<220> FEATURE:
<223> OTHER INFORMATION: Description of Artificial Sequence: Synthetic
      >IGH7_3.25p sequence

<400> SEQUENCE: 449
tgtgtccgcc aggctccagg gaatgggctg gagttgg                37
```

```
<210> SEQ ID NO 450
<211> LENGTH: 37
<212> TYPE: DNA
<213> ORGANISM: Artificial Sequence
<220> FEATURE:
<223> OTHER INFORMATION: Description of Artificial Sequence: Synthetic
      >IGH8_3.54p sequence

<400> SEQUENCE: 450
tcagattccc aagctccagg gaagggggctg gagtgag                37
```

```
<210> SEQ ID NO 451
<211> LENGTH: 37
<212> TYPE: DNA
<213> ORGANISM: Artificial Sequence
<220> FEATURE:
<223> OTHER INFORMATION: Description of Artificial Sequence: Synthetic
```

>IGH9_3.63p sequence

<400> SEQUENCE: 451
tgggtcaatg agactctagg gaagggctg gagggag                                37

<210> SEQ ID NO 452
<211> LENGTH: 48
<212> TYPE: DNA
<213> ORGANISM: Artificial Sequence
<220> FEATURE:
<223> OTHER INFORMATION: Description of Artificial Sequence: Synthetic
      >IGHJ4*01/1-48 sequence

<400> SEQUENCE: 452
actactttga ctactggggc caaggaaccc tggtcaccgt ctcctcag                   48

<210> SEQ ID NO 453
<211> LENGTH: 48
<212> TYPE: DNA
<213> ORGANISM: Artificial Sequence
<220> FEATURE:
<223> OTHER INFORMATION: Description of Artificial Sequence: Synthetic
      >IGHJ4*03/1-48 sequence

<400> SEQUENCE: 453
gctactttga ctactggggc caagggaccc tggtcaccgt ctcctcag                   48

<210> SEQ ID NO 454
<211> LENGTH: 48
<212> TYPE: DNA
<213> ORGANISM: Artificial Sequence
<220> FEATURE:
<223> OTHER INFORMATION: Description of Artificial Sequence: Synthetic
      >IGHJ4*02/1-48 sequence

<400> SEQUENCE: 454
actactttga ctactggggc cagggaaccc tggtcaccgt ctcctcag                   48

<210> SEQ ID NO 455
<211> LENGTH: 50
<212> TYPE: DNA
<213> ORGANISM: Artificial Sequence
<220> FEATURE:
<223> OTHER INFORMATION: Description of Artificial Sequence: Synthetic
      >IGHJ3*01/1-50 sequence

<400> SEQUENCE: 455
tgatgctttt gatgtctggg gccaagggac aatggtcacc gtctcttcag                 50

<210> SEQ ID NO 456
<211> LENGTH: 50
<212> TYPE: DNA
<213> ORGANISM: Artificial Sequence
<220> FEATURE:
<223> OTHER INFORMATION: Description of Artificial Sequence: Synthetic
      >IGHJ3*02/1-50 sequence

<400> SEQUENCE: 456
tgatgctttt gatatctggg gccaagggac aatggtcacc gtctcttcag                 50

<210> SEQ ID NO 457
<211> LENGTH: 63
<212> TYPE: DNA
<213> ORGANISM: Artificial Sequence
<220> FEATURE:
<223> OTHER INFORMATION: Description of Artificial Sequence: Synthetic
      >IGHJ6*01/1-63 sequence

<400> SEQUENCE: 457
attactacta ctactacggt atggacgtct gggggcaagg gaccacggtc accgtctcct    60
cag                                                                 63

<210> SEQ ID NO 458
<211> LENGTH: 63
<212> TYPE: DNA
<213> ORGANISM: Artificial Sequence
<220> FEATURE:
<223> OTHER INFORMATION: Description of Artificial Sequence: Synthetic
      >IGHJ6*02/1-62 sequence

<400> SEQUENCE: 458
attactacta ctactacggt atggacgtct ggggccaagg gaccacggtc accgtctcct    60
cag                                                                 63

<210> SEQ ID NO 459
<211> LENGTH: 63
<212> TYPE: DNA
<213> ORGANISM: Artificial Sequence
<220> FEATURE:
<223> OTHER INFORMATION: Description of Artificial Sequence: Synthetic
      >IGHJ6*04/1-63 sequence

<400> SEQUENCE: 459
attactacta ctactacggt atggacgtct ggggcaaagg gaccacggtc accgtctcct    60
cag                                                                 63

<210> SEQ ID NO 460
<211> LENGTH: 63
<212> TYPE: DNA
<213> ORGANISM: Artificial Sequence
<220> FEATURE:
<223> OTHER INFORMATION: Description of Artificial Sequence: Synthetic
      >IGHJ6*03/1-62 sequence

<400> SEQUENCE: 460
attactacta ctactactac atggacgtct ggggcaaagg gaccacggtc accgtctcct    60
cag                                                                 63

<210> SEQ ID NO 461
<211> LENGTH: 53
<212> TYPE: DNA
<213> ORGANISM: Artificial Sequence
<220> FEATURE:
<223> OTHER INFORMATION: Description of Artificial Sequence: Synthetic
      >IGHJ2*01/1-53 sequence

<400> SEQUENCE: 461
ctactggtac ttcgatctct ggggccgtgg caccctggtc actgtctcct cag           53

<210> SEQ ID NO 462
<211> LENGTH: 51
<212> TYPE: DNA
<213> ORGANISM: Artificial Sequence
<220> FEATURE:
<223> OTHER INFORMATION: Description of Artificial Sequence: Synthetic
      >IGHJ5*01/1-51 sequence

<400> SEQUENCE: 462
acaactggtt cgactcctgg ggccaaggaa ccctggtcac cgtctcctca g             51

```
<210> SEQ ID NO 463
<211> LENGTH: 51
<212> TYPE: DNA
<213> ORGANISM: Artificial Sequence
<220> FEATURE:
<223> OTHER INFORMATION: Description of Artificial Sequence: Synthetic
      >IGHJ5*02/1-51 sequence

<400> SEQUENCE: 463
acaactggtt cgacccctgg ggccagggaa ccctggtcac cgtctcctca g            51

<210> SEQ ID NO 464
<211> LENGTH: 52
<212> TYPE: DNA
<213> ORGANISM: Artificial Sequence
<220> FEATURE:
<223> OTHER INFORMATION: Description of Artificial Sequence: Synthetic
      >IGHJ1*01/1-52 sequence

<400> SEQUENCE: 464
gctgaatact tccagcactg gggccagggc accctggtca ccgtctcctc ag           52

<210> SEQ ID NO 465
<211> LENGTH: 61
<212> TYPE: DNA
<213> ORGANISM: Artificial Sequence
<220> FEATURE:
<223> OTHER INFORMATION: Description of Artificial Sequence: Synthetic
      >IGHJ2P*01/1-61 sequence

<400> SEQUENCE: 465
ctacaagtgc ttggagcact ggggcagggc agcccggaca ccgtctccct gggaacgtca   60
g                                                                   61

<210> SEQ ID NO 466
<211> LENGTH: 54
<212> TYPE: DNA
<213> ORGANISM: Artificial Sequence
<220> FEATURE:
<223> OTHER INFORMATION: Description of Artificial Sequence: Synthetic
      >IGHJ1P*01/1-54 sequence

<400> SEQUENCE: 466
aaaggtgctg ggggtcccct gaacccgacc cgccctgaga ccgcagccac atca         54

<210> SEQ ID NO 467
<211> LENGTH: 52
<212> TYPE: DNA
<213> ORGANISM: Artificial Sequence
<220> FEATURE:
<223> OTHER INFORMATION: Description of Artificial Sequence: Synthetic
      >IGHJ3P*01/1-52 sequence

<400> SEQUENCE: 467
cttgcggttg gacttcccag ccgacagtgg tggtctggct tctgaggggt ca           52

<210> SEQ ID NO 468
<211> LENGTH: 58
<212> TYPE: DNA
<213> ORGANISM: Artificial Sequence
<220> FEATURE:
<223> OTHER INFORMATION: Description of Artificial Sequence: Synthetic
      TRBJ1-2 sequence

<400> SEQUENCE: 468
aatgatacgg cgaccaccga gatctaccta caacggttaa cctggtcccc gaaccgaa     58
```

<210> SEQ ID NO 469
<211> LENGTH: 284
<212> TYPE: DNA
<213> ORGANISM: Artificial Sequence
<220> FEATURE:
<223> OTHER INFORMATION: Description of Artificial Sequence: Synthetic
      TRBV2*02 sequence

<400> SEQUENCE: 469
gaacctgaag tcacccagac tcccagccat caggtcacac agatgggaca ggaagtgatc      60
ttgcactgtg tccccatctc taatcactta tacttctatt ggtacagaca aatcttgggg     120
cagaaagtcg agtttctggt ttcctttat aataatgaaa tctcagagaa gtctgaaata     180
ttcgatgatc aattctcagt tgaaaggcct gatggatcaa atttcactct gaagatccgg    240
tccacaaagc tggaggactc agccatgtac ttctgtgcca gcag                      284

<210> SEQ ID NO 470
<211> LENGTH: 33
<212> TYPE: DNA
<213> ORGANISM: Artificial Sequence
<220> FEATURE:
<223> OTHER INFORMATION: Description of Artificial Sequence: Synthetic
      Jseq 1-1 sequence

<400> SEQUENCE: 470
acaactgtga gtctggtgcc ttgtccaaag aaa                                   33

<210> SEQ ID NO 471
<211> LENGTH: 33
<212> TYPE: DNA
<213> ORGANISM: Artificial Sequence
<220> FEATURE:
<223> OTHER INFORMATION: Description of Artificial Sequence: Synthetic
      Jseq 1-2 sequence

<400> SEQUENCE: 471
acaacggtta acctggtccc cgaaccgaag gtg                                   33

<210> SEQ ID NO 472
<211> LENGTH: 33
<212> TYPE: DNA
<213> ORGANISM: Artificial Sequence
<220> FEATURE:
<223> OTHER INFORMATION: Description of Artificial Sequence: Synthetic
      Jseq 1-3 sequence

<400> SEQUENCE: 472
acaacagtga gccaacttcc ctctccaaaa tat                                   33

<210> SEQ ID NO 473
<211> LENGTH: 33
<212> TYPE: DNA
<213> ORGANISM: Artificial Sequence
<220> FEATURE:
<223> OTHER INFORMATION: Description of Artificial Sequence: Synthetic
      Jseq 1-4 sequence

<400> SEQUENCE: 473
aagacagaga gctgggttcc actgccaaaa aac                                   33

<210> SEQ ID NO 474
<211> LENGTH: 33
<212> TYPE: DNA
<213> ORGANISM: Artificial Sequence
<220> FEATURE:

```
<223> OTHER INFORMATION: Description of Artificial Sequence: Synthetic
      Jseq 1-5 sequence

<400> SEQUENCE: 474
aggatggaga gtcgagtccc atcaccaaaa tgc                                33

<210> SEQ ID NO 475
<211> LENGTH: 33
<212> TYPE: DNA
<213> ORGANISM: Artificial Sequence
<220> FEATURE:
<223> OTHER INFORMATION: Description of Artificial Sequence: Synthetic
      Jseq 1-6 sequence

<400> SEQUENCE: 475
gtcacagtga gcctggtccc gttcccaaag tgg                                33

<210> SEQ ID NO 476
<211> LENGTH: 33
<212> TYPE: DNA
<213> ORGANISM: Artificial Sequence
<220> FEATURE:
<223> OTHER INFORMATION: Description of Artificial Sequence: Synthetic
      Jseq 2-1 sequence

<400> SEQUENCE: 476
agcacggtga gccgtgtccc tggcccgaag aac                                33

<210> SEQ ID NO 477
<211> LENGTH: 33
<212> TYPE: DNA
<213> ORGANISM: Artificial Sequence
<220> FEATURE:
<223> OTHER INFORMATION: Description of Artificial Sequence: Synthetic
      Jseq 2-2 sequence

<400> SEQUENCE: 477
agtacggtca gcctagagcc ttctccaaaa aac                                33

<210> SEQ ID NO 478
<211> LENGTH: 33
<212> TYPE: DNA
<213> ORGANISM: Artificial Sequence
<220> FEATURE:
<223> OTHER INFORMATION: Description of Artificial Sequence: Synthetic
      Jseq 2-3 sequence

<400> SEQUENCE: 478
agcactgtca gccgggtgcc tgggccaaaa tac                                33

<210> SEQ ID NO 479
<211> LENGTH: 33
<212> TYPE: DNA
<213> ORGANISM: Artificial Sequence
<220> FEATURE:
<223> OTHER INFORMATION: Description of Artificial Sequence: Synthetic
      Jseq 2-4 sequence

<400> SEQUENCE: 479
agcactgaga gccgggtccc ggcgccgaag tac                                33

<210> SEQ ID NO 480
<211> LENGTH: 33
<212> TYPE: DNA
<213> ORGANISM: Artificial Sequence
<220> FEATURE:
<223> OTHER INFORMATION: Description of Artificial Sequence: Synthetic
```

```
                            Jseq 2-5 sequence

<400> SEQUENCE: 480
agcaccagga gccgcgtgcc tggcccgaag tac                                      33

<210> SEQ ID NO 481
<211> LENGTH: 33
<212> TYPE: DNA
<213> ORGANISM: Artificial Sequence
<220> FEATURE:
<223> OTHER INFORMATION: Description of Artificial Sequence: Synthetic
      Jseq 2-6 sequence

<400> SEQUENCE: 481
agcacggtca gcctgctgcc ggccccgaaa gtc                                      33

<210> SEQ ID NO 482
<211> LENGTH: 33
<212> TYPE: DNA
<213> ORGANISM: Artificial Sequence
<220> FEATURE:
<223> OTHER INFORMATION: Description of Artificial Sequence: Synthetic
      Jseq 2-7 sequence

<400> SEQUENCE: 482
gtgaccgtga gcctggtgcc cggcccgaag tac                                      33

<210> SEQ ID NO 483
<211> LENGTH: 34
<212> TYPE: DNA
<213> ORGANISM: Artificial Sequence
<220> FEATURE:
<223> OTHER INFORMATION: Description of Artificial Sequence: Synthetic
      TRBJ1-5 sequence
<220> FEATURE:
<221> NAME/KEY: modified_base
<222> LOCATION: (1)..(1)
<223> OTHER INFORMATION: a, c, g or t
<220> FEATURE:
<221> NAME/KEY: misc_feature
<222> LOCATION: (1)..(1)
<223> OTHER INFORMATION: 5' end modified with universal reverse primer

<400> SEQUENCE: 483
nacctaggat ggagagtcga gtcccatcac caaa                                     34

<210> SEQ ID NO 484
<211> LENGTH: 58
<212> TYPE: DNA
<213> ORGANISM: Artificial Sequence
<220> FEATURE:
<223> OTHER INFORMATION: Description of Artificial Sequence: Synthetic
      TRBJ1-5 sequence

<400> SEQUENCE: 484
aatgatacgg cgaccaccga gatctaccta ggatggagag tcgagtccca tcaccaaa           58
```

METHOD OF MEASURING ADAPTIVE IMMUNITY

CROSS-REFERENCE TO RELATED APPLICATIONS

This application is a continuation of U.S. application Ser. No. 14/243,875, filed on Apr. 2, 2014, which is a continuation of U.S. application Ser. No. 12/794,507, filed on Jun. 4, 2010, which claims the benefit of U.S. Provisional Application No. 61/220,344, filed on Jun. 25, 2009, which are all herein incorporated by reference in their entireties.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: SequenceListing.txt, date recorded: Mar. 4, 2016, file size 228,046 bytes).

TECHNICAL FIELD

What is described is a method to measure the adaptive immunity of a patient by analyzing the diversity of T cell receptor genes or antibody genes using large scale sequencing of nucleic acid extracted from adaptive immune system cells.

BACKGROUND

Immunocompetence is the ability of the body to produce a normal immune response (i.e., antibody production and/or cell-mediated immunity) following exposure to a pathogen, which might be a live organism (such as a bacterium or fungus), a virus, or specific antigenic components isolated from a pathogen and introduced in a vaccine. Immunocompetence is the opposite of immunodeficiency or immuno-incompetent or immunocompromised. Several examples would be a newborn that does not yet have a fully functioning immune system but may have maternally transmitted antibody (immunodeficient); a late stage AIDS patient with a failed or failing immune system (immuno-incompetent); a transplant recipient taking medication so their body will not reject the donated organ (immunocompromised); age-related attenuation of T cell function in the elderly; or individuals exposed to radiation or chemotherapeutic drugs. There may be cases of overlap but these terms are all indicators of a dysfunctional immune system. In reference to lymphocytes, immunocompetence means that a B cell or T cell is mature and can recognize antigens and allow a person to mount an immune response.

Immunocompetence depends on the ability of the adaptive immune system to mount an immune response specific for any potential foreign antigens, using the highly polymorphic receptors encoded by B cells (immunoglobulins, Igs) and T cells (T cell receptors, TCRs).

Igs expressed by B cells are proteins consisting of four polypeptide chains, two heavy chains (H chains) and two light chains (L chains), forming an $H_2L_2$ structure. Each pair of H and L chains contains a hypervariable domain, consisting of a $V_L$ and a $V_H$ region, and a constant domain. The H chains of Igs are of several types, $\mu$, $\delta$, $\gamma$, $\alpha$, and $\beta$. The diversity of Igs within an individual is mainly determined by the hypervariable domain. The V domain of H chains is created by the combinatorial joining of three types of germline gene segments, the $V_H$, $D_H$, and $J_H$ segments. Hypervariable domain sequence diversity is further increased by independent addition and deletion of nucleotides at the $V_H$-$D_H$, $D_H$-$J_H$, and $V_H$-$J_H$ junctions during the process of Ig gene rearrangement. In this respect, immunocompetence is reflected in the diversity of Igs.

TCRs expressed by $\alpha\beta$ T cells are proteins consisting of two transmembrane polypeptide chains ($\alpha$ and $\beta$), expressed from the TCRA and TCRB genes, respectively. Similar TCR proteins are expressed in gamma-delta T cells, from the TCRD and TCRG loci. Each TCR peptide contains variable complementarity determining regions (CDRs), as well as framework regions (FRs) and a constant region. The sequence diversity of $\alpha\beta$ T cells is largely determined by the amino acid sequence of the third complementarity-determining region (CDR3) loops of the $\alpha$ and $\beta$ chain variable domains, which diversity is a result of recombination between variable ($V_\beta$), diversity ($D_\beta$), and joining ($J_\beta$) gene segments in the $\beta$ chain locus, and between analogous $V_\alpha$ and $J_\alpha$ gene segments in the $\alpha$ chain locus, respectively. The existence of multiple such gene segments in the TCR $\alpha$ and $\beta$ chain loci allows for a large number of distinct CDR3 sequences to be encoded. CDR3 sequence diversity is further increased by independent addition and deletion of nucleotides at the $V_\beta$-$D_\beta$, $D_\beta$-$J_\beta$, and $V_\alpha$-$J_\alpha$ junctions during the process of TCR gene rearrangement. In this respect, immunocompetence is reflected in the diversity of TCRs.

There exists a long-felt need for methods of assessing or measuring the adaptive immune system of patients in a variety of settings, whether immunocompetence in the immunocompromised, or dysregulated adaptive immunity in autoimmune disease. A demand exists for methods of diagnosing a disease state or the effects of aging by assessing the immunocompetence of a patient. In the same way results of therapies that modify the immune system need to be monitored by assessing the immunocompetence of the patient while undergoing the treatment. Conversely, a demand exists for methods to monitor the adaptive immune system in the context of autoimmune disease flares and remissions, in order to monitor response to therapy, or the need to initiate prophylactic therapy pre-symptomatically.

SUMMARY

One aspect of the invention is composition comprising:
  a multiplicity of V-segment primers, wherein each primer comprises a sequence that is complementary to a single functional V segment or a small family of V segments; and
  a multiplicity of J-segment primers, wherein each primer comprises a sequence that is complementary to a J segment;
wherein the V segment and J-segment primers permit amplification of a TCR CDR3 region by a multiplex polymerase chain reaction (PCR) to produce a multiplicity of amplified DNA molecules sufficient to quantify the diversity of the TCR genes. One embodiment of the invention is the composition, wherein each V-segment primer comprises a sequence that is complementary to a single V$\beta$ segment, and each J segment primer comprises a sequence that is complementary to a J$\beta$ segment, and wherein V segment and J-segment primers permit amplification of a TCR$\beta$ CDR3 region. Another embodiment is the composition, wherein each V-segment primer comprises a sequence that is complementary to a single functional V$\alpha$ segment, and each J segment primer comprises a sequence that is complementary to a Jα segment, and wherein V segment and J-segment primers permit amplification of a TCRα CDR3 region.

Another embodiment of the invention is the composition, wherein the V segment primers hybridize with a conserved segment, and have similar annealing strength. Another embodiment is wherein the V segment primer is anchored at position −43 in the Vβ segment relative to the recombination signal sequence (RSS). Another embodiment is wherein the multiplicity of V segment primers consist of at least 45 primers specific to 45 different Vβ genes. Another embodiment is wherein the V segment primers have sequences that are selected from the group consisting of SEQ ID NOS:1-45. Another embodiment is wherein the V segment primers have sequences that are selected from the group consisting of SEQ ID NOS:58-102. Another embodiment is wherein there is a V segment primer for each Vβ segment.

Another embodiment of the invention is the composition, wherein the J segment primers hybridize with a conserved framework region element of the Jβ segment, and have similar annealing strength. The composition of claim 2, wherein the multiplicity of J segment primers consist of at least thirteen primers specific to thirteen different Jβ genes. Another embodiment is The composition of claim 2, wherein the J segment primers have sequences that are selected from the group consisting of SEQ ID NOS:46-57. Another embodiment is wherein the J segment primers have sequences that are selected from the group consisting of SEQ ID NOS:102-113. Another embodiment is wherein there is a J segment primer for each Jβ segment. Another embodiment is wherein all J segment primers anneal to the same conserved motif.

Another embodiment of the invention is the composition, wherein the amplified DNA molecule starts from said conserved motif and amplifies adequate sequence to diagnostically identify the J segment and includes the CDR3 junction and extends into the V segment. Another embodiment is wherein the amplified Jβ gene segments each have a unique four base tag at positions +11 through +14 downstream of the RSS site.

Another aspect of the invention is the composition further comprising a set of sequencing oligonucleotides, wherein the sequencing oligonucleotides hybridize to a regions within the amplified DNA molecules. An embodiment is wherein the sequencing oligonucleotides hybridize adjacent to a four base tag within the amplified Jβ gene segments at positions +11 through +14 downstream of the RSS site. Another embodiment is wherein the sequencing oligonucleotides are selected from the group consisting of SEQ ID NOS:58-70. Another embodiment is wherein the V-segment or J-segment are selected to contain a sequence error-correction by merger of closely related sequences. Another embodiment is the composition, further comprising a universal C segment primer for generating cDNA from mRNA.

Another aspect of the invention is a composition comprising:
a multiplicity of V segment primers, wherein each V segment primer comprises a sequence that is complementary to a single functional V segment or a small family of V segments; and
a multiplicity of J segment primers, wherein each J segment primer comprises a sequence that is complementary to a J segment;
wherein the V segment and J segment primers permit amplification of the TCRG CDR3 region by a multiplex polymerase chain reaction (PCR) to produce a multiplicity of amplified DNA molecules sufficient to quantify the diversity of antibody heavy chain genes.

Another aspect of the invention is a composition comprising:
a multiplicity of V segment primers, wherein each V segment primer comprises a sequence that is complementary to a single functional V segment or a small family of V segments; and
a multiplicity of J segment primers, wherein each J segment primer comprises a sequence that is complementary to a J segment;
wherein the V segment and J segment primers permit amplification of antibody heavy chain (IGH) CDR3 region by a multiplex polymerase chain reaction (PCR) to produce a multiplicity of amplified DNA molecules sufficient to quantify the diversity of antibody heavy chain genes.

Another aspect of the invention is a composition comprising:
a multiplicity of V segment primers, wherein each V segment primer comprises a sequence that is complementary to a single functional V segment or a small family of V segments; and
a multiplicity of J segment primers, wherein each J segment primer comprises a sequence that is complementary to a J segment;
wherein the V segment and J segment primers permit amplification of antibody light chain (IGL) $V_L$ region by a multiplex polymerase chain reaction (PCR) to produce a multiplicity of amplified DNA molecules sufficient to quantify the diversity of antibody light chain genes.

Another aspect of the invention is a method comprising:
selecting a multiplicity of V segment primers, wherein each V segment primer comprises a sequence that is complementary to a single functional V segment or a small family of V segments; and
selecting a multiplicity of J segment primers, wherein each J segment primer comprises a sequence that is complementary to a J segment;
combining the V segment and J segment primers with a sample of genomic DNA to permit amplification of a CDR3 region by a multiplex polymerase chain reaction (PCR) to produce a multiplicity of amplified DNA molecules sufficient to quantify the diversity of the TCR genes.

One embodiment of the invention is the method wherein each V segment primer comprises a sequence that is complementary to a single functional Vβ segment, and each J segment primer comprises a sequence that is complementary to a Jβ segment; and wherein combining the V segment and J segment primers with a sample of genomic DNA permits amplification of a TCR CDR3 region by a multiplex polymerase chain reaction (PCR) and produces a multiplicity of amplified DNA molecules. Another embodiment is wherein each V segment primer comprises a sequence that is complementary to a single functional Vα segment, and each J segment primer comprises a sequence that is complementary to a Jα segment; and wherein combining the V segment and J segment primers with a sample of genomic DNA permits amplification of a TCR CDR3 region by a multiplex polymerase chain reaction (PCR) and produces a multiplicity of amplified DNA molecules.

Another embodiment of the invention is the method further comprising a step of sequencing the amplified DNA molecules. Another embodiment is wherein the sequencing step utilizes a set of sequencing oligonucleotides, that hybridize to regions within the amplified DNA molecules. Another embodiment is the method, further comprising a step of calculating the total diversity of TCRβ CDR3 sequences among the amplified DNA molecules. Another embodiment is wherein the method shows that the total diversity of a normal human subject is greater than $1*10^6$ sequences, greater than $2*10^6$ sequences, or greater than $3*10^6$ sequences.

Another aspect of the invention is a method of diagnosing immunodeficiency in a human patient, comprising measuring the diversity of TCR CDR3 sequences of the patient, and comparing the diversity of the subject to the diversity obtained from a normal subject. An embodiment of the invention is the method, wherein measuring the diversity of TCR sequences comprises the steps of:
- selecting a multiplicity of V segment primers, wherein each V segment primer comprises a sequence that is complementary to a single functional V segment or a small family of V segments; and
- selecting a multiplicity of J segment primers, wherein each J segment primer comprises a sequence that is complementary to a J segment;
- combining the V segment and J segment primers with a sample of genomic DNA to permit amplification of a TCR CDR3 region by a multiplex polymerase chain reaction (PCR) to produce a multiplicity of amplified DNA molecules;
- sequencing the amplified DNA molecules;
- calculating the total diversity of TCR CDR3 sequences among the amplified DNA molecules.

An embodiment of the invention is the method, wherein comparing the diversity is determined by calculating using the following equation:

$$\Delta(t) = \sum_x E(n_x)_{measurement1+2} - \sum_x E(n_x)_{measurement2} = S \int_0^\infty e^{-\lambda}(1 - e^{-\lambda t}) dG(\lambda)$$

wherein $G(\lambda)$ is the empirical distribution function of the parameters $\lambda_1, \ldots, \lambda_S$, $n_x$ is the number of clonotypes sequenced exactly x times, and $$E(n_x) = S \int_0^\infty \left( \frac{e^{-\lambda} \lambda^x}{x!} \right) dG(\lambda).$$

Another embodiment of the invention is the method, wherein the diversity of at least two samples of genomic DNA are compared. Another embodiment is wherein one sample of genomic DNA is from a patient and the other sample is from a normal subject. Another embodiment is wherein one sample of genomic DNA is from a patient before a therapeutic treatment and the other sample is from the patient after treatment. Another embodiment is wherein the two samples of genomic DNA are from the same patient at different times during treatment. Another embodiment is wherein a disease is diagnosed based on the comparison of diversity among the samples of genomic DNA. Another embodiment is wherein the immunocompetence of a human patient is assessed by the comparison.

DETAILED DESCRIPTION OF ILLUSTRATIVE EMBODIMENTS

The TCR and Ig genes can generate millions of distinct proteins via somatic mutation. Because of this diversity-generating mechanism, the hypervariable complementarity-determining regions of these genes can encode sequences that can interact with millions of ligands, and these regions are linked to a constant region that can transmit a signal to the cell indicating binding of the protein's cognate ligand.

The adaptive immune system employs several strategies to generate a repertoire of T- and B-cell antigen receptors with sufficient diversity to recognize the universe of potential pathogens. In $\alpha\beta$ and $\gamma\delta$ T cells, which primarily recognize peptide antigens presented by MHC molecules, most of this receptor diversity is contained within the third complementarity-determining region (CDR3) of the T cell receptor (TCR) $\alpha$ and $\beta$ chains (or $\gamma$ and $\delta$ chains). Although it has been estimated that the adaptive immune system can generate up to $10^{18}$ distinct TCR $\alpha\beta$ pairs, direct experimental assessment of TCR CDR3 diversity has not been possible.

What is described herein is a novel method of measuring TCR CDR3 diversity that is based on single molecule DNA sequencing, and use this approach to sequence the CDR3 regions in millions of rearranged TCR$\beta$ genes isolated from peripheral blood T cells of two healthy adults.

The ability of the adaptive immune system to mount an immune response specific for any of the vast number of potential foreign antigens to which an individual might be exposed relies on the highly polymorphic receptors encoded by B cells (immunoglobulins) and T cells (T cell receptors; TCRs). The TCRs expressed by $\alpha\beta$ T cells, which primarily recognize peptide antigens presented by major histocompatibility complex (MHC) class I and II molecules, are heterodimeric proteins consisting of two transmembrane polypeptide chains ($\alpha$ and $\beta$), each containing one variable and one constant domain. The peptide specificity of $\alpha\beta$ T cells is in large part determined by the amino acid sequence encoded in the third complementarity-determining region (CDR3) loops of the $\alpha$ and $\beta$ chain variable domains. The CDR3 regions of the $\beta$ and $\alpha$ chains are formed by recombination between noncontiguous variable ($V_\beta$), diversity ($D_\beta$), and joining ($J_\beta$) gene segments in the $\beta$ chain locus, and between analogous $V_\alpha$ and $J_\alpha$ gene segments in the $\alpha$ chain locus, respectively. The existence of multiple such gene segments in the TCR $\alpha$ and $\beta$ chain loci allows for a large number of distinct CDR3 sequences to be encoded. CDR3 sequence diversity is further increased by template-independent addition and deletion of nucleotides at the $V_\beta$-$D_\beta$, $D_\beta$-$J_\beta$, and $V_\alpha$-$J_\alpha$ junctions during the process of TCR gene rearrangement.

Previous attempts to assess the diversity of receptors in the adult human $\alpha\beta$ T cell repertoire relied on examining rearranged TCR $\alpha$ and $\beta$ chain genes expressed in small, well-defined subsets of the repertoire, followed by extrapolation of the diversity present in these subsets to the entire repertoire, to estimate approximately $10^6$ unique TCR$\beta$ chain CDR3 sequences per individual, with 10-20% of these unique TCR$\beta$ CDR3 sequences expressed by cells in the antigen-experienced CD45RO$^+$ compartment. The accuracy and precision of this estimate is severely limited by the need to extrapolate the diversity observed in hundreds of sequences to the entire repertoire, and it is possible that the actual number of unique TCR$\beta$ chain CDR3 sequences in the $\alpha\beta$ T cell repertoire is significantly larger than $1\times10^6$.

Recent advances in high-throughput DNA sequencing technology have made possible significantly deeper sequencing than capillary-based technologies. A complex library of template molecules carrying universal PCR adapter sequences at each end is hybridized to a lawn of complementary oligonucleotides immobilized on a solid surface. Solid phase PCR is utilized to amplify the hybridized library, resulting in millions of template clusters on the surface, each comprising multiple (~1,000) identical copies of a single DNA molecule from the original library. A 30-54 bp interval in the molecules in each cluster is sequenced using reversible dye-termination chemistry, to permit simultaneous sequencing from genomic DNA of the rearranged TCRβ chain CDR3 regions carried in millions of T cells. This approach enables direct sequencing of a significant fraction of the uniquely rearranged TCRβ CDR3 regions in populations of αβ T cells, which thereby permits estimation of the relative frequency of each CDR3 sequence in the population.

Accurate estimation of the diversity of TCRβ CDR3 sequences in the entire αβ T cell repertoire from the diversity measured in a finite sample of T cells requires an estimate of the number of CDR3 sequences present in the repertoire that were not observed in the sample. TCRβ chain CDR3 diversity in the entire αβ T cell repertoire were estimated using direct measurements of the number of unique TCRβ CDR3 sequences observed in blood samples containing millions of αβ T cells. The results herein identify a lower bound for TCRβ CDR3 diversity in the CD4$^+$ and CD8$^+$ T cell compartments that is several fold higher than previous estimates. In addition, the results herein demonstrate that there are at least $1.5 \times 10^6$ unique TCRβ CDR3 sequences in the CD45RO$^+$ compartment of antigen-experienced T-cells, a large proportion of which are present at low relative frequency. The existence of such a diverse population of TCRβ CDR3 sequences in antigen-experienced cells has not been previously demonstrated.

The diverse pool of TCRβ chains in each healthy individual is a sample from an estimated theoretical space of greater than $10^{11}$ possible sequences. However, the realized set of rearranged of TCRs is not evenly sampled from this theoretical space. Different Vβ's and Jβ's are found with over a thousand-fold frequency difference. Additionally, the insertion rates of nucleotides are strongly biased. This reduced space of realized TCRβ sequences leads to the possibility of shared β chains between people. With the sequence data generated by the methods described herein, the in vivo J usage, V usage, mono- and di-nucleotide biases, and position dependent amino acid usage can be computed. These biases significantly narrow the size of the sequence space from which TCRβ are selected, suggesting that different individuals share TCRβ chains with identical amino acid sequences. Results herein show that many thousands of such identical sequences are shared pairwise between individual human genomes.

The assay technology uses two pools of primers to provide for a highly multiplexed PCR reaction. The "forward" pool has a primer specific to each V segment in the gene (several primers targeting a highly conserved region are used, to simultaneously capture many V segments). The "reverse" pool primers anneal to a conserved sequence in the joining ("J") segment. The amplified segment pool includes adequate sequence to identify each J segment and also to allow for a J-segment-specific primer to anneal for resequencing. This enables direct observation of a large fraction of the somatic rearrangements present in an individual. This in turn enables rapid comparison of the TCR repertoire in individuals with an autoimmune disorder (or other target disease indication) against the TCR repertoire of controls.

The adaptive immune system can in theory generate an enormous diversity of T cell receptor CDR3 sequences—far more than are likely to be expressed in any one individual at any one time. Previous attempts to measure what fraction of this theoretical diversity is actually utilized in the adult αβ T cell repertoire, however, have not permitted accurate assessment of the diversity. What is described herein is the development of a novel approach to this question that is based on single molecule DNA sequencing and an analytic computational approach to estimation of repertoire diversity using diversity measurements in finite samples. The analysis demonstrated that the number of unique TCRβ CDR3 sequences in the adult repertoire significantly exceeds previous estimates based on exhaustive capillary sequencing of small segments of the repertoire. The TCRβ chain diversity in the CD45RO$^-$ population (enriched for naïve T cells) observed using the methods described herein is five-fold larger than previously reported. A major discovery is the number of unique TCRβ CDR3 sequences expressed in antigen-experienced CD45RO$^+$ T cells—the results herein show that this number is between 10 and 20 times larger than expected based on previous results of others. The frequency distribution of CDR3 sequences in CD45RO$^+$ cells suggests that the T cell repertoire contains a large number of clones with a small clone size.

The results herein show that the realized set of TCRβ chains are sampled non-uniformly from the huge potential space of sequences. In particular, the β chains sequences closer to germ line (few insertions and deletions at the V-D and D-J boundaries) appear to be created at a relatively high frequency. TCR sequences close to germ line are shared between different people because the germ line sequence for the V's, D's, and J's are shared, modulo a small number of polymorphisms, among the human population.

The T cell receptors expressed by mature αβ T cells are heterodimers whose two constituent chains are generated by independent rearrangement events of the TCR α and β chain variable loci. The α chain has less diversity than the β chain, so a higher fraction of α's are shared between individuals, and hundreds of exact TCR αβ receptors are shared between any pair of individuals.

Cells

B cells and T cells can be obtained from a variety of tissue samples including marrow, thymus, lymph glands, peripheral tissues and blood, but peripheral blood is most easily accessed. Peripheral blood samples are obtained by phlebotomy from subjects. Peripheral blood mononuclear cells (PBMC) are isolated by techniques known to those of skill in the art, e.g., by Ficoll-Hypaque® density gradient separation. Preferably, whole PBMCs are used for analysis. The B and/or T lymphocytes, instead, may be flow sorted into multiple compartments for each subject: e.g. CD8$^+$ CD45RO$^{+/-}$ and CD4$^+$CD45RO$^{+/-}$ using fluorescently labeled anti-human antibodies, e.g., CD4 FITC (clone M-T466, Miltenyi Biotec), CD8 PE (clone RPA-T8, BD Biosciences), CD45RO ECD (clone UCHL-1, Beckman Coulter), and CD45RO APC (clone UCHL-1, BD Biosciences) Staining of total PBMCs may be done with the appropriate combination of antibodies, followed by washing cells before analysis. Lymphocyte subsets can be isolated by FACS sorting, e.g., by a BD FACSAria™ cell-sorting system (BD Biosciences) and by analyzing results with FlowJo software (Treestar Inc.), and also by conceptually similar methods involving specific antibodies immobilized to surfaces or beads.

Nucleic Acid Extraction

Total genomic DNA is extracted from cells, e.g., by using the QIAamp® DNA blood Mini Kit (QIAGEN®). The approximate mass of a single haploid genome is 3 pg. Preferably, at least 100,000 to 200,000 cells are used for analysis of diversity, i.e., about 0.6 to 1.2 μg DNA from diploid T cells. Using PBMCs as a source, the number of T cells can be estimated to be about 30% of total cells.

Alternatively, total nucleic acid can be isolated from cells, including both genomic DNA and mRNA. If diversity is to be measured from mRNA in the nucleic acid extract, the mRNA must be converted to cDNA prior to measurement. This can readily be done by methods of one of ordinary skill.

DNA Amplification

A multiplex PCR system is used to amplify rearranged TCR loci from genomic DNA, preferably from a CDR3 region, more preferably from a TCRα, TCRγ or TCRδ CDR3 region, most preferably from a TCRβ CDR3 region.

In general, a multiplex PCR system may use at least 14, 15, 16, 17, 18, 19, 20, 21, 22, 23, 24, or 25, preferably 26, 27, 28, 29, 30, 31, 32, 33, 34, 35, 36, 37, 38, or 39, most preferably 40, 41, 42, 43, 44, or 45 forward primers, in which each forward primer is specific to a sequence corresponding to one or more TRB V region segments shown in SEQ ID NOS:114-248; and at least 3, 4, 5, 6, or 7, preferably 8, 9, 10, 11, 12 or 13 reverse primers, in which each reverse primer is specific to a sequence corresponding to one or more TRB J region segments shown in SEQ ID NOS:249-261. Most preferably, there is a J segment primer for every J segment.

Preferably, the primers are designed not to cross an intron/exon boundary. The forward primers must preferably anneal to the V segments in a region of relatively strong sequence conservation between V segments so as to maximize the conservation of sequence among these primers. Accordingly, this minimizes the potential for differential annealing properties of each primer, and so that the amplified region between V and J primers contains sufficient TCR V sequence information to identify the specific V gene segment used.

Preferably, the J segment primers hybridize with a conserved element of the J segment, and have similar annealing strength. Most preferably, all J segment primers anneal to the same conserved framework region motif. The forward and reverse primers are both preferably modified at the 5' end with the universal forward primer sequence compatible with a DNA sequencer.

For example, a multiplex PCR system may use 45 forward primers (Table 1), each specific to a functional TCR Vβ segment, and thirteen reverse primers (Table 2), each specific to a TCR Jβ segment. Xn and Yn correspond to polynucleotides of lengths n and m, respectively, which would be specific to the single molecule sequencing technology being used to read out the assay.

TABLE 1

TCR-Vβ Forward primer sequences

| TRBV gene segment(s) | SEQ ID NO: | Primer sequence* |
|---|---|---|
| TRBV2 | 1 | XnTCAAATTTCACTCTGAAGATCCGGTCCACAA |
| TRBV3-1 | 2 | XnGCTCACTTAAATCTTCACATCAATTCCCTGG |
| TRBV4-1 | 3 | XnCTTAAACCTTCACCTACACGCCCTGC |
| TRBV(4-2, 4-3) | 4 | XnCTTATTCCTTCACCTACACACCCTGC |
| TRBV5-1 | 5 | XnGCTCTGAGATGAATGTGAGCACCTTG |
| TRBV5-3 | 6 | XnGCTCTGAGATGAATGTGAGTGCCTTG |

TABLE 1-continued

TCR-Vβ Forward primer sequences

| TRBV gene segment(s) | SEQ ID NO: | Primer sequence* |
|---|---|---|
| TRBV(5-4, 5-5, 5-6, 5-7, 5-8) | 7 | XnGCTCTGAGCTGAATGTGAACGCCTTG |
| TRBV6-1 | 8 | XnTCGCTCAGGCTGGAGTCGGCTG |
| TRBV(6-2, 6-3) | 9 | XnGCTGGGGTTGGAGTCGGCTG |
| TRBV6-4 | 10 | XnCCCTCACGTTGGCGTCTGCTG |
| TRBV6-5 | 11 | XnGCTCAGGCTGCTGTCGGCTG |
| TRBV6-6 | 12 | XnCGCTCAGGCTGGAGTTGGCTG |
| TRBV6-7 | 13 | XnCCCCTCAAGCTGGAGTCAGCTG |
| TRBV6-8 | 14 | XnCACTCAGGCTGGTGTCGGCTG |
| TRBV6-9 | 15 | XnCGCTCAGGCTGGAGTCAGCTG |
| TRBV7-1 | 16 | XnCCACTCTGAAGTTCCAGCGCACAC |
| TRBV7-2 | 17 | XnCACTCTGACGATCCAGCGCACAC |
| TRBV7-3 | 18 | XnCTCTACTCTGAAGATCCAGCGCACAG |
| TRBV7-4 | 19 | XnCCACTCTGAAGATCCAGCGCACAG |
| TRBV7-6 | 20 | XnCACTCTGACGATCCAGCGCACAG |
| TRBV7-7 | 21 | XnCCACTCTGACGATTCAGCGCACAG |
| TRBV7-8 | 22 | XnCCACTCTGAAGATCCAGCGCACAC |
| TRBV7-9 | 23 | XnCACCTTGGAGATCCAGCGCACAG |
| TRBV9 | 24 | XnGCACTCTGAACTAAACCTGAGCTCTCTG |
| TRBV10-1 | 25 | XnCCCCTCACTCTGGAGTCTGCTG |
| TRBV10-2 | 26 | XnCCCCCTCACTCTGGAGTCAGCTA |
| TRBV10-3 | 27 | XnCCTCCTCACTCTGGAGTCCGCTA |
| TRBV(11-1, 11-3) | 28 | XnCCACTCTCAAGATCCAGCCTGCAG |
| TRBV11-2 | 29 | XnCTCCACTCTCAAGATCCAGCCTGCAA |
| TRBV(12-3, 12-4, 12-5) | 30 | XnCCACTCTGAAGATCCAGCCCTCAG |
| TRBV13 | 31 | XnCATTCTGAACTGAACATGAGCTCCTTGG |
| TRBV14 | 32 | XnCTACTCTGAAGGTGCAGCCTGCAG |
| TRBV15 | 33 | XnGATAACTTCCAATCCAGGAGGCCGAACA |
| TRBV16 | 34 | XnCTGTAGCCTTGAGATCCAGGCTACGA |
| TRBV17 | 35 | XnCTTCCACGCTGAAGATCCATCCCG |
| TRBV18 | 36 | XnGCATCCTGAGGATCCAGCAGGTAG |
| TRBV19 | 37 | XnCCTCTCACTGTGACATCGGCCC |
| TRBV20-1 | 38 | XnCTTGTCCACTCTGACAGTGACCAGTG |
| TRBV23-1 | 39 | XnCAGCCTGGCAATCCTGTCCTCAG |
| TRBV24-1 | 40 | XnCTCCCTGTCCCTAGAGTCTGCCAT |

TABLE 1-continued

TCR-Vβ Forward primer sequences

| TRBV gene segment(s) | SEQ ID NO: | Primer sequence* |
|---|---|---|
| TRBV25-1 | 41 | XnCCCTGACCCTGGAGTCTGCCA |
| TRBV27 | 42 | XnCCCTGATCCTGGAGTCGCCCA |
| TRBV28 | 43 | XnCTCCCTGATTCTGGAGTCCGCCA |
| TRBV29-1 | 44 | XnCTAACATTCTCAACTCTGACTGTGAGCAACA |
| TRBV30 | 45 | XnCGGCAGTTCATCCTGAGTTCTAAGAAGC |

TABLE 2

TCR-Jβ Reverse Primer Sequences

| TRBJ gene segment | SEQ ID NO: | Primer sequence* |
|---|---|---|
| TRBJ1-1 | 46 | YmTTACCTACAACTGTGAGTCTGGTGCCTTGTCCAAA |
| TRBJ1-2 | 47 | YmACCTACAACGGTTAACCTGGTCCCCGAACCGAA |
| TRBJ1-3 | 48 | YmACCTACAACAGTGAGCCAACTTCCCTCTCCAAA |
| TRBJ1-4 | 49 | YmCCAAGACAGAGAGCTGGGTTCCACTGCCAAA |
| TRBJ1-5 | 483 | YmACCTAGGATGGAGAGTCGAGTCCCATCACCAAA |
| TRBJ1-6 | 50 | YmCTGTCACAGTGAGCCTGGTCCCGTTCCCAAA |
| TRBJ2-1 | 51 | YmCGGTGAGCCGTGTCCCTGGCCCGAA |
| TRBJ2-2 | 52 | YmCCAGTACGGTCAGCCTAGAGCCTTCTCCAAA |
| TRBJ2-3 | 53 | YmACTGTCAGCCGGGTGCCTGGGCCAAA |
| TRBJ2-4 | 54 | YmAGAGCCGGGTCCCGGCGCCGAA |
| TRBJ2-5 | 55 | YmGGAGCCGCGTGCCTGGCCCGAA |
| TRBJ2-6 | 56 | YmGTCAGCCTGCTGCCGGCCCCGAA |
| TRBJ2-7 | 57 | YmGTGAGCCTGGTGCCCGGCCCGAA |

The 45 forward PCR primers of Table 1 are complementary to each of the 48 functional Variable segments, and the thirteen reverse PCR primers of Table 2 are complementary to each of the functional joining (J) gene segments from the TRB locus (TRBJ). The TRB V region segments are identified in the Sequence Listing at SEQ ID NOS:114-248 and the TRB J region segments are at SEQ ID NOS:249-261. The primers have been designed such that adequate information is present within the amplified sequence to identify both the V and J genes uniquely (>40 base pairs of sequence upstream of the V gene recombination signal sequence (RSS), and >30 base pairs downstream of the J gene RSS). Alternative primers may be selected by one of ordinary skill from the V and J regions of the genes of each TCR subunit.

The forward primers are modified at the 5' end with the universal forward primer sequence compatible with the DNA sequencer (Xn of Table 1). Similarly, all of the reverse primers are modified with a universal reverse primer sequence (Ym of Table 2). One example of such universal primers is shown in Tables 3 and 4, for the Illumina GAIT single-end read sequencing system. The 45 TCR Vβ forward primers anneal to the Vβ segments in a region of relatively strong sequence conservation between Vβ segments so as to maximize the conservation of sequence among these primers.

TABLE 3

TCR-Vβ Forward primer sequences

| TRBV gene segment(s) | SEQ ID NO: | Primer sequence* |
|---|---|---|
| TRBV2 | 58 | CAAGCAGAAGACGGCATACGAGCTCTTCCGATCTTCAAATTTCACTCTGAAGATCCGGTCCACAA |
| TRBV3-1 | 59 | CAAGCAGAAGACGGCATACGAGCTCTTCCGATCTGCTCACTTAAATCTTCACATCAATTCCCTGG |
| TRBV4-1 | 60 | CAAGCAGAAGACGGCATACGAGCTCTTCCGATCTCTTAAACCTTCACCTACACGCCCTGC |
| TRBV(4-2, 4-3) | 61 | CAAGCAGAAGACGGCATACGAGCTCTTCCGATCTCTTATTCCTTCACCTACACACCCTGC |
| TRBV5-1 | 62 | CAAGCAGAAGACGGCATACGAGCTCTTCCGATCTGCTCTGAGATGAATGTGAGCACCTTG |
| TRBV5-3 | 63 | CAAGCAGAAGACGGCATACGAGCTCTTCCGATCTGCTCTGAGATGAATGTGAGTGCCTTG |
| TRBV(5-4, 5-5, 5-6, 5-7, 5-8) | 64 | CAAGCAGAAGACGGCATACGAGCTCTTCCGATCTGCTCTGAGCTGAATGTGAACGCCTTG |
| TRBV6-1 | 65 | CAAGCAGAAGACGGCATACGAGCTCTTCCGATCTTCGCTCAGGCTGGAGTCGGCTG |
| TRBV(6-2, 6-3) | 66 | CAAGCAGAAGACGGCATACGAGCTCTTCCGATCTGCTGGGGTTGGAGTCGGCTG |
| TRBV6-4 | 67 | CAAGCAGAAGACGGCATACGAGCTCTTCCGATCTCCCTCACGTTGGCGTCTGCTG |
| TRBV6-5 | 68 | CAAGCAGAAGACGGCATACGAGCTCTTCCGATCTGCTCAGGCTGCTGTCGGCTG |
| TRBV6-6 | 69 | CAAGCAGAAGACGGCATACGAGCTCTTCCGATCTCGCTCAGGCTGGAGTTGGCTG |
| TRBV6-7 | 70 | CAAGCAGAAGACGGCATACGAGCTCTTCCGATCTCCCCTCAAGCTGGAGTCAGCTG |
| TRBV6-8 | 71 | CAAGCAGAAGACGGCATACGAGCTCTTCCGATCTCACTCAGGCTGGTGTCGGCTG |
| TRBV6-9 | 72 | CAAGCAGAAGACGGCATACGAGCTCTTCCGATCTCGCTCAGGCTGGAGTCAGCTG |
| TRBV7-1 | 73 | CAAGCAGAAGACGGCATACGAGCTCTTCCGATCTCCACTCTGAAGTTCCAGCGCACAC |
| TRBV7-2 | 74 | CAAGCAGAAGACGGCATACGAGCTCTTCCGATCTCACTCTGACGATCCAGCGCACAC |
| TRBV7-3 | 75 | CAAGCAGAAGACGGCATACGAGCTCTTCCGATCTCTCTACTCTGAAGATCCAGCGCACAG |
| TRBV7-4 | 76 | CAAGCAGAAGACGGCATACGAGCTCTTCCGATCTCCACTCTGAAGATCCAGCGCACAG |
| TRBV7-6 | 77 | CAAGCAGAAGACGGCATACGAGCTCTTCCGATCTCACTCTGACGATCCAGCGCACAG |
| TRBV7-7 | 78 | CAAGCAGAAGACGGCATACGAGCTCTTCCGATCTCCACTCTGACGATTCAGCGCACAG |
| TRBV7-8 | 79 | CAAGCAGAAGACGGCATACGAGCTCTTCCGATCTCCACTCTGAAGATCCAGCGCACAC |

TABLE 3-continued

TCR-Vβ Forward primer sequences

| TRBV gene segment(s) | SEQ ID NO: | Primer sequence* |
|---|---|---|
| TRBV7-9 | 80 | CAAGCAGAAGACGGCATACGAGCTCTTCCGATCTCACCTTGGAGATCCAGCGCACAG |
| TRBV9 | 81 | CAAGCAGAAGACGGCATACGAGCTCTTCCGATCTGCACTCTGAACTAAACCTGAGCTCTCTG |
| TRBV10-1 | 82 | CAAGCAGAAGACGGCATACGAGCTCTTCCGATCTCCCCTCACTCTGGAGTCTGCTG |
| TRBV10-2 | 83 | CAAGCAGAAGACGGCATACGAGCTCTTCCGATCTCCCCCTCACTCTGGAGTCAGCTA |
| TRBV10-3 | 84 | CAAGCAGAAGACGGCATACGAGCTCTTCCGATCTCCTCCTCACTCTGGAGTCCGCTA |
| TRBV(11-1, 11-3) | 85 | CAAGCAGAAGACGGCATACGAGCTCTTCCGATCTCCACTCTCAAGATCCAGCTGCAG |
| TRBV11-2 | 86 | CAAGCAGAAGACGGCATACGAGCTCTTCCGATCTCTCCACTCTCAAGATCCAGCTGCAA |
| TRBV(12-3, 12-4, 12-5) | 87 | CAAGCAGAAGACGGCATACGAGCTCTTCCGATCTCCACTCTGAAGATCCAGCCCTCAG |
| TRBV13 | 88 | CAAGCAGAAGACGGCATACGAGCTCTTCCGATCTCATTCTGAACTGAACATGAGCTCCTTGG |
| TRBV14 | 89 | CAAGCAGAAGACGGCATACGAGCTCTTCCGATCTCTACTCTGAAGGTGCAGCCTGCAG |
| TRBV15 | 90 | CAAGCAGAAGACGGCATACGAGCTCTTCCGATCTATAACTTCCAATCCAGGAGGCCGAACA |
| TRBV16 | 91 | CAAGCAGAAGACGGCATACGAGCTCTTCCGATCTCTGTAGCCTTGAGATCCAGGCTACGA |
| TRBV17 | 92 | CAAGCAGAAGACGGCATACGAGCTCTTCCGATCTCTTCCACGCTGAAGATCCATCCCG |
| TRBV18 | 93 | CAAGCAGAAGACGGCATACGAGCTCTTCCGATCTGCATCCTGAGGATCCAGCAGGTAG |
| TRBV19 | 94 | CAAGCAGAAGACGGCATACGAGCTCTTCCGATCTCCTCTCACTGTGACATCGGCCC |
| TRBV20-1 | 95 | CAAGCAGAAGACGGCATACGAGCTCTTCCGATCTCTTGTCCACTCTGACAGTGACCAGTG |
| TRBV23-1 | 96 | CAAGCAGAAGACGGCATACGAGCTCTTCCGATCTCAGCCTGGCAATCCTGTCCTCAG |
| TRBV24-1 | 97 | CAAGCAGAAGACGGCATACGAGCTCTTCCGATCTCTCCCTGTCCCTAGAGTCTGCCAT |
| TRBV25-1 | 98 | CAAGCAGAAGACGGCATACGAGCTCTTCCGATCTCCCTGACCCTGGAGTCTGCCA |
| TRBV27 | 99 | CAAGCAGAAGACGGCATACGAGCTCTTCCGATCTCCCTGATCCTGGAGTCGCCCA |
| TRBV28 | 100 | CAAGCAGAAGACGGCATACGAGCTCTTCCGATCTCTCCCTGATTCTGGAGTCCGCCA |
| TRBV29-1 | 101 | CAAGCAGAAGACGGCATACGAGCTCTTCCGATCTCTAACATTCTCAACTCTGACTGTGAGCAACA |
| TRBV30 | 102 | CAAGCAGAAGACGGCATACGAGCTCTTCCGATCTCGGCAGTTCATCCTGAGTTCTAAGAAGC |

TABLE 4

TCR-Jβ Reverse Primer Sequences

| TRBJ gene segment | SEQ ID NO: | Primer sequence* |
|---|---|---|
| TRBJ1-1 | 103 | AATGATACGGCGACCACCGAGATCTTTACCTACAACTGTGAGTCTGGTGCCTTGTCCAAA |
| TRBJ1-2 | 468 | AATGATACGGCGACCACCGAGATCTACCTACAACGGTTAACCTGGTCCCCGAACCGAA |
| TRBJ1-3 | 104 | AATGATACGGCGACCACCGAGATCTACCTACAACAGTGAGCCAACTTCCCTCTCCAAA |
| TRBJ1-4 | 105 | AATGATACGGCGACCACCGAGATCTCCAAGACAGAGAGCTGGGTTCCACTGCCAAA |
| TRBJ1-5 | 484 | AATGATACGGCGACCACCGAGATCTACCTAGGATGGAGAGTCGAGTCCCATCACCAAA |
| TRBJ1-6 | 106 | AATGATACGGCGACCACCGAGATCTCTGTCACAGTGAGCCTGGTCCCGTTCCCAAA |
| TRBJ2-1 | 107 | AATGATACGGCGACCACCGAGATCTCGGTGAGCCGTGTCCCTGGCCCGAA |
| TRBJ2-2 | 108 | AATGATACGGCGACCACCGAGATCTCCAGTACGGTCAGCCTAGAGCCTTCTCCAAA |
| TRBJ2-3 | 109 | AATGATACGGCGACCACCGAGATCTACTGTCAGCCGGGTGCCTGGGCCAAA |
| TRBJ2-4 | 110 | AATGATACGGCGACCACCGAGATCTAGAGCCGGGTCCCGGCGCCGAA |
| TRBJ2-5 | 111 | AATGATACGGCGACCACCGAGATCTGGAGCCGCGTGCCTGGCCCGAA |
| TRBJ2-6 | 112 | AATGATACGGCGACCACCGAGATCTGTCAGCCTGCTGCCGGCCCCGAA |
| TRBJ2-7 | 113 | AATGATACGGCGACCACCGAGATCTGTGAGCCTGGTGCCCGGCCCGAA |

*bold sequence indicates universal R oligonucleotide for the sequence analysis

The total PCR product for a rearranged TCRβ CDR3 region using this system is expected to be approximately 200 bp long. Genomic templates are PCR amplified using a pool of the 45 TCR Vβ F primers (the "VF pool") and a pool of the twelve TCR Jβ R primers (the "JR pool"). For example, 50 µl PCR reactions may be used with 1.0 µM VF pool (22 nM for each unique TCR Vβ F primer), 1.0 µM JR pool (77 nM for each unique TCRBJR primer), 1× QIAGEN Multiple PCR master mix (QIAGEN part number 206145), 10% Q-solution (QIAGEN), and 16 ng/ul gDNA.

The IGH primer set was designed to try to accommodate the potential for somatic hypermutation within the rearranged IGH genes, as is observed after initial stimulation of naïve B cells. Consequently all primers were designed to be slightly longer than normal, and to anchor the 3' ends of each primer into highly conserved sequences of three or more nucleotides that should be resistant to both functional and non-functional somatic mutations.

The IGHJ reverse primers were designed to anchor the 3' end of each PCR primer on a highly conserved GGGG sequence motif within the IGHJ segments. These sequences are shown in Table 5. Underlined sequence are ten base pairs in from RSS that may be deleted. These were excluded from barcode design. Bold sequence is the reverse complement of the IGH J reverse PCR primers. Italicized sequence is the barcode for J identity (eight barcodes reveal six genes, and two alleles within genes). Further sequence within underlined segment may reveal additional allelic identities.

TABLE 5

| IgH J segment | SEQ ID NO: | Sequence |
|---|---|---|
| >IGHJ4*01/1-48 | 452 | ACTACTTTGACTACTGGGGCCAAGGAACCCTGGTCACCGTCTCCTCAG |
| >IGHJ4*03/1-48 | 453 | GCTACTTTGACTACTGGGGCCAAGGGACCCTGGTCACCGTCTCCTCAG |
| >IGHJ4*02/1-48 | 454 | ACTACTTTGACTACTGGGGCCAGGGAACCCTGGTCACCGTCTCCTCAG |
| >IGHJ3*01/1-50 | 455 | TGATGCTTTTGATGTCTGGGGCCAAGGGACAATGGTCACCGTCTCTTCAG |
| >IGHJ3*02/1-50 | 456 | TGATGCTTTTGATATCTGGGGCCAAGGGACAATGGTCACCGTCTCTTCAG |
| >IGHJ6*01/1-63 | 457 | ATTACTACTACTACTACGGTATGGACGTCTGGGGGCAAGGGACCACGGTCACCGTCTCCTCAG |
| >IGHJ6*02/1-62 | 458 | ATTACTACTACTACTACGGTATGGACGTCTGGGGCCAAGGGACCACGGTCACCGTCTCCTCAG |
| >IGHJ6*04/1-63 | 459 | ATTACTACTACTACTACGGTATGGACGTCTGGGGCAAAGGGACCACGGTCACCGTCTCCTCAG |
| >IGHJ6*03/1-62 | 460 | ATTACTACTACTACTACATGGACGTCTGGGGCAAAGGGACCACGGTCACCGTCTCCTCAG |
| >IGHJ2*01/1-53 | 461 | CTACTGGTACTTCGATCTCTGGGGCCGTGGCACCCTGGTCACTGTCTCCTCAG |
| >IGHJ5*01/1-51 | 462 | ACAACTGGTTCGACTCCTGGGGCCAAGGAACCCTGGTCACCGTCTCCTCAG |
| >IGHJ5*02/1-51 | 463 | ACAACTGGTTCGACCCCTGGGGCCAGGGAACCCTGGTCACCGTCTCCTCAG |
| >IGHJ1*01/1-52 | 464 | GCTGAATACTTCCAGCACTGGGGCCAGGGCACCCTGGTCACCGTCTCCTCAG |
| >IGHJ2P*01/1-61 | 465 | CTACAAGTGCTTGGAGCACTGGGGCAGGGCAGCCCGGACACCGTCTCCCTGGGAACGTCAG |
| >IGHJ1P*01/1-54 | 466 | AAAGGTGCTGGGGGTCCCCTGAACCCGACCCGCCCTGAGACCGCAGCCACATCA |
| >IGHJ3P*01/1-52 | 467 | CTTGCGGTTGGACTTCCCAGCCGACAGTGGTGGTCTGGCTTCTGAGGGGTCA |

Sequences of the IGHJ reverse PCR primers are shown in Table 6.

TABLE 6

| IgH J segment | SEQ ID NO: | sequence |
|---|---|---|
| >IGHJ4_1 | 421 | TGAGGAGACGGTGACCAGGGTTCCTTGGCCC |
| >IGHJ4_3 | 422 | TGAGGAGACGGTGACCAGGGTCCCTTGGCCC |
| >IGHJ4_2 | 423 | TGAGGAGACGGTGACCAGGGTTCCCTGGCCC |
| >IGHJ3_12 | 424 | CTGAAGAGACGGTGACCATTGTCCCTTGGCCC |
| >IGHJ6_1 | 425 | CTGAGGAGACGGTGACCGTGGTCCCTTGCCCC |
| >IGHJ6_2 | 426 | TGAGGAGACGGTGACCGTGGTCCCTTGGCCC |
| >IGHJ6_34 | 427 | CTGAGGAGACGGTGACCGTGGTCCCTTTGCCC |
| >IGHJ2_1 | 428 | CTGAGGAGACAGTGACCAGGGTGCCACGGCCC |
| >IGHJ5_1 | 429 | CTGAGGAGACGGTGACCAGGGTTCCTTGGCCC |
| >IGHJ5_2 | 430 | CTGAGGAGACGGTGACCAGGGTTCCCTGGCCC |
| >IGHJ1_1 | 431 | CTGAGGAGACGGTGACCAGGGTGCCCTGGCCC |

V primers were designed in a conserved in region of FR2 between the two conserved tryptophan (W) codons.

The primer sequences are anchored at the 3' end on a tryptophan codon for all IGHV families that conserve this codon. This allows for the last three nucleotides (tryptophan's TGG) to anchor on sequence that is expected to be resistant to somatic hypermutation, providing a 3' anchor of five out of six nucleotides for each primer. The upstream sequence is extended further than normal, and includes degenerate nucleotides to allow for mismatches induced by hypermutation (or between closely relate IGH V families) without dramatically changing the annealing characteristics of the primer, as shown in Table 7. The sequences of the V gene segments are SEQ ID NOS:262-420.

TABLE 7

| IgH V segment | SEQ ID NO: | sequence |
|---|---|---|
| >IGHV1 | 443 | TGGGTGCACCAGGTCCANGNACAAGGGCTTGAGTGG |
| >IGHV2 | 444 | TGGGTGCGACAGGCTCGNGNACAACGCCTTGAGTGG |
| >IGHV3 | 445 | TGGGTGCGCCAGATGCCNGNGAAAGGCCTGGAGTGG |
| >IGHV4 | 446 | TGGGTCCGCCAGSCYCCNGNGAAGGGGCTGGAGTGG |
| >IGHV5 | 447 | TGGGTCCGCCAGGCTCCNGNAAAGGGGCTGGAGTGG |
| >IGHV6 | 448 | TGGGTCTGCCAGGCTCCNGNGAAGGGGCAGGAGTGG |
| >IGH7_3.25p | 449 | TGTGTCCGCCAGGCTCCAGGGAATGGGCTGGAGTTGG |
| >IGH8_3.54p | 450 | TCAGATTCCCAAGCTCCAGGGAAGGGGCTGGAGTGAG |
| >IGH9_3.63p | 451 | TGGGTCAATGAGACTCTAGGGAAGGGGCTGGAGGGAG |

Thermal cycling conditions may follow methods of those skilled in the art. For example, using a PCR Express thermal cycler (Hybaid, Ashford, UK), the following cycling conditions may be used: 1 cycle at 95° C. for 15 minutes, 25 to 40 cycles at 94° C. for 30 seconds, 59° C. for 30 seconds and 72° C. for 1 minute, followed by one cycle at 72° C. for 10 minutes.

Sequencing

Sequencing is achieved using a set of sequencing oligonucleotides that hybridize to a defined region within the amplified DNA molecules.

Preferably, the amplified J gene segments each have a unique four base tag at positions +11 through +14 downstream from the RSS site. Accordingly, the sequencing oligonucleotides hybridize adjacent to a four base tag within the amplified Jβ gene segments at positions +11 through +14 downstream of the RSS site.

For example, sequencing oligonucleotides for TCRB may be designed to anneal to a consensus nucleotide motif observed just downstream of this "tag", so that the first four bases of a sequence read will uniquely identify the J segment (Table 8).

TABLE 8

Sequencing oligonucleotides

| Sequencing oligo-nucleotide | SEQ ID NO: | Oligonucleotide sequence |
|---|---|---|
| Jseq 1-1 | 470 | ACAACTGTGAGTCTGGTGCCTTGTCCAAAGAAA |
| Jseq 1-2 | 471 | ACAACGGTTAACCTGGTCCCCGAACCGAAGGTG |
| Jseq 1-3 | 472 | ACAACAGTGAGCCAACTTCCCTCTCCAAAATAT |
| Jseq 1-4 | 473 | AAGACAGAGAGCTGGGTTCCACTGCCAAAAAAC |
| Jseq 1-5 | 474 | AGGATGGAGAGTCGAGTCCCATCACCAAAATGC |
| Jseq 1-6 | 475 | GTCACAGTGAGCCTGGTCCCGTTCCCAAAGTGG |
| Jseq 2-1 | 476 | AGCACGGTGAGCCGTGTCCCTGGCCCGAAGAAC |
| Jseq 2-2 | 477 | AGTACGGTCAGCCTAGAGCCTTCTCCAAAAAAC |
| Jseq 2-3 | 478 | AGCACTGTCAGCCGGGTGCCTGGGCCAAAATAC |
| Jseq 2-4 | 479 | AGCACTGAGAGCCGGGTCCCGGCGCCGAAGTAC |
| Jseq 2-5 | 480 | AGCACCAGGAGCCGCGTGCCTGGCCCGAAGTAC |
| Jseq 2-6 | 481 | AGCACGGTCAGCCTGCTGCCGGCCCCGAAAGTC |
| Jseq 2-7 | 482 | GTGACCGTGAGCCTGGTGCCCGGCCCGAAGTAC |

The information used to assign the J and V segment of a sequence read is entirely contained within the amplified sequence, and does not rely upon the identity of the PCR primers. These sequencing oligonucleotides were selected such that promiscuous priming of a sequencing reaction for one J segment by an oligonucleotide specific to another J segment would generate sequence data starting at exactly the same nucleotide as sequence data from the correct sequencing oligonucleotide. In this way, promiscuous annealing of the sequencing oligonucleotides did not impact the quality of the sequence data generated.

The average length of the CDR3 region, defined as the nucleotides between the second conserved cysteine of the V segment and the conserved phenylalanine of the J segment, is 35+/−3, so sequences starting from the Jβ segment tag will nearly always capture the complete V-D-J junction in a 50 base pair read.

TCR βJ gene segments are roughly 50 base pair in length. PCR primers that anneal and extend to mismatched sequences are referred to as promiscuous primers. The TCR Jβ Reverse PCR primers were designed to minimize overlap with the sequencing oligonucleotides to minimize promiscuous priming in the context of multiplex PCR. The 13 TCR Jβ reverse primers are anchored at the 3' end on the consensus splice site motif, with minimal overlap of the sequencing primers. The TCR Jβ primers provide consistent annealing temperature using the sequencer program under default parameters.

For the sequencing reaction, the IGHJ sequencing primers extend three nucleotides across the conserved CAG sequences as shown in Table 9.

TABLE 9

| IgH J segment | SEQ ID NO: | sequence |
|---|---|---|
| >IGHJSEQ4_1 | 432 | TGAGGAGACGGTGACCAGGGTTCCTTGGCCCCAG |
| >IGHJSEQ4_3 | 433 | TGAGGAGACGGTGACCAGGGTCCCTTGGCCCCAG |
| >IGHJSEQ4_2 | 434 | TGAGGAGACGGTGACCAGGGTTCCCTGGCCCCAG |
| >IGHJSEQ3_12 | 435 | CTGAAGAGACGGTGACCATTGTCCCTTGGCCCCAG |
| >IGHJSEQ6_1 | 436 | CTGAGGAGACGGTGACCGTGGTCCCTTGCCCCCAG |
| >IGHJSEQ6_2 | 437 | TGAGGAGACGGTGACCGTGGTCCCTTGGCCCCAG |
| >IGHJSEQ6_34 | 438 | CTGAGGAGACGGTGACCGTGGTCCCTTTGCCCCAG |
| >IGHJSEQ2_1 | 439 | CTGAGGAGACAGTGACCAGGGTGCCACGGCCCCAG |
| >IGHJSEQ5_1 | 440 | CTGAGGAGACGGTGACCAGGGTTCCTTGGCCCCAG |
| >IGHJSEQ5_2 | 441 | CTGAGGAGACGGTGACCAGGGTTCCCTGGCCCCAG |
| >IGHJSEQ1_1 | 442 | CTGAGGAGACGGTGACCAGGGTGCCCTGGCCCCAG |

Processing Sequence Data

For rapid analysis of sequencing results, an algorithm can be developed by one of ordinary skill. A preferred method is as follows.

The use of a PCR step to amplify the TCRβ CDR3 regions prior to sequencing could potentially introduce a systematic bias in the inferred relative abundance of the sequences, due to differences in the efficiency of PCR amplification of CDR3 regions utilizing different Vβ and Jβ gene segments. Each cycle of PCR amplification potentially introduces a bias of average magnitude $1.5^{1/15}=1.027$. Thus, the 25 cycles of PCR introduces a total bias of average magnitude $1.027^{25}=1.95$ in the inferred relative abundance of distinct CDR3 region sequences.

Sequenced reads were filtered for those including CDR3 sequences. Sequencer data processing involves a series of steps to remove errors in the primary sequence of each read, and to compress the data. A complexity filter removes approximately 20% of the sequences that are misreads from the sequencer. Then, sequences were required to have a minimum of a six base match to both one of the thirteen TCRB J-regions and one of 54 V-regions. Applying the filter to the control lane containing phage sequence, on average only one sequence in 7-8 million passed these steps. Finally, a nearest neighbor algorithm was used to collapse the data into unique sequences by merging closely related sequences, in order to remove both PCR error and sequencing error.

Analyzing the data, the ratio of sequences in the PCR product must be derived working backward from the sequence data before estimating the true distribution of clonotypes in the blood. For each sequence observed a given number of times in the data herein, the probability that that sequence was sampled from a particular size PCR pool is estimated. Because the CDR3 regions sequenced are sampled randomly from a massive pool of PCR products, the number of observations for each sequence are drawn from Poisson distributions. The Poisson parameters are quantized according to the number of T cell genomes that provided the template for PCR. A simple Poisson mixture model both estimates these parameters and places a pairwise probability for each sequence being drawn from each distribution. This is an expectation maximization method which reconstructs the abundances of each sequence that was drawn from the blood.

To estimate diversity, the "unseen species" formula is employed. To apply this formula, unique adaptive immune receptors (e.g. TCRB) clonotypes takes the place of species. The mathematical solution provides that for a total number of TCRβ "species" or clonotypes, S, a sequencing experiment observes $x_s$ copies of sequence s. For all of the unobserved clonotypes, $x_s$ equals 0, and each TCR clonotype is "captured" in a blood draw according to a Poisson process with parameter $\lambda_s$. The number of T cell genomes sequenced in the first measurement 1, and in the second measurement. Since there are a large number of unique sequences, an integral will represent the sum. If $G(\lambda)$ is the empirical distribution function of the parameters $\lambda_1, \ldots, \lambda_S$, and $n_x$ is the number of clonotypes sequenced exactly x times, then the total number of clonotypes, i.e., the measurement of diversity E, is given by the following formula:

$$E(n_x) = S \int_0^\infty \left(\frac{e^{-\lambda}\lambda^x}{x!}\right) dG(\lambda).$$

For a given experiment, where T cells are sampled from some arbitrary source (e.g. a blood draw), the formula is used to estimate the total diversity of species in the entire source. The idea is that the sampled number of clonotypes at each size contains sufficient information to estimate the underlying distribution of clonotypes in the whole source. To derive the formula, the number of new species expected if the exact measurement was repeated was estimated. The limit of the formula as if repeating the measurements an infinite number of times. The result is the expect number of species in the total underlying source population. The value for $\Delta(t)$, the number of new clonotypes observed in a second measurement, should be determined, preferably using the following equation:

$$\Delta(t) = \sum_x E(n_x)_{msmt1+msmt2} - \sum_x E(n_x)_{msmt1} = S \int_0^\infty e^{-\lambda}(1 - e^{-\lambda t}) dG(\lambda)$$

in which msmt1 and msmt2 are the number of clonotypes from measurement 1 and 2, respectively. Taylor expansion of $1-e^{-\lambda t}$ gives $\Delta(t)=E(x_1)t-E(x_2)t^2+E(x_3)t^3-\ldots$, which can be approximated by replacing the expectations $E(n_x)$ with the observed numbers in the first measurement. Using in the numbers observed in the first measurement, this formula predicts that $1.6*10^5$ new unique sequences should be observed in the second measurement. The actual value of the second measurement was $1.8*10^5$ new TCRβ sequences, which implies that the prediction provided a valid lower bound on total diversity. An Euler's transformation was used to regularize $\Delta(t)$ to produce a lower bound for $\Delta(\infty)$.

Using a Measurement of Diversity to Diagnose Disease

The measurement of diversity can be used to diagnose disease or the effects of a treatment, as follows. T cell and/or B cell receptor repertoires can be measured at various time points, e.g., after hematopoietic stem cell transplant (HSCT) treatment for leukemia. Both the change in diversity and the overall diversity of TCRB repertoire can be utilized to measure immunocompetence. A standard for the expected rate of immune reconstitution after transplant can be utilized. The rate of change in diversity between any two time points may be used to actively modify treatment. The overall diversity at a fixed time point is also an important measure, as this standard can be used to compare between different patients. In particular, the overall diversity is the measure that should correlate with the clinical definition of immune reconstitution. This information may be used to modify prophylactic drug regiments of antibiotics, antivirals, and antifungals, e.g., after HSCT.

The assessment of immune reconstitution after allogeneic hematopoietic cell transplantation can be determined by measuring changes in diversity. These techniques will also enhance the analysis of how lymphocyte diversity declines with age, as measured by analysis of T cell responses to vaccination. Further, the methods of the invention provide a means to evaluate investigational therapeutic agents (e.g., Interleukin-7 (IL-7)) that have a direct effect on the generation, growth, and development of αβ T cells. Moreover, application of these techniques to the study of thymic T cell populations will provide insight into the processes of both T cell receptor gene rearrangement as well as positive and negative selection of thymocytes.

A newborn that does not yet have a fully functioning immune system but may have maternally transmitted antibody is immunodeficient. A newborn is susceptible to a number of diseases until its immune system autonomously develops, and our measurement of the adaptive immune system may will likely prove useful with newborn patients.

Lymphocyte diversity can be assessed in other states of congenital or acquired immunodeficiency. An AIDS patient with a failed or failing immune system can be monitored to determine the stage of disease, and to measure a patient's response to therapies aimed to reconstitute immunocompetence.

Another application of the methods of the invention is to provide diagnostic measures for solid organ transplant recipients taking medication so their body will not reject the donated organ. Generally, these patients are under immunosuppressive therapies. Monitoring the immunocompetence of the host will assist before and after transplantation.

Individuals exposed to radiation or chemotherapeutic drugs are subject to bone marrow transplantations or otherwise require replenishment of T cell populations, along with associated immunocompetence. The methods of the invention provide a means for qualitatively and quantitatively assessing the bone marrow graft, or reconstitution of lymphocytes in the course of these treatments.

One manner of determining diversity is by comparing at least two samples of genomic DNA, preferably in which one sample of genomic DNA is from a patient and the other sample is from a normal subject, or alternatively, in which one sample of genomic DNA is from a patient before a therapeutic treatment and the other sample is from the patient after treatment, or in which the two samples of genomic DNA are from the same patient at different times during treatment. Another manner of diagnosis may be based on the comparison of diversity among the samples of genomic DNA, e.g., in which the immunocompetence of a human patient is assessed by the comparison.

Biosciences), CD45RO ECD (clone UCHL-1, Beckman Coulter), and CD45RO APC (clone UCHL-1, BD Biosciences) Staining of total PBMCs was done with the appropriate combination of antibodies for 20 minutes at 4° C., and stained cells were washed once before analysis. Lymphocyte subsets were isolated by FACS sorting in the BD FACSAria™ cell-sorting system (BD Biosciences). Data were analyzed with FlowJo software (Treestar Inc.).

Total genomic DNA was extracted from sorted cells using the QIAamp® DNA blood Mini Kit (QIAGEN®). The approximate mass of a single haploid genome is 3 pg. In order to sample millions of rearranged TCRB in each T cell compartment, 6 to 27 micrograms of template DNA were obtained from each compartment (see Table 10).

TABLE 10

|  | CD8+/CD45RO− | CD8+/CD45RO+ | CD4+/CD45RO− | CD4+/CD45RO+ | Donor |
|---|---|---|---|---|---|
| cells ($\times 10^6$) | 9.9 | 6.3 | 6.3 | 10 | 2 |
| DNA (μg) | 27 | 13 | 19 | 25 |  |
| PCR cycles | 25 | 25 | 30 | 30 |  |
| clusters (K/tile) | 29.3 | 27 | 102.3* | 118.3* |  |
| VJ sequences ($\times 10^6$) | 3.0 | 2.0 | 4.4 | 4.2 |  |
| Cells | 4.9 | 4.8 | 3.3 | 9 | 1 |
| DNA | 12 | 13 | 6.6 | 19 |  |
| PCR cycles | 30 | 30 | 30 | 30 |  |
| Clusters | 116.3 | 121 | 119.5 | 124.6 |  |
| VJ sequences | 3.2 | 3.7 | 4.0 | 3.8 |  |
| Cells | NA | NA | NA | 0.03 | PCR Bias assessment |
| DNA | NA | NA | NA | 0.015 |  |
| PCR cycles | NA | NA | NA | 25 + 15 |  |
| clusters | NA | NA | NA | 1.4/23.8 |  |
| VJ sequences | NA | NA | NA | 1.6 |  |

Biomarkers

Shared TCR sequences between individuals represent a new class of potential biomarkers for a variety of diseases, including cancers, autoimmune diseases, and infectious diseases. These are the public T cells that have been reported for multiple human diseases. TCRs are useful as biomarkers because T cells are a result of clonal expansion, by which the immune system amplifies these biomarkers through rapid cell division. Following amplification, the TCRs are readily detected even if the target is small (e.g. an early stage tumor). TCRs are also useful as biomarkers because in many cases the T cells might additionally contribute to the disease causally and, therefore could constitute a drug target. T cells self interactions are thought to play a major role in several diseases associated with autoimmunity, e.g., multiple sclerosis, Type I diabetes, and rheumatoid arthritis.

EXAMPLES

Example 1: Sample Acquisition, PBMC Isolation, FACS Sorting and Genomic DNA Extraction Peripheral blood samples from two healthy male donors aged 35 and 37 were obtained with written informed consent using forms approved by the Institutional Review Board of the Fred Hutchinson Cancer Research Center (FHCRC). Peripheral blood mononuclear cells (PBMC) were isolated by Ficoll-Hypaque® density gradient separation. The T-lymphocytes were flow sorted into four compartments for each subject: $CD8^+CD45RO^{+/-}$ and $CD4^+CD45RO^{+/-}$. For the characterization of lymphocytes the following conjugated anti-human antibodies were used: CD4 FITC (clone M-T466, Miltenyi Biotec), CD8 PE (clone RPA-T8, BD Example 2: Virtual T Cell Receptor β Chain Spectratyping Virtual TCR β chain spectratyping was performed as follows. Complementary DNA was synthesized from RNA extracted from sorted T cell populations and used as template for multiplex PCR amplification of the rearranged TCR β chain CDR3 region. Each multiplex reaction contained a 6-FAM-labeled antisense primer specific for the TCR β chain constant region, and two to five TCR β chain variable (TRBV) gene-specific sense primers. All 23 functional Vβ families were studied. PCR reactions were carried out on a Hybaid PCR Express thermal cycler (Hybaid, Ashford, UK) under the following cycling conditions: 1 cycle at 95° C. for 6 minutes, 40 cycles at 94° C. for 30 seconds, 58° C. for 30 seconds, and 72° C. for 40 seconds, followed by 1 cycle at 72° C. for 10 minutes. Each reaction contained cDNA template, 500 μM dNTPs, 2 mM $MgCl_2$ and 1 unit of AmpliTaq Gold DNA polymerase (Perkin Elmer) in AmpliTaq Gold buffer, in a final volume of 20 μL. After completion, an aliquot of the PCR product was diluted 1:50 and analyzed using a DNA analyzer. The output of the DNA analyzer was converted to a distribution of fluorescence intensity vs. length by comparison with the fluorescence intensity trace of a reference sample containing known size standards.

Example 3: Multiplex PCR Amplification of TCRβ CDR3 Regions

The CDR3 junction region was defined operationally, as follows. The junction begins with the second conserved cysteine of the V-region and ends with the conserved phenylalanine of the J-region. Taking the reverse complements of the observed sequences and translating the flanking regions, the amino acids defining the junction boundaries were identified. The number of nucleotides between these boundaries determines the length and therefore the frame of the CDR3 region. In order to generate the template library for sequencing, a multiplex PCR system was selected to amplify rearranged TCRβ loci from genomic DNA. The multiplex PCR system uses 45 forward primers (Table 3), each specific to a functional TCR Vβ segment, and thirteen reverse primers (Table 4), each specific to a TCR Jβ segment. The primers were selected to provide that adequate information is present within the amplified sequence to identify both the V and J genes uniquely (>40 base pairs of sequence upstream of the V gene recombination signal sequence (RSS), and >30 base pairs downstream of the J gene RSS).

The forward primers are modified at the 5' end with the universal forward primer sequence compatible with the Illumina GA2 cluster station solid-phase PCR. Similarly, all of the reverse primers are modified with the GA2 universal reverse primer sequence. The 3' end of each forward primer is anchored at position −43 in the Vβ segment, relative to the recombination signal sequence (RSS), thereby providing a unique Vβ tag sequence within the amplified region. The thirteen reverse primers specific to each Jβ segment are anchored in the 3' intron, with the 3' end of each primer crossing the intron/exon junction. Thirteen sequencing primers complementary to the Jβ segments were designed that are complementary to the amplified portion of the Jβ segment, such that the first few bases of sequence generated will capture the unique Jβ tag sequence.

On average J deletions were 4 bp+/−2.5 bp, which implies that J deletions greater than 10 nucleotides occur in less than 1% of sequences. The thirteen different TCR Jβ gene segments each had a unique four base tag at positions +11 through +14 downstream of the RSS site. Thus, sequencing oligonucleotides were designed to anneal to a consensus nucleotide motif observed just downstream of this "tag", so that the first four bases of a sequence read will uniquely identify the J segment (Table 5).

The information used to assign the J and V segment of a sequence read is entirely contained within the amplified sequence, and does not rely upon the identity of the PCR primers. These sequencing oligonucleotides were selected such that promiscuous priming of a sequencing reaction for one J segment by an oligonucleotide specific to another J segment would generate sequence data starting at exactly the same nucleotide as sequence data from the correct sequencing oligonucleotide. In this way, promiscuous annealing of the sequencing oligonucleotides did not impact the quality of the sequence data generated.

The average length of the CDR3 region, defined following convention as the nucleotides between the second conserved cysteine of the V segment and the conserved phenylalanine of the J segment, is 35+/−3, so sequences starting from the Jβ segment tag will nearly always capture the complete VNDNJ junction in a 50 bp read.

TCR βJ gene segments are roughly 50 bp in length. PCR primers that anneal and extend to mismatched sequences are referred to as promiscuous primers. Because of the risk of promiscuous priming in the context of multiplex PCR, especially in the context of a gene family, the TCR Jβ Reverse PCR primers were designed to minimize overlap with the sequencing oligonucleotides. Thus, the 13 TCR Jβ reverse primers are anchored at the 3' end on the consensus splice site motif, with minimal overlap of the sequencing primers. The TCR Jβ primers were designed for a consistent annealing temperature (58 degrees in 50 mM salt) using the OligoCalc program under default parameters (http://www-.basic.northwestern.edu/biotools/oligocalc.html).

The 45 TCR Vβ forward primers were designed to anneal to the Vβ segments in a region of relatively strong sequence conservation between Vβ segments, for two express purposes. First, maximizing the conservation of sequence among these primers minimizes the potential for differential annealing properties of each primer. Second, the primers were chosen such that the amplified region between V and J primers will contain sufficient TCR Vβ sequence information to identify the specific Vβ gene segment used. This obviates the risk of erroneous TCR Vβ gene segment assignment, in the event of promiscuous priming by the TCR Vβ primers. TCR Vβ forward primers were designed for all known non-pseudogenes in the TCRβ locus.

The total PCR product for a successfully rearranged TCRβ CDR3 region using this system is expected to be approximately 200 bp long. Genomic templates were PCR amplified using an equimolar pool of the 45 TCR Vβ F primers (the "VF pool") and an equimolar pool of the thirteen TCR Jβ R primers (the "JR pool"). 50 μl PCR reactions were set up at 1.0 μM VF pool (22 nM for each unique TCR Vβ F primer), 1.0 μM JR pool (77 nM for each unique TCRBJR primer), 1× QIAGEN Multiple PCR master mix (QIAGEN part number 206145), 10% Q-solution (QIAGEN), and 16 ng/ul gDNA. The following thermal cycling conditions were used in a PCR Express thermal cycler (Hybaid, Ashford, UK) under the following cycling conditions: 1 cycle at 95° C. for 15 minutes, 25 to 40 cycles at 94° C. for 30 seconds, 59° C. for 30 seconds and 72° C. for 1 minute, followed by one cycle at 72° C. for 10 minutes. 12-20 wells of PCR were performed for each library, in order to sample hundreds of thousands to millions of rearranged TCRβ CDR3 loci.

Example 4: Pre-Processing of Sequence Data

Sequencer data processing involves a series of steps to remove errors in the primary sequence of each read, and to compress the data. First, a complexity filter removes approximately 20% of the sequences which are misreads from the sequencer. Then, sequences were required to have a minimum of a six base match to both one of the thirteen J-regions and one of 54 V-regions. Applying the filter to the control lane containing phage sequence, on average only one sequence in 7-8 million passed these steps without false positives. Finally, a nearest neighbor algorithm was used to collapse the data into unique sequences by merging closely related sequences, in order to remove both PCR error and sequencing error (see Table 10).

Example 5: Estimating Relative CDR3 Sequence Abundance in PCR Pools and Blood Samples After collapsing the data, the underlying distribution of T-cell sequences in the blood reconstructing were derived from the sequence data. The procedure used three steps; 1) flow sorting T-cells drawn from peripheral blood, 2) PCR amplification, and 3) sequencing. Analyzing the data, the ratio of sequences in the PCR product must be derived working backward from the sequence data before estimating the true distribution of clonotypes in the blood.

For each sequence observed a given number of times in the data herein, the probability that that sequence was sampled from a particular size PCR pool is estimated. Because the CDR3 regions sequenced are sampled randomly from a massive pool of PCR products, the number of observations for each sequence are drawn from Poisson distributions. The Poisson parameters are quantized according to the number of T cell genomes that provided the template for PCR. A simple Poisson mixture model both estimates these parameters and places a pairwise probability for each sequence being drawn from each distribution. This is an expectation maximization method which reconstructs the abundances of each sequence that was drawn from the blood.

Example 6: Unseen Species Model for Estimation of True Diversity

A mixture model can reconstruct the frequency of each TCRβ CDR3 species drawn from the blood, but the larger question is how many unique CDR3 species were present in the donor? This is a fundamental question that needs to be answered as the available sample is limited in each donor, and will be more important in the future as these techniques are extrapolated to the smaller volumes of blood that can reasonably be drawn from patients undergoing treatment.

The mathematical solution provides that for a total number of TCRβ "species" or clonotypes, S, a sequencing experiment observes $x_s$ copies of sequence s. For all of the unobserved clonotypes, $x_s$ equals 0, and each TCR clonotype is "captured" in a blood draw according to a Poisson process with parameter $\lambda_s$. The number of T cell genomes sequenced in the first measurement 1, and in the second measurement. Since there are a large number of unique sequences, an integral will represent the sum. If $G(\lambda)$ is the empirical distribution function of the parameters $\lambda_1, \ldots, \lambda_S$, and $n_x$ is the number of clonotypes sequenced exactly x times, then $$E(n_x) = S \int_0^\infty \left(\frac{e^{-\lambda}\lambda^x}{x!}\right) dG(\lambda).$$

The value $\Delta(t)$ is the number of new clonotypes observed in the second sequencing experiment.

$$\Delta(t) = \sum_x E(n_x)_{exp1+exp2} - \sum_x E(n_x)_{exp1} = S \int_0^\infty e^{-\lambda}(1 - e^{-\lambda t}) dG(\lambda)$$

Taylor expansion of $1-e^{-\lambda t}$ gives $\Delta(t)=E(x_1)t-E(x_2)t^2+E(x_3)t^3- \ldots$, which can be approximated by replacing the expectations ($E(n_x)$) with the observed numbers in the first measurement. Using in the numbers observed in the first measurement, this formula predicts that $1.6*10^5$ new unique sequences should be observed in the second measurement. The actual value of the second measurement was $1.8*10^5$ new TCRβ sequences, which implies that the prediction provided a valid lower bound on total diversity. An Euler's transformation was used to regularize $\Delta(t)$ to produce a lower bound for $\Delta(\infty)$.

Example 7: Error Correction and Bias Assessment

Sequence error in the primary sequence data derives primarily from two sources: (1) nucleotide misincorporation that occurs during the amplification by PCR of TCRβ CDR3 template sequences, and (2) errors in base calls introduced during sequencing of the PCR-amplified library of CDR3 sequences. The large quantity of data allows us to implement a straightforward error correcting code to correct most of the errors in the primary sequence data that are attributable to these two sources. After error correction, the number of unique, in-frame CDR3 sequences and the number of observations of each unique sequence were tabulated for each of the four flow-sorted T cell populations from the two donors. The relative frequency distribution of CDR3 sequences in the four flow cytometrically-defined populations demonstrated that antigen-experienced CD45RO+ populations contained significantly more unique CDR3 sequences with high relative frequency than the CD45RO− populations. Frequency histograms of TCRβ CDR3 sequences observed in four different T cell subsets distinguished by expression of CD4, CD8, and CD45RO and present in blood showed that ten unique sequences were each observed 200 times in the CD4+CD45RO+ (antigen-experienced) T cell sample, which was more than twice as frequent as that observed in the CD4+CD45RO− populations.

The use of a PCR step to amplify the TCRβ CDR3 regions prior to sequencing could potentially introduce a systematic bias in the inferred relative abundance of the sequences, due to differences in the efficiency of PCR amplification of CDR3 regions utilizing different Vβ and Jβ gene segments. To estimate the magnitude of any such bias, the TCRβ CDR3 regions from a sample of approximately 30,000 unique CD4+CD45RO+ T lymphocyte genomes were amplified through 25 cycles of PCR, at which point the PCR product was split in half. Half was set aside, and the other half of the PCR product was amplified for an additional 15 cycles of PCR, for a total of 40 cycles of amplification. The PCR products amplified through 25 and 40 cycles were then sequenced and compared. Over 95% of the 25 cycle sequences were also found in the 40-cycle sample: a linear correlation is observed when comparing the frequency of sequences between these samples. For sequences observed a given number of times in the 25 cycle lane, a combination of PCR bias and sampling variance accounts for the variance around the mean of the number of observations at 40 cycles. Conservatively attributing the mean variation about the line (1.5-fold) entirely to PCR bias, each cycle of PCR amplification potentially introduces a bias of average magnitude $1.5^{1/15}=1.027$. Thus, the 25 cycles of PCR introduces a total bias of average magnitude $1.027^{25}=1.95$ in the inferred relative abundance of distinct CDR3 region sequences.

Example 8: Jβ Gene Segment Usage

The CDR3 region in each TCR β chain includes sequence derived from one of the thirteen $J_\beta$ gene segments. Analysis of the CDR3 sequences in the four different T cell populations from the two donors demonstrated that the fraction of total sequences which incorporated sequences derived from the thirteen different $J_\beta$ gene segments varied more than 20-fold. Jβ utilization among four different T flow cytometrically-defined T cells from a single donor is was relatively constant within a given donor. Moreover, the $J_\beta$ usage patterns observed in two donors, which were inferred from analysis of genomic DNA from T cells sequenced using the GA, are qualitatively similar to those observed in T cells from umbilical cord blood and from healthy adult donors, both of which were inferred from analysis of cDNA from T cells sequenced using exhaustive capillary-based techniques.

Example 9: Nucleotide Insertion Bias

Much of the diversity at the CDR3 junctions in TCR α and β chains is created by non-templated nucleotide insertions by the enzyme Terminal Deoxynucloetidyl Transferase (TdT). However, in vivo, selection plays a significant role in shaping the TCR repertoire giving rise to unpredictability. The TdT nucleotide insertion frequencies, independent of selection, were calculated using out of frame TCR sequences. These sequences are non-functional rearrangements that are carried on one allele in T cells where the second allele has a functional rearrangement. The mononucleotide insertion bias of TdT favors C and G (Table 11).

TABLE 11

Mono-nucleotide bias in out of frame data

| | A | C | G | T |
|---|---|---|---|---|
| Lane 1 | 0.24 | 0.294 | 0.247 | 0.216 |
| Lane 2 | 0.247 | 0.284 | 0.256 | 0.211 |
| Lane 3 | 0.25 | 0.27 | 0.268 | 0.209 |
| Lane 4 | 0.255 | 0.293 | 0.24 | 0.21 |

Similar nucleotide frequencies are observed in the in frame sequences (Table 12).

TABLE 12

Mono-nucleotide bias in in-frame data

| | A | C | G | T |
|---|---|---|---|---|
| Lane 1 | 0.21 | 0.285 | 0.275 | 0.228 |
| Lane 2 | 0.216 | 0.281 | 0.266 | 0.235 |
| Lane 3 | 0.222 | 0.266 | 0.288 | 0.221 |
| Lane 4 | 0.206 | 0.294 | 0.228 | 0.27 |

The N regions from the out of frame TCR sequences were used to measure the di-nucleotide bias. To isolate the marginal contribution of a di-nucleotide bias, the di-nucleotide frequencies was divided by the mononucleotide frequencies of each of the two bases. The measure is $$m = \frac{f(n_1 n_2)}{f(n_1) f(n_2)}.$$

The matrix for m is found in Table 13.

TABLE 13

Di-nucleotide odd ratios for out of frame data

| | A | C | G | T |
|---|---|---|---|---|
| A | 1.198 | 0.938 | 0.945 | 0.919 |
| C | 0.988 | 1.172 | 0.88 | 0.931 |
| G | 0.993 | 0.701 | 1.352 | 0.964 |
| T | 0.784 | 1.232 | 0.767 | 1.23 |

Many of the dinucleotides are under or over represented. As an example, the odds of finding a GG pair are very high. Since the codons GGN translate to glycine, many glycines are expected in the CDR3 regions.

Example 10: Amino Acid Distributions in the CDR3 Regions

The distribution of amino acids in the CDR3 regions of TCRβ chains are shaped by the germline sequences for V, D, and J regions, the insertion bias of TdT, and selection. The distribution of amino acids in this region for the four different T cell sub-compartments is very similar between different cell subtypes. Separating the sequences into β chains of fixed length, a position dependent distribution among amino acids, which are grouped by the six chemical properties: small, special, and large hydrophobic, neutral polar, acidic and basic. The distributions are virtually identical except for the CD8+ antigen experienced T cells, which have a higher proportion of acidic bases, particularly at position 5.

Of particular interest is the comparison between CD8+ and CD4+ TCR sequences as they bind to peptides presented by class I and class II HLA molecules, respectively. The CD8+ antigen experienced T cells have a few positions with a higher proportion of acidic amino acids. This could be do binding with a basic residue found on HLA Class I molecules, but not on Class II.

Example 11: TCR β Chains with Identical Amino Acid Sequences Found in Different People The TCR β chain sequences were translated to amino acids and then compared pairwise between the two donors. Many thousands of exact sequence matches were observed. For example, comparing the CD4+ CD45RO− sub-compartments, approximately 8,000 of the 250,000 unique amino acid sequences from donor 1 were exact matches to donor 2. Many of these matching sequences at the amino acid level have multiple nucleotide differences at third codon positions. Following the example mentioned above, 1,500/8,000 identical amino acid matches had >5 nucleotide mismatches. Between any two T cell sub-types, 4-5% of the unique TCRβ sequences were found to have identical amino acid matches.

Two possibilities were examined: that 1) selection during TCR development is producing these common sequences and 2) the large bias in nucleotide insertion frequency by TdT creates similar nucleotide sequences. The in-frame pairwise matches were compared to the out-of-frame pairwise matches (see Examples 1-4, above). Changing frames preserved all of the features of the genetic code and so the same number of matches should be found if the sequence bias was responsible for the entire observation. However, almost twice as many in-frame matches as out-of-frame matches were found, suggesting that selection at the protein level is playing a significant role.

To confirm this finding of thousands of identical TCR β chain amino acid sequences, two donors were compared with respect to the CD8+ CD62L+ CD45RA+ (naïve-like) TCRs from a third donor, a 44 year old CMV+ Caucasian female. Identical pairwise matches of many thousands of sequences at the amino acid level between the third donor and each of the original two donors were found. In contrast, 460 sequences were shared between all three donors. The large variation in total number of unique sequences between the donors is a product of the starting material and variations in loading onto the sequencer, and is not representative of a variation in true diversity in the blood of the donors.

Example 12: Higher Frequency Clonotypes are Closer to Germline

The variation in copy number between different sequences within every T cell sub-compartment ranged by a factor of over 10,000-fold. The only property that correlated with copy number was (the number of insertions plus the number of deletions), which inversely correlated. Results of the analysis showed that deletions play a smaller role than insertions in the inverse correlation with copy number.

Sequences with less insertions and deletions have receptor sequences closer to germ line. One possibility for the increased number of sequences closer to germ line is that they are the created multiple times during T cell development. Since germ line sequences are shared between people, shared TCRβ chains are likely created by TCRs with a small number of insertions and deletions.

Example 13: "Spectratype" Analysis of TCRβ CDR3 Sequences by V Gene Segment Utilization and CDR3 Length TCR diversity has commonly been assessed using the technique of TCR spectratyping, an RT-PCR-based technique that does not assess TCR CDR3 diversity at the sequence level, but rather evaluates the diversity of TCRα or TCRβ CDR3 lengths expressed as mRNA in subsets of αβ T cells that use the same $V_\alpha$ or $V_\beta$ gene segment. The spectratypes of polyclonal T cell populations with diverse repertoires of TCR CDR3 sequences, such as are seen in umbilical cord blood or in peripheral blood of healthy young adults typically contain CDR3 sequences of 8-10 different lengths that are multiples of three nucleotides, reflecting the selection for in-frame transcripts. Spectratyping also provides roughly quantitative information about the relative frequency of CDR3 sequences with each specific length. To assess whether direct sequencing of TCRβ CDR3 regions from T cell genomic DNA using the sequencer could faithfully capture all of the CDR3 length diversity that is identified by spectratyping, "virtual" TCRβ spectratypes (see Examples above) were generated from the sequence data and compared with TCRβ spectratypes generated using conventional PCR techniques. The virtual spectratypes contained all of the CDR3 length and relative frequency information present in the conventional spectratypes. Direct TCRβ CDR3 sequencing captures all of the TCR diversity information present in a conventional spectratype. A comparison of standard TCRβ spectratype data and calculated TCRβ CDR3 length distributions for sequences utilizing representative TCR Vβ gene segments and present in $CD4^+$ $CD45RO^+$ cells from donor 1. Reducing the information contained in the sequence data to a frequency histogram of the unique CDR3 sequences with different lengths within each Vβ family readily reproduces all of the information contained in the spectratype data. In addition, the virtual spectratypes revealed the presence within each $V_\beta$ family of rare CDR3 sequences with both very short and very long CDR3 lengths that were not detected by conventional PCR-based spectratyping.

Example 14: Estimation of Total CDR3 Sequence Diversity

After error correction, the number of unique CDR3 sequences observed in each lane of the sequencer flow cell routinely exceeded $1 \times 10^5$. Given that the PCR products sequenced in each lane were necessarily derived from a small fraction of the T cell genomes present in each of the two donors, the total number of unique TCRβ CDR3 sequences in the entire T cell repertoire of each individual is likely to be far higher. Estimating the number of unique sequences in the entire repertoire, therefore, requires an estimate of the number of additional unique CDR3 sequences that exist in the blood but were not observed in the sample. The estimation of total species diversity in a large, complex population using measurements of the species diversity present in a finite sample has historically been called the "unseen species problem" (see Examples above). The solution starts with determining the number of new species, or TCRβ CDR3 sequences, that are observed if the experiment is repeated, i.e., if the sequencing is repeated on an identical sample of peripheral blood T cells, e.g., an identically prepared library of TCRβ CDR3 PCR products in a different lane of the sequencer flow cell and counting the number of new CDR3 sequences. For $CD8^+CD45RO^-$ cells from donor 2, the predicted and observed number of new CDR3 sequences in a second lane are within 5% (see Examples above), suggesting that this analytic solution can, in fact, be used to estimate the total number of unique TCRβ CDR3 sequences in the entire repertoire.

The resulting estimates of the total number of unique TCRβ CDR3 sequences in the four flow cytometrically-defined T cell compartments are shown in Table 14.

TABLE 14

| | TCR repertoire diversity | | | |
|---|---|---|---|---|
| Donor | CD8 | CD4 | CD45RO | Diversity |
| 1 | + | − | + | $6.3 * 10^5$ |
| | + | − | − | $1.24 * 10^6$ |
| | − | + | + | $8.2 * 10^5$ |
| | − | + | − | $1.28 * 10^6$ |
| | Total T cell diversity | | | $3.97 * 10^6$ |
| 2 | + | − | + | $4.4 * 10^5$ |
| | + | − | − | $9.7 * 10^5$ |
| | − | + | + | $8.7 * 10^5$ |
| | − | + | − | $1.03 * 10^6$ |
| | Total T cell diversity | | | $3.31 * 10^6$ |

Of note, the total TCRβ diversity in these populations is between 3-4 million unique sequences in the peripheral blood. Surprisingly, the $CD45RO^+$, or antigen-experienced, compartment constitutes approximately 1.5 million of these sequences. This is at least an order of magnitude larger than expected. This discrepancy is likely attributable to the large number of these sequences observed at low relative frequency, which could only be detected through deep sequencing. The estimated TCRβ CDR3 repertoire sizes of each compartment in the two donors are within 20% of each other.

The results herein demonstrate that the realized TCRβ receptor diversity is at least five-fold higher than previous estimates (~$4*10^6$ distinct CDR3 sequences), and, in particular, suggest far greater TCRβ diversity among $CD45RO^+$ antigen-experienced αβ T cells than has previously been reported (~$1.5*10^6$ distinct CDR3 sequences). However, bioinformatic analysis of the TCR sequence data shows strong biases in the mono- and di-nucleotide content, implying that the utilized TCR sequences are sampled from a distribution much smaller than the theoretical size. With the large diversity of TCRβ chains in each person sampled from a severely constrict space of sequences, overlap of the TCR sequence pools can be expected between each person. In fact, the results showed about 5% of $CD8^+$ naïve TCRβ chains with exact amino acid matches are shared between each pair of three different individuals. As the TCRα pool has been previously measured to be substantially smaller than the theoretical TCRβ diversity, these results show that hundreds to thousands of truly public αβ TCRs can be found.

What is claimed:

1. A method for generating a clonotype profile of rearranged T cell receptor (TCR) and/or immunoglobulins (Ig) in a biological sample comprising:
   (a) combining a plurality of V segment primers and a plurality of J segment primers with DNA from a biological sample comprising T cells and/or B cells wherein the V segment primers for TCR amplification comprise the primers of SEQ ID Nos: 1-45, the J segment primers for TCR amplification comprise the primers of SEQ ID Nos: 46-57, the V segment primers for Ig amplification comprise the primers of SEQ ID Nos:443-451 and the J segment primers for amplification of Ig comprise the primers of SEQ ID Nos: 452-467, wherein the terminal "n" position in SEQ ID NO: 1-45 and SEQ ID Nos: 46-57 comprises a universal primer sequence, and wherein SEQ ID Nos:443-451 and SEQ ID Nos: 452-467 comprise a universal primer sequence;
   (b) amplifying rearranged TCR and/or Ig using the plurality of V segment primers and J segment primers in a multiplex polymerase chain reaction (PCR) to produce amplified rearranged TCR and/or Ig DNA molecules;

(c) immobilizing said amplified rearranged TCR and/or Ig DNA molecules on a solid surface and performing solid phase PCR to form template clusters on the solid surface; and (d) sequencing the TCR and/or Ig DNA molecules in the template clusters to produce sequence reads that encompasses a CDR3 encoding region of the TCR and/or Ig thereby generating a clonotype profile TCRs and/or Igs in the biological sample.

2. The method of claim 1 wherein the universal primer sequence is a GA2 universal primer sequence.

3. The method of claim 2 wherein the V segment primers for TCR amplification comprise SEQ ID NOS: 58-102 and the J segment primers for TCR amplification comprise SEQ ID Nos: 103-113.

4. The method of claim 1 wherein the total diversity of rearranged TCR is greater than $1 \times 10^6$.

5. The method of claim 1 wherein sequencing in step (d) is done by reversible dye termination chemistry.

6. The method of claim 5 wherein the sequencing reads 30-54 base pair intervals.

7. The method of claim 1 wherein the sample comprises genomic DNA.

8. The method of claim 1 wherein the sample comprises cDNA.

9. The method of claim 1 wherein the biological sample is a blood sample.

* * * * *